US012496347B2

(12) United States Patent
Zhang et al.

(10) Patent No.: US 12,496,347 B2
**(45) Date of Patent: *Dec. 16, 2025**

(54) NUCLEIC ACID, COMPOSITION AND CONJUGATE CONTAINING NUCLEIC ACID, PREPARATION METHOD THEREFOR AND USE THEREOF

(71) Applicant: SUZHOU RIBO LIFE SCIENCE CO., LTD., Jiangsu (CN)

(72) Inventors: Hongyan Zhang, Jiangsu (CN); Shan Gao, Jiangsu (CN); Daiwu Kang, Jiangsu (CN)

(73) Assignee: SUZHOU RIBO LIFE SCIENCE CO., LTD., Jiangsu (CN)

( * ) Notice: Subject to any disclaimer, the term of this patent is extended or adjusted under 35 U.S.C. 154(b) by 1062 days.

This patent is subject to a terminal disclaimer.

(21) Appl. No.: 17/418,946

(22) PCT Filed: Dec. 27, 2019

(86) PCT No.: PCT/CN2019/129016

§ 371 (c)(1),
(2) Date: Jun. 28, 2021

(87) PCT Pub. No.: WO2020/135673

PCT Pub. Date: Jul. 2, 2020

(65) Prior Publication Data

US 2022/0062427 A1 Mar. 3, 2022

(30) Foreign Application Priority Data

Dec. 28, 2018 (CN) ......................... 201811622633.0

(51) Int. Cl.

| | |
|---|---|
| ***A61K 47/54*** | (2017.01) |
| ***A61P 3/06*** | (2006.01) |
| ***C12N 15/113*** | (2010.01) |

(52) U.S. Cl.

CPC .............. *A61K 47/549* (2017.08); *A61P 3/06* (2018.01); *C12N 15/113* (2013.01); *C12N 2310/14* (2013.01); *C12N 2310/315* (2013.01); *C12N 2310/322* (2013.01); *C12N 2310/351* (2013.01); *C12N 2320/30* (2013.01)

(58) Field of Classification Search

CPC ....... A61K 47/549; A61P 3/06; C12N 15/113; C12N 2310/14; C12N 2310/315; C12N 2310/322; C12N 2310/351; C12N 2320/30

See application file for complete search history.

(56) References Cited

U.S. PATENT DOCUMENTS

| | | | |
|---|---|---|---|
| 8,030,474 B2 | 10/2011 | Khvorova et al. | |
| 8,106,022 B2 | 1/2012 | Manoharan et al. | |
| 8,334,372 B2 | 12/2012 | Freier et al. | |
| 8,344,125 B2 | 1/2013 | Manoharan et al. | |
| 9,428,751 B2 | 8/2016 | Macdonald et al. | |
| 9,670,492 B2 | 6/2017 | Freier et al. | |
| 10,130,651 B2 | 11/2018 | Wooddell et al. | |
| 10,246,708 B2 | 4/2019 | Kasperkovitz et al. | |
| 10,294,477 B2 | 5/2019 | Swayze | |
| 10,370,453 B2 | 8/2019 | Sexton et al. | |
| 10,934,544 B2 | 3/2021 | Akinc et al. | |
| 11,084,884 B2 | 8/2021 | Sexton et al. | |
| 11,414,661 B2 | 8/2022 | Zhang et al. | |
| 11,414,665 B2 | 8/2022 | Zhang et al. | |
| 11,492,620 B2 | 11/2022 | Zhang et al. | |
| 11,633,482 B2 * | 4/2023 | Zhang .................. | A61K 47/549 514/25 |
| 11,660,347 B2 * | 5/2023 | Zhang .................. | A61K 47/549 536/1.11 |
| 11,918,600 B2 | 3/2024 | Zhang et al. | |

(Continued)

FOREIGN PATENT DOCUMENTS

| | | |
|---|---|---|
| AU | 2014208251 A1 | 8/2014 |
| CA | 2930393 A1 | 6/2009 |

(Continued)

OTHER PUBLICATIONS

Lorenzer et al., "Going beyond the liver: Progress and Challenges of Targeted Delivery of siRNA Therapeutics", Journal of Controlled Release, vol. 203, Apr. 10, 2015, pp. 1-15. (Year: 2015).*

Fedin A.I. et al., "Review of clinical recommendations for treatment and prevention of ischemic stroke", S. S. Korsakov Journal of Neurology and Psychiatry, 2019, vol. 119, No. 8, pp. 91-96, doi: 10.17116/jnevro201911908291, with English abstract. (Cited in Office Action issued on Mar. 6, 2024, in corresponding Russian Application No. 2021130601) (6 pages).

Meijers J.C. et al., "High levels of coagulation factor XI as a risk factor for venous thrombosis", N. Engl. J. Med., 2000, vol. 342, No. 10, pp. 696-701, doi: 10.1056/NEJM200003093421004. (Cited in Office Action issued on Mar. 6, 2024, in corresponding Russian Application No. 2021130601) (6 pages).

(Continued)

*Primary Examiner* — Abigail Vanhorn
*Assistant Examiner* — Stephanie L Sullivan
(74) *Attorney, Agent, or Firm* — Panitch Schwarze Belisario & Nadel LLP

(57) ABSTRACT

Provided are an siRNA for inhibiting the expression of the apolipoprotein C3 gene, and a pharmaceutical composition and a conjugate containing the siRNA. Each nucleotide in the siRNA is, respectively and independently, a modified or unmodified nucleotide; the siRNA contains a sense strand and an anti-sense strand; the sense strand includes nucleotide sequence I; nucleotide sequence I has the same length as the nucleotide sequence as shown in SEQ ID NO: 1, and not more than three nucleotides are different; the anti-sense strand contains nucleotide sequence II; and nucleotide sequence II has the same length as the nucleotide sequence as shown in SEQ ID NO: 2, and not more than three nucleotides are different. The siRNA provided by the present disclosure and the pharmaceutical composition and the conjugate thereof can effectively treat and/or prevent dyslipidemia.

24 Claims, 10 Drawing Sheets

Specification includes a Sequence Listing.

(56) References Cited

U.S. PATENT DOCUMENTS

2003/0206887 A1 11/2003 Morrissey et al.
2004/0266707 A1 12/2004 Leake et al.
2005/0245475 A1 11/2005 Khvorova et al.
2005/0246794 A1 11/2005 Khvorova et al.
2005/0255487 A1 11/2005 Khvorova et al.
2008/0113351 A1 5/2008 Naito et al.
2008/0146788 A1 6/2008 Bhat et al.
2010/0063132 A1 3/2010 Kim et al.
2010/0137414 A1 6/2010 Freier et al.
2011/0015252 A1 1/2011 Fitzgerald et al.
2011/0039914 A1 2/2011 Pavco et al.
2011/0054005 A1 3/2011 Naito et al.
2012/0052487 A9 3/2012 Khvorova et al.
2012/0108803 A1 5/2012 Han et al.
2012/0172412 A1 7/2012 Rozema et al.
2012/0184595 A1 7/2012 Macdonald et al.
2012/0201756 A1 8/2012 Sexton
2012/0227119 A1 9/2012 Doran et al.
2013/0005793 A1 1/2013 Chin et al.
2013/0023579 A1 1/2013 Crooke et al.
2013/0041133 A1* 2/2013 Aaronson ............ A61K 47/645 530/324
2013/0096288 A1 4/2013 Han et al.
2013/0123482 A1 5/2013 Xi et al.
2013/0158021 A1 6/2013 Dong et al.
2013/0190484 A1 7/2013 Rozema et al.
2014/0099666 A1 4/2014 Rossomando et al.
2014/0128453 A1 5/2014 Mullick et al.
2014/0179768 A1 6/2014 Bettencourt et al.
2014/0194489 A1 7/2014 Bumcrot et al.
2014/0343123 A1 11/2014 Prakash et al.
2015/0093444 A1 4/2015 Zhang et al.
2015/0152436 A1 6/2015 Musunuru et al.
2015/0174260 A1 6/2015 Yang et al.
2015/0191726 A1 7/2015 Manoharan et al.
2015/0247143 A1 9/2015 Fitzgerald et al.
2015/0263948 A1 9/2015 Jan et al.
2015/0291958 A1 10/2015 Albaek et al.
2015/0315584 A1 11/2015 Macdonald et al.
2015/0315594 A1 11/2015 Prakash et al.
2016/0017335 A1 1/2016 Borodovsky et al.
2016/0186180 A1 6/2016 Bettencourt et al.
2016/0237438 A1 8/2016 Brown et al.
2016/0283653 A1 9/2016 Staudt et al.
2016/0354404 A1 12/2016 Hinkle et al.
2017/0000815 A1 1/2017 Fitzgerald et al.
2017/0002094 A1 1/2017 Sexton et al.
2017/0114341 A1 4/2017 Bradshaw et al.
2018/0087054 A1 3/2018 Querbes et al.
2018/0148722 A1 5/2018 Fitzgerald et al.
2018/0216114 A1 8/2018 Fitzgerald et al.
2018/0245077 A1 8/2018 Chiu et al.
2019/0062749 A1 2/2019 Zhang
2019/0078088 A1* 3/2019 Li ........................ C12N 15/113
2019/0202855 A1 7/2019 Sakamuri et al.
2019/0255091 A1 8/2019 Li et al.
2019/0292547 A1 9/2019 Li et al.
2020/0199591 A1 6/2020 Fitzgerald et al.
2020/0338201 A1 10/2020 Zhang et al.
2020/0360522 A1 11/2020 Zhang et al.
2021/0032623 A1 2/2021 Zhang et al.
2021/0275564 A1 9/2021 Zhang et al.
2021/0277400 A1 9/2021 Zhang et al.
2021/0401994 A1 12/2021 Zhang et al.
2022/0049249 A1 2/2022 Zhang et al.
2022/0186221 A1 6/2022 Zhang et al.
2022/0235359 A1 7/2022 Zhang et al.
2022/0315929 A1 10/2022 Zhang et al.
2022/0356474 A1 11/2022 Zhang et al.
2022/0389428 A1 12/2022 Zhang et al.
2022/0395526 A1 12/2022 Zhang et al.
2023/0076803 A1 3/2023 Zhang et al.
2023/0132756 A1 5/2023 Zhang et al.
2023/0257827 A1 8/2023 Zhang et al.
2023/0313195 A1 10/2023 Zhang et al.
2024/0200060 A1 6/2024 Zhang et al.
2024/0200076 A1 6/2024 Zhang et al.

FOREIGN PATENT DOCUMENTS

CA 2 677 068 A1 3/2011
CN 101603042 A 12/2009
CN 102006890 A 4/2011
CN 102016036 A 4/2011
CN 102124107 A 7/2011
CN 102140458 A 8/2011
CN 102140459 A 8/2011
CN 102140460 A 8/2011
CN 102140461 A 8/2011
CN 102344477 A 2/2012
CN 102439148 A 5/2012
CN 102719434 A 10/2012
CN 102753186 A 10/2012
CN 102869774 A 1/2013
CN 103380113 A 10/2013
CN 102083983 B 4/2014
CN 103890000 A 6/2014
CN 104107437 A 10/2014
CN 104232644 A 12/2014
CN 104328121 A 2/2015
CN 104717982 A 6/2015
CN 104854242 A 8/2015
CN 104922141 A 9/2015
CN 105324485 A 2/2016
CN 105378082 A 3/2016
CN 105392488 A 3/2016
CN 105452465 A 3/2016
CN 105517556 A 4/2016
CN 105713092 A 6/2016
CN 105814204 A 7/2016
CN 106132442 A 11/2016
CN 106146591 A 11/2016
CN 106232831 A 12/2016
CN 106255755 A 12/2016
CN 106460025 A 2/2017
CN 107075516 A 8/2017
CN 107109405 A 8/2017
CN 107250362 A 10/2017
CN 107854478 A 3/2018
CN 108271386 A 3/2018
CN 108064294 A 5/2018
CN 108064313 A 5/2018
CN 108220293 A 6/2018
CN 108239644 A 7/2018
CN 108265052 A 7/2018
CN 108348541 A 7/2018
CN 110945131 A 3/2020
CN 110959011 A 4/2020
CN 111050807 A 4/2020
CN 111973617 A 11/2020
CN 111973618 A 11/2020
CN 111973619 A 11/2020
CN 111979237 A 11/2020
CN 112423795 A 2/2021
CN 113330117 A 8/2021
EP 1 752 536 A1 2/2007
EP 2 194 128 A1 6/2010
EP 2 213 738 A2 8/2010
EP 2 376 641 A 10/2011
EP 2669377 A2 12/2013
EP 2990410 A1 3/2016
EP 3312281 A2 4/2018
EP 3315608 A1 5/2018
EP 3 335 715 A2 6/2018
EP 3409780 A1 12/2018
EP 3 719 128 A1 10/2020
EP 3 862 024 A1 8/2021
JP 2013523149 A 6/2013
JP 2013537423 A 10/2013
JP 2016501195 A 1/2016
JP 2016523087 A 8/2016
JP 2017521045 A 8/2017
JP 2017534290 A 11/2017

(56) References Cited

FOREIGN PATENT DOCUMENTS

| | | | |
|---|---|---|---|
| RU | 2013 134 745 | A | 2/2015 |
| RU | 2 558 258 | C2 | 7/2015 |
| RU | 2015 133 167 | A | 3/2017 |
| TW | 201925471 | A | 7/2019 |
| TW | 201929905 | A | 8/2019 |
| WO | 00/27795 | A1 | 5/2000 |
| WO | 2004/045543 | A2 | 6/2004 |
| WO | 2004/078181 | A1 | 9/2004 |
| WO | 2005/116204 | A1 | 12/2005 |
| WO | 2006/006948 | A2 | 1/2006 |
| WO | 2006/096018 | A1 | 9/2006 |
| WO | 2007/134161 | A2 | 11/2007 |
| WO | 2008/011431 | A2 | 1/2008 |
| WO | 2008/109472 | A2 | 9/2008 |
| WO | 2009/073809 | A2 | 6/2009 |
| WO | 2009/082607 | A2 | 7/2009 |
| WO | 2009/134487 | A2 | 11/2009 |
| WO | 2010/012244 | A1 | 2/2010 |
| WO | 2010/045509 | A2 | 4/2010 |
| WO | 2010/068978 | A1 | 6/2010 |
| WO | 2010/083615 | A1 | 7/2010 |
| WO | 2010/101951 | A1 | 9/2010 |
| WO | 2010/121074 | A1 | 10/2010 |
| WO | 2010/131916 | A2 | 11/2010 |
| WO | 2010147992 | A1 | 12/2010 |
| WO | 2011005793 | A1 | 1/2011 |
| WO | 2011/028938 | A1 | 3/2011 |
| WO | 2011/085271 | A2 | 7/2011 |
| WO | 2011/104169 | A1 | 9/2011 |
| WO | 2011126974 | A1 | 10/2011 |
| WO | 2011/139702 | A2 | 11/2011 |
| WO | 2011/154331 | A1 | 12/2011 |
| WO | 2012/013127 | A1 | 2/2012 |
| WO | 2012/024170 | A2 | 2/2012 |
| WO | 2012/037254 | A1 | 3/2012 |
| WO | 2012/068176 | A1 | 5/2012 |
| WO | 2012/083185 | A2 | 6/2012 |
| WO | 2012/089352 | A1 | 7/2012 |
| WO | 2012/130086 | A1 | 10/2012 |
| WO | 2012/139081 | A2 | 10/2012 |
| WO | 2012/139469 | A1 | 10/2012 |
| WO | 2012/177784 | A2 | 12/2012 |
| WO | 2013/060261 | A1 | 5/2013 |
| WO | 2013/070771 | A1 | 5/2013 |
| WO | 2013061295 | A1 | 5/2013 |
| WO | 2013/166155 | A1 | 11/2013 |
| WO | 2014/025805 | A1 | 2/2014 |
| WO | 2014076195 | A1 | 5/2014 |
| WO | 2014/089313 | A1 | 6/2014 |
| WO | 2014/118267 | A2 | 11/2014 |
| WO | 2014/179626 | A2 | 11/2014 |
| WO | 2014/179627 | A2 | 11/2014 |
| WO | 2014/179629 | A2 | 11/2014 |
| WO | 2014205451 | A1 | 12/2014 |
| WO | 2015/006498 | A2 | 1/2015 |
| WO | 2015/006740 | A2 | 1/2015 |
| WO | 2015/015496 | A1 | 2/2015 |
| WO | 2015/031679 | A2 | 3/2015 |
| WO | 2015/051366 | A2 | 4/2015 |
| WO | 2015/100394 | A1 | 7/2015 |
| WO | 2015/113922 | A1 | 8/2015 |
| WO | 2015/148580 | A2 | 10/2015 |
| WO | 2015/168532 | A2 | 11/2015 |
| WO | 2015168589 | A1 | 11/2015 |
| WO | 2015/188197 | A2 | 12/2015 |
| WO | 2015188194 | A1 | 12/2015 |
| WO | 2016/011123 | A1 | 1/2016 |
| WO | 2016/028649 | A1 | 2/2016 |
| WO | 2016/040589 | A1 | 3/2016 |
| WO | 2016/077321 | A1 | 5/2016 |
| WO | 2016/081444 | A1 | 5/2016 |
| WO | 2016077349 | A1 | 5/2016 |
| WO | 2016/099982 | A2 | 6/2016 |
| WO | 2016/149331 | A2 | 9/2016 |
| WO | 2016/154127 | A2 | 9/2016 |
| WO | 2016/168286 | A1 | 10/2016 |
| WO | 2016/179342 | A2 | 11/2016 |
| WO | 2016/188473 | A1 | 12/2016 |
| WO | 2016/201301 | A1 | 12/2016 |
| WO | 2016/206626 | A1 | 12/2016 |
| WO | 2017/015175 | A1 | 1/2017 |
| WO | 2017/019660 | A1 | 2/2017 |
| WO | 2017/019891 | A2 | 2/2017 |
| WO | 2017/035340 | A1 | 3/2017 |
| WO | 2017055627 | A1 | 4/2017 |
| WO | 2017/100542 | A1 | 6/2017 |
| WO | 2017/120397 | A1 | 7/2017 |
| WO | 2017131236 | A1 | 8/2017 |
| WO | 2017/184689 | A1 | 10/2017 |
| WO | 2017/189813 | A1 | 11/2017 |
| WO | 2018/027106 | A2 | 2/2018 |
| WO | 2018/035380 | A1 | 2/2018 |
| WO | 2018/044350 | A1 | 3/2018 |
| WO | 2018/075658 | A1 | 4/2018 |
| WO | 2018/140920 | A1 | 8/2018 |
| WO | 2018/191278 | A2 | 10/2018 |
| WO | 2018/209848 | A1 | 11/2018 |
| WO | 2018/223073 | A1 | 12/2018 |
| WO | 2019/105403 | A1 | 6/2019 |
| WO | 2019/105404 | A1 | 6/2019 |
| WO | 2019/105418 | A1 | 6/2019 |
| WO | 2019/105419 | A1 | 6/2019 |
| WO | 2019/105435 | A1 | 6/2019 |
| WO | 2019/105437 | A1 | 6/2019 |
| WO | 2019/128611 | A1 | 7/2019 |
| WO | 2020038377 | A1 | 2/2020 |
| WO | 2020/063198 | A1 | 4/2020 |
| WO | 2020/093053 | A1 | 5/2020 |
| WO | 2020/135581 | A1 | 7/2020 |
| WO | 2020/147847 | A1 | 7/2020 |
| WO | 2020233651 | A1 | 11/2020 |
| WO | 2020233655 | A1 | 11/2020 |
| WO | 2020233680 | A1 | 11/2020 |
| WO | 2020238763 | A1 | 12/2020 |
| WO | 2020238766 | A1 | 12/2020 |

OTHER PUBLICATIONS

Soodabeh S. et al., "From in vitro Experiments to in vivo and Clinical Studies; Pros and Cons", Curr. Drug Discov. Technol., 2015, vol. 12, No. 4, pp. 218-224. (Cited in Office Action issued on Mar. 6, 2024, in corresponding Russian Application No. 2021130601) (7 pages).

Shafer A.I. et al., "Thrombotic Disorders Diagnosis and Treatment", Am. Soc. Hematol. Educ. Program, 2003, v. 1, pp. 520-539, doi 10.1182asheducation-2003.1.520. (Cited in Office Action issued on Mar. 6, 2024, in corresponding Russian Application No. 2021130601) (20 pages).

Sehgal, Alfica et al., "Liver as a target for oligonucleotide therapeutics", Journal of hepatology, 2013, vol. 59, pp. 1354-1359. (Cited in Office Action issued on Mar. 11, 2024, in corresponding Taiwanese Patent Application No. 109116935) (6 pages).

Diaz-Torné, Cesar et al., "New medications in development for the treatment of hyperuricemia of gout", Current opinion in rheumatology. 2015, vol. 27, No. 2, pp. 164-169. (Cited in Office Action issued on Mar. 11, 2024, in corresponding Taiwanese Patent Application No. 109116934) (6 pages).

Kojima, S. et al., "Tumour suppressors miR-1 and miR-133a target the oncogenic function ofphosphorylase (PNP) in prostate cancer", Br. J. Cancer, 2012, vol. 106(2), pp. 405-413. (Cited in Office Action issued May 21, 2024, in corresponding Japanese Patent Application No. JP2021-569112) (9 pages).

Chen et al., "Proof-of-concept Studies for siRNA-mediated Gene Silencing for Coagulation Factors in Rat and Rabbit", Molecular Therapy—Nucleic Acids, Jan. 27, 2015, vol. 4, No. 1, p. e224.

Ferrone et al., "IONIS-PKK Rx a Novel Antisense Inhibitor of Prekallikrein and Bradykinin Production", Nucleic Acid Therapeutics, Apr. 1, 2019, vol. 29, No. 2, pp. 82-91.

Ghosh et al., "Effectiveness and Safety of Inclisiran, A Novel Long-Acting RNA Therapeutic Inhibitor of Proprotein Convertase

(56) References Cited

OTHER PUBLICATIONS

Subtilisin/Kexin 9", American Journal of Cardiology, Cahners Publishing Co., Newton, MA, US, Jul. 3, 2018, vol. 122, No. 7, pp. 1272-1277.
Joshi et al., "siRNA: novel therapeutics from functional genomics", Biotechnology and Genetic Engineering Reviews, Jan. 2, 2014, vol. 30, No. 1, pp. 1-30.
Pawluczyk et al., "Kallikrein gene 'knock-down' by small interfering RNA transfection induces a profibrotic phenotype in rat mesangial cells", Journal of Hypertension, Lippincott Williams & Wilkens, Ltd., Jan. 1, 2008, vol. 26, No. 1, pp. 93-101.
Revenko et al., "Selective depletion of plasma prekallikrein or coagulation factor XII inhibits thrombosis in mice without increased risk of bleeding", Blood, American Society of Hematology, Nov. 10, 2011, vol. 118, No. 19, pp. 5302-5311.
Yamasaki et al., "Novel molecular targets regulated by tumor suppressors microRNA-1 and microRNA-133a in bladder cancer", International Journal of Oncology, Feb. 29, 2012, vol. 40, pp. 1821-1830.
Supplementary European Search Report issued on Jun. 14, 2023, by the European Patent Office in European Patent Application No. 20809702.2 (12 pages).
Supplementary European Search Report issued on Jun. 16, 2023, by the European Patent Office in European Patent Application No. 20814338.8 (10 pages).
Partial Supplementary European Search Report issued on Jul. 5, 2023, by the European Patent Office in European Patent Application No. 20810635.1 (13 pages).
Partial Supplementary European Search Report issued on Jul. 10, 2023, by the European Patent Office in European Patent Application No. 20815633.1 (17 pages).
Qui, S. et al., "Dickkopf 3 attenuates xanthine dehydrogenase expression to prevent oxidative stress-induced apoptosis," Genes to Cells, 2017, vol. 22, pp. 406-417. (cited in Extended European Search Report issued on Jan. 30, 2024, in European Patent Application No. 20813863.6).
Yasuda, T. et al., "Anti-Gout Agent Allopurinol Exerts Cytotoxicity to Human Hormone-Refractory Prostate Cancer Cells in Combination with Tumor Necrosis Factor-Related Apoptosis-Inducing Ligand," Mol Cancer Res, Dec. 2008, vol. 6, No. 12, pp. 1852-1860. (cited in Extended European Search Report issued on Jan. 30, 2024, in European Patent Application No. 20813863.6).
Hashimoto, K. et al., "Sulfotransferase-1A1-dependent bioactivation of aristolochic acid I and N-hydroxyaristolactam I in human cells," Carcinogenesis, 2016, vol. 37, No. 7, pp. 647-655. (cited in Extended European Search Report issued on Jan. 30, 2024, in European Patent Application No. 20813863.6).
The First Office Action and Search Report issued on Jun. 23, 2021, by the State Intellectual Property Office of People's Republic of China in corresponding Chinese Patent Application No. 201980046892.X, and an English Translation of the Office Action. (13 pages).
Rajeev, K. G. et al., "Hepatocyte-Specific Delivery of siRNAs Conjugated to Novel Non-nucleosidic Trivalent N-Acetylgalactosamine Elicits Robust Gene Silencing in Vivo," ChemBioChem, 2015, vol. 16, pp. 903-908.
Nair, J.K. et al., "Multivalent N-Acetylgalactosamine-Conjugated siRNA Localizes in Hepatocytes and Elicits Robust RNAi-Mediated Gene Silencing," J. Am. Chem. Soc. 2014, vol. 136, pp. 16958-16961.
Love, T. K. et al., "Lipid-like materials for low-dose, in vivo gene silencing," PNAS, Feb. 2, 2010, vol. 107, No. 21, pp. 1864-1869.
Dong, Y, et al., "Lipopeptide nanoparticles for potent and selective siRNA delivery in rodents and nonhuman primates," PNAS Early Edition, 2014, pp. 1-6.
Protective Groups in Organic Synthesis, Chapter 2, Protection for the Hydroxylgroup, Including 1,2- And 1,3-DIOLS, 3rd edition, John Wiley & Sons, Inc., 1999, 229 pages.
Matsuda, S. et al., "siRNA Conjugates Carrying Sequentially Assembled Trivalent N-Acetylgalactosamine Linked Through Nucleosides Elicit Robust Gene Silencing in Vivo in Hepatocytes," ACS Chemical Biology, 2015, 7 pages.
Khvorova, A. et al., "The chemical evolution of oligonucleotide therapies of clinical utility," Nature Biotechnology, advance online publication, 2017, pp. 842-855.
Watts, J. K. et al., "Chemically modified siRNA: tools and applications," Drug Discovery Today, vol. 13, Nos. 19/20, Oct. 2008, Elsevier Ltd., 14 pages.
Beaucage, S. et al., "Advances in the Synthesis of Oligonucleotides by the Phosphoramidite Approach," Tetrahedron Report No. 309, Tetrahedron, 1992, vol. 48. No. 12, pp. 2223-2311.
Nordestgaard et al., "Advances in lipid-lowering therapy through gene-silencing technologies," Nature Reviews Cardiology, May 2018, published online Feb. 8, 2018, vol. 15, pp. 261-272.
The First Office Action issued on Jan. 30, 2022, by the State Intellectual Property Office of the People's Republic of China in Chinese Patent Application No. 201880049520.8 and an English translation of the Action (11 pages).
Decision of Rejection issued on Mar. 3, 2022, by the State Intellectual Property Office of the People's Republic of China in Chinese Patent Application No. 202010426194.7 and an English translation of the Action. (20 pages).
The Second Office Action issued on Mar. 21, 2022, by the State Intellectual Property Office of the People's Republic of China in Chinese Patent Application No. 201980046893.4 and an English translation of the Action. (19 pages).
The First Office Action issued on May 7, 2022, by the State Intellectual Property Office of the People's Republic of China in Chinese Patent Application No. 201980010095.6 and an English translation of the Action. (27 pages).
The First Office Action issued on May 7, 2022, by the State Intellectual Property Office of the People's Republic of China in Chinese Patent Application No. 201980010175.1 and an English translation of the Action. (30 pages).
The First Office Action issued on May 7, 2022, by the State Intellectual Property Office of the People's Republic of China in Chinese Patent Application No. 201880049190.2 and an English translation of the Action. (31 pages).
The First Office Action issued on May 7, 2022, by the State Intellectual Property Office of the People's Republic of China in Chinese Patent Application No. 201880049191.7 and an English translation of the Action. (30 pages).
The First Office Action issued on May 7, 2022, by the State Intellectual Property Office of the People's Republic of China in Chinese Patent Application No. 202080007282.1 and an English translation of the Action. (33 pages).
The First Office Action issued on May 7, 2022, by the State Intellectual Property Office of the People's Republic of China in Chinese Patent Application No. 201880049564.0 and an English translation of the Action. (29 pages).
The First Office Action issued on May 7, 2022, by the State Intellectual Property Office of the People's Republic of China in Chinese Patent Application No. 201880049586.7 and an English translation of the Action. (33 pages).
The First Office Action issued on May 7, 2022, by the State Intellectual Property Office of the People's Republic of China in Chinese Patent Application No. 201880048597.3 and an English translation of the Action. (34 pages).
The First Office Action issued on May 7, 2022, by the State Intellectual Property Office of the People's Republic of China in Chinese Patent Application No. 201880048600.1 and an English translation of the Action. (34 pages).
The First Office Action issued on May 7, 2022, by the State Intellectual Property Office of the People's Republic of China in Chinese Patent Application No. 202080009787.1 and an English translation of the Action. (50 pages).
The First Office Action issued on May 7, 2022, by the State Intellectual Property Office of the People's Republic of China in Chinese Patent Application No. 201880048949.5 and an English translation of the Action. (33 pages).

(56) References Cited

OTHER PUBLICATIONS

The First Office Action issued on May 20, 2021, by the State Intellectual Property Office of the People's Republic of China in Chinese Patent Application No. 202010426194.7 and an English translation of the Action. (20 pages).
The First Office Action issued on Jun. 23, 2021, by the State Intellectual Property Office of the People's Republic of China in Chinese Patent Application No. 201980046893.4 and an English translation of the Action. (12 pages).
Decision of Rejection issued on Jun. 29, 2022, by the State Intellectual Property Office of the People's Republic of China in Chinese Patent Application No. 201980046892.X and an English translation of the Decision. (8 pages).
Decision of Rejection issued on Jun. 29, 2022, by the State Intellectual Property Office of the People's Republic of China in Chinese Patent Application No. 201980046893.4 and an English translation of the Decision. (8 pages).
The First Office Action issued on Oct. 25, 2021, by the State Intellectual Property Office of the People's Republic of China in Chinese Patent Application No. 202010426196.6 and an English translation of the Action. (16 pages).
The Second Office Action issued on Nov. 12, 2021, by the State Intellectual Property Office of the People's Republic of China in Chinese Patent Application No. 202010426194.7 and an English translation of the Action. (16 pages).
The Extended European Search Report issued on Jun. 9, 2022, by the European Patent Office in European Patent Application Publication No. 19851738.5. (64 pages).
The Extended European Search Report and Supplementary European Search Report issued on Aug. 9, 2021, by the European Patent Office in European Patent Application Publication No. 18883362.8. (9 pages).
Extended European Search Report dated Sep. 17, 2021, issued by the European Patent Office in corresponding European Application No. 18883982.3. (9 pages).
Extended European Search Report dated Sep. 29, 2021, issued by the European Patent Office in corresponding European Application No. 18884492.2. (45 pages).
The Extended European Search Report issued on Oct. 7, 2021, by the European Patent Office in European Patent Application Publication No. 18896766.5. (19 pages).
The Extended European Search Report issued on Sep. 16, 2021, by the European Patent Office in European Patent Application No. 18883803.1. (10 pages).
Invitation to remedy deficiencies pursuant to Rule 30(3) EPC / Rule 163(3) EPC issued on Feb. 22, 2022, by the European Patent Office in European Patent Application No. 20809029.0. (2 pages).
Communication pursuant to Rule 159 and Rule 58 EPC Invitation to remedy deficiencies in the application documents issued on Jan. 24, 2022, by the European Patent Office in European Patent Application No. 20815633.1 (2 pages).
Supplementary European Search Report issued on Jul. 27, 2022, by the European Patent Office in European Patent Application No. 18883153. (7 pages).
Notification of Substantive Examination Result issued on Dec. 2, 2021, by the Intellectual Property Office of the Republic of Indonesia in Indonesian Patent Application No. P00202003125 and an English translation of the Notification. (6 pages).
Notification of Substantive Examination Result issued on Aug. 24, 2021, by the Intellectual Property Office of the Republic of Indonesia in Indonesian Patent Application No. P00202003131 and an English translation of the Notification. (6 pages).
Examination report under sections 12 & 13 of the Patents Act, 1970 and the Patents Rules, 2003 issued on Nov. 24, 2021, by the Intellectual Property Office of India in Indian Patent Application No. 202047017398 and English translation of the Report. (7 pages).
International Preliminary Report on Patentability issued on Jun. 2, 2020, by the International Bureau of WIPO in International Patent Application No. PCT/CN2018/118191. (6 pages).
International Preliminary Report on Patentability issued on Jun. 16, 2021, by the International Bureau of WIPO in International Patent Application No. PCT/CN2019/128686 and English translation of the Report. (16 pages).
International Preliminary Report on Patentability issued on Jun. 23, 2020, by the International Bureau of WIPO in International Patent Application No. PCT/CN2018/118232 and English translation of the Report. (13 pages).
International Preliminary Report on Patentability issued on Sep. 3, 2021, by the State Intellectual Property Office of the People's Republic of China in International Patent Application No. PCT/CN2020/091489 and English translation of the Report. (12 pages).
Written Opinion of the International Searching Authority and International Search Report issued on Feb. 20, 2019, by the State Intellectual Property Office of the People's Republic of China in International Patent Application No. PCT/CN2018/118107 and English translation. (22 pages).
Written Opinion of the International Searching Authority and International Search Report issued on Feb. 25, 2019, by the State Intellectual Property Office of the People's Republic of China in International Patent Application No. PCT/CN2018/118212 and English translation. (23 pages).
English translation of the Written Opinion of the International Searching Authority and International Search Report issued on Feb. 27, 2019, by the State Intellectual Property Office of the People's Republic of China in International Patent Application No. PCT/CN2018/118224. (13 pages).
Written Opinion of the International Searching Authority and International Search Report issued on Feb. 28, 2019, by the State Intellectual Property Office of the People's Republic of China in International Patent Application No. PCT/CN2018/118300 and English translation. (20 pages).
Written Opinion of the International Searching Authority and International Search Report issued on Mar. 6, 2019, by the State Intellectual Property Office of the People's Republic of China in International Patent Application No. PCT/CN2018/118106 and English translation. (20 pages).
Written Opinion of the International Searching Authority and International Search Report issued on Mar. 6, 2019, by the State Intellectual Property Office of the People's Republic of China in International Application No. PCT/CN2018/118191 and English translation. (17 pages).
Written Opinion of the International Searching Authority and International Search Report issued on Mar. 7, 2019, by the State Intellectual Property Office of the People's Republic of China in International Patent Application No. PCT/CN2018/118303 and English translation. (22 pages).
Written Opinion of the International Searching Authority and International Search Report issued on Mar. 7, 2019, by the State Intellectual Property Office of the People's Republic of China in International Patent Application No. PCT/CN2018/118232 and English translation. (24 pages).
Written Opinion of the International Searching Authority and International Search Report issued on Mar. 26, 2020, by the State Intellectual Property Office of the People's Republic of China in International Patent Application No. PCT/CN2019/128686 and English translation. (27 pages).
Written Opinion of the International Searching Authority and International Search Report issued on Aug. 19, 2020, by the State Intellectual Property Office of the People's Republic of China in International Patent Application No. PCT/CN2020/091489 and English translation. (26 pages).
Written Opinion of the International Searching Authority and International Search Report issued on Aug. 21, 2020, by the State Intellectual Property Office of the People's Republic of China in International Patent Application No. PCT/CN2020/091484 and English translation. (29 pages).
Written Opinion of the International Searching Authority and International Search Report issued on Aug. 21, 2020, by the State Intellectual Property Office of the People's Republic of China in International Patent Application No. PCT/CN2020/091614 and English translation. (24 pages).

(56) References Cited

OTHER PUBLICATIONS

Written Opinion of the International Searching Authority and International Search Report issued on Aug. 24, 2020, by the State Intellectual Property Office of the People's Republic of China in International Patent Application No. PCT/CN2020/091624 and English translation. (26 pages).
Written Opinion of the International Searching Authority and International Search Report issued on Aug. 25, 2020, by the State Intellectual Property Office of the People's Republic of China in International Patent Application No. PCT/CN2020/091485 and English translation. (30 pages).
Written Opinion of the International Searching Authority and International Search Report issued on Aug. 28, 2020, by the State Intellectual Property Office of the People's Republic of China in International Patent Application No. PCT/CN2020/091649 and English translation. (25 pages).
Written Opinion of the International Searching Authority and International Search Report issued on Sep. 2, 2020, by the State Intellectual Property Office of the People's Republic of China in International Patent Application No. PCT/CN2020/091606 and English translation. (22 pages).
Written Opinion of the International Searching Authority and International Search Report issued on Nov. 21, 2019, by the State Intellectual Property Office of the People's Republic of China in International Patent Application No. PCT/CN2019/101653 and English translation. (23 pages).
Written Opinion of the International Searching Authority and International Search Report issued on Nov. 28, 2019, by the State Intellectual Property Office of the People's Republic of China in International Patent Application No. PCT/CN2019/101656 and English translation. (21 pages).
Written Opinion of the International Searching Authority and International Search Report issued on Apr. 17, 2020, by the State Intellectual Property Office of the People's Republic of China in International Patent Application No. PCT/CN2020/072813 and English translation. (32 pages).
Office Action issued on Mar. 9, 2022, by the Russian Agency for Patents and Trademarks in Russian Patent Application No. 2020118025/10(030488) and English translation of the Action. (14 pages).
Office Action issued on May 11, 2022, by the Russian Agency for Patents and Trademarks in Russian Patent Application No. 2020121741/04(037329) and English translation of the Action. (18 pages).
Office Action issued on Jan. 28, 2022, by the U.S. Patent and Trademark Office in U.S. Appl. No. 16/758,532. (28 pages).
Office Action issued on Mar. 11, 2022, by the U.S. Patent and Trademark Office in U.S. Appl. No. 16/758,720. (21 pages).
Notice of Allowance issued on Mar. 31, 2022, by the U.S. Patent and Trademark Office in U.S. Appl. No. 16/764,307. (7 pages).
Notice of Allowance issued on Apr. 5, 2022, by the U.S. Patent and Trademark Office in U.S. Appl. No. 16/763,058. (7 pages).
Office Action issued on May 27, 2022, by the U.S. Patent and Trademark Office in U.S. Appl. No. 16/758,532. (8 pages).
Notice of Allowance issued on Jul. 25, 2022, by the U.S. Patent and Trademark Office in U.S. Appl. No. 16/758,720. (5 pages).
Office Action issued on Oct. 29, 2021, by the U.S. Patent and Trademark Office in U.S. Appl. No. 16/764,307. (17 pages).
Office Action issued on Nov. 16, 2021, by the U.S. Patent and Trademark Office in U.S. Appl. No. 16/763,058. (26 pages).
Office Action issued Aug. 14, 2020, by the Intellectual Property Office of Vietnam in Vietnamese Patent Application No. 1-2020-03065 and an English translation of the Action. (3 pages).
Office Action issued Aug. 28, 2020, by the Intellectual Property Office of Vietnam in Vietnamese Patent Application No. 1-2020-03777 and an English translation of the Action. (3 pages).
Payment and Certificate of Renewal issued on May 30, 2022 by the Patent Office of South Africa in South African Patent Application No. 2020/03833. (1 page).
Ahmad Dar et al., "siRNAmod: A database of experimentally validated chemically modified siRNAs," Scientific Reports, Jan. 28, 2016, vol. 6, No. 1. (8 pages).
Behlke, Mark A., "Chemical Modification of siRNAs for in Vivo Use," Oligonucleotides, 2008, vol. 18, pp. 305-320.
Berthold et al., "Cellular Delivery and Antisense Effects of Peptide Nucleic Acid Conjugated to Polyethyleneimine via Disulfide Linkers," Bioconjugate Chemistry, 2010, vol. 21, No. 10, pp. 1933-1938.
Chen et al., "Research progress on factor XI as a novel target for antithrombotic therapy," Chinese Pharmacological Bulletin, Apr. 15, 2015, vol. 31, No. 5, with English abstract, pp. 619-622.
Dai et al., "A vital role for Angpll3 in the PAN-induced podocyte loss by affecting detachment and apoptosis in vitro," BMC Nephrology, 2015, vol. 16, No. 1. (10 pages).
Ding et al., "Limited role of kininogen in the host response during gram-negative pneumonia derived sepsis," American Journal of Physiology Lung Cellular and Molecular Physiology, Nov. 9, 2017. (33 pages).
Dong et al., "A novel packaging system of recombinant AAV5/5 vector," Chinese Journal of Biotechnology, May 25, 2010, vol. 26, No. 5, pp. 679-686.
Common knowledge "RNAi technology" with English translation. (5 pages).
"*Homo sapiens* Kininogen 1 (KNG1), Transcript Variant 1, mRNA" GenBank, May 2, 2018, NM 00102416.2. (8 pages).
Khaitmetova et al., "Synthesis and Study of the Properties of Polymer Complexes of Ethacizin with Carboxymethylcellulose," Chemistry of Plant Raw Materials, No. 4, with English translation. (18 pages).
Khan et al., "High-Molecular-Weight Kininogen Fragments Stimulate the Secretion of Cytokines and Chemokines Through uPAR, Mac-1, and gC1qR in Monocytes," Arteriosclerosis, Thrombosis, and Vascular Biology, Oct. 2006, vol. 26, No. 10, pp. 2260-2266.
Kim et al., "Bifunctional compounds for targeted hepatic gene delivery," Gene Therapy, 2007, vol. 14, pp. 704-708.
Liu et al., "Determination of Human Plasma Pre-Kallikrein," Journal of China Medical University, 1988, vol. 17, No. 6, with English abstract, pp. 432-436.
Liu et al., "Coagulation factor XI induces Ca2+ response and accelerates cell migration in vascular smooth muscle cells via proteinase-activated receptor 1," American Journal of Physiology, Cell Physiology, Mar. 1, 2019, vol. 316, No. 3, pp. C377-C392.
Montagne et al., "Pericyte degeneration causes white matter dysfunction in the mouse CNS," Nature Medicine, 2018, vol. 24, vol. 3, pp. 326-337.
Nakagawa et al., "The RNAi-Mediated Silencing of Xanthine Dehydrogenase Impairs Growth and Fertility and Accelerates Leaf Senescence in Transgenic *Arabidopsis* Plants," Plant & Cell Physiology, 2007, vol. 48, No. 10, pp. 1484-1495.
Norata et al., "Gene silencing approaches for the management of dyslipidaemia," Trends in Pharmacological Sciences, Apr. 13, 2013, vol. 34, No. 4, pp. 198-205.
Papulov, Yu. G., "Relationship between Properties of Compounds with Their Structures: Math Modeling," Advances in Modern Natural Sciences, 2006, with English translation, pp. 75-76.
Paris et al., "Conjugating Phosphospermines to siRNAs for Improved Stability in Serum, Intracellular Delivery and RNAi-Mediated Gene Silencing," Molecular Pharmaceutics, 2012, vol. 9, No. 12, pp. 3464-3475.
Peña-Altamira, et al., "Release of soluble and vesicular purine nucleoside phosphorylase from rat astrocytes and microglia induced by pro-inflammatory stimulation with extracellular ATP via P2X7 receptors," Neurochemistry International, May 31, 2018, vol. 115, pp. 37-49.
Pessentheiner et al., "ANGPTL3 targeting: The power of versatile lipid-lowering," Atherosclerosis, Jan. 2018, vol. 268, pp. 185-187.
Prakash et al., "Comprehensive Structure-Activity Relationship of Triantennary N-Acetylgalactosamine Conjugated Antisense Oligonucleotides for Targeted Delivery to Hepatocytes," Journal of Medicinal Chemistry, 2016, vol. 59, pp. 2718-2733.
Ren et al., "Synthesis of bifunctional cationic compound for gene delivery," Tetrahedron Letters, 2001, vol. 42, pp. 1007-1010.
Ren et al., "Gene Expression Profile of Transgenic Mouse Kidney Reveals Pathogenesis of Hepatitis B Virus Associated Nephropathy," Journal of Medical Virology, 2006, vol. 78, pp. 551-560.

(56) References Cited

OTHER PUBLICATIONS

Ren et al., "Stable Inhibition of Hepatitis B Virus Expression and Replication by Expressed siRNA", Biochemical and Biophysical Research Communications, Oct. 7, 2005, vol. 335, No. 4, with English abstract, pp. 1051-1058.
Springer et al., "GalNAc-siRNA Conjugates: Leading the Way for Delivery of RNAi Therapeutics," Nucleic Acid Therapeutics, May 2018, vol. 28, No. 3, pp. 109-118.
Su et al., "Progress on the Inhibition of Hepatitis B virus by siRNA Strategy," China Biotechnology, 2014, vol. 34, No. 9, with English abstract, pp. 102-107.
Tangkijvanich et al., "Low pretreatment serum HBsAg level and viral mutations as predictors of response to PEG-interferon alpha-2b therapy in chronic hepatitis B," Journal of Clinical Virology, vol. 46, 2009, pp. 117-123.
Ui-Tei et al., "Functional dissection of siRNA sequence by systematic DNA substitution: modified siRNA with a DNA seed arm is a powerful tool for mammalian gene silencing with significantly reduced off-target effect", Nucleic Acids Research, 2008, vol. 36, No. 7, pp. 2136-2151.
Wooddell et al., "Hepatocyte-targeted RNAi Therapeutics for the Treatment of Chronic Hepatitis B Virus Infection" The American Society of Gene & Cell Therapy, 2013, doi:10.1038/mt.2013.31. (13 pages).
Wu et al., "Cleaved high molecular weight kininogen inhibits tube formation of endothelial progenitor cells via suppression of matrix metalloproteinase 2," Journal of Thrombosis and Haemostasis, 2010, vol. 8, pp. 185-193.
Wu et al., "Contact pathway of coagulation and inflammation," Thrombosis Journal, 2015, pp. 13-17.
Xu et al., "Role of angiopoielin-like 3 (ANGPTL3) in regulating plasma level of low-density lipoprotein cholesterol," Atherosclerosis, 2018, vol. 268, pp. 196-206.
Yang et al., "A critical role for plasma kallikrein in the pathogenesis of autoantibody-induced arthritis," Federation of American Societies for Experimental Biology, Nov. 2017, vol. 31, No. 12, pp. 5419-5431.
Yang et al., "An essential role of high-molecular-weight kininogen in endotoxemia," Journal of Experimental Medicine, Sep. 4, 2017, vol. 214, No. 9, pp. 2649-2670.
International Search Report (PCT/ISA/210) with an English translation, and Written Opinion (PCT/ISA/237) mailed on Mar. 26, 2020, by the Chinese Patent Office as the International Searching Authority for International Application No. PCT/CN2019/129016.
Durnov, et al., "Children's Oncology", Paediatric Oncology, Second Edition, Moscow Publishing House Medicine, 2002, p. 139 and its English translation. Cited in Office Action issued on Oct. 10, 2022 in Russian Application No. 2020121741). (4 pages).
Dysop, "Chemistry of Synthetic Drugs", Publishing House MIR, 1964, pp. 12-19 and its English translation. Cited in Office Action issued on Oct. 10, 2022 in Russian Application No. 2020121741). (18 pages).
Belikov, V.G., "Pharmaceutical Chemistry", textbook, Moscow, 11th Edition, MEDpress-inform, 2007, pp. 27-29 and its English translation. (Cited in Office Action issued on Oct. 10, 2022 in Russian Application No. 2020121741). (8 pages).
Examination Report No. 2 issued on Feb. 3, 2023, by the Australian Government IP Australia in Australian Patent Application No. 2018394875 (4 pages).
Ren et al., "Synthesis of Galactosyl Compounds for Targeted Gene Delivery", Bioorganic & Medicinal Chemistry, 2001, 9(11), pp. 2969-2978.
Extended European Search Report issued on Mar. 27, 2023, by the European Patent Office in European Patent Application No. 19902173.4 (11 pages).
Li et al., "The silencing of ApoC3 suppresses oxidative stress and inflammatory responses in placenta cells from mice with preeclampsia via inhibition of the NF-B signaling pathway", Biomedicine & Pharmacotherapy, Aug. 31, 2018, vol. 107, pp. 1377-1384.
Notice of Reasons for Refusal issued on Jun. 1, 2023, by the Japanese Patent Office in Japanese Patent Application No. 2021-537877, with an English translation of the Notice (6 pages).
Kanasty et al., "Delivery materials for siRNA therapeutics", Nature Materials, Nov. 2023, vol. 12, pp. 967-977.
Notice of Reasons for Refusal issued on Jun. 6, 2023, by the Japanese Patent Office in Japanese Patent Application No. 2021-509880, with an English translation of the Notice (6 pages).
Foster et al., "Advanced siRNA Designs Further Improve in Vivo Performance of GalNAc-siRNA Conjugates," Molecular Therapy, Mar. 2018, vol. 26, No. 3, pp. 708-717.
Office Action issued on Mar. 16, 2022, by the Intellectual Property Office of the People's Republic of China in corresponding Chinese Patent Application No. 201980046892.X. (10 pages).
Office Action issued on Aug. 24, 2022, by the U.S. Patent and Trademark Office in U.S. Appl. No. 16/758,532. (13 pages).
Extended European Search Report issued on Jul. 19, 2022, by the European Patent Office in corresponding European Patent Application No. 19867686.8. (12 pages).
Nakamoto et al., "Enhanced Intercellular Delivery of cRGD-siRNA Conjugates by an Additional Oligospermine Modification," ACS Omega, 2018, vol. 3, pp. 8226-8232. (7 pages).
Nothisen et al., "Cationic siRNAs Provide Carrier-Free Gene Silencing in Animal Cells," Journal of the American Chemical Society, 2009, vol. 131, No. 29, pp. 17730-17731. (2 pages).
Bertrand, et al., "Comparison of antisense oligonucleotides and siRNAs in cell culture and in vivo," Biochemical and Biophysical Research Communications, 2002, vol. 296, Issue 4, pp. 1000-1004, ISSN 0006-291X.

* cited by examiner

NUCLEIC ACID, COMPOSITION AND CONJUGATE CONTAINING NUCLEIC ACID, PREPARATION METHOD THEREFOR AND USE THEREOF

SEQUENCE LISTING

Incorporated by reference herein in its entirety is a computer-readable sequence listing submitted via EFS-Web and identified as follows: One (80,502 byte ASCII (Text)) file named "US-The Sequence Listing.txt" created on Aug. 12, 2021.

TECHNICAL FIELD

The present disclosure relates to a nucleic acid capable of inhibiting the expression of Apolipoprotein C3 (APOC3) gene, a composition and a conjugate comprising the same. The present disclosure also relates to a preparation method and use of such nucleic acids, compositions and conjugates.

BACKGROUND ART

Dyslipidemia (also known as hyperlipidemia), referring to a systemic disease in which abnormal metabolism and transportation of fat cause a higher plasma lipid content than the normal value, severely threatens the health of patients worldwide. The currently available medicines for treating dyslipidemia include mainly statins, cholesterol absorption inhibitors, resins, probucol, fibrates, niacins, and derivatives thereof.

Apolipoprotein C3 (APOC3) plays a crucial role in lipid metabolism. In the people carrying APOC3 mutant gene, the expression level of APOC3 in blood circulation reduces by 46%, and the triglyceride level in plasma reduces by 39% as compared with normal population. Meanwhile, the relatively low blood lipid level can reduce the risk of developing heart diseases in people carrying APOC3 mutant gene by 35.1% as compared with those not carrying said gene. Thus, silencing gene expression of APOC3 gene at genetic level to block APOC3 production is undoubtedly the most ideal treatment means. Based on the mechanism of RNA interference (RNAi), small interfering RNA (siRNA) could inhibit or block the expression of any target gene of interest in a sequence-specific manner, so as to achieve the purpose of treating diseases.

Suitable sequences and modification of siRNA and the delivery system thereof are two crucial technologies in the development of siRNA medicines.

SUMMARY OF THE INVENTION

In some embodiments, the present disclosure provides a siRNA conjugate having a structure as shown by Formula (308):

Formula (308)

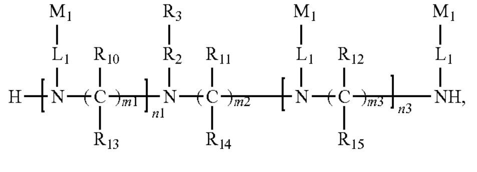

wherein n1 is an integer of 1-3, and n3 is an integer of 0-4;

m1, m2, and m3 independently of one another are an integer of 2-10;

$R_{10}$, $R_{11}$, $R_{12}$, $R_{13}$, $R_{14}$, and $R_{15}$ independently of one another are H, or selected from the group consisting of $C_1$-$C_{10}$ alkyl, $C_1$-$C_{10}$ haloalkyl, and $C_1$-$C_{10}$ alkoxy;

$R_3$ is a group having a structure as shown by Formula (A59):

Formula (A59)

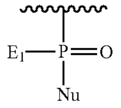

wherein, $E_1$ is OH, SH or $BH_2$;

Nu is a siRNA;

the siRNA comprises a sense strand and an antisense strand; each nucleotide in the siRNA is independently a modified or unmodified nucleotide; wherein the sense strand comprises a nucleotide sequence I, and the antisense strand comprises a nucleotide sequence II; the nucleotide sequence I and the nucleotide sequence II are at least partly reverse complementary to form a double-stranded region; the nucleotide sequence I and the nucleotide sequence II are the sequences selected from one of the following groups i)-v):

i) the nucleotide sequence I and the nucleotide sequence as shown by SEQ ID NO: 1 have an equal length and no more than 3 nucleotide differences, and the nucleotide sequence II and the nucleotide sequence as shown by SEQ ID NO: 2 have an equal length and no more than 3 nucleotide differences:

(SEQ ID NO: 1)
5'-UUAAAAGGGACAGUAUUCZ$_{a1}$-3', (SEQ ID NO: 2)
5'-Z$_{a2}$GAAUACUGUCCCUUUUAA-3', wherein, $Z_{a1}$ is A and $Z_{a2}$ is U, and the nucleotide sequence I comprises a nucleotide $Z_{a3}$ at the position corresponding to $Z_{a1}$; the nucleotide sequence II comprises a nucleotide $Z_{a4}$ at the position corresponding to $Z_{a2}$, wherein $Z_{a4}$ is the first nucleotide at 5' terminal of the antisense strand; or ii) the nucleotide sequence I and the nucleotide sequence as shown by SEQ ID NO: 13 have an equal length and no more than 3 nucleotide differences, and the nucleotide sequence II and the nucleotide sequence as shown by SEQ ID NO: 14 have an equal length and no more than 3 nucleotide differences:

(SEQ ID NO: 13)
5'-ACAGUAUUCUCAGUGCUCZ$_{b1}$-3', (SEQ ID NO: 14)
5'-Z$_{b2}$GAGCACUGAGAAUACUGU-3', wherein, $Z_{b1}$ is A and $Z_{b2}$ is U, and the nucleotide sequence I comprises a nucleotide $Z_{b3}$ at the position corresponding to $Z_{b1}$; the nucleotide sequence II comprises a nucleotide $Z_{b4}$ at the position corresponding to $Z_{b2}$, wherein $Z_{b4}$ is the first nucleotide at 5' terminal of the antisense strand; or iii) the nucleotide sequence I and the nucleotide sequence as shown by SEQ ID NO: 25 have an equal length and no more than 3 nucleotide differences, and the nucleotide sequence II and the nucleotide sequence as shown by SEQ ID NO: 26 have an equal length and no more than 3 nucleotide differences:

(SEQ ID NO: 25)
5'-UAUUCUCAGUGCUCUCCU$Z_{c1}$-3', (SEQ ID NO: 26)
5'-$Z_{c2}$AGGAGAGCACUGAGAAUA-3', wherein, $Z_{c1}$ is A and $Z_{c2}$ is U, and the nucleotide sequence I comprises a nucleotide $Z_{c3}$ at the position corresponding to $Z_{c1}$; the nucleotide sequence II comprises a nucleotide $Z_{c4}$ at the position corresponding to $Z_{c2}$, wherein $Z_{c4}$ is the first nucleotide at 5' terminal of the antisense strand; or iv) the nucleotide sequence I and the nucleotide sequence as shown by SEQ ID NO: 37 have an equal length and no more than 3 nucleotide differences, and the nucleotide sequence II and the nucleotide sequence as shown by SEQ ID NO: 38 have an equal length and no more than 3 nucleotide differences:

(SEQ ID NO: 37)
5'-AGUAUUCUCAGUGCUCUC$Z_{d1}$-3', (SEQ ID NO: 38)
5'-$Z_{d2}$GAGAGCACUGAGAAUACU-3', wherein, $Z_{d1}$ is A and $Z_{d2}$ is U, and the nucleotide sequence I comprises a nucleotide $Z_{d3}$ at the position corresponding to $Z_{d1}$; the nucleotide sequence II comprises a nucleotide $Z_{d4}$ at the position corresponding to $Z_{d2}$, wherein $Z_{d4}$ is the first nucleotide at 5' terminal of the antisense strand; or v) the nucleotide sequence I and the nucleotide sequence as shown by SEQ ID NO: 49 have an equal length and no more than 3 nucleotide differences, and the nucleotide sequence II and the nucleotide sequence as shown by SEQ ID NO: 50 have an equal length and no more than 3 nucleotide differences:

(SEQ ID NO: 49)
5'-GGACAGUAUUCUCAGUGC$Z_{e1}$-3', (SEQ ID NO: 50)
5'-$Z_{e2}$GCACUGAGAAUACUGUCC-3', wherein, $Z_{e1}$ is A and $Z_{e2}$ is U, and the nucleotide sequence I comprises a nucleotide $Z_{e3}$ at the position corresponding to $Z_{e1}$; the nucleotide sequence II comprises a nucleotide $Z_{e4}$ at the position corresponding to $Z_{e2}$, wherein $Z_{e4}$ is the first nucleotide at 5' terminal of the antisense strand;

$R_2$ is a linear alkylene of 1 to 20 carbon atoms in length, wherein one or more carbon atoms are optionally replaced with one or more groups selected from the group consisting of: C(O), NH, O, S, CH═N, $S(O)_2$, $C_2$-$C_{10}$ alkenylene, $C_2$-$C_{10}$ alkynylene, $C_1$-$C_{10}$ arylene, $C_3$-$C_{18}$ heterocyclylene, and $C_5$-$C_{10}$ heteroarylene; and wherein $R_2$ optionally has any one or more substituents selected from the group consisting of: $C_1$-$C_{10}$ alkyl, $C_1$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —N($C_1$-$C_{10}$ alkyl) ($C_1$-$C_{10}$ alkylphenyl), —NH($C_1$-$C_{10}$ alkylphenyl), cyano, nitro, —$CO_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-$C_{10}$ alkyl), —$SO_2$NH(phenyl), —$NHSO_2$($C_1$-$C_{10}$ alkyl), —$NHSO_2$(phenyl), and —$NHSO_2$($C_1$-$C_{10}$ haloalkyl); each $L_1$ is a linear alkylene of 1 to 70 carbon atoms in length, wherein one or more carbon atoms are optionally replaced with one or more groups selected from the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene; and wherein $L_1$ optionally has any one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —N($C_1$-$C_{10}$ alkyl) ($C_1$-$C_{10}$ alkylphenyl), —NH($C_1$-$C_{10}$ alkylphenyl), cyano, nitro, —$CO_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-$C_{10}$ alkyl), —$SO_2$NH(phenyl), —$NHSO_2$($C_1$-$C_{10}$ alkyl), —$NHSO_2$(phenyl), and —$NHSO_2$($C_1$-$C_{10}$ haloalkyl);

∿∿∿ represents the site where a group is linked to the rest of the molecule; and $M_1$ represents a targeting group.

In some embodiments, the present disclosure provides a siRNA capable of inhibiting the expression of APOC3 gene, wherein the siRNA comprises a sense strand and an antisense strand; each nucleotide in the sense strand and the antisense strand is independently a fluoro modified nucleotide and a non-fluoro modified nucleotide; wherein the sense strand comprises a nucleotide sequence I and the antisense strand comprises a nucleotide sequence II; the nucleotide sequence I and the nucleotide sequence II are at least partly reverse complementary to form a double-stranded region; the fluoro modified nucleotides are located in the nucleotide sequence I and the nucleotide sequence II; and in the direction from 5' terminal to 3' terminal, the nucleotides at positions 7, 8 and 9 of the nucleotide sequence I in the sense strand are fluoro modified nucleotides, and the nucleotides at the rest of positions in the sense strand of the siRNA are non-fluoro modified nucleotides; in the direction from 5' terminal to 3' terminal, the nucleotides at positions 2, 6, 14, and 16 of the nucleotide sequence II in the antisense strand are fluoro modified nucleotides, and the nucleotides at the rest of positions in the antisense strand of the siRNA are non-fluoro modified nucleotides; and the nucleotide sequence I and the nucleotide sequence II are the sequences selected from one of the following groups i)-v):

i) the nucleotide sequence I and the nucleotide sequence as shown by SEQ ID NO: 1 have an equal length and no more than 3 nucleotide differences, and the nucleotide sequence II and the nucleotide sequence as shown by SEQ ID NO: 2 have an equal length and no more than 3 nucleotide differences:

(SEQ ID NO: 1)
5′-UUAAAAGGGACAGUAUUCZ$_{a1}$-3′, (SEQ ID NO: 2)
5′-Z$_{a2}$GAAUACUGUCCCUUUUAA-3′, wherein, $Z_{a1}$ is A and $Z_{a2}$ is U, and the nucleotide sequence I comprises a nucleotide $Z_{a3}$ at the position corresponding to $Z_{a1}$; the nucleotide sequence II comprises a nucleotide $Z_{a4}$ at the position corresponding to $Z_{a2}$, wherein $Z_{a4}$ is the first nucleotide at 5' terminal of the antisense strand; or ii) the nucleotide sequence I and the nucleotide sequence as shown by SEQ ID NO: 13 have an equal length and no more than 3 nucleotide differences, and the nucleotide sequence II and the nucleotide sequence as shown by SEQ ID NO: 14 have an equal length and no more than 3 nucleotide differences:

(SEQ ID NO: 13)
5′-ACAGUAUUCUCAGUGCUCZ$_{b1}$-3′, (SEQ ID NO: 14)
5′-Z$_{b2}$GAGCACUGAGAAUACUGU-3′, wherein, $Z_{b1}$ is A and $Z_{b2}$ is U, and the nucleotide sequence I comprises a nucleotide $Z_{b3}$ at the position corresponding to $Z_{b1}$; the nucleotide sequence II comprises a nucleotide $Z_{b4}$ at the position corresponding to $Z_{b2}$, wherein $Z_{b4}$ is the first nucleotide at 5' terminal of the antisense strand; or iii) the nucleotide sequence I and the nucleotide sequence as shown by SEQ ID NO: 25 have an equal length and no more than 3 nucleotide differences, and the nucleotide sequence II and the nucleotide sequence as shown by SEQ ID NO: 26 have an equal length and no more than 3 nucleotide differences:

(SEQ ID NO: 25)
5′-UAUUCUCAGUGCUCUCCUZ$_{c1}$-3′, (SEQ ID NO: 26)
5′-Z$_{c2}$AGGAGAGCACUGAGAAUA-3′, wherein, $Z_{c1}$ is A and $Z_{c2}$ is U, and the nucleotide sequence I comprises a nucleotide $Z_{c3}$ at the position corresponding to $Z_{c1}$; the nucleotide sequence II comprises a nucleotide $Z_{c4}$ at the position corresponding to $Z_{c2}$, wherein $Z_{c4}$ is the first nucleotide at 5' terminal of the antisense strand; or iv) the nucleotide sequence I and the nucleotide sequence as shown by SEQ ID NO: 37 have an equal length and no more than 3 nucleotide differences, and the nucleotide sequence II and the nucleotide sequence as shown by SEQ ID NO: 38 have an equal length and no more than 3 nucleotide differences:

(SEQ ID NO: 37)
5′-AGUAUUCUCAGUGCUCUCZ$_{a1}$-3′, (SEQ ID NO: 38)
5′-Z$_{a2}$GAGAGCACUGAGAAUACU-3′, wherein, $Z_{d1}$ is A and $Z_{d2}$ is U, and the nucleotide sequence I comprises a nucleotide $Z_{d3}$ at the position corresponding to $Z_{d1}$; the nucleotide sequence II comprises a nucleotide $Z_{d4}$ at the position corresponding to $Z_{d2}$, wherein $Z_{d4}$ is the first nucleotide at 5' terminal of the antisense strand; or v) the nucleotide sequence I and the nucleotide sequence as shown by SEQ ID NO: 49 have an equal length and no more than 3 nucleotide differences, and the nucleotide sequence II and the nucleotide sequence as shown by SEQ ID NO: 50 have an equal length and no more than 3 nucleotide differences:

(SEQ ID NO: 49)
5′-GGACAGUAUUCUCAGUGCZ$_{e1}$-3′, (SEQ ID NO: 50)
5′-Z$_{e2}$GCACUGAGAAUACUGUCC-3′, wherein, $Z_{e1}$ is A and $Z_{e2}$ is U, and the nucleotide sequence I comprises a nucleotide $Z_{e3}$ at the position corresponding to $Z_{e1}$; the nucleotide sequence II comprises a nucleotide $Z_{e4}$ at the position corresponding to $Z_{e2}$, wherein $Z_{e4}$ is the first nucleotide at 5' terminal of the antisense strand.

In some embodiments, each non-fluoro modified nucleotide is independently selected from one of a nucleotide formed by substituting the 2'-hydroxy of the ribose group thereof with a non-fluoro group, and a nucleotide analogue.

In some embodiments, the nucleotide formed by substituting the 2'-hydroxy of the ribose group with a non-fluoro group is selected from the group consisting of 2'-alkoxy modified nucleotide, 2'-substituted alkoxy modified nucleotide, 2'-alkyl modified nucleotide, 2'-substituted alkyl modified nucleotide, 2'-amino modified nucleotide, 2'-substituted amino modified nucleotide and 2'-deoxy nucleotide; and the nucleotide analogue is selected from the group consisting of an isonucleotide, LNA, ENA, cET, UNA, and GNA.

In some embodiments, each non-fluoro modified nucleotide is a methoxy modified nucleotide.

In some embodiments, the present disclosure provides a pharmaceutical composition, comprising the above siRNA of the present disclosure, and a pharmaceutically acceptable carrier.

In some embodiments, the present disclosure provides use of the siRNA, and/or the pharmaceutical composition, and/or the siRNA conjugate of the present disclosure in the manufacture of a medicament for treating and/or preventing dyslipidemia caused by abnormal expression of the APOC3 gene.

In some embodiments, the present disclosure provides a method for treating and/or preventing dyslipidemia, comprising administering an effective amount of the siRNA, and/or the pharmaceutical composition, and/or the siRNA conjugate of the present disclosure to a subject suffering from dyslipidemia.

In some embodiments, the present disclosure provides a method for inhibiting the expression of APOC3 gene in hepatocytes, comprising contacting an effective amount of the siRNA, and/or the pharmaceutical composition, and/or the siRNA conjugate of the present disclosure with the hepatocytes.

In some embodiments, the present disclosure provides a kit, comprising the siRNA, and/or the pharmaceutical composition, and/or the siRNA conjugate of the present disclosure.

Beneficial Effects

The siRNA, the composition comprising the siRNA, and the siRNA conjugate of the present disclosure could exhibit good stability, higher gene suppression activity, and/or significantly reduced blood lipid level.

In some embodiments, the siRNA conjuage of the present disclosure exhibits excellent property of suppressing APOC3 mRNA: inhibiting at least 82.0% of the expression of APOC3 mRNA in the liver of high-fat model mice at a dose of 1 mg/kg.

The experiments show that as compared with the conjugates formed from conjugation molecules as provided in the prior art, the siRNA conjugate of the present disclosure exhibits excellent capability of reducing blood lipid. Moreover, the siRNA conjugate of the present disclosure could continuously exhibit excellent effect of reducing blood lipid level over a period of up to 189 days under low administration dose and low administration frequency.

For example, after single administrations of 3 mg/kg, Conjugates 2, 4 and 5 maintain an inhibition rate of 70% to 90% against TG over a period of up to 77 days, substantially maintain an inhibition rate of 50% against total cholesterol (CHO) over a period of up to 77 days, and maintain an inhibition rate of about 50% or higher against TG over a period of up to 147 days; after single administrations of 3 mg/kg, the three conjugates exhibit an inhibition rate of up to about 80% against TG on day 7, and continuously exhibit an effect of reducing the TG content by no less than 50% over a period of up to 49 days; and on day 35 after single administration, the three conjugates in the 1 mg/kg dose group still show an effect of reducing the CHO content by at least about 50%. For Conjugate 1, in both of the dose groups of 3 mg/kg and 1 mg/kg, Conjugate 1 could significantly reduce the TG and CHO levels in the transgenic mice over a period of up to 112 days; and such reduction effects are significantly superior to that of Comparative Conjugate 2. In both of the dose groups of 3 mg/kg and 1 mg/kg, Conjugate 1 exhibits inhibition rates of 50% or higher against TG and CHO over a period of 56 days after single administration; and the inhibitory effects on TG are more significant: the two doses of Conjugate 1 continuously maintain the TG level of about 50% over a period of up to 112 days.

As another example, Conjugate 3 could significantly reduce the TG and CHO levels in transgenic mice over a period of up to 98 days. On day 14 after single administration of 3 mg/kg, Conjugate 3 shows an inhibition rate of up to 93.6% against TG, and on day 7 after single administration shows an inhibition rate of up to 63.0% against CHO. Conjugates 4, 6 and 7 in the two doses could exhibit an effect of significantly reducing blood lipid level in human APOC3 transgenic mice, and in the 3 mg/kg dose group, continuously maintain an inhibition rate of 50% or higher against TG and an inhibition rate of 30% or higher against CHO over a period of 84 days after administration. It is noteworthy that at the doses of 3 mg/kg and 1 mg/kg, Conjugates 4, 6 and 7 continuously show higher inhibitory effects on TG than that of Comparative Conjugate 2; and the same tendency is also observed for the inhibitory effect on CHO.

As for Conjugates 8 and 9, the $ED_{50}$ values for inhibiting TG at different time points are measured. It can be seen that for human APOC3 transgenic mouse, even half a month after administration, a single subcutaneous injection of 0.16 mg/kg Conjugate 8 or 0.11 mg/kg Conjugate 9 could still realize the efficacy of reducing half of the serum TG content; and even one month after administration, a single subcutaneous injection of less than 1 mg/kg of the conjugates of the present disclosure could still realize the effect of reducing half of the serum TG content.

Therefore, the siRNA, the pharmaceutical composition and the siRNA conjugate of the present disclosure could inhibit the expression of APOC3 gene, effectively treat and/or prevent dyslipidemia caused by the overexpression of APOC3 gene, and thus show a promising prospect of application.

Additional features and advantages of the present disclosure will be detailedly illustrated in the following part "detailed description of the invention".

BRIEF DESCRIPTION OF THE DRAWINGS

In order to more clearly illustrate the examples of the present invention and the technical solutions of the prior art, the following parts briefly describe the figures used in the examples and the prior art. Obviously, the figures in the following description represent only some examples of the present invention.

DETAILED DESCRIPTION OF THE INVENTION

Figure 1:
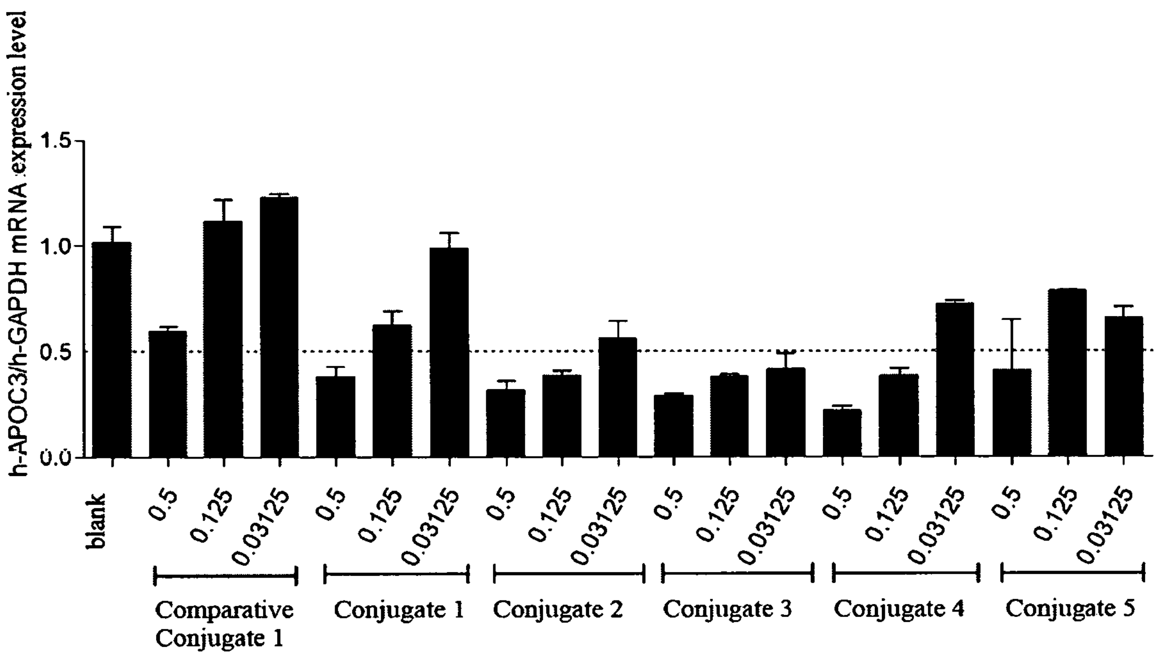
FIG. 1 is a histogram showing the expression levels of APOC3 mRNA in untransfected Huh7 cells and in Huh7 cells transfected with different conjugates at different final concentrations.

The following is the detailed description of the specific embodiments of the present disclosure. It should be understood that the specific embodiments described herein are only used to illustrate and explain the present disclosure and are not intended to limit the present disclosure.

In the present disclosure, the sequence of APOC3 mRNA is the sequence as shown in Genbank Accession No. NM_000040.1. Further, unless otherwise specified, the term "target gene" used in the present disclosure refers to the gene expressing the above APOC3 mRNA; and the term "target mRNA" refers to the above APOC3 mRNA.

Definitions

In the context of the present disclosure, unless otherwise specified, C, G, U, and A represent the base composition of a nucleotide; m represents that the nucleotide adjacent to the left side of the letter m is a methoxy modified nucleotide; f represents that the nucleotide adjacent to the left side of the letter f is a fluoro modified nucleotide; s represents the two nucleotides adjacent to both sides of the letter s are linked by a thiophosphate linkage; P1 represents that the nucleotide adjacent to the right side of P1 is a 5'-phosphate nucleotide or a 5'-phosphate analogue modified nucleotide; in some embodiments, P1 represents the specific modified nucleotide VP, Ps or P, wherein VP represents that the nucleotide adjacent to the right side of VP is a vinyl phosphate (5'-(E)-vinylphosphonate, E-VP) modified nucleotide; Ps represents that the nucleotide adjacent to the right side of Ps is a thiophosphate modified nucleotide; and P represents that the nucleotide adjacent to the right side of the letter P is a 5'-phosphate nucleotide.

In the context of the present disclosure, a "fluoro modified nucleotide" refers to a nucleotide formed by substituting 2'-hydroxy of the ribose group with a fluorine atom. A "non-fluoro modified nucleotide" refers to a nucleotide formed by substituting 2'-hydroxy of the ribose group with a non-fluoro group, or a nucleotide analogue. A "nucleotide analogue" refers to a group that can replace a nucleotide in a nucleic acid, while structurally differs from an adenine ribonucleotide, a guanine ribonucleotide, a cytosine ribonucleotide, a uracil ribonucleotide, or thymine deoxyribonucleotide, such as an isonucleotide, a bridged nucleotide (bridged nucleic acid, BNA) or an acyclic nucleotide. The "methoxy modified nucleotide" refers to a nucleotide formed by substituting 2'-hydroxy of the ribose group with a methoxy group.

In the context of the present disclosure, expressions "complementary" and "reverse complementary" can be interchangeably used, and have a well-known meaning in the art, namely, the bases in one strand are complementarily paired with those in the other strand in a double-stranded nucleic acid molecule. In DNAs, a purine base adenine (A) is always paired with a pyrimidine base thymine (T) (or a uracil (U) in RNAs); and a purine base guanine (G) is always paired with a pyrimidine base cytosine (C). Each base pair comprises a purine and a pyrimidine. While adenines in one strand are always paired with thymines (or uracils) in another strand, and guanines are always paired with cytosines, the two strands are considered as being complementary with each other; and the sequence of a strand may be deduced from the sequence of its complementary strand. Correspondingly, a "mispairing" means that the bases at corresponding positions are not present in a manner of complementary pairing in a double-stranded nucleic acid.

In the context of the present disclosure, unless otherwise specified, "basically reverse complementary" means that there are no more than 3 base mispairings between two nucleotide sequences. "Substantially reverse complementary" means that there is no more than 1 base mispairing between two nucleotide sequences. "Completely reverse complementary" means that there is no base mispairing between two nucleotide sequences.

In the context of the present disclosure, when a nucleotide sequence has a "nucleotide difference" from another nucleotide sequence, the bases of the nucleotides at the same position therebetween are changed. For example, if a nucleotide base in the latter sequence is A and the nucleotide base at the same position in the former sequence is U, C, G, or T, the two nucleotide sequences are considered as having a nucleotide difference at this position. In some embodiments, if a nucleotide at a position is replaced with an abasic nucleotide or a nucleotide analogue, it is also considered that there is a nucleotide difference at the position.

In the context of the present disclosure, particularly in the description of the siRNA, the composition comprising the siRNA, or the method for preparing the siRNA conjugate of the present disclosure, unless otherwise specified, the "nucleoside monomer" refers to, according to the type and sequence of the nucleotides in the siRNA or siRNA conjugate to be prepared, unmodified or modified nucleoside phosphoramidite monomer (unmodified or modified RNA phosphoramidites; sometimes RNA phosphoramidites are referred to as nucleoside phosphoramidites) used in a phosphoramidite solid phase synthesis. The phosphoramidite solid phase synthesis is a well-known method for RNA synthesis by those skilled in the art. Nucleoside monomers used in the present disclosure are all commercially available.

In the context of the present disclosure, unless otherwise specified, "conjugation" means that two or more chemical moieties each having specific function are linked to each other via a covalent linkage. Correspondingly, a "conjugate" refers to a compound formed by covalent linkage of individual chemical moieties. Furthermore, a "siRNA conjugate" represents a compound formed by covalently attaching one or more chemical moieties each with specific functions to a siRNA. In the following text, the siRNA conjugate of the present disclosure is sometimes abbreviated as "conjugate". According to the context of the present disclosure, the siRNA conjugate should be understood as the generic term of siRNA conjugates, the generic term of siRNA conjugates of many specific chemical molecules, or each siRNA conjugate among the siRNA conjugates of many specific chemical molecules. In the context of the present disclosure, "conjugation molecules" should be interpreted as a class of compounds or specific compounds capable of being conjugated to a siRNA via reactions, thereby finally forming the siRNA conjugate of the present disclosure.

As used herein, a dash ("-") that is not present between two letters or symbols is used to indicate the position that is an attachment point for a substituent. For example, the dash on the far left side in the structure formula "$—C_1$-$C_{10}$alkyl-$NH_2$" means being attached through the $C_1$-$C_{10}$alkyl.

As used herein, "optional" or "optionally" means that the subsequently described event or circumstance may or may not occur, and that the description includes instances in which the event or circumstance occurs and instances in which it does not. For example, "optionally substituted alkyl" encompasses both "alkyl" and "substituted alkyl" as defined below. Those skilled in the art would understand, with respect to any group containing one or more substituents, that such groups are not intended to introduce any substitution or substitution patterns that are sterically impractical, synthetically infeasible and/or inherently unstable.

As used herein, "alkyl" refers to straight chain and branched chain alkyl having the indicated number of carbon atoms, usually from 1 to 20 carbon atoms, for example 1 to 10 carbon atoms, such as 1 to 8 or 1 to 6 carbon atoms. For example, $C_1$-$C_6$ alkyl encompasses both straight and branched chain alkyl of from 1 to 6 carbon atoms. When an alkyl residue having a specific number of carbon atoms is named, all branched and straight chain forms having that number of carbon atoms are intended to be encompassed; thus, for example, "butyl" is meant to encompass n-butyl, sec-butyl, isobutyl, and t-butyl; "propyl" includes n-propyl and isopropyl. Alkylene is a subset of alkyl, referring to the same residues as alkyl, but having two attachment points.

As used herein, "alkenyl" refers to an unsaturated branched or straight-chain alkyl group having at least one carbon-carbon double bond obtained by respectively removing one hydrogen molecule from two adjacent carbon atoms of the parent alkyl. The group may be in either the cis or trans configuration of the double bond(s). Typical alkenyl groups include, but are not limited to, ethenyl; propenyl, such as prop-1-en-1-yl, prop-1-en-2-yl, prop-2-en-1-yl (allyl), prop-2-en-2-yl; butenyl, such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms, and in other embodiments, from 2 to 10, 2 to 8, or 2 to 6 carbon atoms. Alkenylene is a subset of alkenyl, referring to the same residues as alkenyl, but having two attachment points.

As used herein, "alkynyl" refers to an unsaturated branched or straight-chain alkyl group having at least one carbon-carbon triple bond obtained by respectively removing two hydrogen molecules from two adjacent carbon atoms of the parent alkyl. Typical alkynyl groups include, but are not limited to, ethynyl; propynyl, such as prop-1-yn-1-yl, prop-2-yn-1-yl; butynyl, such as but-1-yn-1-yl, but-1-yn-3-yl, but-3-yn-1-yl; and the like. In certain embodiments, an alkynyl group has from 2 to 20 carbon atoms, and in other embodiments, from 2 to 10, 2 to 8, or 2 to 6 carbon atoms. Alkynylene is a subset of alkynyl, referring to the same residues as alkynyl, but having two attachment points.

As used herein, "alkoxy" refers to an alkyl group of the indicated number of carbon atoms attached through an oxygen bridge, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy group usually has from 1 to 10, 1 to 8, 1 to 6, or 1 to 4 carbon atoms attached through oxygen bridge.

As used herein, "aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon, including from 6 to 18 carbon atoms, wherein at least one ring in the ring system is fully unsaturated, i.e., it contains a cyclic, delocalized $(4n+2)\pi$-electron system in accordance with the Hückel theory. Aryl groups include, but are not limited to, groups such as phenyl, fluorenyl, and naphthyl. Arylene is a subset of aryl, referring to the same residues as aryl, but having two attachment points.

As used herein, "cycloalkyl" refers to a non-aromatic carbon ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "halo substituent" or "halo" refers to fluoro, chloro, bromo, and iodo, and the term "halogen" includes fluorine, chlorine, bromine, and iodine.

As used herein, "haloalkyl" refers to alkyl as defined above in which the specified number of carbon atoms are substituted with one or more (up to the maximum allowable number) halogen atoms. Examples of haloalkyl include, but are not limited to, trifluoromethyl, difluoromethyl, 2-fluoroethyl, and penta-fluoroethyl.

"Heterocyclyl" refers to a stable 3 to 18 membered non-aromatic ring radical that comprises 2 to 12 carbon atoms and 1 to 6 heteroatoms selected from nitrogen, oxygen or sulfur. Unless stated otherwise in the specification, the heterocyclyl is a monocyclic, bicyclic, tricyclic, or tetracyclic ring system, which may include fused or bridged ring system(s). The heteroatom(s) in the heterocyclyl may be optionally oxidized. One or more nitrogen atoms, if present, are optionally quaternized. The heterocyclyl is partially or fully saturated. The heterocyclyl may be attached to the rest of the molecule through any ring atom. Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxapiperazinyl, 2-oxapiperidinyl, 2-oxapyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

"Heteroaryl" refers to a radical derived from a 3 to 18 membered aromatic ring radical that comprises 2 to 17 carbon atoms and 1 to 6 heteroatoms selected from nitrogen, oxygen or sulfur. As used herein, the heteroaryl may be a monocyclic, bicyclic, tricyclic or tetracyclic ring system, wherein at least one ring in the ring system is fully unsaturated, i.e., it contains a cyclic, delocalized $(4n+2)\pi$-electron system in accordance with the Hückel theory. Heteroaryl includes fused or bridged ring system(s). The heteroatom(s) in the heteroaryl is optionally oxidized. One or more nitrogen atoms, if present, are optionally quaternized. The heteroaryl is attached to the rest of the molecule through any ring atom. Examples of heteroaryl include, but are not limited to, azepinyl, acridinyl, benzimidazolyl, benzindolyl, 1,3-benzodioxazolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzooxazolyl, benzodioxolyl, benzodioxinyl, benzopyranyl, benzopyranonyl, benzofuranyl, benzofuranonyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothienyl, furanyl, furanonyl, furo[3,2-c]pyridinyl, 5,6,7,8,9,10 hexahydrocycloocta[d]pyrimidinyl, 5,6,7,8,9,10-hexahydrocyclohepta[d]pyridazinyl, 5,6,7,8,9,10-hexahydrocycloocta[d]pyridinyl, isothiazolyl, imidazolyl, indazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinonyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl and thiophenyl/thienyl.

Various hydroxyl protection groups may be used in the present disclosure. In general, protection groups render chemical functional groups inert to specific reaction conditions, and may be appended to and removed from such functional groups in a molecule without substantially damaging the remainder of the molecule. Representative hydroxyl protection groups are disclosed in Beaucage et al., Tetrahedron 1992, 48, 2223-2311, and also in Greene and Wuts, Protective Groups in Organic Synthesis, Chapter 2, 2d ed, John Wiley & Sons, New York, 1991, which are incorporated herein by reference in their entirety. In some embodiments, the protection group is stable under basic conditions but may be removed under acidic conditions. In some embodiments, non-exclusive examples of the hydroxyl protection groups that may be used herein include dimethoxytrityl (DMT), monomethoxytrityl, 9-phenylxanthen-9-yl (Pixyl) and 9-(p-methoxyphenyl)xanthen-9-yl (Mox). In some embodiments, non-exclusive examples of the hydroxyl protection groups that may be used herein comprises Tr (trityl), MMTr (4-methoxytrityl), DMTr (4,4'-dimethoxytrityl), and TMTr (4,4',4"-trimethoxytrityl).

The term "subject", as used herein, refers to any animal, e.g., a mammal or marsupial. The subject of the present disclosure includes, but are not limited to, human, non-human primate (e.g., rhesus or other types of macaques), mouse, pig, horse, donkey, cow, sheep, rat, and any kind of poultry.

As used herein, "treatment" or "treating", or "alleviating" or "ameliorating" can be used interchangeably herein. These terms refer to an approach for obtaining beneficial or desirable results, including but not limited to therapeutic benefit. By "therapeutic benefit" is meant eradication or amelioration of the underlying disorder being treated. Also, a therapeutic benefit is achieved by eradicating or ameliorating one or more physiological symptoms associated with the underlying disorder, thereby observing amelioration in the subject, although the subject may still be afflicted with the underlying disorder.

As used herein, "prevention" and "preventing" can be used interchangeably. These terms refer to an approach for obtaining beneficial or desirable results, including but not limited to a prophylactic benefit. In order to obtain "prophylactic benefit", the conjugates or compositions may be administered to a subject at risk of developing a particular disease, or to a subject reporting one or more physiological symptoms of a disease, even a diagnosis of this disease has not been made.

The siRNA of the present disclosure comprises nucleotide groups as basic structural units. It is well known to those skilled in the art that the nucleotide group comprises a phosphate group, a ribose group and a base. Detailed illustrations of these groups are omitted herein.

First siRNA

According to the present disclosure, the siRNA may be a first siRNA.

The first siRNA comprises a sense strand and an antisense strand; each nucleotide in the first siRNA is independently a modified or unmodified nucleotide; wherein the sense strand comprises a nucleotide sequence I, and the antisense strand comprises a nucleotide sequence II; the nucleotide sequence I and the nucleotide sequence II are at least partly reverse complementary to form a double-stranded region; for the first siRNA, the nucleotide sequence I and the nucleotide sequence as shown by SEQ ID NO: 1 have an equal length and no more than 3 nucleotide differences, and the nucleotide sequence II and the nucleotide sequence as shown by SEQ ID NO: 2 have an equal length and no more than 3 nucleotide differences:

(SEQ ID NO: 1)
5'-UUAAAAGGGACAGUAUUCZ$_{a1}$-3', (SEQ ID NO: 2)
5'-Z$_{a2}$GAAUACUGUCCCUUUUAA-3', wherein, $Z_{a1}$ is A and $Z_{a2}$ is U, and the nucleotide sequence I comprises a nucleotide $Z_{a3}$ at the position corresponding to $Z_{a1}$; the nucleotide sequence II comprises a nucleotide $Z_{a4}$ at the position corresponding to $Z_{a2}$, wherein $Z_{a4}$ is the first nucleotide at 5' terminal of the antisense strand;

In the context of the present disclosure, "corresponding position" refers to, the same position in the nucleotide sequence when counting from the same terminal of the nucleotide sequence. For example, for the first siRNA, the first nucleotide at 3' terminal of the nucleotide sequence I is a nucleotide at the position corresponding to the first nucleotide at 3' terminal of SEQ ID NO: 1.

In some embodiments, the sense strand comprises only the nucleotide sequence I, and the antisense strand comprises only the nucleotide sequence II.

In some embodiments, the nucleotide sequence I and the nucleotide sequence as shown by SEQ ID NO: 1 have no more than 1 nucleotide difference, and/or the nucleotide sequence II and the nucleotide sequence as shown by SEQ ID NO: 2 have no more than 1 nucleotide difference.

In some embodiments, the nucleotide difference between the nucleotide sequence II and the nucleotide sequence as shown by SEQ ID NO: 2 includes a difference at the position $Z_{a4}$, wherein $Z_{a4}$ is selected from A, C or G. In some embodiments, the nucleotide difference is a difference at the position $Z_{a4}$, wherein $Z_{a4}$ is selected from A, C or G. In some embodiments, $Z_{a3}$ is a nucleotide complementary to $Z_{a4}$. These nucleotide differences will not significantly reduce the ability of the siRNA conjugates of inhibiting the target gene, and thus these siRNA conjugates comprising the nucleotide differences are within the protection scope of the present disclosure.

In some embodiments, the nucleotide sequence I and the nucleotide sequence II are basically reverse complementary, substantially reverse complementary, or completely reverse complementary to each other; the "basically reverse complementary" means that there is no more than 3 base mispairings between two nucleotide sequences; the "substantially reverse complementary" means that there is no more than 1 base mispairing between two nucleotide sequences; the "completely reverse complementary" means that there is no mispairing between two nucleotide sequences.

In some embodiments, the nucleotide sequence I is the nucleotide sequence as shown by SEQ ID NO: 3, and the nucleotide sequence II is the nucleotide sequence as shown by SEQ ID NO: 4:

(SEQ ID NO: 3)
5'-UUAAAAGGGACAGUAUUCZ$_{a3}$-3', (SEQ ID NO: 4)
5'-Z$_{a4}$GAAUACUGUCCCUUUUAA-3', wherein, $Z_{a4}$ is the first nucleotide at 5' terminal of the antisense strand, $Z_{a3}$ is selected from A, U, G, or C, and $Z_{a4}$ is a nucleotide complementary to $Z_{a3}$; in some embodiments, $Z_{a3}$ is U, and $Z_{a4}$ is A.

Moreover, the sense strand and the antisense strand have the same or different length, wherein the sense strand has a length of 19 to 23 nucleotides, and the antisense strand has a length of 20 to 26 nucleotides.

In some embodiments, the sense strand further comprises a nucleotide sequence III, the antisense strand further comprises a nucleotide sequence IV, and the nucleotide sequence III and the nucleotide sequence IV independently of one another have a length of 1 to 4 nucleotides; the nucleotide sequence III is linked to 5' terminal of the nucleotide sequence I, the nucleotide sequence IV is linked to 3' terminal of the nucleotide sequence II; and the nucleotide sequence III and the nucleotide sequence IV have an equal length.

In some embodiments, the nucleotide sequence III and the nucleotide sequence IV both have a length of 1 nucleotide, and the base of the nucleotide sequence III is C, and the base of the nucleotide sequence IV is G; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the bases of the nucleotide sequence III is GC, and the bases of the nucleotide sequence IV is GC; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the bases of the nucleotide sequence III is UGC, and the bases of the nucleotide sequence IV is GCA; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the bases of the nucleotide sequence III is UUGC, and the bases of the nucleotide sequence IV is GCAA; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the bases of the nucleotide sequence III is GC, and the bases of the nucleotide sequence IV is GC; in this case, the length ratio of the sense strand and the antisense strand thereof is 21/21.

In some embodiments, the nucleotide sequence III and the nucleotide sequence IV have an equal length and are completely reverse complementary. Hence, where the base(s) of nucleotide sequence III is(are) provided, the base(s) of nucleotide sequence IV is(are) also determined.

Second siRNA

According to the present disclosure, the siRNA may be a second siRNA.

The second siRNA comprises a sense strand and an antisense strand; each nucleotide in the second siRNA is independently a modified or unmodified nucleotide; wherein the sense strand comprises a nucleotide sequence I, and the antisense strand comprises a nucleotide sequence II; the nucleotide sequence I and the nucleotide sequence II are at least partly reverse complementary to form a double-stranded region; wherein, the nucleotide sequence I and the nucleotide sequence as shown by SEQ ID NO: 13 have an equal length and no more than 3 nucleotide differences, and the nucleotide sequence II and the nucleotide sequence as shown by SEQ ID NO: 14 have an equal length and no more than 3 nucleotide differences:

(SEQ ID NO: 13)
5'-ACAGUAUUCUCAGUGCUC$Z_{b1}$-3', (SEQ ID NO: 14)
5'-$Z_{b2}$GAGCACUGAGAAUACUGU-3', wherein, $Z_{b1}$ is A and $Z_{b2}$ is U, and the nucleotide sequence I comprises a nucleotide $Z_{b3}$ at the position corresponding to $Z_{b1}$; the nucleotide sequence II comprises a nucleotide $Z_{b4}$ at the position corresponding to $Z_{b2}$, wherein $Z_{b4}$ is the first nucleotide at 5' terminal of the antisense strand;

In some embodiments, the sense strand comprises only the nucleotide sequence I, and the antisense strand comprises only the nucleotide sequence II.

In some embodiments, the nucleotide sequence I and the nucleotide sequence as shown by SEQ ID NO: 13 have no more than 1 nucleotide difference, and/or the nucleotide sequence II and the nucleotide sequence as shown by SEQ ID NO: 14 have no more than 1 nucleotide difference.

In some embodiments, the nucleotide difference between the nucleotide sequence II and the nucleotide sequence as shown by SEQ ID NO: 14 includes a difference at the position $Z_{b4}$, wherein $Z_{b4}$ is selected from A, C or G. In some embodiments, the nucleotide difference is a difference at the position $Z_{b4}$, wherein $Z_{b4}$ is selected from A, C or G. In some embodiments, $Z_{b3}$ is a nucleotide complementary to $Z_{b4}$. These nucleotide differences will not significantly reduce the ability of the siRNA conjugates of inhibiting the target gene, and thus these siRNA conjugates comprising the nucleotide differences are within the protection scope of the present disclosure.

In some embodiments, the nucleotide sequence I and the nucleotide sequence II are basically reverse complementary, substantially reverse complementary, or completely reverse complementary to each other.

In some embodiments, the nucleotide sequence I is the nucleotide sequence as shown by SEQ ID NO: 15, and the nucleotide sequence II is the nucleotide sequence as shown by SEQ ID NO: 16:

(SEQ ID NO: 15)
5'-ACAGUAUUCUCAGUGCUC$Z_{b3}$-3', (SEQ ID NO: 16)
5'-$Z_{b4}$GAGCACUGAGAAUACUGU-3', wherein, $Z_{b4}$ is the first nucleotide at 5' terminal of the antisense strand, $Z_{b3}$ is selected from A, U, G, or C, and $Z_{b4}$ is a nucleotide complementary to $Z_{b3}$; in some embodiments, $Z_{b3}$ is U, and $Z_{b4}$ is A.

Moreover, the sense strand and the antisense strand have the same or different length, wherein the sense strand has a length of 19 to 23 nucleotides, and the antisense strand has a length of 20 to 26 nucleotides.

In some embodiments, the sense strand further comprises a nucleotide sequence III, the antisense strand further comprises a nucleotide sequence IV, and the nucleotide sequence III and the nucleotide sequence IV independently of one another have a length of 1 to 4 nucleotides; the nucleotide sequence III is linked to 5' terminal of the nucleotide sequence I, the nucleotide sequence IV is linked to 3' terminal of the nucleotide sequence II; and the nucleotide sequence III and the nucleotide sequence IV have an equal length.

In some embodiments, the nucleotide sequence III and the nucleotide sequence IV both have a length of 1 nucleotide, and the base of the nucleotide sequence III is G, and the base of the nucleotide sequence IV is C; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the bases of the nucleotide sequence III is GG, and the bases of the nucleotide sequence IV is CC; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the bases of the nucleotide sequence III is GGG, and the bases of the nucleotide sequence IV is CCC; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the bases of the nucleotide sequence III is AGGG, and the bases of the nucleotide sequence IV is CCCU; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the bases of the nucleotide sequence III is GG, and the bases of the nucleotide sequence IV is CC; in this case, the length ratio of the sense strand and the antisense strand thereof is 21/21.

In some embodiments, the nucleotide sequence III and the nucleotide sequence IV have an equal length and are completely reverse complementary. Hence, where the base(s) of nucleotide sequence III is(are) provided, the base(s) of nucleotide sequence IV is(are) also determined.

Third siRNA

According to the present disclosure, the siRNA may be a third siRNA.

The third siRNA comprises a sense strand and an antisense strand; each nucleotide in the third siRNA is independently a modified or unmodified nucleotide; wherein the sense strand comprises a nucleotide sequence I, and the antisense strand comprises a nucleotide sequence II; the nucleotide sequence I and the nucleotide sequence II are at least partly reverse complementary to form a double-stranded region; wherein, the nucleotide sequence I and the nucleotide sequence as shown by SEQ ID NO: 25 have an equal length and no more than 3 nucleotide differences, and the nucleotide sequence II and the nucleotide sequence as shown by SEQ ID NO: 26 have an equal length and no more than 3 nucleotide differences:

(SEQ ID NO: 25)
5'-UAUUCUCAGUGCUCUCCUZ$_{c1}$-3', (SEQ ID NO: 26)
5'-Z$_{c2}$AGGAGAGCACUGAGAAUA-3', wherein, $Z_{c1}$ is A and $Z_{c2}$ is U, and the nucleotide sequence I comprises a nucleotide $Z_{c3}$ at the position corresponding to $Z_{c1}$; the nucleotide sequence II comprises a nucleotide $Z_{c4}$ at the position corresponding to $Z_{c2}$, wherein $Z_{c4}$ is the first nucleotide at 5' terminal of the antisense strand;

In some embodiments, the sense strand comprises only the nucleotide sequence I, and the antisense strand comprises only the nucleotide sequence II.

In some embodiments, the nucleotide sequence I and the nucleotide sequence as shown by SEQ ID NO: 25 have no more than 1 nucleotide difference, and/or the nucleotide sequence II and the nucleotide sequence as shown by SEQ ID NO: 26 have no more than 1 nucleotide difference.

In some embodiments, the nucleotide difference between the nucleotide sequence II and the nucleotide sequence as shown by SEQ ID NO: 26 includes a difference at the position $Z_{c4}$, wherein $Z_{c4}$ is selected from A, C or G. In some embodiments, the nucleotide difference is a difference at the position $Z_{c4}$, wherein $Z_{c4}$ is selected from A, C or G. In some embodiments, $Z_{c3}$ is a nucleotide complementary to $Z_{c4}$. These nucleotide differences will not significantly reduce the ability of the siRNA conjugates of inhibiting the target gene, and thus these siRNA conjugates comprising the nucleotide differences are within the protection scope of the present disclosure.

In some embodiments, the nucleotide sequence I and the nucleotide sequence II are basically reverse complementary, substantially reverse complementary, or completely reverse complementary to each other.

In some embodiments, the nucleotide sequence I is the nucleotide sequence as shown by SEQ ID NO: 27, and the nucleotide sequence II is the nucleotide sequence as shown by SEQ ID NO: 28:

(SEQ ID NO: 27)
5'-UAUUCUCAGUGCUCUCCUZ$_{c3}$-3';

(SEQ ID NO: 28)
5'-Z$_{c4}$AGGAGAGCACUGAGAAUA-3', wherein, $Z_{c4}$ is the first nucleotide at 5' terminal of the antisense strand, $Z_{c3}$ is selected from A, U, G, or C, and $Z_{c4}$ is a nucleotide complementary to $Z_{c3}$; in some embodiments, $Z_{c3}$ is U, and $Z_{c4}$ is A.

Moreover, the sense strand and the antisense strand have the same or different length, wherein the sense strand has a length of 19 to 23 nucleotides, and the antisense strand has a length of 20 to 26 nucleotides.

In some embodiments, the sense strand further comprises a nucleotide sequence III, the antisense strand further comprises a nucleotide sequence IV, and the nucleotide sequence III and the nucleotide sequence IV independently of one another have a length of 1 to 4 nucleotides; the nucleotide sequence III is linked to 5' terminal of the nucleotide sequence I, the nucleotide sequence IV is linked to 3' terminal of the nucleotide sequence II; and the nucleotide sequence III and the nucleotide sequence IV have an equal length.

In some embodiments, the nucleotide sequence III and the nucleotide sequence IV both have a length of 1 nucleotide, and the base of the nucleotide sequence III is G, and the base of the nucleotide sequence IV is C; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the bases of the nucleotide sequence III is AG, and the bases of the nucleotide sequence IV is CU; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the bases of the nucleotide sequence III is CAG, and the bases of the nucleotide sequence IV is CUG; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the bases of the nucleotide sequence III is ACAG, and the bases of the nucleotide sequence IV is CUGU; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the bases of the nucleotide sequence III is AG, and the bases of the nucleotide sequence IV is CU; in this case, the length ratio of the sense strand and the antisense strand thereof is 21/21.

In some embodiments, the nucleotide sequence III and the nucleotide sequence IV have an equal length, and are completely reverse complementary. Hence, where the base(s) of nucleotide sequence III is(are) provided, the base(s) of nucleotide sequence IV is(are) also determined.

Fourth siRNA

According to the present disclosure, the siRNA may be a fourth siRNA.

The fourth siRNA comprises a sense strand and an antisense strand; each nucleotide in the fourth siRNA is independently a modified or unmodified nucleotide; wherein the sense strand comprises a nucleotide sequence I, and the antisense strand comprises a nucleotide sequence II; the nucleotide sequence I and the nucleotide sequence II are at least partly reverse complementary to form a double-stranded region; wherein, the nucleotide sequence I and the nucleotide sequence as shown by SEQ ID NO: 37 have an equal length and no more than 3 nucleotide differences, and the nucleotide sequence II and the nucleotide sequence as shown by SEQ ID NO: 38 have an equal length and no more than 3 nucleotide differences:

(SEQ ID NO: 37)
5'-AGUAUUCUCAGUGCUCUC$Z_{a1}$-3';

(SEQ ID NO: 38)
5'-$Z_{a2}$GAGAGCACUGAGAAUACU-3', wherein, $Z_{d1}$ is A and $Z_{d2}$ is U, and the nucleotide sequence I comprises a nucleotide $Z_{d3}$ at the position corresponding to $Z_{d1}$, the nucleotide sequence II comprises a nucleotide $Z_{d4}$ at the position corresponding to $Z_{d2}$, wherein $Z_{d4}$ is the first nucleotide at 5' terminal of the antisense strand.

In some embodiments, the sense strand comprises only the nucleotide sequence I, and the antisense strand comprises only the nucleotide sequence II.

In some embodiments, the nucleotide sequence I and the nucleotide sequence as shown by SEQ ID NO: 37 have no more than 1 nucleotide difference, and/or the nucleotide sequence II and the nucleotide sequence as shown by SEQ ID NO: 38 have no more than 1 nucleotide difference.

In some embodiments, the nucleotide difference between the nucleotide sequence II and the nucleotide sequence as shown by SEQ ID NO: 38 includes a difference at the position $Z_{d4}$, wherein $Z_{d4}$ is selected from A, C or G. In some embodiments, the nucleotide difference is a difference at the position $Z_{d4}$, wherein $Z_{d4}$ is selected from A, C or G. In some embodiments, $Z_{d3}$ is a nucleotide complementary to $Z_{d4}$. These nucleotide differences will not significantly reduce the ability of the siRNA conjugates of inhibiting the target gene, and thus these siRNA conjugates comprising the nucleotide differences are within the protection scope of the present disclosure.

In some embodiments, the nucleotide sequence I and the nucleotide sequence II are basically reverse complementary, substantially reverse complementary, or completely reverse complementary to each other.

In some embodiments, the nucleotide sequence I is the nucleotide sequence as shown by SEQ ID NO: 39, and the nucleotide sequence II is the nucleotide sequence as shown by SEQ ID NO: 40:

(SEQ ID NO: 39)
5'-AGUAUUCUCAGUGCUCUC$Z_{a3}$-3';

(SEQ ID NO: 40)
5'-$Z_{a4}$GAGAGCACUGAGAAUACU-3', wherein, $Z_{d4}$ is the first nucleotide at 5' terminal of the antisense strand, $Z_{d3}$ is selected from A, U, G, or C, and $Z_{d4}$ is a nucleotide complementary to $Z_{d3}$; in some embodiments, $Z_{d3}$ is U, and $Z_{d4}$ is A.

Moreover, the sense strand and the antisense strand have the same or different length, wherein the sense strand has a length of 19 to 23 nucleotides, and the antisense strand has a length of 20 to 26 nucleotides.

In some embodiments, the sense strand further comprises a nucleotide sequence III, the antisense strand further comprises a nucleotide sequence IV, and the nucleotide sequence III and the nucleotide sequence IV independently of one another have a length of 1 to 4 nucleotides; the nucleotide sequence III is linked to 5' terminal of the nucleotide sequence I, the nucleotide sequence IV is linked to 3' terminal of the nucleotide sequence II; and the nucleotide sequence III and the nucleotide sequence IV have an equal length.

In some embodiments, the nucleotide sequence III and the nucleotide sequence IV both have a length of 1 nucleotide, and the base of the nucleotide sequence III is C, and the base of the nucleotide sequence IV is G; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the bases of the nucleotide sequence III is AC, and the bases of the nucleotide sequence IV is GU; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the bases of the nucleotide sequence III is GAC, and the bases of the nucleotide sequence IV is GUC; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the bases of the nucleotide sequence III is GGAC, and the bases of the nucleotide sequence IV is GUCC; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the bases of the nucleotide sequence III is AC, and the bases of the nucleotide sequence IV is GU; in this case, the length ratio of the sense strand and the antisense strand thereof is 21/21.

In some embodiments, the nucleotide sequence III and the nucleotide sequence IV have an equal length, and are completely reverse complementary. Hence, where the base(s) of nucleotide sequence III is(are) provided, the base(s) of nucleotide sequence IV is(are) also determined.

Fifth siRNA

According to the present disclosure, the siRNA may be a fifth siRNA.

The fifth siRNA comprises a sense strand and an antisense strand; each nucleotide in the fifth siRNA is independently a modified or unmodified nucleotide; wherein the sense strand comprises a nucleotide sequence I, and the antisense strand comprises a nucleotide sequence II; the nucleotide sequence I and the nucleotide sequence II are at least partly reverse complementary to form a double-stranded region; wherein, the nucleotide sequence I and the nucleotide sequence as shown by SEQ ID NO: 49 have an equal length and no more than 3 nucleotide differences, and the nucleotide sequence II and the nucleotide sequence as shown by SEQ ID NO: 50 have an equal length and no more than 3 nucleotide differences:

```
(SEQ ID NO: 49)
5'-GGACAGUAUUCUCAGUGCZe1-3';

(SEQ ID NO: 50)
5'-Ze2GCACUGAGAAUACUGUCC-3',
```

wherein, $Z_{e1}$ is A and $Z_{e2}$ is U, and the nucleotide sequence I comprises a nucleotide $Z_{e3}$ at the position corresponding to $Z_{e1}$, the nucleotide sequence II comprises a nucleotide $Z_{e4}$ at the position corresponding to $Z_{e2}$, wherein $Z_{e4}$ is the first nucleotide at 5' terminal of the antisense strand.

In some embodiments, the sense strand comprises only the nucleotide sequence I, and the antisense strand comprises only the nucleotide sequence II.

In some embodiments, the nucleotide sequence I and the nucleotide sequence as shown by SEQ ID NO: 49 have no more than 1 nucleotide difference, and/or the nucleotide sequence II and the nucleotide sequence as shown by SEQ ID NO: 50 have no more than 1 nucleotide difference.

In some embodiments, the nucleotide difference between the nucleotide sequence II and the nucleotide sequence as shown by SEQ ID NO: 50 includes a difference at the position $Z_{e4}$, wherein $Z_{e4}$ is selected from A, C or G. In some embodiments, the nucleotide difference is a difference at the position $Z_{e4}$, wherein $Z_{e4}$ is selected from A, C or G. In some embodiments, $Z_{e3}$ is a nucleotide complementary to $Z_{e4}$. These nucleotide differences will not significantly reduce the ability of the siRNA conjugates of inhibiting the target gene, and thus these siRNA conjugates comprising the nucleotide differences are within the protection scope of the present disclosure.

In some embodiments, the nucleotide sequence I and the nucleotide sequence II are basically reverse complementary, substantially reverse complementary, or completely reverse complementary to each other.

In some embodiments, the nucleotide sequence I is the nucleotide sequence as shown by SEQ ID NO: 51, and the nucleotide sequence II is the nucleotide sequence as shown by SEQ ID NO: 52:

```
(SEQ ID NO: 51)
5'-GGACAGUAUUCUCAGUGCZe3-3';

(SEQ ID NO: 52)
5'-Ze4GCACUGAGAAUACUGUCC-3',
```

wherein, $Z_{e4}$ is the first nucleotide at 5' terminal of the antisense strand, $Z_{e3}$ is selected from A, U, G, or C, and $Z_{e4}$ is a nucleotide complementary to $Z_{e3}$; in some embodiments, $Z_{e3}$ is U, and $Z_{e4}$ is A.

Moreover, the sense strand and the antisense strand have the same or different length, wherein the sense strand has a length of 19 to 23 nucleotides, and the antisense strand has a length of 20 to 26 nucleotides.

In some embodiments, the sense strand further comprises a nucleotide sequence III, the antisense strand further comprises a nucleotide sequence IV, and the nucleotide sequence III and the nucleotide sequence IV independently of one another have a length of 1 to 4 nucleotides; the nucleotide sequence III is linked to 5' terminal of the nucleotide sequence I, the nucleotide sequence IV is linked to 3' terminal of the nucleotide sequence II; and the nucleotide sequence III and the nucleotide sequence IV have an equal length.

In some embodiments, the nucleotide sequence III and the nucleotide sequence IV both have a length of 1 nucleotide, and the base of the nucleotide sequence III is G, and the base of the nucleotide sequence IV is C; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the bases of the nucleotide sequence III is AG, and the bases of the nucleotide sequence IV is CU; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the bases of the nucleotide sequence III is AAG, and the bases of the nucleotide sequence IV is CUU; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the bases of the nucleotide sequence III is AAAG, and the bases of the nucleotide sequence IV is CUUU; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the bases of the nucleotide sequence III is AG, and the bases of the nucleotide sequence IV is CU; in this case, the length ratio of the sense strand and the antisense strand thereof is 21/21.

In some embodiments, the nucleotide sequence III and the nucleotide sequence IV have an equal length, and are completely reverse complementary. Hence, where the base(s) of nucleotide sequence III is(are) provided, the base(s) of nucleotide sequence IV is(are) also determined.

Overhang Terminal and Modification of siRNA

The following description regarding the nucleotide sequence V, the nucleic acid sequence, or the nucleotide modification and the modified sequence of the siRNA is applicable to any one of the first siRNA to the fifth siRNA. Namely, unless stated otherwise, the following description of the siRNA should be regarded as the description of each of the first, second, third, fourth and fifth siRNAs. For example, if no particular siRNA is specifically indicated, "the siRNA further comprises a nucleotide sequence V" means that "the first siRNA, the second siRNA, the third siRNA, the fourth siRNA or the fifth siRNA further comprise a nucleotide sequence V".

In some embodiments, the siRNA further comprises a nucleotide sequence V. The nucleotide sequence V has a length of 1 to 3 nucleotides and is linked to 3' terminal of the antisense strand (i.e., linking to the terminal of the nucleotide sequence II or the nucleotide sequence IV), thereby forming a 3' overhang terminal of the antisense strand. In this case, the length ratio of the sense strand and the antisense strand of the siRNA may be 19/20, 19/21, 19/22, 20/21, 20/22, 20/23, 21/22, 21/23, 21/24, 22/23, 22/24, 22/25, 23/24, 23/25, or 23/26. In some embodiments, the nucleotide sequence V has a length of 2 nucleotides. Thus, the length ratio of the sense strand and the antisense strand of the siRNA of the present disclosure may be 19/21, 21/23 or 23/25.

Each nucleotide in the nucleotide sequence V may be any nucleotide. In order to facilitate the synthesis and to save synthesis cost, the nucleotide sequence V is 2 consecutive thymine deoxyribonucleotides (dTdT) or 2 consecutive uracil ribonucleotides (UU); in order to enhance the affinity between the antisense strand of the siRNA and the target mRNA, the nucleotide sequence V is complementary to the nucleotides at the corresponding positions of the target mRNA. Thus, in some embodiments, the length ratio of the sense strand and the antisense strand of the siRNA of the present disclosure is 19/21 or 21/23. In this case, the siRNA of the present disclosure exhibits better mRNA silencing activity.

The nucleotides at the corresponding positions of the target mRNA refer to the nucleotides or nucleotide sequence adjacent to 5' terminal of a segment of the nucleotide sequence of the target mRNA. This segment of the nucleotide sequence of the target mRNA refers to the segment of the nucleotide sequence which is substantially reverse complementary or completely reverse complementary with the nucleotide sequence II, or is substantially reverse complementary or completely reverse complementary with the nucleotide sequence consisted of the nucleotide sequence II and the nucleotide sequence IV.

In some embodiments, for the first siRNA, the sense strand of the siRNA comprises the nucleotide sequence as shown by SEQ ID NO: 5, and the antisense strand of the siRNA comprises the nucleotide sequence as shown by SEQ ID NO: 6:

(SEQ ID NO: 5)
5'-UUAAAAGGGACAGUAUUC$Z_{a3}$-3';

(SEQ ID NO: 6)
5'-$Z_{a4}$GAAUACUGUCCCUUUUAAGC-3';

Alternatively, the sense strand of the siRNA comprises the nucleotide sequence as shown by SEQ ID NO: 7, and the antisense strand of the siRNA comprises the nucleotide sequence as shown by SEQ ID NO: 8:

(SEQ ID NO: 7)
5'-GCUUAAAAGGGACAGUAUUC$Z_{a3}$-3';

(SEQ ID NO: 8)
5'-$Z_{a4}$GAAUACUGUCCCUUUUAAGCAA-3';

wherein, $Z_{a4}$ is the first nucleotide at 5' terminal of the antisense strand; $Z_{a3}$ is selected from A, U, G or C, and $Z_{a4}$ is a nucleotide complementary to $Z_{a3}$.

In some embodiments, for the second siRNA, the sense strand of the siRNA comprises the nucleotide sequence as shown by SEQ ID NO: 17, and the antisense strand of the siRNA comprises the nucleotide sequence as shown by SEQ ID NO: 18:

(SEQ ID NO: 17)
5'-ACAGUAUUCUCAGUGCUC$Z_{b3}$-3';

(SEQ ID NO: 18)
5'- $Z_{b4}$GAGCACUGAGAAUACUGUCC-3';

Alternatively, the sense strand of the siRNA comprises the nucleotide sequence as shown by SEQ ID NO: 19, and the antisense strand of the siRNA comprises the nucleotide sequence as shown by SEQ ID NO: 20:

(SEQ ID NO: 19)
5'-GGACAGUAUUCUCAGUGCUC$Z_{b3}$-3';

(SEQ ID NO: 20)
5'-$Z_{b4}$GAGCACUGAGAAUACUGUCCCU-3';

wherein, $Z_{b4}$ is the first nucleotide at 5' terminal of the antisense strand; $Z_{b3}$ is selected from A, U, G or C, and $Z_{b4}$ is a nucleotide complementary to $Z_{b3}$.

In some embodiments, for the third siRNA, the sense strand of the siRNA comprises the nucleotide sequence as shown by SEQ ID NO: 29, and the antisense strand of the siRNA comprises the nucleotide sequence as shown by SEQ ID NO: 30:

(SEQ ID NO: 29)
5'-UAUUCUCAGUGCUCUCCU$Z_{c3}$-3';

(SEQ ID NO: 30)
5'-$Z_{c4}$AGGAGAGCACUGAGAAUACU-3';

Alternatively, the sense strand of the siRNA comprises the nucleotide sequence as shown by SEQ ID NO: 31, and the antisense strand of the siRNA comprises the nucleotide sequence as shown by SEQ ID NO: 32:

(SEQ ID NO: 31)
5'-AGUAUUCUCAGUGCUCUCCU$Z_{c3}$-3';

(SEQ ID NO: 32)
5'-$Z_{c4}$AGGAGAGCACUGAGAAUACUGU-3';

wherein, $Z_{c4}$ is the first nucleotide at 5' terminal of the antisense strand; $Z_{c3}$ is selected from A, U, G or C, and $Z_{c4}$ is a nucleotide complementary to $Z_{c3}$.

In some embodiments, for the fourth siRNA, the sense strand of the siRNA comprises the nucleotide sequence as shown by SEQ ID NO: 41, and the antisense strand of the siRNA comprises the nucleotide sequence as shown by SEQ ID NO: 42:

(SEQ ID NO: 41)
5'-AGUAUUCUCAGUGCUCUC$Z_{a3}$-3';

(SEQ ID NO: 42)
5'-$Z_{a4}$GAGAGCACUGAGAAUACUGU-3';

Alternatively, the sense strand of the siRNA comprises the nucleotide sequence as shown by SEQ ID NO: 43, and the antisense strand of the siRNA comprises the nucleotide sequence as shown by SEQ ID NO: 44:

(SEQ ID NO: 43)
5'-ACAGUAUUCUCAGUGCUCUC$Z_{a3}$-3';

(SEQ ID NO: 44)
5'-$Z_{a4}$GAGAGCACUGAGAAUACUGUCC-3';

wherein, $Z_{d4}$ is the first nucleotide at 5' terminal of the antisense strand; $Z_{d3}$ is selected from A, U, G or C, and $Z_{d4}$ is a nucleotide complementary to $Z_{d3}$.

In some embodiments, for the fifth siRNA, the sense strand of the siRNA comprises the nucleotide sequence as shown by SEQ ID NO: 53, and the antisense strand of the siRNA comprises the nucleotide sequence as shown by SEQ ID NO: 54:

(SEQ ID NO: 53)
5'-GGACAGUAUUCUCAGUGCZ$_{e3}$-3';

(SEQ ID NO: 54)
5'-Z$_{e4}$GCACUGAGAAUACUGUCCCU-3';

Alternatively, the sense strand of the siRNA comprises the nucleotide sequence as shown by SEQ ID NO: 55, and the antisense strand of the siRNA comprises the nucleotide sequence as shown by SEQ ID NO: 56:

(SEQ ID NO: 55)
5'-AGGGACAGUAUUCUCAGUGCZ$_{e3}$-3';

(SEQ ID NO: 56)
5'-Z$_{e4}$GCACUGAGAAUACUGUCCCUUU-3';

wherein, $Z_{e4}$ is the first nucleotide at 5' terminal of the antisense strand; $Z_{e3}$ is selected from A, U, G or C, and $Z_{e4}$ is a nucleotide complementary to $Z_{e3}$.

In some embodiments, the siRNA of the present disclosure is siAPa1, siAPa2, siAPb1, siAPb2, siAPc1, siAPc2, siAPd1, siAPd2, siAPe1, or siAPe2:

siAPa1
sense strand:
(SEQ ID NO: 9)
5'-UUAAAAGGGACAGUAUUCU-3' antisense strand:
(SEQ ID NO: 10)
5'-AGAAUACUGUCCCUUUUAAGC-3' siAPa2
sense strand:
(SEQ ID NO: 11)
5'-GCUUAAAAGGGACAGUAUUCU-3' antisense strand:
(SEQ ID NO: 12)
5'-AGAAUACUGUCCCUUUUAAGCAA-3' siAPb1
sense strand:
(SEQ ID NO: 21)
5'-ACAGUAUUCUCAGUGCUCU-3' antisense strand:
(SEQ ID NO: 22)
5'-AGAGCACUGAGAAUACUGUCC-3' siAPb2
sense strand:
(SEQ ID NO: 23)
5'-GGACAGUAUUCUCAGUGCUCU-3' antisense strand:
(SEQ ID NO: 24)
5'-AGAGCACUGAGAAUACUGUCCCU-3' siAPc1
sense strand:
(SEQ ID NO: 33)
5'-UAUUCUCAGUGCUCUCCUA-3' antisense strand:
(SEQ ID NO: 34)
5'-UAGGAGAGCACUGAGAAUACU-3' siAPc2
sense strand:
(SEQ ID NO: 35)
5'-AGUAUUCUCAGUGCUCUCCUA-3'

-continued antisense strand:
(SEQ ID NO: 36)
5'-UAGGAGAGCACUGAGAAUACUGU-3' siAPd1
sense strand:
(SEQ ID NO: 45)
5'-AGUAUUCUCAGUGCUCUCC-3' antisense strand:
(SEQ ID NO: 46)
5'-GGAGAGCACUGAGAAUACUGU-3' siAPd2
sense strand:
(SEQ ID NO: 47)
5'-ACAGUAUUCUCAGUGCUCUCC-3' antisense strand:
(SEQ ID NO: 48)
5'-GGAGAGCACUGAGAAUACUGUCC-3' siAPe1
sense strand:
(SEQ ID NO: 57)
5'-GGACAGUAUUCUCAGUGCU-3' antisense strand:
(SEQ ID NO: 58)
5'-AGCACUGAGAAUACUGUCCCU-3' siAPe2
sense strand:
(SEQ ID NO: 59)
5'-AGGGACAGUAUUCUCAGUGCU-3' antisense strand:
(SEQ ID NO: 60)
5'-AGCACUGAGAAUACUGUCCCUUU-3'.

In some embodiments, the siRNA has the nucleotide sequence (i.e., nucleic acid or base sequence) as shown by siAPa1, siAPa2, siAPb1, siAPb2, siAPc1, siAPc2, siAPd1, siAPd2, siAPe1, or siAPe2.

As mentioned above, in the siRNA of the present disclosure, each nucleotide is independently a modified or unmodified nucleotide. In some embodiments, the nucleotide in the siRNA of the present disclosure is an unmodified nucleotide; in some embodiments, in the siRNA of the present disclosure, some or all of the nucleotides are modified nucleotides. These modifications on the nucleotide groups would not lead to significant decrease or loss of the functions for inhibiting the expression of APOC3 gene of the siRNA conjugate of the present disclosure.

In some embodiments, the siRNA of the present disclosure comprises at least 1 modified nucleotide. In the context of the present disclosure, the term "modified nucleotide" used refers to a nucleotide formed by substituting 2'-hydroxy of the ribose group with other groups, or nucleotide analogue, or a nucleotide of which the base is a modified base. The modified nucleotide would not lead to significant impairment or loss of the functions for inhibiting gene expression of the siRNA conjugate. For example, the modified nucleotides disclosed in Watts, J. K., G. F. Deleavey and M. J. Damha, Chemically Modified siRNA: tools and applications. Drug Discov Today, 2008.13(19-20): p. 842-55 may be selected.

In some embodiments, at least one nucleotide in the sense strand or the antisense strand of the siRNA of the present disclosure is a modified nucleotide, and/or at least one phosphate group is a phosphate group with modified group (s). In other words, at least a portion of the phosphate and/or ribose groups in the phosphate-ribose backbone of at least one single strand in the sense strand and the antisense strand are phosphate groups with modified groups and/or ribose groups with modified groups.

In some embodiments, all the nucleotides in the sense strand and/or the antisense strand are modified nucleotides. In some embodiments, each nucleotide in the sense strand and antisense strand of the siRNA of the present disclosure is independently a fluoro modified nucleotide or a non-fluoro modified nucleotide.

The inventors of the present disclosure surprisingly found that the siRNA of the present disclosure achieves high balance between plasma stability and gene silencing efficiency in animal experiments.

In some embodiments, the fluoro modified nucleotides are located in the nucleotide sequence I and the nucleotide sequence II; and in the direction from 5' terminal to 3' terminal, the nucleotides at positions 7, 8 and 9 of the nucleotide sequence I are fluoro modified nucleotides; and in the direction from 5'terminal to 3' terminal, the nucleotides at positions 2, 6, 14, and 16 of the nucleotide sequence II are fluoro modified nucleotides.

In some embodiments, the fluoro modified nucleotides are located in the nucleotide sequence I and the nucleotide sequence II; and the nucleotide sequence I comprises no more than 5 fluoro modified nucleotides; and in the direction from 5' terminal to 3' terminal, the nucleotides at positions 7, 8 and 9 of the nucleotide sequence I are fluoro modified nucleotides; the nucleotide sequence II comprises no more than 7 fluoro modified nucleotides; and the nucleotides at positions 2, 6, 14, and 16 of the nucleotide sequence II are fluoro modified nucleotides.

In some embodiments, in the direction from 5' terminal to 3' terminal, the nucleotides at positions 7, 8 and 9 or at positions 5, 7, 8 and 9 of the nucleotide sequence I in the sense strand are fluoro modified nucleotides, and the nucleotides at the other positions in the sense strand are non-fluoro modified nucleotides; in the direction from 5' terminal to 3' terminal, the nucleotides at positions 2, 6, 14, and 16 or at positions 2, 6, 8, 9, 14, and 16 of the nucleotide sequence II in the antisense strand are fluoro modified nucleotides, and the nucleotides at the other positions in the antisense strand are non-fluoro modified nucleotides.

In the context of the present disclosure, a "fluoro modified nucleotide" refers to a nucleotide formed by substituting 2'-hydroxy of the ribose group with a fluorine atom, which has a structure as shown by the following Formula (7). A "non-fluoro modified nucleotide" refers to a nucleotide formed by substituting 2'-hydroxy of the ribose group with a non-fluoro group, or a nucleotide analogue. In some embodiments, each non-fluoro modified nucleotide is independently selected from a nucleotide formed by substituting 2'-hydroxy of the ribose group thereof with a non-fluoro group, or a nucleotide analogue.

The nucleotides formed by replacing 2'-hydroxy of the ribose group with a non-fluoro group are well-known in the art, and can be one selected from the group consisting of 2'-alkoxy modified nucleotides, 2'-substituted alkoxy modified nucleotides, 2'-alkyl modified nucleotides, 2'-substituted alkyl modified nucleotides, 2'-amino modified nucleotides, 2'-substituted amino modified nucleotides, and 2'-deoxy nucleotides.

In some embodiments, the 2'-alkoxy modified nucleotide is a 2'-methoxy (2'-OMe) modified nucleotide, as shown by Formula (8). In some embodiments, the 2'-substituted alkoxy modified nucleotide is for example a 2'-O-methoxyethyl (2'-MOE) modified nucleotide, as shown by Formula (9). In some embodiments, the 2'-amino (2'-$NH_2$) modified nucleotide is as shown by Formula (10). In some embodiments, the 2'-deoxy nucleotide (DNA) is as shown by Formula (11).

Formula (7)

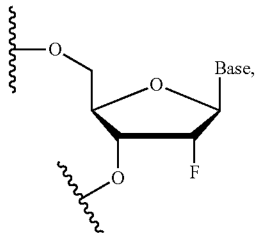

Formula (8)

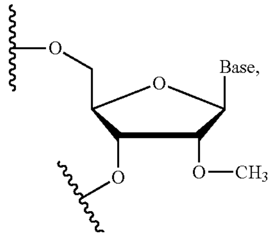

Formula (9)

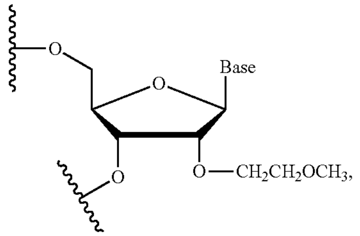

Formula (10)

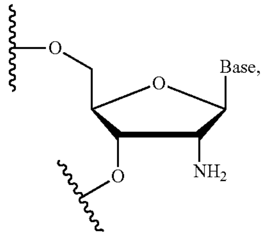

Formula (11)

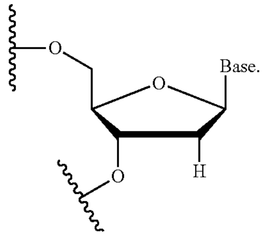

A nucleotide analogue refers to a group that can replace a nucleotide in a nucleic acid, while structurally differs from an adenine ribonucleotide, a guanine ribonucleotide, a cytosine ribonucleotide, a uracil ribonucleotide, or thymine deoxyribonucleotide. In some embodiments, the nucleotide analogue may be an isonucleotide, a bridged nucleotide or an acyclic nucleotide.

A BNA nucleotide (bridged nucleic acid, BNA) is a nucleotide that is constrained or inaccessible. BNA can contain a 5-, 6-membered or a 7-membered ring bridged structure with a "fixed" C3'-endo sugar puckering. The bridge is typically incorporated at the 2'- and 4'-positions of the ribose to afford a 2', 4'-BNA nucleotide. In some embodiments, BNA may be LNA, ENA, cET BNA and so on, which are shown by Formulae (12), (13) and (14), respectively.

Formula (112)

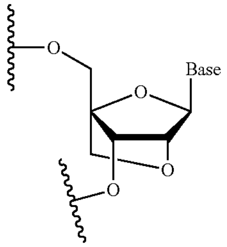

Formula (113)

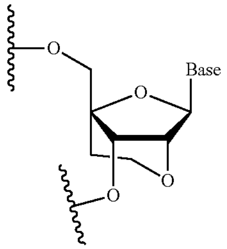

Formula (114)

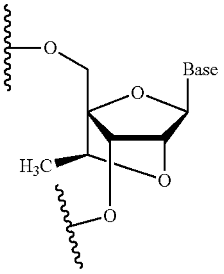

An acyclic nucleotide refers to a class of nucleotides in which the sugar ring is opened. In some embodiments, the acrylic nucleotide is an unlocked nucleic acid (UNA) or a glycerol nucleic acid (GNA), which are as shown by Formulae (15) and (16), respectively.

Formula (115)

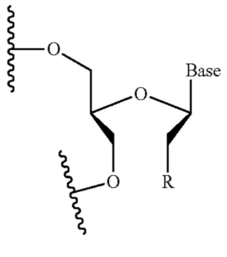

Formula (116)

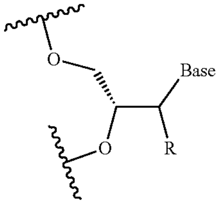

In the above Formulae (15) and (16), R is selected from H, OH or alkoxy (O-alkyl).

An isonucleotide is a compound formed by changing the position of the base on the ribose ring in the nucleotide. In some embodiments, the isonucleotide is a compound formed by transposing the base from 1-position to 2'-position or 3'-position on the ribose ring, as shown by Formula (17) or (18), respectively.

Formula (17)

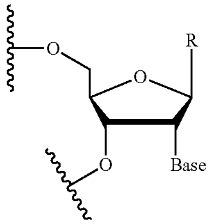

Formula (18)

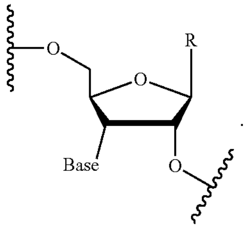

In the above compounds of Formulae (17)-(18), "Base" represents a base of a nucleic acid, such as A, U, G, C, or T; R is selected from H, OH, F, or the above non-fluoro group.

In some embodiments, a nucleotide analogue is one selected from the group consisting of isonucleotide, LNA, ENA, cET, UNA, and GNA. In some embodiments, each non-fluoro modified nucleotide is a methoxy modified nucleotide. In the context of the present disclosure, the methoxy modified nucleotide refers to a nucleotide formed by substituting 2'-hydroxy of the ribose group with a methoxy group.

In the context of the disclosure, a "fluoro modified nucleotide", a "2'-fluoro modified nucleotide", a "nucleotide in which 2'-hydroxy of a ribose group is substituted with a fluorine atom", and a "nucleotide with 2'-fluororibosyl" have the same meaning, referring to a compound in which 2'-hydroxy of the nucleotide is substituted with a flurorin atom, which has a structure as shown by Formula (7). A "methoxy modified nucleotide", a "2'-methoxy modified nucleotide", a "nucleotide in which 2'-hydroxy of a ribose group is substituted with a methoxy" and a "nucleotide with 2'-methoxyribosyl" have the same meaning, referring to a compound in which 2'-hydroxy of the ribose group in the nucleotide is substituted with a methoxy, which has a structure as shown by Formula (8).

In some embodiments, the siRNA of the present disclosure is a siRNA with the following modifications: in the direction from 5' terminal to 3' terminal, the nucleotides at positions 7, 8 and 9 or at positions 5, 7, 8 and 9 of the nucleotide sequence I in the sense strand are fluoro modified nucleotides, and the nucleotides at the other positions in the sense strand are methoxy modified nucleotides; the nucleotides at positions 2, 6, 14, and 16 or at positions 2, 6, 8, 9, 14, and 16 of the nucleotide sequence II in the antisense strand are fluoro modified nucleotides, and the nucleotides at the other positions in the antisense strand are methoxy modified nucleotides.

In some embodiments, the siRNA of the present disclosure is a siRNA with the following modifications: in the direction from 5' terminal to 3' terminal, the nucleotides at positions 5, 7, 8, and 9 of the nucleotide sequence I in the sense strand of the siRNA are fluoro modified nucleotides, and the nucleotides at the other positions of the sense strand of the siRNA are methoxy modified nucleotides; and in the direction from 5' terminal to 3' terminal, the nucleotides at positions 2, 6, 8, 9, 14, and 16 of the nucleotide sequence II in the antisense strand of the siRNA are fluoro modified nucleotides, and the nucleotides at the other positions in the antisense strand of the siRNA are methoxy modified nucleotides;

Alternatively, in the direction from 5' terminal to 3' terminal, the nucleotides at positions 5, 7, 8, and 9 of the nucleotide sequence I in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14, and 16 of the nucleotide sequence II in the antisense strand of the siRNA are fluoro modified nucleotides, and the nucleotides at the other positions in the antisense strand of the siRNA are methoxy modified nucleotides.

Alternatively, in the direction from 5' terminal to 3' terminal, the nucleotides at positions 7, 8 and 9 of the nucleotide sequence I in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14, and 16 of the nucleotide sequence II in the antisense strand of the siRNA are fluoro modified nucleotides, and the nucleotides at the other positions in the antisense strand of the siRNA are methoxy modified nucleotides.

In some embodiments, the siRNA of the present disclosure is any one of siAPa1-M1, siAPa2-M1, siAPa1-M2, siAPa2-M2, siAPa1-M3, siAPa2-M3, siAPb1-M1, siAPb2-M1, siAPb1-M2, siAPb2-M2, siAPb1-M3, siAPb2-M3, siAPc1-M1, siAPc2-M1, siAPc1-M2, siAPc2-M2, siAPc1-M3, siAPc2-M3, siAPd1-M1, siAPd2-M1, siAPd1-M2, siAPd2-M2, siAPd1-M3, siAPd2-M3, siAPe1-M1, siAPe2-M1, siAPe1-M2, siAPe2-M2, siAPe1-M3, or siAPe2-M3:

```
siAPa1-M1
sense strand:
                                                  (SEQ ID NO: 61)
5'-UmUmAmAmAfAmGfGfGfAmCmAmGmUmAmUmUmCmUm-3'

antisense strand:
                                                  (SEQ ID NO: 62)
5'-AmGfAmAmUmAfCmUfGfUmCmCmCmUfUmUfUmAmAmGmCm-3'

siAPa2-M1
sense strand:
                                                  (SEQ ID NO: 63)
5'-GmCmUmUmAmAmAfAmGfGfGfAmCmAmGmUmAmUmUmCmUm-3'

antisense strand:
                                                  (SEQ ID NO: 64)
5'-AmGfAmAmUmAfCmUfGfUmCmCmCmUfUmUfUmAmAmGmCmAmAm-3'

siAPa1-M2
sense strand:
                                                  (SEQ ID NO: 65)
5'-UmUmAmAmAfAmGfGfGfAmCmAmGmUmAmUmUmCmUm-3'

antisense strand:
                                                  (SEQ ID NO: 66)
5'-AmGfAmAmUmAfCmUmGmUmCmCmCmUfUmUfUmAmAmGmCm-3'

siAPa2-M2
sense strand:
                                                  (SEQ ID NO: 67)
5'-GmCmUmUmAmAmAfAmGfGfGfAmCmAmGmUmAmUmUmCmUm-3'

antisense strand:
                                                  (SEQ ID NO: 68)
5'-AmGfAmAmUmAfCmUmGmUmCmCmCmUfUmUfUmAmAmGmCmAmAm-3'

siAPa1-M3
sense strand:
                                                  (SEQ ID NO: 69)
5'-UmUmAmAmAmAmGfGfGfAmCmAmGmUmAmUmUmCmUm-3'

antisense strand:
                                                  (SEQ ID NO: 70)
5'-AmGfAmAmUmAfCmUmGmUmCmCmCmUfUmUfUmAmAmGmCm-3'

siAPa2-M3
sense strand:
                                                  (SEQ ID NO: 71)
5'-GmCmUmUmAmAmAmAmGfGfGfAmCmAmGmUmAmUmUmCmUm-3'

antisense strand:
                                                  (SEQ ID NO: 72)
5'-AmGfAmAmUmAfCmUmGmUmCmCmCmUfUmUfUmAmAmGmCmAmAm-3'
```

-continued siAPb1-M1
sense strand:
(SEQ ID NO: 73)
5'-AmCmAmGmUfAmUfUfCfUmCmAmGmUmGmCmUmCmUm-3' antisense strand:
(SEQ ID NO: 74)
5'-AmGfAmGmCmAfCmUfGfAmGmAmAmUfAmCfUmGmUmCmCm-3' siAPb2-M1
sense strand:
(SEQ ID NO: 75)
5'-GmGmAmCmAmGmUfAmUfUfCfUmCmAmGmUmGmCmUmCmUm-3' antisense strand:
(SEQ ID NO: 76)
5'-AmGfAmGmCmAfCmUfGfAmGmAmAmUfAmCfUmGmUmCmCmCmUm-3' siAPb1-M2
sense strand:
(SEQ ID NO: 77)
5'-AmCmAmGmUfAmUfUfCfUmCmAmGmUmGmCmUmCmUm-3' antisense strand:
(SEQ ID NO: 78)
5'-AmGfAmGmCmAfCmUmGmAmGmAmAmUfAmCfUmGmUmCmCm-3' siAPb2-M2
sense strand:
(SEQ ID NO: 79)
5'-GmGmAmCmAmGmUfAmUfUfCfUmCmAmGmUmGmCmUmCmUm-3' antisense strand:
(SEQ ID NO: 80)
5'-AmGfAmGmCmAfCmUmGmAmGmAmAmUfAmCfUmGmUmCmCmCmUm-3' siAPb1-M3
sense strand:
(SEQ ID NO: 81)
5'-AmCmAmGmUmAmUfUfCfUmCmAmGmUmGmCmUmCmUm-3' antisense strand:
(SEQ ID NO: 82)
5'-AmGfAmGmCmAfCmUmGmAmGmAmAmUfAmCfUmGmUmCmCm-3' siAPb2-M3
sense strand:
(SEQ ID NO: 83)
5'-GmGmAmCmAmGmUmAmUfUfCfUmCmAmGmUmGmCmUmCmUm-3' antisense strand:
(SEQ ID NO: 84)
5'-AmGfAmGmCmAfCmUmGmAmGmAmAmUfAmCfUmGmUmCmCmCmUm-3' siAPc1-M1
sense strand:
(SEQ ID NO: 85)
5'-UmAmUmUmCfUmCfAfGfUmGmCmUmCmUmCmCmUmAm-3' antisense strand:
(SEQ ID NO: 86)
5'-UmAfGmGmAmGfAmGfCfAmCmUmGmAfGmAfAmUmAmCmUm-3' siAPc2-M1
sense strand:
(SEQ ID NO: 87)
5'-AmGmUmAmUmUmCfUmCfAfGfUmGmCmUmCmUmCmCmUmAm-3' antisense strand:
(SEQ ID NO: 88)
5'-UmAfGmGmAmGfAmGfCfAmCmUmGmAfGmAfAmUmAmCmUmGmUm-3' siAPc1-M2
sense strand:
(SEQ ID NO: 89)
5'-UmAmUmUmCfUmCfAfGfUmGmCmUmCmUmCmCmUmAm-3' antisense strand:
(SEQ ID NO: 90)
5'-UmAfGmGmAmGfAmGmCmAmCmUmGmAfGmAfAmUmAmCmUm-3'

-continued siAPc2-M2
sense strand:
(SEQ ID NO: 91)
5'-AmGmUmAmUmUmCfUmCfAfGfUmGmCmUmCmUmCmCmUmAm-3' antisense strand:
(SEQ ID NO: 92)
5'-UmAfGmGmAmGfAmGmCmAmCmUmGmAfGmAfAmUmAmCmUmGmUm-3' siAPc1-M3
sense strand:
(SEQ ID NO: 93)
5'-UmAmUmUmCmUmCfAfGfUmGmCmUmCmUmCmCmUmAm-3' antisense strand:
(SEQ ID NO: 94)
5'-UmAfGmGmAmGfAmGmCmAmCmUmGmAfGmAfAmUmAmCmUm-3' siAPc2-M3
sense strand:
(SEQ ID NO: 95)
5'-AmGmUmAmUmUmCmUmCfAfGfUmGmCmUmCmUmCmCmUmAm-3' antisense strand:
(SEQ ID NO: 96)
5'-UmAfGmGmAmGfAmGmCmAmCmUmGmAfGmAfAmUmAmCmUmGmUm-3' siAPd1-M1
sense strand:
(SEQ ID NO: 97)
5'-AmGmUmAmUfUmCfUfCfAmGmUmGmCmUmCmUmCmCm-3' antisense strand:
(SEQ ID NO: 98)
5'-GmGfAmGmAmGfCmAfCfUmGmAmGmAfAmUfAmCmUmGmUm-3' siAPd2-M1
sense strand:
(SEQ ID NO: 99)
5'-AmCmAmGmUmAmUfUmCfUfCfAmGmUmGmCmUmCmUmCmCm-3' antisense strand:
(SEQ ID NO: 100)
5'-GmGfAmGmAmGfCmAfCfUmGmAmGmAfAmUfAmCmUmGmUmCmCm-3' siAPd1-M2
sense strand:
(SEQ ID NO: 101)
5'-AmGmUmAmUfUmCfUfCfAmGmUmGmCmUmCmUmCmCm-3' antisense strand:
(SEQ ID NO: 102)
5'-GmGfAmGmAmGfCmAmCmUmGmAmGmAfAmUfAmCmUmGmUm-3' siAPd2-M2
sense strand:
(SEQ ID NO: 103)
5'-AmCmAmGmUmAmUfUmCfUfCfAmGmUmGmCmUmCmUmCmCm-3' antisense strand:
(SEQ ID NO: 104)
5'-GmGfAmGmAmGfCmAmCmUmGmAmGmAfAmUfAmCmUmGmUmCmCm-3' siAPd1-M3
sense strand:
(SEQ ID NO: 105)
5'-AmGmUmAmUmUmCfUfCfAmGmUmGmCmUmCmUmCmCm-3' antisense strand:
(SEQ ID NO: 106)
5'-GmGfAmGmAmGfCmAmCmUmGmAmGmAfAmUfAmCmUmGmUm-3' siAPd2-M3
sense strand:
(SEQ ID NO: 107)
5'-AmCmAmGmUmAmUmUmCfUfCfAmGmUmGmCmUmCmUmCmCm-3' antisense strand:
(SEQ ID NO: 108)
5'-GmGfAmGmAmGfCmAmCmUmGmAmGmAfAmUfAmCmUmGmUmCmCm-3'

-continued

```
siAPe1-M1
sense strand:
                                      (SEQ ID NO: 109)
5'-GmGmAmCmAfGmUfAfUfUmCmUmCmAmGmUmGmCmUm-3'

antisense strand:
                                      (SEQ ID NO: 110)
5'-AmGfCmAmCmUfGmAfGfAmAmUmAmCfUmGfUmCmCmCmUm-3'

siAPe2-M1
sense strand:
                                      (SEQ ID NO: 111)
5'-AmGmGmGmAmCmAfGmUfAfUfUmCmUmCmAmGmUmGmCmUm-3'

antisense strand:
                                      (SEQ ID NO: 112)
5'-AmGfCmAmCmUfGmAfGfAmAmUmAmCfUmGfUmCmCmCmUmUmUm-3'

siAPe1-M2
sense strand:
                                      (SEQ ID NO: 113)
5'-GmGmAmCmAfGmUfAfUfUmCmUmCmAmGmUmGmCmUm-3'

antisense strand:
                                      (SEQ ID NO: 114)
5'-AmGfCmAmCmUfGmAmGmAmAmUmAmCfUmGfUmCmCmCmUm-3'

siAPe2-M2
sense strand:
                                      (SEQ ID NO: 115)
5'-AmGmGmGmAmCmAfGmUfAfUfUmCmUmCmAmGmUmGmCmUm-3'

antisense strand:
                                      (SEQ ID NO: 116)
5'-AmGfCmAmCmUfGmAmGmAmAmUmAmCfUmGfUmCmCmCmUmUmUm-3'

siAPe1-M3
sense strand:
                                      (SEQ ID NO: 117)
5'-GmGmAmCmAmGmUfAfUfUmCmUmCmAmGmUmGmCmUm-3'

antisense strand:
                                      (SEQ ID NO: 118)
5'-AmGfCmAmCmUfGmAmGmAmAmUmAmCfUmGfUmCmCmCmUm-3'

siAPe2-M3
sense strand:
                                      (SEQ ID NO: 119)
5'-AmGmGmGmAmCmAmGmUfAfUfUmCmUmCmAmGmUmGmCmUm-3'

antisense strand:
                                      (SEQ ID NO: 120)
5'-AmGfCmAmCmUfGmAmGmAmAmUmAmCfUmGfUmCmCmCmUmUmUm-3'
```

The siRNAs with the above modifications not only have lower costs, but also cause that the ribonucleases in the blood cannot easily cleave the nucleic acid, thereby increasing the stability of the nucleic acid and rendering the nucleic acid to have stronger resistance against nuclease hydrolysis.

In some embodiments, at least a portion of the phosphate groups in the phosphate-ribose backbone of at least one single strand in the sense strand and the antisense strand of the siRNA of the present disclosure are phosphate groups with modified groups. In some embodiments, the phosphate group with modified group(s) is a phosphorothioate group formed by substituting at least one oxygen atom in a phosphodiester bond in a phosphate groups with a sulfur atom. In some embodiments, the phosphate group with modified group(s) is a phosphorothioate group having a structure as shown by Formula (1):

Formula (1)

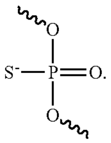

This modification stabilizes the double-stranded structure of the siRNA, thereby maintaining high specificity and high affinity of base pairing.

In some embodiments, in the siRNA of the present disclosure, the phosphorothioate linkage is located in at least one of the group consisting of the following positions: the position between the first and the second nucleotides at either terminal of the sense or antisense strand, the position between the second and the third nucleotides at either terminal of the sense or antisense strand, or any combination thereof. In some embodiments, the phosphorothioate linkage is located in all the above positions except 5' terminal of the sense strand. In some embodiments, the phosphorothioate linkage is located in all the above positions except 3' terminal of the sense strand. In some embodiments, the phosphorothioate linkage is located in at least one of the following positions:

- the position between the first and second nucleotides at 5' terminal of the sense strand;
- the position between the second and third nucleotides at 5' terminal of the sense strand;
- the position between the first and second nucleotides at 3' terminal of the sense strand;
- the position between the second and third nucleotides at 3' terminal of the sense strand;
- the position between the first and second nucleotides at 5' terminal of the antisense strand;
- the position between the second and third nucleotides at 5' terminal of the antisense strand;
- the position between the first and second nucleotides at 3' terminal of the antisense strand; and
- the position between the second and third nucleotides at 3' terminal of the antisense strand.

In some embodiments, the siRNA of the present disclosure is siAPa1-M1S, siAPa2-M1S, siAPa1-M2S, siAPa2-M2S, siAPa1-M3S, siAPa2-M3S, siAPb1-M1S, siAPb2-M1S, siAPb1-M2S, siAPb2-M2S, siAPb1-M3S, siAPb2-M3S, siAPc1-M1S, siAPc2-M1S, siAPc1-M2S, siAPc2-M2S, siAPc1-M3S, siAPc2-M3S, siAPd1-M1S, siAPd2-M1S, siAPd1-M2S, siAPd2-M2S, siAPd1-M3S, siAPd2-M3S, siAPe1-M1S, siAPe2-M1S, siAPe1-M2S, siAPe2-M2S, siAPe1-M3S, and siAPe2-M3S.

```
siAPa1-M1S
sense strand:
                                          (SEQ ID NO: 121)
5'-UmsUmsAmAmAfAmGfGfGfAmCmAmGmUmAmUmUmCmUm-3'

antisense strand:
                                          (SEQ ID NO: 122)
5'-AmsGfsAmAmUmAfCmUfGfUmCmCmCmUfUmUfUmAmAmsGmsCm-3'

siAPa2-M1S
sense strand:
                                          (SEQ ID NO: 123)
5'-GmsCmsUmUmAmAmAfAmGfGfGfAmCmAmGmUmAmUmUmCmUm-3'

antisense strand:
                                          (SEQ ID NO: 124)
5'-AmsGfsAmAmUmAfCmUfGfUmCmCmCmUfUmUfUmAmAmGmCmsAmsAm-3'

siAPa1-M2S
sense strand:
                                          (SEQ ID NO: 125)
5'-UmsUmsAmAmAfAmGfGfGfAmCmAmGmUmAmUmUmCmUm-3'

antisense strand:
                                          (SEQ ID NO: 126)
5'-AmsGfsAmAmUmAfCmUmGmUmCmCmCmUfUmUfUmAmAmsGmsCm-3'

siAPa2-M2S
sense strand:
                                          (SEQ ID NO: 127)
5'-GmsCmsUmUmAmAmAfAmGfGfGfAmCmAmGmUmAmUmUmCmUm-3'

antisense strand:
                                          (SEQ ID NO: 128)
5'-AmsGfsAmAmUmAfCmUmGmUmCmCmCmUfUmUfUmAmAmGmCmsAmsAm-3'

siAPa1-M3S
sense strand:
                                          (SEQ ID NO: 129)
5'-UmsUmsAmAmAmAmGfGfGfAmCmAmGmUmAmUmUmCmUm-3'

antisense strand:
                                          (SEQ ID NO: 130)
5'-AmsGfsAmAmUmAfCmUmGmUmCmCmCmUfUmUfUmAmAmsGmsCm-3'

siAPa2-M3S
sense strand:
                                          (SEQ ID NO: 131)
5'-GmsCmsUmUmAmAmAmAmGfGfGfAmCmAmGmUmAmUmUmCmUm-3'

antisense strand:
                                          (SEQ ID NO: 132)
5'-AmsGfsAmAmUmAfCmUmGmUmCmCmCmUfUmUfUmAmAmGmCmsAmsAm-3'

siAPb1-M1S
sense strand:
                                          (SEQ ID NO: 133)
5'-AmsCmsAmGmUfAmUfUfCfUmCmAmGmUmGmCmUmCmUm-3'

antisense strand:
                                          (SEQ ID NO: 134)
5'-AmsGfsAmGmCmAfCmUfGfAmGmAmAmUfAmCfUmGmUmsCmsCm-3'
```

-continued siAPb2-M1S
sense strand:
(SEQ ID NO: 135)
5'-GmsGmsAmCmAmGmUfAmUfUfCfUmCmAmGmUmGmCmUmCmUm-3' antisense strand:
(SEQ ID NO: 136)
5'-AmsGfsAmGmCmAfCmUfGfAmGmAmAmUfAmCfUmGmUmCmCmsCmsUm-3' siAPb1-M2S
sense strand:
(SEQ ID NO: 137)
5'-AmsCmsAmGmUfAmUfUfCfUmCmAmGmUmGmCmUmCmUm-3' antisense strand:
(SEQ ID NO: 138)
5'-AmsGfsAmGmCmAfCmUmGmAmGmAmAmUfAmCfUmGmUmsCmsCm-3' siAPb2-M2S
sense strand:
(SEQ ID NO: 139)
5'-GmsGmsAmCmAmGmUfAmUfUfCfUmCmAmGmUmGmCmUmCmUm-3' antisense strand:
(SEQ ID NO: 140)
5'-AmsGfsAmGmCmAfCmUmGmAmGmAmAmUfAmCfUmGmUmCmCmsCmsUm-3' siAPb1-M3S
sense strand:
(SEQ ID NO: 141)
5'-AmsCmsAmGmUmAmUfUfCfUmCmAmGmUmGmCmUmCmUm-3' antisense strand:
(SEQ ID NO: 142)
5'-AmsGfsAmGmCmAfCmUmGmAmGmAmAmUfAmCfUmGmUmsCmsCm-3' siAPb2-M3S
sense strand:
(SEQ ID NO: 143)
5'-GmsGmsAmCmAmGmUmAmUfUfCfUmCmAmGmUmGmCmUmCmUm-3' antisense strand:
(SEQ ID NO: 144)
5'-AmsGfsAmGmCmAfCmUmGmAmGmAmAmUfAmCfUmGmUmCmCmsCmsUm-3' siAPc1-M1S
sense strand:
(SEQ ID NO: 145)
5'-UmsAmsUmUmCfUmCfAfGfUmGmCmUmCmUmCmCmUmAm-3' antisense strand:
(SEQ ID NO: 146)
5'-UmsAfsGmGmAmGfAmGfCfAmCmUmGmAfGmAfAmUmAmsCmsUm-3' siAPc2-M1S
sense strand:
(SEQ ID NO: 147)
5'-AmsGmsUmAmUmUmCfUmCfAfGfUmGmCmUmCmUmCmCmUmAm-3' antisense strand:
(SEQ ID NO: 148)
5'-UmsAfsGmGmAmGfAmGfCfAmCmUmGmAfGmAfAmUmAmCmUmsGmsUm-3' siAPc1-M2S
sense strand:
(SEQ ID NO: 149)
5'-UmsAmsUmUmCfUmCfAfGfUmGmCmUmCmUmCmCmUmAm-3' antisense strand:
(SEQ ID NO: 150)
5'-UmsAfsGmGmAmGfAmGmCmAmCmUmGmAfGmAfAmUmAmsCmsUm-3' siAPc2-M2S
sense strand:
(SEQ ID NO: 151)
5'-AmsGmsUmAmUmUmCfUmCfAfGfUmGmCmUmCmUmCmCmUmAm-3' antisense strand:
(SEQ ID NO: 152)
5'-UmsAfsGmGmAmGfAmGmCmAmCmUmGmAfGmAfAmUmAmCmUmsGmsUm-3'

-continued siAPc1-M3S
sense strand:
(SEQ ID NO: 153)
5'-UmsAmsUmUmCmUmCfAfGfUmGmCmUmCmUmCmCmUmAm-3' antisense strand:
(SEQ ID NO: 154)
5'-UmsAfsGmGmAmGfAmGmCmAmCmUmGmAfGmAfAmUmAmsCmsUm-3' siAPc2-M3S
sense strand:
(SEQ ID NO: 155)
5'-AmsGmsUmAmUmUmCmUmCfAfGfUmGmCmUmCmUmCmCmUmAm-3' antisense strand:
(SEQ ID NO: 156)
5'-UmsAfsGmGmAmGfAmGmCmAmCmUmGmAfGmAfAmUmAmCmUmsGmsUm-3' siAPd1-M1S
sense strand:
(SEQ ID NO: 157)
5'-AmsGmsUmAmUfUmCfUfCfAmGmUmGmCmUmCmUmCmCm-3' antisense strand:
(SEQ ID NO: 158)
5'-GmsGfsAmGmAmGfCmAfCfUmGmAmGmAfAmUfAmCmUmsGmsUm-3' siAPd2-M1S
sense strand:
(SEQ ID NO: 159)
5'-AmsCmsAmGmUmAmUfUmCfUfCfAmGmUmGmCmUmCmUmCmCm-3' antisense strand:
(SEQ ID NO: 160)
5'-GmsGfsAmGmAmGfCmAfCfUmGmAmGmAfAmUfAmCmUmGmUmsCmsCm-3' siAPd1-M2S
sense strand:
(SEQ ID NO: 161)
5'-AmsGmsUmAmUfUmCfUfCfAmGmUmGmCmUmCmUmCmCm-3' antisense strand:
(SEQ ID NO: 162)
5'-GmsGfsAmGmAmGfCmAmCmUmGmAmGmAfAmUfAmCmUmsGmsUm-3' siAPd2-M2S
sense strand:
(SEQ ID NO: 163)
5'-AmsCmsAmGmUmAmUfUmCfUfCfAmGmUmGmCmUmCmUmCmCm-3' antisense strand:
(SEQ ID NO: 164)
5'-GmsGfsAmGmAmGfCmAmCmUmGmAmGmAfAmUfAmCmUmGmUmsCmsCm-3' siAPd1-M3S
sense strand:
(SEQ ID NO: 165)
5'-AmsGmsUmAmUmUmCfUfCfAmGmUmGmCmUmCmUmCmCm-3' antisense strand:
(SEQ ID NO: 166)
5'-GmsGfsAmGmAmGfCmAmCmUmGmAmGmAfAmUfAmCmUmsGmsUm-3' siAPd2-M3S
sense strand:
(SEQ ID NO: 167)
5'-AmsCmsAmGmUmAmUmUmCfUfCfAmGmUmGmCmUmCmUmCmCm-3' antisense strand:
(SEQ ID NO: 168)
5'-GmsGfsAmGmAmGfCmAmCmUmGmAmGmAfAmUfAmCmUmGmUmsCmsCm-3' siAPe1-M1S
sense strand:
(SEQ ID NO: 169)
5'-GmsGmsAmCmAfGmUfAfUfUmCmUmCmAmGmUmGmCmUm-3' antisense strand:
(SEQ ID NO: 170)
5'-AmsGfsCmAmCmUfGmAfGfAmAmUmAmCfUmGfUmCmCmsCmsUm-3'

-continued siAPe2-M1S
sense strand:
(SEQ ID NO: 171)
5'-AmsGmsGmGmAmCmAfGmUfAfUfUmCmUmCmAmGmUmGmCmUm-3';

antisense strand:
(SEQ ID NO: 172)
5'-AmsGfsCmAmCmUfGmAfGfAmAmUmAmCfUmGfUmCmCmCmUmsUmsUm-3' siAPe1-M2S
sense strand:
(SEQ ID NO: 173)
5'-GmsGmsAmCmAfGmUfAfUfUmCmUmCmAmGmUmGmCmUm-3' antisense strand:
(SEQ ID NO: 174)
5'-AmsGfsCmAmCmUfGmAmGmAmAmUmAmCfUmGfUmCmCmsCmsUm-3' siAPe2-M2S
sense strand:
(SEQ ID NO: 175)
5'-AmsGmsGmGmAmCmAfGmUfAfUfUmCmUmCmAmGmUmGmCmUm-3' antisense strand:
(SEQ ID NO: 176)
5'-AmsGfsCmAmCmUfGmAmGmAmAmUmAmCfUmGfUmCmCmCmUmsUmsUm-3' siAPe1-M3S
sense strand:
(SEQ ID NO: 177)
5'-GmsGmsAmCmAmGmUfAfUfUmCmUmCmAmGmUmGmCmUm-3' antisense strand:
(SEQ ID NO: 178)
5'-AmsGfsCmAmCmUfGmAmGmAmAmUmAmCfUmGfUmCmCmsCmsUm-3' siAPe2-M3S
sense strand:
(SEQ ID NO: 179)
5'-AmsGmsGmGmAmCmAmGmUfAfUfUmCmUmCmAmGmUmGmCmUm-3' antisense strand:
(SEQ ID NO: 180)
5'-AmsGfsCmAmCmUfGmAmGmAmAmUmAmCfUmGfUmCmCmCmUmsUmsUm-3'

In some embodiments, the nucleotide at 5'-terminal in the antisense strand of the siRNA is a 5'-phosphate nucleotide or a 5'-phosphate analogue modified nucleotide.

Typical 5'-phosphate nucleotides or 5'-phosphate analogue modified nucleotides are well known to those skilled in the art. For example, the 5'-phosphate nucleotides may have the following structure:

Formula (2)

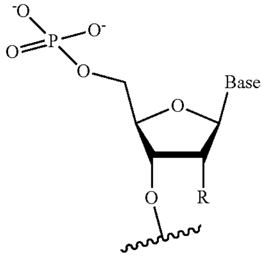

As another example, Anastasia Khvorova and Jonathan K. Watts, The chemical evolution of oligonucleotide therapies of clinical utility. Nature Biotechnology, 2017, 35(3): 238-48 discloses the following four 5'-phosphate analogue modified nucleotides:

Formula (3)

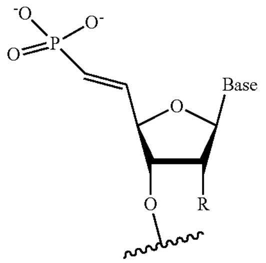

Formula (4)

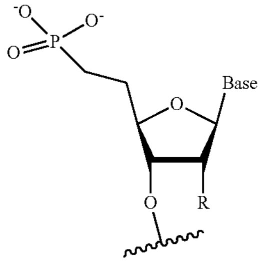

-continued

Formula (5)

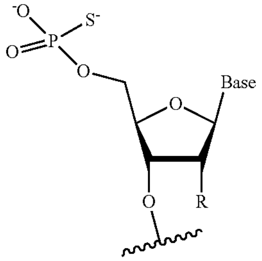

Formula (6)

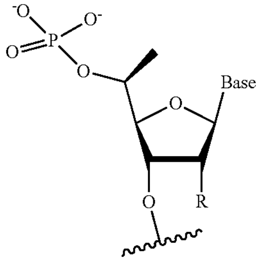

wherein R is selected from H, OH, methoxy, and F;

"Base" represents a base selected from A, U, C, G, or T.

In some embodiments, the 5'-phosphate nucleotide is a nucleotide with 5'-phosphate modification as shown by Formula (2); the 5'-phosphate analogue modified nucleotide is a nucleotide with vinylphosphonate modification as shown by Formula (3), or a phosphorothioate modified nucleotide as shown by Formula (5).

In some embodiments, the siRNA of the present disclosure is any one of siAPa1-M1P1, siAPa2-M1P1, siAPa1-M2P1, siAPa2-M2P1, siAPa1-M3P1, siAPa2-M3P1, siAPa1-M1SP1, siAPa2-M1SP1, siAPa1-M2SP1, siAPa2-M2SP1, siAPa1-M3SP1, siAPa2-M3SP1, siAPa1U-M1P1, siAPa2U-M1P1, siAPa1U-M2P1, siAPa2U-M2P1, siAPa1U-M3P1, siAPa2U-M3P1, siAPa1U-M1SP1, siAPa2U-M1SP1, siAPa1U-M2SP1, siAPa2U-M2SP1, siAPa1U-M3SP1, siAPa2U-M3SP1, siAPb1-M1P1, siAPb2-M1P1, siAPb1-M2P1, siAPb2-M2P1, siAPb1-M3P1, siAPb2-M3P1, siAPb1-M1SP1, siAPb2-M1SP1, siAPb1-M2SP1, siAPb2-M2SP1, siAPb1-M3SP1, siAPb2-M3SP1, siAPb1U-M1P1, siAPb2U-M1P1, siAPb1U-M2P1, siAPb2U-M2P1, siAPb1U-M3P1, siAPb2U-M3P1, siAPb1U-M1SP1, siAPb2U-M1SP1, siAPb1U-M2SP1, siAPb2U-M2SP1, siAPb1U-M3SP1, siAPb2U-M3SP1, siAPc1-M1P1, siAPc2-M1P1, siAPc1-M2P1, siAPc2-M2P1, siAPc1-M3P1, siAPc2-M3P1, siAPc1-M1SP1, siAPc2-M1SP1, siAPc1-M2SP1, siAPc2-M2SP1, siAPc1-M3SP1, siAPc2-M3SP1, siAPd1-M1P1, siAPd2-M1P1, siAPd1-M2P1, siAPd2-M2P1, siAPd1-M3P1, siAPd2-M3P1, siAPd1-M1SP1, siAPd2-M1SP1, siAPd1-M2SP1, siAPd2-M2SP1, siAPd1-M3SP1, siAPd2-M3SP1, siAPd1U-M1P1, siAPd2U-M1P1, siAPd1U-M2P1, siAPd2U-M2P1, siAPd1U-M3P1, siAPd2U-M3P1, siAPd1U-M1SP1, siAPd2U-M1SP1, siAPd1U-M2SP1, siAPd2U-M2SP1, siAPd1U-M3SP1, siAPd2U-M3SP1, siAPe1-M1P1, siAPe2-M1P1, siAPe1-M2P1, siAPe2-M2P1, siAPe1-M3P1, siAPe2-M3P1, siAPe1-M1SP1, siAPe2-M1SP1, siAPe1-M2SP1, siAPe2-M2SP1, siAPe1-M3SP1, siAPe2-M3SP1, siAPe1U-M1P1, siAPe2U-M1P1, siAPe1U-M2P1, siAPe2U-M2P1, siAPe1U-M3P1, siAPe2U-M3P1, siAPe1U-M1SP1, siAPe2U-M1SP1, siAPe1U-M2SP1, siAPe2U-M2SP1, siAPe1U-M3SP1, and siAPe2U-M3SP1.

siAPa1-M1P1
sense strand:
(SEQ ID NO: 181)
5'-UmUmAmAmAfAmGfGfGfAmCmAmGmUmAmUmUmCmUm-3' antisense strand:
(SEQ ID NO: 182)
5'-P1-AmGfAmAmUmAfCmUfGfUmCmCmCmUfUmUfUmAmAmGmCm-3' siAPa2-M1P1
sense strand:
(SEQ ID NO: 183)
5'-GmCmUmUmAmAmAfAmGfGfGfAmCmAmGmUmAmUmUmCmUm-3' antisense strand:
(SEQ ID NO: 184)
5'-P1-AmGfAmAmUmAfCmUfGfUmCmCmCmUfUmUfUmAmAmGmCmAmAm-3' siAPa1-M2P1
sense strand:
(SEQ ID NO: 185)
5'-UmUmAmAmAfAmGfGfGfAmCmAmGmUmAmUmUmCmUm-3' antisense strand:
(SEQ ID NO: 186)
5'-P1-AmGfAmAmUmAfCmUmGmUmCmCmCmUfUmUfUmAmAGmCm-3' siAPa2-M2P1
sense strand:
(SEQ ID NO: 187)
5'-GmCmUmUmAmAmAfAmGfGfGfAmCmAmGmUmAmUmUmCmUm-3' antisense strand:
(SEQ ID NO: 188)
5'-P1-AmGfAmAmUmAfCmUmGmUmCmCmCmUfUmUfUmAmAmGmCmAmAm-3'

-continued siAPa1-M3P1
sense strand:
(SEQ ID NO: 189)
5'-UmUmAmAmAmAmGfGfGfAmCmAmGmUmAmUmUmCmUm-3' antisense strand:
(SEQ ID NO: 190)
5'-P1-AmGfAmAmUmAfCmUmGmUmCmCmCmUfUmUfUmAmAmGmCm-3' siAPa2-M3P1
sense strand:
(SEQ ID NO: 191)
5'-GmCmUmUmAmAmAmAmGfGfGfAmCmAmGmUmAmUmUmCmUm-3' antisense strand:
(SEQ ID NO: 192)
5'-P1-AmGfAmAmUmAfCmUmGmUmCmCmCmUfUmUfUmAmAmGmCmAmAm-3' siAPa1-M1SP1
sense strand:
(SEQ ID NO: 193)
5'-UmsUmsAmAmAfAmGfGfGfAmCmAmGmUmAmUmUmCmUm-3' antisense strand:
(SEQ ID NO: 194)
5'-P1-AmsGfsAmAmUmAfCmUfGfUmCmCmCmUfUmUfUmAmAmsGmsCm-3' siAPa2-M1SP1
sense strand:
(SEQ ID NO: 195)
5'-GmsCmsUmUmAmAmAfAmGfGfGfAmCmAmGmUmAmUmUmCmUm-3' antisense strand:
(SEQ ID NO: 196)
5'-P1-AmsGfsAmAmUmAfCmUfGfUmCmCmCmUfUmUfUmAmAmGmCmsAmsAm-3' siAPa1-M2SP1
sense strand:
(SEQ ID NO: 197)
5'-UmsUmsAmAmAfAmGfGfGfAmCmAmGmUmAmUmUmCmUm-3' antisense strand:
(SEQ ID NO: 198)
5'-P1-AmsGfsAmAmUmAfCmUmGmUmCmCmCmUfUmUfUmAmAmsGmsCm-3' siAPa2-M2SP1
sense strand:
(SEQ ID NO: 199)
5'-GmsCmsUmUmAmAmAfAmGfGfGfAmCmAmGmUmAmUmUmCmUm-3' antisense strand:
(SEQ ID NO: 200)
5'-P1-AmsGfsAmAmUmAfCmUmGmUmCmCmCmUfUmUfUmAmAmGmCmsAmsAm-3' siAPa1-M3SP1
sense strand:
(SEQ ID NO: 201)
5'-UmsUmsAmAmAmAmGfGfGfAmCmAmGmUmAmUmUmCmUm-3' antisense strand:
(SEQ ID NO: 202)
5'-P1-AmsGfsAmAmUmAfCmUmGmUmCmCmCmUfUmUfUmAmAmsGmsCm-3' siAPa2-M3SP1
sense strand:
(SEQ ID NO: 203)
5'-GmsCmsUmUmAmAmAmAmGfGfGfAmCmAmGmUmAmUmUmCmUm-3' antisense strand:
(SEQ ID NO: 204)
5'-P1-AmsGfsAmAmUmAfCmUmGmUmCmCmCmUfUmUfUmAmAmGmCmsAmsAm-3' siAPa1U-M1P1
sense strand:
(SEQ ID NO: 327)
5'-UmUmAmAmAfAmGfGfGfAmCmAmGmUmAmUmUmCmAm-3' antisense strand:
(SEQ ID NO: 328)
5'-P1-UmGfAmAmUmAfCmUfGfUmCmCmCmUfUmUfUmAmAmGmCm-3'

-continued siAPa2U-M1P1
sense strand:
(SEQ ID NO: 329)
5'-GmCmUmUmAmAmAfAmGfGfGfAmCmAmGmUmAmUmUmCmAm-3' antisense strand:
(SEQ ID NO: 330)
5'-P1-UmGfAmAmUmAfCmUfGfUmCmCmCmUfUmUfUmAmAmGmCmAmAm-3' siAPa1U-M2P1
sense strand:
(SEQ ID NO: 331)
5'-UmUmAmAmAfAmGfGfGfAmCmAmGmUmAmUmUmCmAm-3' antisense strand:
(SEQ ID NO: 332)
5'-P1-UmGfAmAmUmAfCmUmGmUmCmCmCmUfUmUfUmAmAmGmCm-3' siAPa2U-M2P1
sense strand:
(SEQ ID NO: 333)
5'-GmCmUmUmAmAmAfAmGfGfGfAmCmAmGmUmAmUmUmCmAm-3' antisense strand:
(SEQ ID NO: 334)
5'-P1-UmGfAmAmUmAfCmUmGmUmCmCmCmUfUmUfUmAmAmGmCmAmAm-3' siAPa1U-M3P1
sense strand:
(SEQ ID NO: 335)
5'-UmUmAmAmAmAmGfGfGfAmCmAmGmUmAmUmUmCmAm-3' antisense strand:
(SEQ ID NO: 336)
5'-P1-UmGfAmAmUmAfCmUmGmUmCmCmCmUfUmUfUmAmAmGmCm-3' siAPa2U-M3P1
sense strand:
(SEQ ID NO: 337)
5'-GmCmUmUmAmAmAmAmGfGfGfAmCmAmGmUmAmUmUmCmAm-3' antisense strand:
(SEQ ID NO: 338)
5'-P1-UmGfAmAmUmAfCmUmGmUmCmCmCmUfUmUfUmAmAmGmCmAmAm-3' siAPa1U-M1SP1
sense strand:
(SEQ ID NO: 339)
5'-UmsUmsAmAmAfAmGfGfGfAmCmAmGmUmAmUmUmCmAm-3' antisense strand:
(SEQ ID NO: 340)
5'-P1-UmsGfsAmAmUmAfCmUfGfUmCmCmCmUfUmUfUmAmAmsGmsCm-3' siAPa2U-M1SP1
sense strand:
(SEQ ID NO: 341)
5'-GmsCmsUmUmAmAmAfAmGfGfGfAmCmAmGmUmAmUmUmCmAm-3' antisense strand:
(SEQ ID NO: 342)
5'-P1-UmsGfsAmAmUmAfCmUfGfUmCmCmCmUfUmUfUmAmAmGmCmsAmsAm-3' siAPa1U-M2SP1
sense strand:
(SEQ ID NO: 343)
5'-UmsUmsAmAmAfAmGfGfGfAmCmAmGmUmAmUmUmCmAm-3' antisense strand:
(SEQ ID NO: 344)
5'-P1-UmsGfsAmAmUmAfCmUmGmUmCmCmCmUfUmUfUmAmAmsGmsCm-3' siAPa2U-M2SP1
sense strand:
(SEQ ID NO: 345)
5'-GmsCmsUmUmAmAmAfAmGfGfGfAmCmAmGmUmAmUmUmCmAm-3' antisense strand:
(SEQ ID NO: 346)
5'-P1-UmsGfsAmAmUmAfCmUmGmUmCmCmCmUfUmUfUmAmAmGmCmsAmsAm-3'

-continued siAPa1U-M3SP1
sense strand:
(SEQ ID NO: 347)
5'-UmsUmsAmAmAmAmGfGfGfAmCmAmGmUmAmUmUmCmAm-3' antisense strand:
(SEQ ID NO: 348)
5'-P1-UmsGfsAmAmUmAfCmUmGmUmCmCmCmUfUmUfUmAmAmsGmsCm-3' siAPa2U-M3SP1
sense strand:
(SEQ ID NO: 349)
5'-GmsCmsUmUmAmAmAmAmGfGfGfAmCmAmGmUmAmUmUmCmAm-3' antisense strand:
(SEQ ID NO: 350)
5'-P1-UmsGfsAmAmUmAfCmUmGmUmCmCmCmUfUmUfUmAmAmGmCmsAmsAm-3' siAPb1-M1P1
sense strand:
(SEQ ID NO: 205)
5'-AmCmAmGmUfAmUfUfCfUmCmAmGmUmGmCmUmCmUm-3' antisense strand:
(SEQ ID NO: 206)
5'-P1-AmGfAmGmCmAfCmUfGfAmGmAmAmUfAmCfUmGmUmCmCm-3' siAPb2-M1P1
sense strand:
(SEQ ID NO: 207)
5'-GmGmAmCmAmGmUfAmUfUfCfUmCmAmGmUmGmCmUmCmUm-3' antisense strand:
(SEQ ID NO: 208)
5'-P1-AmGfAmGmCmAfCmUfGfAmGmAmAmUfAmCfUmGmUmCmCmCmUm-3' siAPb1-M2P1
sense strand:
(SEQ ID NO: 209)
5'-AmCmAmGmUfAmUfUfCfUmCmAmGmUmGmCmUmCmUm-3' antisense strand:
(SEQ ID NO: 210)
5'-P1-AmGfAmGmCmAfCmUmGmAmGmAmAmUfAmCfUmGmUmCmCm-3' siAPb2-M2P1
sense strand:
(SEQ ID NO: 211)
5'-GmGmAmCmAmGmUfAmUfUfCfUmCmAmGmUmGmCmUmCmUm-3' antisense strand:
(SEQ ID NO: 212)
5'-P1-AmGfAmGmCmAfCmUmGmAmGmAmAmUfAmCfUmGmUmCmCmCmUm-3' siAPb1-M3P1
sense strand:
(SEQ ID NO: 213)
5'-AmCmAmGmUmAmUfUfCfUmCmAmGmUmGmCmUmCmUm-3' antisense strand:
(SEQ ID NO: 214)
5'-P1-AmGfAmGmCmAfCmUmGmAmGmAmAmUfAmCfUmGmUmCmCm-3' siAPb2-M3P1
sense strand:
(SEQ ID NO: 215)
5'-GmGmAmCmAmGmUmAmUfUfCfUmCmAmGmUmGmCmUmCmUm-3' antisense strand:
(SEQ ID NO: 216)
5'-P1-AmGfAmGmCmAfCmUmGmAmGmAmAmUfAmCfUmGmUmCmCmCmUm-3' siAPb1-M1SP1
sense strand:
(SEQ ID NO: 217)
5'-AmsCmsAmGmUfAmUfUfCfUmCmAmGmUmGmCmUmCmUm-3' antisense strand:
(SEQ ID NO: 218)
5'-P1-AmsGfsAmGmCmAfCmUfGfAmGmAmAmUfAmCfUmGmUmsCmsCm-3'

-continued siAPb2-M1SP1
sense strand:
(SEQ ID NO: 219)
5'-GmsGmsAmCmAmGmUfAmUfUfCfUmCmAmGmUmGmCmUmCmUm-3' antisense strand:
(SEQ ID NO: 220)
5'-P1-AmsGfsAmGmCmAfCmUfGfAmGmAmAmUfAmCfUmGmUmCmCmsCmsUm-3' siAPb1-M2SP1
sense strand:
(SEQ ID NO: 221)
5'-AmsCmsAmGmUfAmUfUfCfUmCmAmGmUmGmCmUmCmUm-3' antisense strand:
(SEQ ID NO: 222)
5'-P1-AmsGfsAmGmCmAfCmUmGmAmGmAmAmUfAmCfUmGmUmsCmsCm-3' siAPb2-M2SP1
sense strand:
(SEQ ID NO: 223)
5'-GmsGmsAmCmAmGmUfAmUfUfCfUmCmAmGmUmGmCmUmCmUm-3' antisense strand:
(SEQ ID NO: 224)
5'-P1-AmsGfsAmGmCmAfCmUmGmAmGmAmAmUfAmCfUmGmUmCmCmsCmsUm-3' siAPb1-M3SP1
sense strand:
(SEQ ID NO: 225)
5'-AmsCmsAmGmUmAmUfUfCfUmCmAmGmUmGmCmUmCmUm-3' antisense strand:
(SEQ ID NO: 226)
5'-P1-AmsGfsAmGmCmAfCmUmGmAmGmAmAmUfAmCfUmGmUmsCmsCm-3' siAPb2-M3SP1
sense strand:
(SEQ ID NO: 227)
5'-GmsGmsAmCmAmGmUmAmUfUfCfUmCmAmGmUmGmCmUmCmUm-3' antisense strand:
(SEQ ID NO: 228)
5'-P1-AmsGfsAmGmCmAfCmUmGmAmGmAmAmUfAmCfUmGmUmCmCmsCmsUm-3' siAPb1U-M1P1
sense strand:
(SEQ ID NO: 351)
5'-AmCmAmGmUfAmUfUfCfUmCmAmGmUmGmCmUmCmAm-3' antisense strand:
(SEQ ID NO: 352)
5'-P1-UmGfAmGmCmAfCmUfGfAmGmAmAmUfAmCfUmGmUmCmCm-3' siAPb2U-M1P1
sense strand:
(SEQ ID NO: 353)
5'-GmGmAmCmAmGmUfAmUfUfCfUmCmAmGmUmGmCmUmCmAm-3' antisense strand:
(SEQ ID NO: 354)
5'-P1-UmGfAmGmCmAfCmUfGfAmGmAmAmUfAmCfUmGmUmCmCmCmUm-3' siAPb1U-M2P1
sense strand:
(SEQ ID NO: 355)
5'-AmCmAmGmUfAmUfUfCfUmCmAmGmUmGmCmUmCmAm-3' antisense strand:
(SEQ ID NO: 356)
5'-P1-UmGfAmGmCmAfCmUmGmAmGmAmAmUfAmCfUmGmUmCmCm-3' siAPb2U-M2P1
sense strand:
(SEQ ID NO: 357)
5'-GmGmAmCmAmGmUfAmUfUfCfUmCmAmGmUmGmCmUmCmAm-3'

-continued antisense strand:
(SEQ ID NO: 358)
5'-P1-UmGfAmGmCmAfCmUmGmAmGmAmAmUfAmCfUmGmUmCmCmCmUm-3' siAPb1U-M3P1
sense strand:
(SEQ ID NO: 359)
5'-AmCmAmGmUmAmUfUfCfUmCmAmGmUmGmCmUmCmAm-3' antisense strand:
(SEQ ID NO: 360)
5'-P1-UmGfAmGmCmAfCmUmGmAmGmAmAmUfAmCfUmGmUmCmCm-3' siAPb2U-M3P1
sense strand:
(SEQ ID NO: 361)
5'-GmGmAmCmAmGmUmAmUfUfCfUmCmAmGmUmGmCmUmCmAm-3' antisense strand:
(SEQ ID NO: 362)
5'-P1-UmGfAmGmCmAfCmUmGmAmGmAmAmUfAmCfUmGmUmCmCmCmUm-3' siAPb1U-M1SP1
sense strand:
(SEQ ID NO: 363)
5'-AmsCmsAmGmUfAmUfUfCfUmCmAmGmUmGmCmUmCmAm-3' antisense strand:
(SEQ ID NO: 364)
5'-P1-UmsGfsAmGmCmAfCmUfGfAmGmAmAmUfAmCfUmGmUmsCmsCm-3' siAPb2U-M1SP1
sense strand:
(SEQ ID NO: 365)
5'-GmsGmsAmCmAmGmUfAmUfUfCfUmCmAmGmUmGmCmUmCmAm-3' antisense strand:
(SEQ ID NO: 366)
5'-P1-UmsGfsAmGmCmAfCmUfGfAmGmAmAmUfAmCfUmGmUmCmCmsCmsUm-3' siAPb1U-M2SP1
sense strand:
(SEQ ID NO: 367)
5'-AmsCmsAmGmUfAmUfUfCfUmCmAmGmUmGmCmUmCmAm-3' antisense strand:
(SEQ ID NO: 368)
5'-P1-UmsGfsAmGmCmAfCmUmGmAmGmAmAmUfAmCfUmGmUmsCmsCm-3' siAPb2U-M2SP1
sense strand:
(SEQ ID NO: 369)
5'-GmsGmsAmCmAmGmUfAmUfUfCfUmCmAmGmUmGmCmUmCmAm-3' antisense strand:
(SEQ ID NO: 370)
5'-P1-UmsGfsAmGmCmAfCmUmGmAmGmAmAmUfAmCfUmGmUmCmCmsCmsUm-3' siAPb1U-M3SP1
sense strand:
(SEQ ID NO: 371)
5'-AmsCmsAmGmUmAmUfUfCfUmCmAmGmUmGmCmUmCmAm-3' antisense strand:
(SEQ ID NO: 372)
5'-P1-UmsGfsAmGmCmAfCmUmGmAmGmAmAmUfAmCfUmGmUmsCmsCm-3' siAPb2U-M3SP1
sense strand:
(SEQ ID NO: 373)
5'-GmsGmsAmCmAmGmUmAmUfUfCfUmCmAmGmUmGmCmUmCmAm-3' antisense strand:
(SEQ ID NO: 374)
5'-P1-UmsGfsAmGmCmAfCmUmGmAmGmAmAmUfAmCfUmGmUmCmCmsCmsUm-3' siAPc1-M1P1
sense strand:
(SEQ ID NO: 229)
5'-UmAmUmUmCfUmCfAfGfUmGmCmUmCmUmCmCmUmAm-3'

-continued antisense strand:
(SEQ ID NO: 230)
5'-P1-UmAfGmGmAmGfAmGfCfAmCmUmGmAfGmAfAmUmAmCmUm-3' siAPc2-M1P1
sense strand:
(SEQ ID NO: 231)
5'-AmGmUmAmUmUmCfUmCfAfGfUmGmCmUmCmUmCmCmUmAm-3' antisense strand:
(SEQ ID NO: 232)
5'-P1-UmAfGmGmAmGfAmGfCfAmCmUmGmAfGmAfAmUmAmCmUmGmUm-3' siAPc1-M2P1
sense strand:
(SEQ ID NO: 233)
5'-UmAmUmUmCfUmCfAfGfUmGmCmUmCmUmCmCmUmAm-3' antisense strand:
(SEQ ID NO: 234)
5'-P1-UmAfGmGmAmGfAmGmCmAmCmUmGmAfGmAfAmUmAmCmUm-3' siAPc2-M2P1
sense strand:
(SEQ ID NO: 235)
5'-AmGmUmAmUmUmCfUmCfAfGfUmGmCmUmCmUmCmCmUmAm-3' antisense strand:
(SEQ ID NO: 236)
5'-P1-UmAfGmGmAmGfAmGmCmAmCmUmGmAfGmAfAmUmAmCmUmGmUm-3' siAPc1-M3P1
sense strand:
(SEQ ID NO: 237)
5'-UmAmUmUmCmUmCfAfGfUmGmCmUmCmUmCmCmUmAm-3' antisense strand:
(SEQ ID NO: 238)
5'-P1-UmAfGmGmAmGfAmGmCmAmCmUmGmAfGmAfAmUmAmCmUm-3' siAPc2-M3P1
sense strand:
(SEQ ID NO: 239)
5'-AmGmUmAmUmUmCmUmCfAfGfUmGmCmUmCmUmCmCmUmAm-3' antisense strand:
(SEQ ID NO: 240)
5'-P1-UmAfGmGmAmGfAmGmCmAmCmUmGmAfGmAfAmUmAmCmUmGmUm-3' siAPc1-M1SP1
sense strand:
(SEQ ID NO: 241)
5'-UmsAmsUmUmCfUmCfAfGfUmGmCmUmCmUmCmCmUmAm-3' antisense strand:
(SEQ ID NO: 242)
5'-P1-UmsAfsGmGmAmGfAmGfCfAmCmUmGmAfGmAfAmUmAmsCmsUm-3' siAPc2-M1SP1
sense strand:
(SEQ ID NO: 243)
5'-AmsGmsUmAmUmUmCfUmCfAfGfUmGmCmUmCmUmCmCmUmAm-3' antisense strand:
(SEQ ID NO: 244)
5'-P1-UmsAfsGmGmAmGfAmGfCfAmCmUmGmAfGmAfAmUmAmCmUmsGmsUm-3' siAPc1-M2SP1
sense strand:
(SEQ ID NO: 245)
5'-UmsAmsUmUmCfUmCfAfGfUmGmCmUmCmUmCmCmUmAm-3' antisense strand:
(SEQ ID NO: 246)
5'-P1-UmsAfsGmGmAmGfAmGmCmAmCmUmGmAfGmAfAmUmAmsCmsUm-3' siAPc2-M2SP1
sense strand:
(SEQ ID NO: 247)
5'-AmsGmsUmAmUmUmCfUmCfAfGfUmGmCmUmCmUmCmCmUmAm-3'

-continued antisense strand:
(SEQ ID NO: 248)
5'-P1-UmsAfsGmGmAmGfAmGmCmAmCmUmGmAfGmAfAmUmAmCmUmsGmsUm-3' siAPc1-M3SP1
sense strand:
(SEQ ID NO: 249)
5'-UmsAmsUmUmCmUmCfAfGfUmGmCmUmCmUmCmCmUmAm-3' antisense strand:
(SEQ ID NO: 250)
5'-P1-UmsAfsGmGmAmGfAmGmCmAmCmUmGmAfGmAfAmUmAmsCmsUm-3' siAPc2-M3SP1
sense strand:
(SEQ ID NO: 251)
5'-AmsGmsUmAmUmUmCmUmCfAfGfUmGmCmUmCmUmCmCmUmAm-3' antisense strand:
(SEQ ID NO: 252)
5'-P1-UmsAfsGmGmAmGfAmGmCmAmCmUmGmAfGmAfAmUmAmCmUmsGmsUm-3' siAPd1-M1P1
sense strand:
(SEQ ID NO: 253)
5'-AmGmUmAmUfUmCfUfCfAmGmUmGmCmUmCmUmCmCm-3' antisense strand:
(SEQ ID NO: 254)
5'-P1-GmGfAmGmAmGfCmAfCfUmGmAmGmAfAmUfAmCmUmGmUm-3' siAPd2-M1P1
sense strand:
(SEQ ID NO: 255)
5'-AmCmAmGmUmAmUfUmCfUfCfAmGmUmGmCmUmCmUmCmCm-3' antisense strand:
(SEQ ID NO: 256)
5'-P1-GmGfAmGmAmGfCmAfCfUmGmAmGmAfAmUfAmCmUmGmUmCmCm-3' siAPd1-M2P1
sense strand:
(SEQ ID NO: 257)
5'-AmGmUmAmUfUmCfUfCfAmGmUmGmCmUmCmUmCmCm-3' antisense strand:
(SEQ ID NO: 258)
5'-P1-GmGfAmGmAmGfCmAmCmUmGmAmGmAfAmUfAmCmUmGmUm-3' siAPd2-M2P1
sense strand:
(SEQ ID NO: 259)
5'-AmCmAmGmUmAmUfUmCfUfCfAmGmUmGmCmUmCmUmCmCm-3' antisense strand:
(SEQ ID NO: 260)
5'-P1-GmGfAmGmAmGfCmAmCmUmGmAmGmAfAmUfAmCmUmGmUmCmCm-3' siAPd1-M3P1
sense strand:
(SEQ ID NO: 261)
5'-AmGmUmAmUmUmCfUfCfAmGmUmGmCmUmCmUmCmCm-3' antisense strand:
(SEQ ID NO: 262)
5'-P1-GmGfAmGmAmGfCmAmCmUmGmAmGmAfAmUfAmCmUmGmUm-3' siAPd2-M3P1
sense strand:
(SEQ ID NO: 263)
5'-AmCmAmGmUmAmUmUmCfUfCfAmGmUmGmCmUmCmUmCmCm-3' antisense strand:
(SEQ ID NO: 264)
5'-P1-GmGfAmGmAmGfCmAmCmUmGmAmGmAfAmUfAmCmUmGmUmCmCm-3' siAPd1-M1SP1
sense strand:
(SEQ ID NO: 265)
5'-AmsGmsUmAmUfUmCfUfCfAmGmUmGmCmUmCmUmCmCm-3'

-continued antisense strand:
(SEQ ID NO: 266)
5'-P1-GmsGfsAmGmAmGfCmAfCfUmGmAmGmAfAmUfAmCmUmsGmsUm-3' siAPd2-M1SP1
sense strand:
(SEQ ID NO: 267)
5'-AmsCmsAmGmUmAmUfUmCfUfCfAmGmUmGmCmUmCmUmCmCm-3' antisense strand:
(SEQ ID NO: 268)
5'-P1-GmsGfsAmGmAmGfCmAfCfUmGmAmGmAfAmUfAmCmUmGmUmsCmsCm-3' siAPd1-M2SP1
sense strand:
(SEQ ID NO: 269)
5'-AmsGmsUmAmUfUmCfUfCfAmGmUmGmCmUmCmUmCmCm-3' antisense strand:
(SEQ ID NO: 270)
5'-P1-GmsGfsAmGmAmGfCmAmCmUmGmAmGmAfAmUfAmCmUmsGmsUm-3' siAPd2-M2SP1
sense strand:
(SEQ ID NO: 271)
5'-AmsCmsAmGmUmAmUfUmCfUfCfAmGmUmGmCmUmCmUmsCmsCm-3' antisense strand:
(SEQ ID NO: 272)
5'-P1-GmsGfsAmGmAmGfCmAmCmUmGmAmGmAfAmUfAmCmUmGmUmsCmsCm-3' siAPd1-M3SP1
sense strand:
(SEQ ID NO: 273)
5'-AmsCmsAmGmUmAmUmUmCfUfCfAmGmUmGmCmUmCmUmCmCm-3' antisense strand:
(SEQ ID NO: 274)
5'-P1-GmsGfsAmGmAmGfCmAmCmUmGmAmGmAfAmUfAmCmUmsGmsUm-3' siAPd2-M3SP1
sense strand:
(SEQ ID NO: 275)
5'-AmsCmsAmGmUmAmUmUmCfUfCfAmGmUmGmCmUmCmUmCmCm-3' antisense strand:
(SEQ ID NO: 276)
5'-P1-GmsGfsAmGmAmGfCmAmCmUmGmAmGmAfAmUfAmCmUmGmUmsCmsCm-3' siAPd1U-M1P1
sense strand:
(SEQ ID NO: 375)
5'-AmGmUmAmUfUmCfUfCfAmGmUmGmCmUmCmUmCmAm-3' antisense strand:
(SEQ ID NO: 376)
5'-P1-UmGfAmGmAmGfCmAfCfUmGmAmGmAfAmUfAmCmUmGmUm-3' siAPd2U-M1P1
sense strand:
(SEQ ID NO: 377)
5'-AmCmAmGmUmAmUfUmCfUfCfAmGmUmGmCmUmCmUmCmAm-3' antisense strand:
(SEQ ID NO: 378)
5'-P1-UmGfAmGmAmGfCmAfCfUmGmAmGmAfAmUfAmCmUmGmUmCmCm-3' siAPd1U-M2P1
sense strand:
(SEQ ID NO: 379)
5'-AmGmUmAmUfUmCfUfCfAmGmUmGmCmUmCmUmCmAm-3;

antisense strand:
(SEQ ID NO: 380)
5'-P1-UmGfAmGmAmGfCmAmCmUmGmAmGmAfAmUfAmCmUmGmUm-3' siAPd2U-M2P1
sense strand:
(SEQ ID NO: 381)
5'-AmCmAmGmUmAmUfUmCfUfCfAmGmUmGmCmUmCmUmCmAm-3'

-continued antisense strand:
(SEQ ID NO: 382)
5'-P1-UmGfAmGmAmGfCmAmCmUmGmAmGmAfAmUfAmCmUmGmUmCmCm-3' siAPd1U-M3P1
sense strand:
(SEQ ID NO: 383)
5'-AmGmUmAmUmUmCfUfCfAmGmUmGmCmUmCmUmCmAm-3' antisense strand:
(SEQ ID NO: 384)
5'-P1-UmGfAmGmAmGfCmAmCmUmGmAmGmAfAmUfAmCmUmGmUm-3' siAPd2U-M3P1
sense strand:
(SEQ ID NO: 385)
5'-AmCmAmGmUmAmUmUmCfUfCfAmGmUmGmCmUmCmUmCmAm-3' antisense strand:
(SEQ ID NO: 386)
5'-P1-UmGfAmGmAmGfCmAmCmUmGmAmGmAfAmUfAmCmUmGmUmCmCm-3' siAPd1U-M1SP1
sense strand:
(SEQ ID NO: 387)
5'-AmsGmsUmAmUfUmCfUfCfAmGmUmGmCmUmCmUmCmAm-3' antisense strand:
(SEQ ID NO: 388)
5'-P1-UmsGfsAmGmAmGfCmAfCfUmGmAmGmAfAmUfAmCmUmsGmsUm-3' siAPd2U-M1SP1
sense strand:
(SEQ ID NO: 389)
5'-AmsCmsAmGmUmAmUfUmCfUfCfAmGmUmGmCmUmCmUmCmAm-3' antisense strand:
(SEQ ID NO: 390)
5'-P1-UmsGfsAmGmAmGfCmAfCfUmGmAmGmAfAmUfAmCmUmGmUmsCmsCm-3' siAPd1U-M2SP1
sense strand:
(SEQ ID NO: 391)
5'-AmsGmsUmAmUfUmCfUfCfAmGmUmGmCmUmCmUmCmAm-3' antisense strand:
(SEQ ID NO: 392)
5'-P1-UmsGfsAmGmAmGfCmAmCmUmGmAmGmAfAmUfAmCmUmsGmsUm-3' siAPd2U-M2SP1
sense strand:
(SEQ ID NO: 393)
5'-AmsCmsAmGmUmAmUfUmCfUfCfAmGmUmGmCmUmCmUmCmAm-3' antisense strand:
(SEQ ID NO: 394)
5'-P1-UmsGfsAmGmAmGfCmAmCmUmGmAmGmAfAmUfAmCmUmGmUmsCmsCm-3' siAPd1U-M3SP1
sense strand:
(SEQ ID NO: 395)
5'-AmsGmsUmAmUmUmCfUfCfAmGmUmGmCmUmCmUmCmAm-3' antisense strand:
(SEQ ID NO: 396)
5'-P1-UmsGfsAmGmAmGfCmAmCmUmGmAmGmAfAmUfAmCmUmsGmsUm-3' siAPd2U-M3SP1
sense strand:
(SEQ ID NO: 397)
5'-AmsCmsAmGmUmAmUmUmCfUfCfAmGmUmGmCmUmCmUmCmAm-3' antisense strand:
(SEQ ID NO: 398)
5'-P1-UmsGfsAmGmAmGfCmAmCmUmGmAmGmAfAmUfAmCmUmGmUmsCmsCm-3' siAPe1-M1P1
sense strand:
(SEQ ID NO: 277)
5'-GmGmAmCmAfGmUfAfUfUmCmUmCmAmGmUmGmCmUm-3'

-continued antisense strand:
(SEQ ID NO: 278)
5'-P1-AmGfCmAmCmUfGmAfGfAmAmUmAmCfUmGfUmCmCmCmUm-3' siAPe2-M1P1
sense strand:
(SEQ ID NO: 279)
5'-AmGmGmGmAmCmAfGmUfAfUfUmCmUmCmAmGmUmGmCmUm-3' antisense strand:
(SEQ ID NO: 280)
5'-P1-AmGfCmAmCmUfGmAfGfAmAmUmAmCfUmGfUmCmCmCmUmUmUm-3' siAPe1-M2P1
sense strand:
(SEQ ID NO: 281)
5'-GmGmAmCmAfGmUfAfUfUmCmUmCmAmGmUmGmCmUm-3' antisense strand:
(SEQ ID NO: 282)
5'-P1-AmGfCmAmCmUfGmAmGmAmAmUmAmCfUmGfUmCmCmCmUm-3' siAPe2-M2P1
sense strand:
(SEQ ID NO: 283)
5'-AmGmGmGmAmCmAfGmUfAfUfUmCmUmCmAmGmUmGmCmUm-3' antisense strand:
(SEQ ID NO: 284)
5'-P1-AmGfCmAmCmUfGmAmGmAmAmUmAmCfUmGfUmCmCmCmUmUmUm-3' siAPe1-M3P1
sense strand:
(SEQ ID NO: 285)
5'-GmGmAmCmAmGmUfAfUfUmCmUmCmAmGmUmGmCmUm-3' antisense strand:
(SEQ ID NO: 286)
5'-P1-AmGfCmAmCmUfGmAmGmAmAmUmAmCfUmGfUmCmCmCmUm-3' siAPe2-M3P1
sense strand:
(SEQ ID NO: 287)
5'-AmGmGmGmAmCmAmGmUfAfUfUmCmUmCmAmGmUmGmCmUm-3';

antisense strand:
(SEQ ID NO: 288)
5'-P1-AmGfCmAmCmUfGmAmGmAmAmUmAmCfUmGfUmCmCmCmUmUmUm-3' siAPe1-M1SP1
sense strand:
(SEQ ID NO: 289)
5'-GmsGmsAmCmAfGmUfAfUfUmCmUmCmAmGmUmGmCmUm-3' antisense strand:
(SEQ ID NO: 290)
5'-P1-AmsGfsCmAmCmUfGmAfGfAmAmUmAmCfUmGfUmCmCmsCmsUm-3' siAPe2-M1SP1
sense strand:
(SEQ ID NO: 291)
5'-AmsGmsGmGmAmCmAfGmUfAfUfUmCmUmCmAmGmUmGmCmUm-3' antisense strand:
(SEQ ID NO: 292)
5'-P1-AmsGfsCmAmCmUfGmAfGfAmAmUmAmCfUmGfUmCmCmCmUmsUmsUm-3' siAPe1-M2SP1
sense strand:
(SEQ ID NO: 293)
5'-GmsGmsAmCmAfGmUfAfUfUmCmUmCmAmGmUmGmCmUm-3' antisense strand:
(SEQ ID NO: 294)
5'-P1-AmsGfsCmAmCmUfGmAmGmAmAmUmAmCfUmGfUmCmCmsCmsUm-3' siAPe2-M2SP1
sense strand:
(SEQ ID NO: 295)
5'-AmsGmsGmGmAmCmAfGmUfAfUfUmCmUmCmAmGmUmGmCmUm-3';

-continued antisense strand:
(SEQ ID NO: 296)
5'-P1-AmsGfsCmAmCmUfGmAmGmAmAmUmAmCfUmGfUmCmCmCmUmsUmsUm-3' siAPe1-M3SP1
sense strand:
(SEQ ID NO: 297)
5'-GmsGmsAmCmAmGmUfAfUfUmCmUmCmAmGmUmGmCmUm-3';

antisense strand:
(SEQ ID NO: 298)
5'-P1-AmsGfsCmAmCmUfGmAmGmAmAmUmAmCfUmGfUmCmCmsCmsUm-3' siAPe2-M3SP1
sense strand:
(SEQ ID NO: 299)
5'-AmsGmsGmGmAmCmAmGmUfAfUfUmCmUmCmAmGmUmGmCmUm-3' antisense strand:
(SEQ ID NO: 300)
5'-P1-AmsGfsCmAmCmUfGmAmGmAmAmUmAmCfUmGfUmCmCmCmUmsUmsUm-3' siAPe1U-M1P1
sense strand:
(SEQ ID NO: 399)
5'-GmGmAmCmAfGmUfAfUfUmCmUmCmAmGmUmGmCmAm-3' antisense strand:
(SEQ ID NO: 400)
5'-P1-UmGfCmAmCmUfGmAfGfAmAmUmAmCfUmGfUmCmCmCmUm-3' siAPe2U-M1P1
sense strand:
(SEQ ID NO: 401)
5'-AmGmGmGmAmCmAfGmUfAfUfUmCmUmCmAmGmUmGmCmAm-3' antisense strand:
(SEQ ID NO: 402)
5'-P1-UmGfCmAmCmUfGmAfGfAmAmUmAmCfUmGfUmCmCmCmUmUmUm-3' siAPe1U-M2P1
sense strand:
(SEQ ID NO: 403)
5'-GmGmAmCmAfGmUfAfUfUmCmUmCmAmGmUmGmCmAm-3' antisense strand:
(SEQ ID NO: 404)
5'-P1-UmGfCmAmCmUfGmAmGmAmAmUmAmCfUmGfUmCmCmCmUm-3' siAPe2U-M2P1
sense strand:
(SEQ ID NO: 405)
5'-AmGmGmGmAmCmAfGmUfAfUfUmCmUmCmAmGmUmGmCmAm-3' antisense strand:
(SEQ ID NO: 406)
5'-P1-UmGfCmAmCmUfGmAmGmAmAmUmAmCfUmGfUmCmCmCmUmUmUm-3' siAPe1U-M3P1
sense strand:
(SEQ ID NO: 407)
5'-GmGmAmCmAmGmUfAfUfUmCmUmCmAmGmUmGmCmAm-3' antisense strand:
(SEQ ID NO: 408)
5'-P1-UmGfCmAmCmUfGmAmGmAmAmUmAmCfUmGfUmCmCmCmUm-3' siAPe2U-M3P1
sense strand:
(SEQ ID NO: 409)
5'-AmGmGmGmAmCmAmGmUfAfUfUmCmUmCmAmGmUmGmCmAm-3';

antisense strand:
(SEQ ID NO: 410)
5'-P1-UmGfCmAmCmUfGmAmGmAmAmUmAmCfUmGfUmCmCmCmUmUmUm-3' siAPe1U-M1SP1
sense strand:
(SEQ ID NO: 411)
5'-GmsGmsAmCmAfGmUfAfUfUmCmUmCmAmGmUmGmCmAm-3'

-continued antisense strand:

(SEQ ID NO: 412)

5'-P1-UmsGfsCmAmCmUfGmAfGfAmAmUmAmCfUmGfUmCmCmsCmsUm-3' siAPe2U-M1SP1 sense strand:

(SEQ ID NO: 413)

5'-AmsGmsGmGmAmCmAfGmUfAfUfUmCmUmCmAmGmUmGmCmAm-3' antisense strand:

(SEQ ID NO: 414)

5'-P1-UmsGfsCmAmCmUfGmAfGfAmAmUmAmCfUmGfUmCmCmCmUmsUmsUm-3' siAPe1U-M2SP1 sense strand:

(SEQ ID NO: 415)

5'-GmsGmsAmCmAfGmUfAfUfUmCmUmCmAmGmUmGmCmAm-3' antisense strand:

(SEQ ID NO: 416)

5'-P1-UmsGfsCmAmCmUfGmAmGmAmAmUmAmCfUmGfUmCmCmsCmsUm-3' siAPe2U-M2SP1 sense strand:

(SEQ ID NO: 417)

5'-AmsGmsGmGmAmCmAfGmUfAfUfUmCmUmCmAmGmUmGmCmAm-3' antisense strand:

(SEQ ID NO: 418)

5'-P1-UmsGfsCmAmCmUfGmAmGmAmAmUmAmCfUmGfUmCmCmCmUmsUmsUm-3' siAPe1U-M3SP1 sense strand:

(SEQ ID NO: 419)

5'-GmsGmsAmCmAmGmUfAfUfUmCmUmCmAmGmUmGmCmAm-3' antisense strand:

(SEQ ID NO: 420)

5'-P1-UmsGfsCmAmCmUfGmAmGmAmAmUmAmCfUmGfUmCmCmsCmsUm-3' siAPe2U-M3SP1 sense strand:

(SEQ ID NO: 421)

5'-AmsGmsGmGmAmCmAmGmUfAfUfUmCmUmCmAmGmUmGmCmAm-3' antisense strand:

(SEQ ID NO: 422)

5'-P1-UmsGfsCmAmCmUfGmAmGmAmAmUmAmCfUmGfUmCmCmCmUmsUmsUm-3'

In some embodiments, the siRNA may be one selected from siAPa1UM3SVP, siAPe1UM3SVP, siAPb1UM3SVP, siAPd1UM3SVP, siAPc1M3SVP, siAPd1UM3SP, siAPd1UM3SPs, siAPa1M3SP, siAPe1M3SP, siAPb1M3SP, and siAPc1M3SP, as shown in Table 7.

In the above siRNAs of the present disclosure, C, G, U, and A represent the base composition of a nucleotide; m represents that the nucleotide adjacent to the left side of the letter m is a methoxy modified nucleotide; f represents that the nucleotide adjacent to the left side of the letter f is a fluoro modified nucleotide; s represents that the two nucleotides adjacent to both sides of the letter s are linked by a phosphorothioate linkage; P1 represents that the nucleotide adjacent to the right side of P1 is a 5'-phosphate nucleotide or a 5'-phosphate analog modified nucleotide. In some embodiments, P1 represents the specific modified nucleotide VP, Ps or P, wherein VP represents that the nucleotide adjacent to the right side of VP is a vinyl phosphate (5'-(E)-vinylphosphonate, E-VP) modified nucleotide; Ps represents that the nucleotide adjacent to the right side of Ps is a thiophosphate modified nucleotide; and P represents that the nucleotide adjacent to the right side of the letter P is a 5'-phosphate nucleotide.

The inventors of the present disclosure surprisingly found that the siRNAs of the present disclosure have significantly enhanced plasma and lysosomal stability, while maintaining high gene-suppressing activity.

The siRNAs of the present disclosure can be obtained by conventional methods for preparing siRNAs in the art, e.g., solid phase synthesis method and liquid phase synthesis method. Commercial customization services have already been available for solid phase synthesis. A modified nucleotide group can be introduced into the siRNA of the present disclosure by using a nucleotide monomer having the corresponding modification. The method for preparing a nucleotide monomer having the corresponding modification and the method for introducing a modified nucleotide group into a siRNA are also well known to those skilled in the art.

Pharmaceutical Composition

The present disclosure provides a pharmaceutical composition, comprising the above siRNA as an active ingredient and a pharmaceutically acceptable carrier.

The pharmaceutically acceptable carrier may be a conventional carrier in the field of siRNA administration, for example, but not limited to, one or more of magnetic nanoparticles (such as $Fe_3O_4$ and $Fe_2O_3$-based nanoparticle), carbon nanotubes, mesoporous silicon, calcium phosphate nanoparticles, polyethylenimine (PEI), polyamidoamine (PAMAM) dendrimer, poly(L-lysine) (PLL), chitosan, 1,2-dioleoyl-3-trimethylammonium-propane (DOTAP), poly(D&L-lactic/glycolic acid) copolymer (PLGA), poly(2-aminoethyl ethylene phosphate) (PPEEA), poly(2-dimethylaminoethyl methacrylate) (PDMAEMA), and derivatives thereof.

In some embodiments, in the pharmaceutical composition, there are no special requirements for the contents of the siRNA and the pharmaceutically acceptable carrier. In some embodiments, the weight ratio of the siRNA to the pharmaceutically acceptable carrier is 1:(1-500), and in some embodiments, the weight ratio is 1:(1-50).

In some embodiments, the pharmaceutical composition may also contain other pharmaceutically acceptable excipients, which may be one or more of various conventional formulations or compounds in the art. For example, said other pharmaceutically acceptable excipients may comprise at least one of a pH buffer, a protection agent and an osmotic pressure regulator.

The pH buffer may be a tris(hydroxymethyl) aminomethane hydrochloride buffer solution with a pH of 7.5-8.5, and/or a phosphate buffer solution with a pH of 5.5-8.5, such as a phosphate buffer solution with a pH of 5.5-8.5.

The protection agent may be at least one of inositol, sorbitol, sucrose, trehalose, mannose, maltose, lactose, and glucose. The content of the protection agent may be from 0.01 wt % to 30 wt % based on the total weight of the pharmaceutical composition.

The osmotic pressure regulator may be sodium chloride and/or potassium chloride. The content of the osmotic pressure regulator renders the osmotic pressure of the pharmaceutical composition to be 200-700 milliosmol/kg. Depending on the desired osmotic pressure, those skilled in the art can readily determine the content of the osmotic pressure regulator.

In some embodiments, the pharmaceutical composition may be a liquid formulation, for example, an injection solution; or a lyophilized powder for injection, which will be mixed with a liquid excipient to form a liquid formulation upon administration. The liquid formulation may be administered by, but not limited to, subcutaneous, intramuscular or intravenous injection, and also may be administered to, but not limited to, lung by spray, or other organs (such as liver) via lung by spray. In some embodiments, the pharmaceutical composition is administered by intravenous injection.

In some embodiments, the pharmaceutical composition may be in the form of a liposome formulation. In some embodiments, the pharmaceutically acceptable carrier used in the liposome formulation comprises an amine-containing transfection compound (hereinafter also referred to as an organic amine), a helper lipid and/or a PEGylated lipid. Therein, the organic amine, the helper lipid and the PEGylated lipid may be respectively one or more selected from the amine-containing transfection compounds or the pharmaceutically acceptable salts or derivatives thereof, the helper lipids and the PEGylated lipids as described in CN103380113A, which is incorporated herein by reference in its entirety.

In some embodiments, the organic amine may be a compound as shown by Formula (201) as described in CN103380113A or a pharmaceutically acceptable salt thereof.

Formula (201)

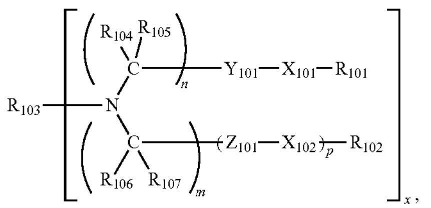

wherein, $X_{101}$ and $X_{102}$ independently of one another are selected from O, S, N-A and C-A, wherein A is hydrogen or a $C_1$-$C_2$M hydrocarbon chain;

$Y_{101}$ and $Z_{101}$ independently of one another are selected from C═O, C═S, S═O, CH—OH and $SO_2$;

$R_{101}$, $R_{102}$, $R_{103}$, $R_{104}$, $R_{105}$, $R_{106}$ and $R_{107}$ independently of one another are selected from hydrogen; a cyclic or an acyclic, substituted or unsubstituted, branched or linear aliphatic group; a cyclic or an acyclic, substituted or unsubstituted, branched or linear heteroaliphatic group; a substituted or unsubstituted, branched or linear acyl group; a substituted or unsubstituted, branched or linear aryl group; and a substituted or unsubstituted, branched or linear heteroaryl group;

x is an integer of 1-10;

n is an integer of 1-3, m is an integer of 0-20, p is 0 or 1, wherein if m=p=0, then $R_{102}$ is hydrogen; and if at least one of n and m is 2, then $R_{103}$ and nitrogen in Formula (201) form a structure as shown by Formula (202) or (203):

Formula (202)

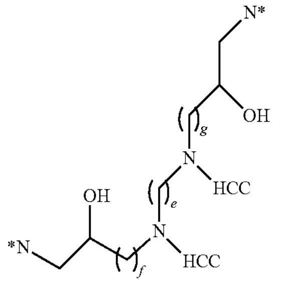

Formula (203)

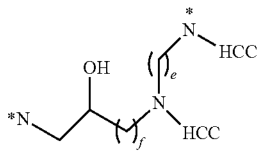

wherein g, e and f independently of one another are an integer of 1-6; "HCC" represents a hydrocarbon chain, and each *N represents a nitrogen atom shown in Formula (201).

In some embodiments, $R_{103}$ is a polyamine. In other embodiments, $R_{103}$ is a ketal. In some embodiments, $R_{101}$ and $R_{102}$ in the Formula (201) independently of one another are any substituted or unsubstituted, branched or linear alkyl or alkenyl, wherein the alkyl or alkenyl has 3-20 carbon atoms (such as 8-18 carbon atoms) and 0-4 double bonds (such as 0-2 double bonds).

In some embodiments, if n and m independently of one another are 1 or 3, $R_{103}$ is any of the following Formulae (204)-(213):

Formula (204)

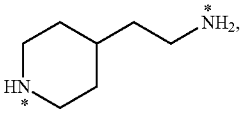

Formula (205)

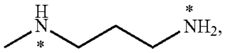

Formula (206)

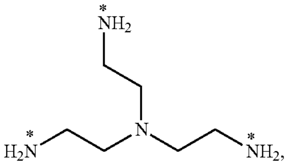

Formula (207)

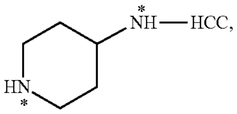

Formula (208)

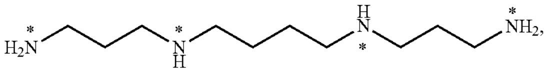

Formula (209)

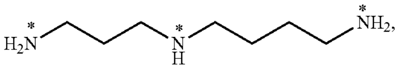

Formula (210)

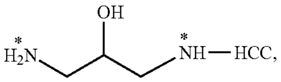

-continued

Formula (211)

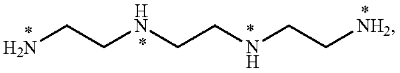

Formula (212)

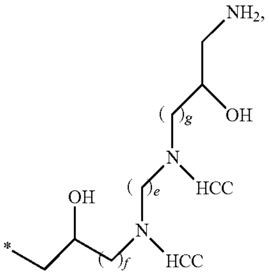

and

Formula (213)

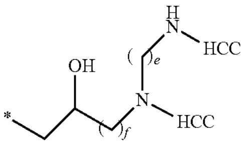

wherein, in Formulae (204)-(213), g, e and f independently of one another are an integer of 1-6, each "HCC" represents a hydrocarbon chain, and each * represents a potential attachment point of $R_{103}$ to the nitrogen atom in Formula (201), wherein each H at any * position can be replaced to achieve the attachment to the nitrogen atom in Formula (201).

The compound as shown by Formula (201) may be prepared as described in CN103380113A.

In some embodiments, the organic amine is an organic amine as shown by Formula (214) and/or an organic amine as shown by Formula (215):

Formula (214)
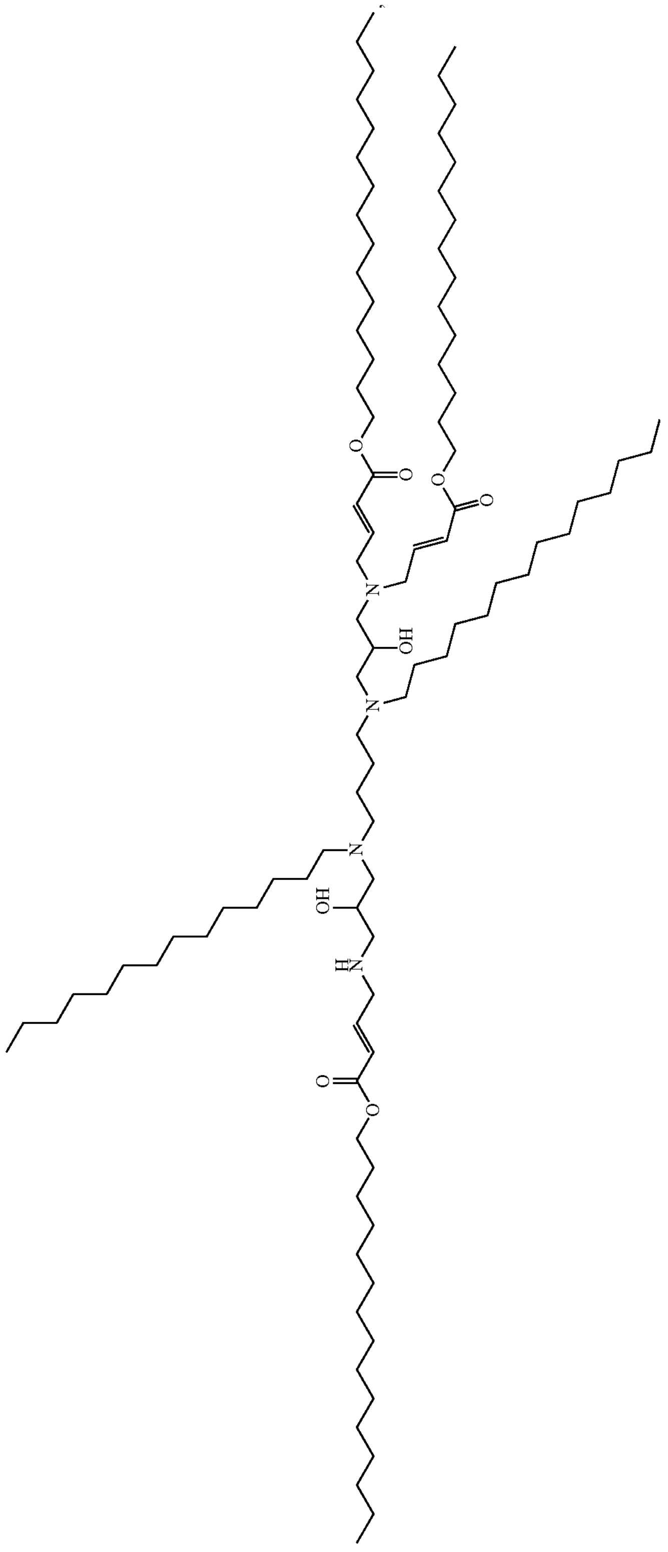

-continued
Formula (215)
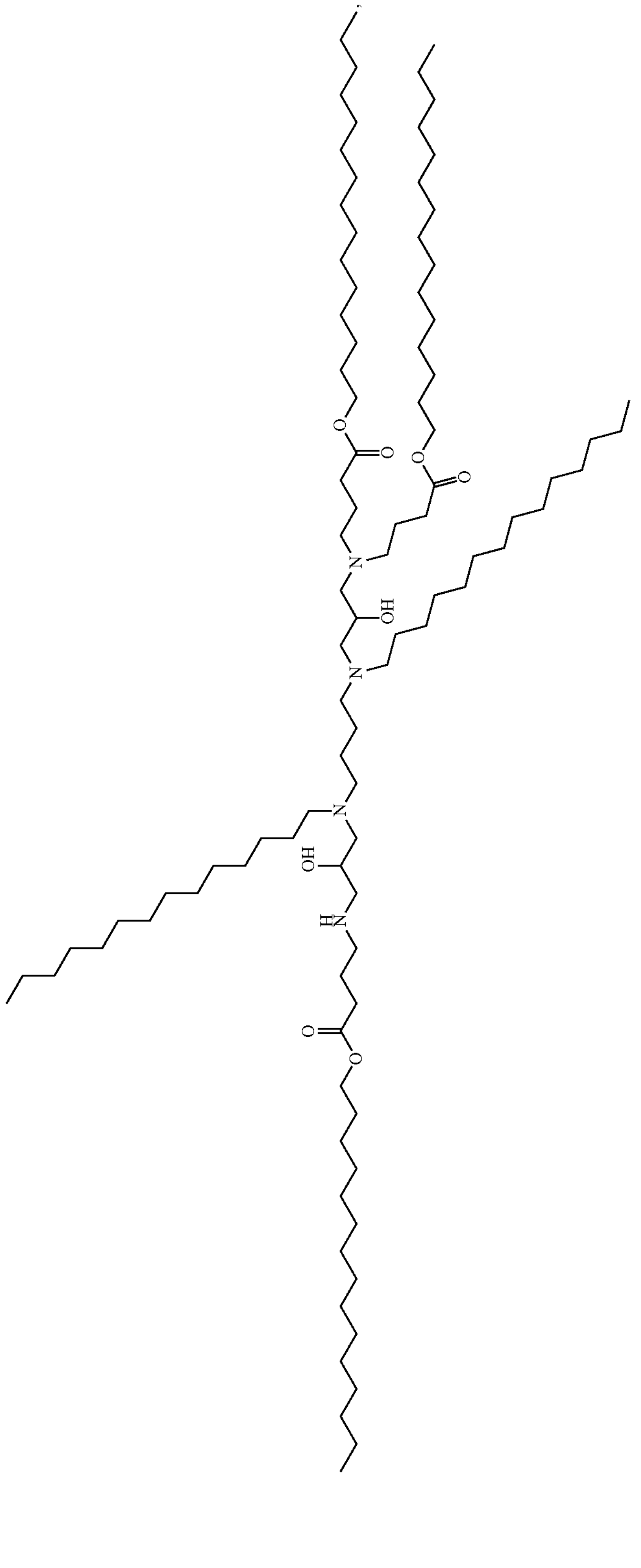

The helper lipid is cholesterol, cholesterol analogs and/or cholesterol derivatives.

The PEGylated lipid is 1,2-dipalmitoyl-sn-glycero-3-phosphatidylethanolamine-N-[methoxy(polyethylene glycol)]-2000.

In some embodiments, the molar ratio among the organic amine, the helper lipid, and the PEGylated lipid in the pharmaceutical composition is (19.7-80):(19.7-80):(0.3-50), for example, the molar ratio may be (50-70):(20-40):(3-20).

In some embodiments, the pharmaceutical composition particles formed by the siRNA of the present disclosure and the above amine-containing transfection reagents have an average diameter from about 30 nm to about 200 nm, typically from about 40 nm to about 135 nm, and more typically, the average diameter of the liposome particles is from about 50 nm to about 120 nm, from about 50 nm to about 100 nm, from about 60 nm to about 90 nm, or from about 70 nm to about 90 nm; for example, the average diameter of the liposome particles is about 30, 40, 50, 60, 70, 75, 80, 85, 90, 100, 110, 120, 130, 140, 150 or 160 nm.

In some embodiments, in the pharmaceutical composition formed by the siRNA of the present disclosure and the above amine-containing transfection reagents, the weight ratio (weight/weight ratio) of the siRNA to total lipids, e.g., the organic amines, the helper lipids and/or the PEGylated lipids, ranges from about 1:1 to about 1:50, from about 1:1 to about 1:30, from about 1:3 to about 1:20, from about 1:4 to about 1:18, from about 1:5 to about 1:17, from about 1:5 to about 1:15, from about 1:5 to about 1:12, from about 1:6 to about 1:12, or from about 1:6 to about 1:10. For example, the weight ratio of the siRNA of the present disclosure to total lipids is about 1:5, 1:6, 1:7, 1:8, 1:9, 1:10, 1:11, 1:12, 1:13, 1:14, 1:15, 1:16, 1:17, or 1:18.

In some embodiments, the pharmaceutical composition may be marketed with each component being separate, and used in the form of a liquid formulation. In some embodiments, the pharmaceutical composition formed by the siRNA of the present disclosure and the above pharmaceutically acceptable carrier may be prepared by various known processes, except for replacing the existing siRNA with the siRNA of the present disclosure. In some specific embodiments, the pharmaceutical composition may be prepared according to the following process:

The organic amines, helper lipids and PEGylated lipids are suspended in alcohol at a molar ratio as described above and mixed homogeneously to yield a lipid solution; the alcohol is used in an amount such that the resultant lipid solution is present at a total mass concentration of 2 to 25 mg/mL (e.g., 8 to 18 mg/mL). The alcohol is a pharmaceutically acceptable alcohol, such as an alcohol that is in liquid form at about room temperature, for example, one or more of ethanol, propylene glycol, benzyl alcohol, glycerol, PEG 200, PEG 300, and PEG 400, such as ethanol.

The siRNA of the present disclosure is dissolved in a buffered salt solution to produce an aqueous solution of the siRNA. The buffered salt solution has a concentration of 0.05 to 0.5 M, such as 0.1 to 0.2 M. The pH of the buffered salt solution is adjusted to 4.0 to 5.5, such as 5.0 to 5.2. The buffered salt solution is used in an amount such that the siRNA is present at a concentration of less than 0.6 mg/ml, such as 0.2 to 0.4 mg/mL. The buffered salt may be one or more selected from the group consisting of soluble acetate and soluble citrate, such as sodium acetate and/or potassium acetate.

The lipid solution and the aqueous solution of the siRNA are mixed. The product obtained by mixing is incubated at a temperature of 40 to 60° C. for at least 2 minutes (e.g., 5 to 30 minutes) to produce an incubated lipid formulation. The volume ratio of the lipid solution to the aqueous solution of the siRNA is 1:(2-5).

The incubated lipid formulation is concentrated or diluted, purified to remove impurities, and then sterilized to afford the pharmaceutical composition of the present disclosure, which has the following physicochemical parameters: a pH of 6.5 to 8, an encapsulation percentage of more than 80%, a particle size of 40 to 200 nm, a polydispersity index of less than 0.30, and an osmotic pressure of 250 to 400 mOsm/kg. For example, the physicochemical parameters may be as follows: a pH of 7.2 to 7.6, an encapsulation percentage of more than 90%, a particle size of 60 to 100 nm, a polydispersity index of less than 0.20, and an osmotic pressure of 300 to 400 mOsm/kg.

Therein, the concentration or dilution step may be performed before, after or simultaneously with removal of the impurities. The method for removing impurities may be any of various existing methods, for example, ultrafiltration with 100 kDa hollow fiber column and PBS at pH 7.4 as ultrafiltration exchange solution using tangential flow system. The method for sterilization may be any of various existing methods, such as filtration sterilization on a 0.22 m filter.

siRNA Conjugate

The present disclosure provides a siRNA conjugate comprising the above siRNA and a conjugation group conjugatively linked to the siRNA.

Generally speaking, the conjugation group comprises at least one pharmaceutically acceptable targeting group and an optional linker. Moreover, the siRNA, the linker and the targeting group are sequentially linked. In some embodiments, the number of the targeting groups is 1 to 6. In some embodiments, the number of target groups is 2 to 4. The siRNA molecule may be non-covalently or covalently conjugated to the conjugation group, for example the siRNA molecule may be covalently conjugated to the conjugation group. The conjugation site between the siRNA and the conjugation group can be at 3' terminal or 5' terminal of the sense strand of the siRNA, or at 5' terminal of the antisense strand of the siRNA, and can be within the internal sequence of the siRNA. In some embodiments, the conjugation site between the siRNA and the conjugation group is at 3' terminal of the sense strand of the siRNA.

In some embodiments, the conjugation group may be linked to the phosphate group, the 2'-hydroxy or the base of a nucleotide. The conjugation group may also be linked to the 3'-hydroxy group when the nucleotides are linked via a 2'-5'-phosphodiester bond. When the conjugation group is linked to a terminal of the siRNA, the conjugation group is typically linked to the phosphate group of a nucleotide; when the conjugation group is linked to an internal sequence of the siRNA, the conjugation group is typically linked to a ribose ring or a base. For various linking modes, reference may be made to: Muthiah Manoharan et. al. siRNA conjugates carrying sequentially assembled trivalent N-acetylgalactosamine linked through nucleosides elicit robust gene silencing in vivo in hepatocytes. ACS Chemical biology, 2015, 10(5): 1181-7.

In some embodiments, the siRNA and the conjugation group can be linked by an acid-labile or reducible chemical bond, and these chemical bonds can be degraded under the acidic environment of cell endosomes, thereby making the siRNA be in free state. For non-degradable conjugation modes, the conjugation group can be linked to the sense strand of the siRNA, thereby minimizing the effect of conjugation on the activity of the siRNA.

In some embodiments, the pharmaceutically acceptable targeting group may be a conventional ligand in the field of siRNA administration, for example, various ligands as described in WO2009082607A2, which is incorporated herein by reference in its entirety.

In some embodiments, the pharmaceutically acceptable targeting group may be one or more selected from the ligands formed by the following targeting molecules or derivatives thereof: lipophilic molecules, such as cholesterol, bile acids, vitamins (such as vitamin E), lipid molecules with different chain lengths; polymers, such as polyethylene glycol; polypeptides, such as cell-penetrating peptide; aptamers; antibodies; quantum dots; saccharides, such as lactose, polylactose, mannose, galactose, N-acetylgalactosamine (GalNAc); folate; or receptor ligands expressed in hepatic parenchymal cells, such as asialoglycoprotein, asialo-sugar residue, lipoproteins (such as high density lipoprotein, low density lipoprotein and the like), glucagon, neurotransmitters (such as adrenaline), growth factors, transferrin and the like.

In some embodiments, each ligand is independently selected from a ligand capable of binding to a cell surface receptor. In some embodiments, at least one ligand is a ligand capable of binding to a surface receptor of a hepatocyte. In some embodiments, at least one ligand is a ligand capable of binding to a surface receptor of a mammalian hepatocyte. In some embodiments, at least one ligand is a ligand capable of binding to a surface receptor of a human hepatocyte. In some embodiments, at least one ligand is a ligand capable of binding to an asialoglycoprotein receptor (ASGPR) on the surface of hepatocytes. The types of these ligands are well-known to those skilled in the art and they typically serve the function of binding to specific receptor on the surface of the target cell, thereby mediating delivery of the siRNA linked to the ligand into the target cell.

In some embodiments, the pharmaceutically acceptable targeting group may be any ligand that binds to the asialoglycoprotein receptors on the surface of mammalian hepatocytes. In some embodiments, each ligand is independently an asialoglycoprotein, such as asialoorosomucoid (ASOR) or asialofetuin (ASF). In some embodiments, the ligand is a saccharide or its derivatives.

In some embodiments, at least one ligand is a saccharide. In some embodiments, each ligand is a saccharide. In some embodiments, at least one ligand is a monosaccharide, polysaccharide, modified monosaccharide, modified polysaccharide, or saccharide derivative. In some embodiments, at least one ligand may be a monosaccharide, disaccharide or trisaccharide. In some embodiments, at least one ligand is a modified saccharide. In some embodiments, each ligand is a modified saccharide. In some embodiments, each ligand is independently selected from a polysaccharide, modified polysaccharide, monosaccharide, modified monosaccharide, polysaccharide derivative, and monosaccharide derivative. In some embodiments, each ligand or at least one ligand may be independently selected from the group consisting of glucose and its derivatives, mannose and its derivatives, galactose and its derivatives, xylose and its derivatives, ribose and its derivatives, fucose and its derivatives, lactose and its derivatives, maltose and its derivatives, arabinose and its derivatives, fructose and its derivatives, and sialic acid.

In some embodiments, each ligand may be independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, L-4-thioribose. Other options of the ligand may be found, for example, in the disclosure of CN105378082A, which is incorporated herein by reference in its entirety.

In some embodiments, the pharmaceutically acceptable targeting group in the siRNA conjugate may be galactose or N-acetylgalactosamine, wherein the galactose or N-acetylgalactosamine molecules may be be mono-, bi-, tri-, or tetra-valent. It should be understood that the terms mono-, bi-, tri-, or tetra-valent described herein respectively mean that the molar ratio of the siRNA molecule to the galactose or N-acetylgalactosamine molecule in the siRNA conjugate is 1:1, 1:2, 1:3 or 1:4, wherein the siRNA conjugate is formed from the siRNA molecule and the conjugation group containing galactose or N-acetylgalactosamine molecule as the targeting group. In some embodiments, the pharmaceutically acceptable targeting group is N-acetylgalactosamine. In some embodiments, when the double-stranded oligonucleotide of the present disclosure is conjugated to a conjugation group comprising N-acetylgalactosamine, the N-acetylgalactosamine molecule is trivalent or tetravalent. In some embodiments, when the siRNA of the present disclosure is conjugated to a conjugation group containing N-acetylgalactosamine, the N-acetylgalactosamine molecule is trivalent.

The targeting group can be linked to the siRNA molecule via an appropriate linker, and the appropriate linker can be selected by those skilled in the art according to the specific type of the targeting group. The types of these linkers and targeting groups and the linking modes with the siRNA may be found in the disclosure of WO2015006740A2, which is incorporated herein by reference in its entirety.

In some embodiments, when the targeting group is N-acetylgalactosamine, a suitable linker may have the following structure as shown by Formula (301):

Formula (301)

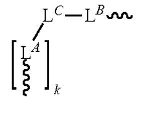

wherein, k is an integer of 1-3;

$L^A$ is an amide bond-comprising chain moiety that has a structure as shown by Formula (302), and two terminals of each $L^A$ are respectively linked to the targeting group and the $L^C$ moiety through an ether bond:

Formula (302)

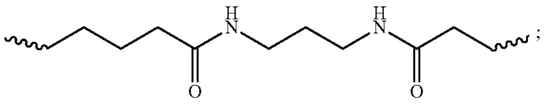

$L^B$ is a N-acylpyrrolidine-comprising chain moiety that has a structure as shown by Formula (303), wherein the chain moiety has a carbonyl group at one terminal and is linked to the $L^C$ moiety through an amide bond, and has an oxy group at the other terminal and is linked to the siRNA via a phosphoester bond:

Formula (303)

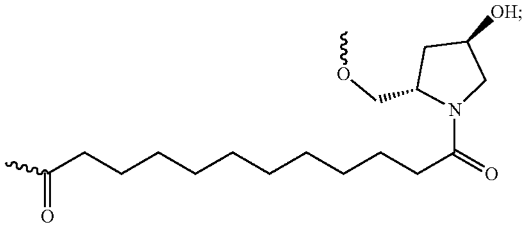

$L^C$ is a bivalent to tetravalent linking group based on hydroxymethyl aminomethane, dihydroxymethyl aminomethane or trihydroxymethyl aminomethane, and $L^C$ is linked to $L^A$ moieties through an ether bond via an oxygen atom, and is linked to $L^B$ moiety through an amide bond via a nitrogen atom.

In some embodiments, when n=3 and $L^C$ is a tetravalent linking group based on trihydroxymethyl aminomethane, the siRNA conjugate formed by linking N-acetylgalactosamine molecules with a siRNA molecule via $-(L^A)_3$-trihydroxymethyl aminomethane-$L^B$- as a linker has a structure as shown by Formula (304):

Formula (304)

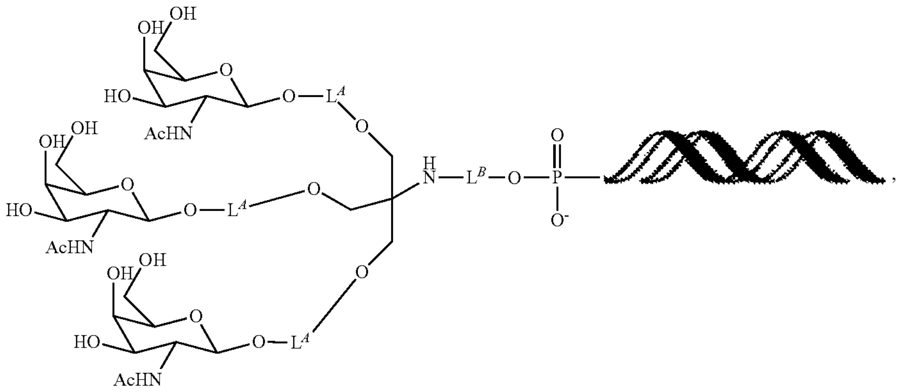

wherein the double helix structure represents a siRNA.

Likewise, the conjugation site between the siRNA and the conjugation group can be at 3'-terminal or 5'-terminal of the sense strand of the siRNA, or at 5'-terminal of the antisense strand, or within the internal sequence of the siRNA.

In some embodiments, the 3'-terminal of the sense strand of the siRNA of the present disclosure is covalently conjugated to three N-acetylgalactosamine molecules via a linker -($L^A$)3-trihydroxymethyl aminomethane-$L^B$-, to afford a siRNA conjugate in which the molar ratio of the siRNA molecule to the GalNAc molecule is 1:3 (hereinafter also referred to as $(GalNAc)_3$-siRNA), and this conjugate has a structure as shown by Formula (305):

Formula (305)

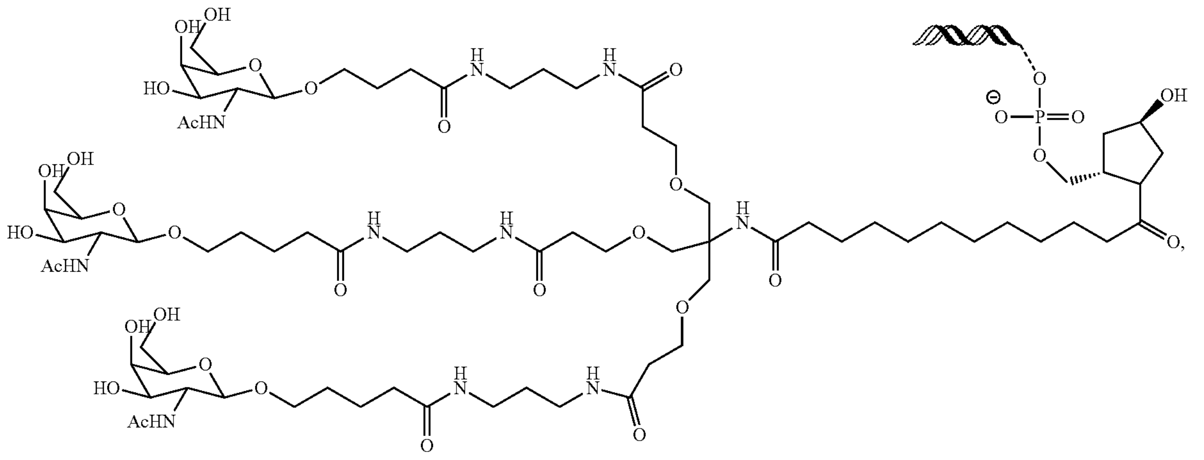

wherein the double helix structure represents a siRNA; and the linker is linked to 3'-terminal of the sense strand of the siRNA.

In some embodiments, when the targeting group is N-acetylgalactosamine, a suitable linker may have a structure as shown by Formula (306):

Formula (306)

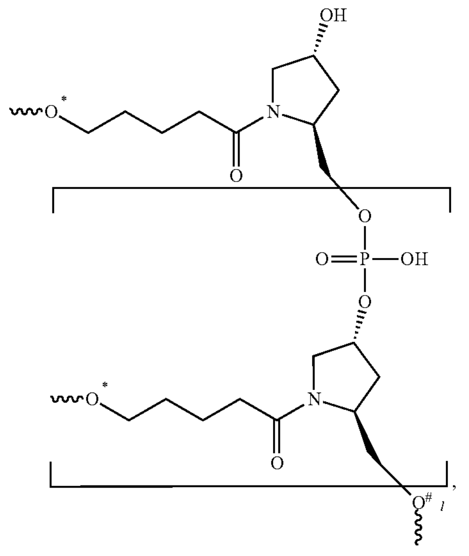

wherein, l is an integer of 0-3;

* represents a site on the linker linked to the targeting group via an ether bond; and # represents a site on the linker linked to the siRNA via a phosphoester bond.

In some specific embodiments, when l=2, the siRNA conjugate has a structure as shown by Formula (307):

Formula (307)

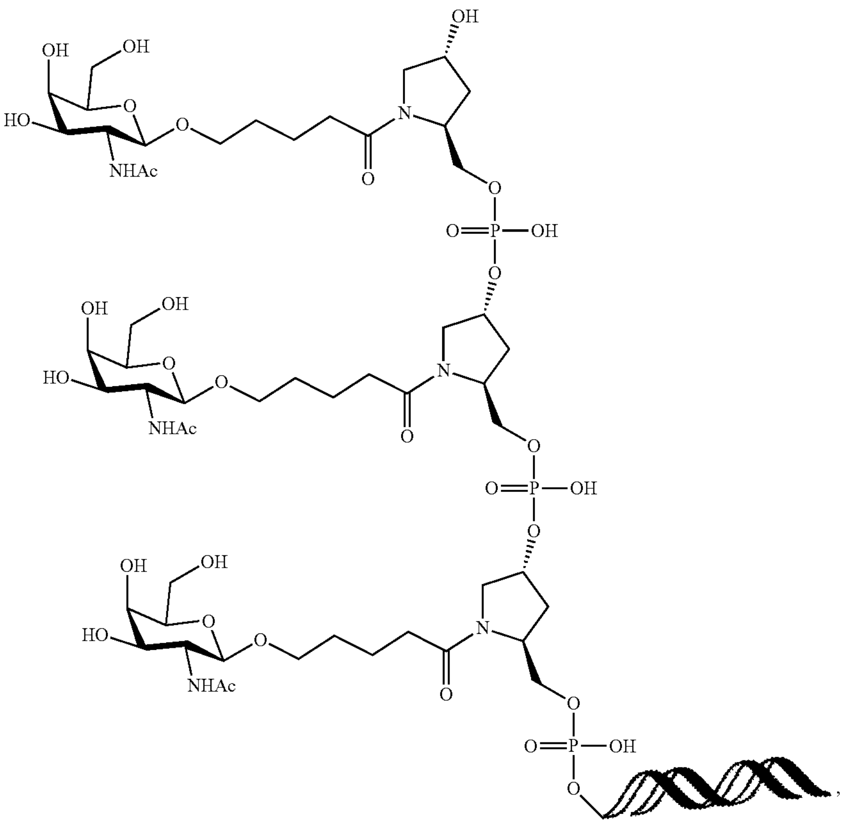

wherein, the double helix structure denotes a siRNA; and the linker is linked to 3'-terminal of the sense strand of the siRNA.

The above conjugates can be synthesized according to the method described in detail in the prior art. For example, WO2015006740 A2 describes in detail the preparation methods of various conjugates. The siRNA conjugate of the present disclosure may be obtained by the methods well-known to those skilled in the art. For example, WO2014025805A1 describes the preparation method of the conjugate having the structure as shown by Formula (305). Rajeev et al., ChemBioChem 2015, 16, 903-908 describes the preparation method of the conjugate having the structure as shown by Formula (307).

In some embodiments, the siRNA conjugate has a structure as shown by Formula (308):

Formula (308)

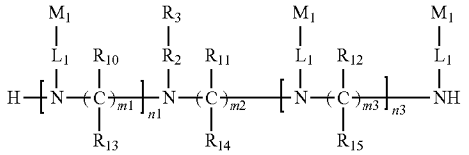

wherein, n1 is an integer of 1-3, and n3 is an integer of 0-4;

m1, m2, and m3 independently of one another are an integer of 2-10;

$R_{10}$, $R_{11}$, $R_{12}$, $R_{13}$, $R_{14}$, and $R_{15}$ independently of one another are H, or selected from the group consisting of $C_1$-$C_{10}$ alkyl, $C_1$-$C_{10}$ haloalkyl, and $C_1$-$C_{10}$ alkoxy, $R_3$ is a group having a structure as shown by Formula (A59):

Formula (A59)

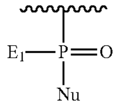

wherein $E_1$ is OH, SH or $BH_2$; and Nu is the siRNA of the present disclosure;

$R_2$ is a linear alkylene of 1 to 20 carbon atoms in length, wherein one or more carbon atoms are optionally replaced with any one or more groups selected from the group consisting of: C(O), NH, O, S, CH═N, $S(O)_2$, $C_2$-$C_{10}$ alkenylene, $C_2$-$C_{10}$ alkynylene, $C_1$-$C_{10}$ arylene, $C_3$-$C_{18}$ heterocyclylene, and $C_5$-$C_{10}$ heteroarylene, and wherein $R_2$ optionally has any one or more substituents selected from the group consisting of: $C_1$-$C_{10}$ alkyl, $C_1$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —NH($C_1$-$C_{10}$ alkylphenyl), —N($C_1$-$C_{10}$ alkyl)($C_1$-$C_{10}$ alkylphenyl), cyano, nitro, —$CO_2H$, —C(O)$OC_1$-$C_{10}$ alkyl, —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2NH$($C_1$-$C_{10}$ alkyl), —$SO_2NH$(phenyl), —$NHSO_2$($C_1$-$C_{10}$ alkyl), —$NHSO_2$(phenyl), and —$NHSO_2$($C_1$-$C_{10}$ haloalkyl);

each $L_1$ is a linear alkylene of 1 to 70 carbon atoms in length, wherein one or more carbon atoms are optionally replaced with any one or more groups selected from the group consisting of: C(O), NH, O, S, CH═N, $S(O)_2$, $C_2$-$C_{10}$ alkenylene, $C_2$-$C_{10}$ alkynylene, $C_1$-$C_{10}$ arylene, $C_3$-$C_{18}$ heterocyclylene, and $C_5$-$C_{10}$ heteroarylene, and wherein $L_1$ optionally has any one or more substituents selected from the group consisting of: $C_1$-$C_{10}$ alkyl, $C_1$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —NH($C_1$-$C_{10}$ alkylphenyl), —N($C_1$-$C_{10}$ alkyl)($C_1$-$C_{10}$ alkylphenyl), cyano, nitro, —$CO_2H$, —C(O)$OC_1$-$C_{10}$ alkyl, —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2NH$($C_1$-$C_{10}$ alkyl), —$SO_2NH$(phenyl), —$NHSO_2$($C_1$-$C_{10}$ alkyl), —$NHSO_2$(phenyl), and —$NHSO_2$($C_1$-$C_{10}$ haloalkyl).

In some embodiments, $L_1$ may be selected from the group consisting of the groups of Formulae (A1)-(A26) and any combination thereof, wherein the structures and definitions of A1-A26 are as follows:

(A1)

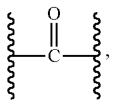

-continued (A2)

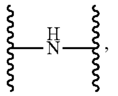

(A3)

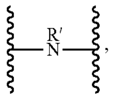

(A4)

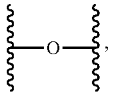

(A5)

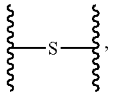

(A6)

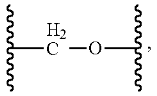

(A7)

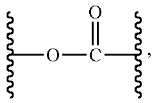

(A8)

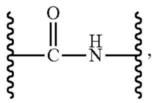

(A9)

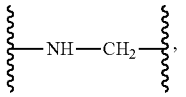

(A10)

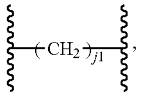

(A11)

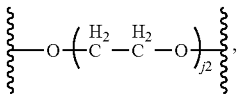

(A12)

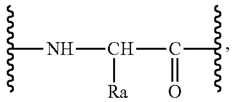

(A13)

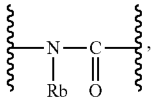

(A14)

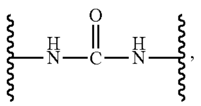

(A15)

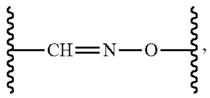

-continued
(A16)
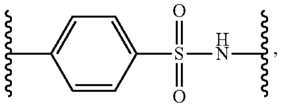
(A17)
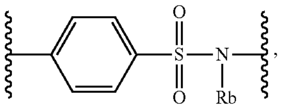
(A18)
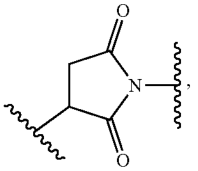
(A19)
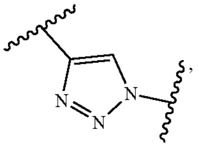
(A20)
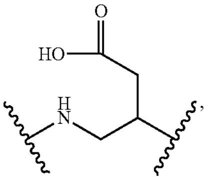
(A21)
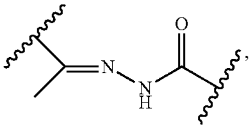
(A22)
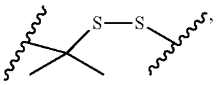
(A23)
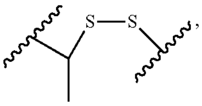
(A24)
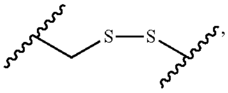
(A25)
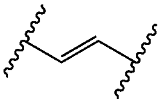
and
(A26)
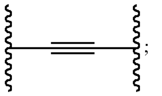
wherein j1 is an integer of 1-20;
j2 is an integer of 1-20;
R' is a $C_1$-$C_{10}$ alkyl;
Ra is selected from the group consisting of the groups of Formulae (A27)-(A45) or any combination thereof:
(A27)
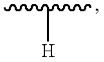
(A28)
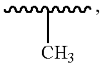
(A29)
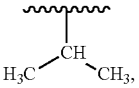
(A30)
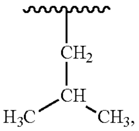
(A31)
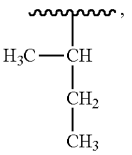
(A32)
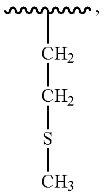
(A33)
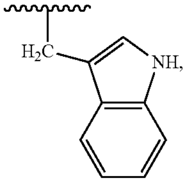
(A34)
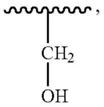
(A35)
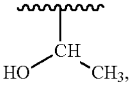
(A36)
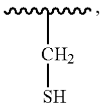
(A37)
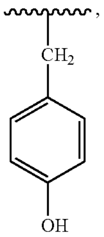

-continued (A38)

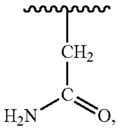

(A39)

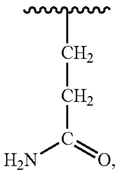

(A40)

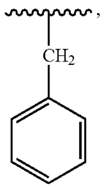

(A41)

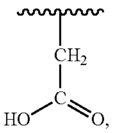

(A42)

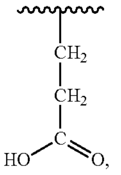

(A43)

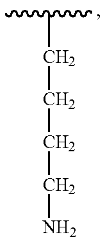

(A44)

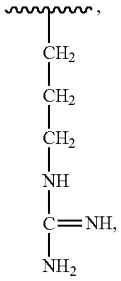

and (A45)

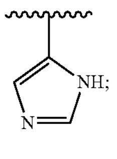

Rb is a $C_1$-$C_{10}$ alkyl; and

~~~~ represents the site where a group is linked to the rest of the molecule.

Those skilled in the art would understand that, though $L_1$ is defined as a linear alkyl for convenience, but it may not be a linear group or be named differently, such as an amine or alkenyl produced by the above replacement and/or substitution. For the purpose of the present disclosure, the length of $L_1$ is the number of the atoms in the chain linking the two attachment points. For this purpose, a ring obtained by replacing a carbon atom in the linear alkylene, such as a heterocyclylene or heteroarylene, is counted as one atom.

$M_1$ represents a targeting group, of which the definitions and options are the same as those of the above targeting groups. In some embodiments, each $M_1$ is independently one selected from the ligands that have affinity to the asialoglycoprotein receptor on the surface of mammalian hepatocytes.

When $M_1$ is a ligand that has affinity to the asialoglycoprotein receptor on the surface of mammalian hepatocyte, in some embodiments, n1 may be an integer of 1-3, and n3 may be an integer of 0-4 to ensure that the number of the $M_1$ targeting group in the conjugate may be at least 2. In some embodiments, $n1+n3 \geq 2$, such that the number of the $M_1$ targeting group is at least 3, thereby rendering the $M_1$ targeting group to more easily bind to the asialoglycoprotein receptor on the surface of hepatocytes, which may facilitates the endocytosis of the conjugate into cells. Experiments have shown that when the number of the $M_1$ ligand is greater than 3, the ease of the binding between the $M_1$ ligand and the asialoglycoprotein receptor on the surface of hepatocytes is not significantly increased. Therefore, in view of various aspects such as synthesis convenience, structure/process costs and delivery efficiency, in some embodiments, n1 is an integer of 1-2, n3 is an integer of 0-1, and $n1+n3=2-3$.

In some embodiments, when m1, m2, and m3 independently of one another are an integer selected from 2-10, the steric positions among many $M_1$ ligands may be suitable for the binding between the $M_1$ ligands and the asialoglycoprotein receptor on the surface of hepatocytes. In order to make the conjugate of the present disclosure have simpler structure, easier synthesis and/or reduced cost, in some embodiments, m1, m2 and m3 independently of one another are an integer of 2-5; in some embodiments, $m1=m2=m3$.

Those skilled in the art would understand that when $R_{10}$, $R_{11}$, $R_{12}$, $R_{13}$, $R_{14}$, and $R_{15}$ independently of one another is one selected from H, $C_1$-$C_{10}$ alkyl, $C_1$-$C_{10}$ haloalkyl, and $C_1$-$C_{10}$ alkoxy, they would not change the properties of the conjugate of the present disclosure and could all achieve the purpose of the present disclosure. In some embodiments, $R_{10}$, $R_{11}$, $R_{12}$, $R_{13}$, $R_{14}$, and $R_{15}$ independently of one another are selected from H, methyl and ethyl. In some embodiments, $R_{10}$, $R_{11}$, $R_{12}$, $R_{13}$, $R_{14}$, and $R_{15}$ are H.

$R_3$ is a group having the structure as shown by Formula A59, wherein $E_1$ is OH, SH or $BH_2$, and considering the easy availability of the starting materials, in some embodiments, $E_1$ is OH or SH.

$R_2$ is selected to achieve the linkage between the group as shown by Formula A59 and the N atom on a nitrogenous backbone. In the context of the present disclosure, a "nitrogenous backbone" refers to a chain structure in which the N atom are coadjacently linked to the carbon atoms to which $R_{10}$, $R_{11}$, $R_{12}$, $R_{13}$, $R_{14}$, and $R_{15}$ are attached. Therefore, $R_2$ may be any linking group capable of linking the group as shown by Formula (A59) to the N atom on the nitrogenous backbone by suitable means. In some embodiments, in the case where the siRNA conjugate as shown by Formula (308) is prepared by a solid phase synthesis process, $R_2$ group needs to have both a site linking to the N atom on the nitrogenous backbone and a site linking to the P atom in $R_3$.
~~~~

In some embodiments, in $R_2$, the site linking to the N atom on the nitrogenous backbone forms an amide bond with the N atom, and the site linking to the P atom in $R_3$ forms a phosphoester bond with the P atom. In some embodiments, $R_2$ may be 135, B6, B5', or B6':

(B5)

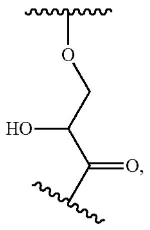

(B8)

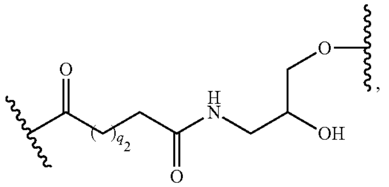

(B5')

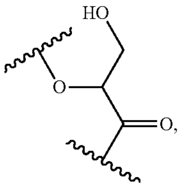

or (B6')

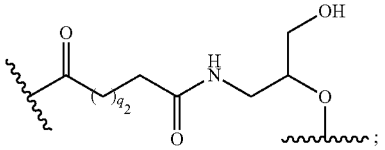

wherein  represents the site where the group is linked via a covalent bond;

$q_2$ is an integer of 1-10; in some embodiments, $q_2$ is an integer of 1-5.

$L_1$ is used to link the $M_1$ targeting group to the N atom on the nitrogenous backbone, thereby providing liver targeting function for the siRNA conjugate as shown by Formula (308). In some embodiments, $L_1$ is selected from the linkage combinations of one or more of Formulae (A1)-(A26). In some embodiments, $L_1$ is selected from the linkage combinations of one or more of Formulae (A1), (A4), (A5), (A6), (A8), (A10), (A11), and (A13). In some embodiments, $L_1$ is selected from the linkage combinations of at least two of Formulae (A1), (A4), (A8), (A10), and (A11). In some embodiments, $L_1$ is selected from the linkage combinations of at least two of Formulae (A1), (A8) and (A10).

In some embodiments, $L_1$ may have a length of 3 to 25, 3 to 20, 4 to 15 or 5 to 12 atoms. In some embodiments, $L_1$ has a length of 3, 4, 5, 6, 7, 8, 9, 10, 11, 12, 13, 14, 15, 16, 17, 18, 19, 20, 21, 22, 23, 24, 25, 30, 35, 40, 45, 50, 55, or 60 atoms.

In some embodiments, j1 is an integer of 2-10, and in some embodiments, j1 is an integer of 3-5. In some embodiments, j2 is an integer of 2-10, and in some embodiments, j2 is an integer of 3-5. R' is a $C_1$-$C_4$ alkyl, and in some embodiments, R' is one of methyl, ethyl and isopropyl. Ra is one of Formulae (A27), (A28), (A29), (A30), and (A31), and in some embodiments, Ra is Formula (A27) or (A28). Rb is a $C_1$-$C_5$ alkyl, and in some embodiments, is one of methyl, ethyl, isopropyl, and butyl. In some embodiments, j1, j2, R', Ra, and Rb in Formulae (A1)-(A26) are respectively selected to achieve the linkage between the $M_1$ targeting groups and the N atom on the nitrogenous backbone, and to make the steric position among the $M_1$ targeting groups more suitable for binding between the $M_1$ targeting groups and the asialoglycoprotein receptor on the surface of hepatocytes.

In some embodiments, the siRNA conjugate has a structure as shown by Formula (403), (404), (405), (406), (407), (408), (409), (410), (411), (412), (413), (414), (415), (416), (417), (418), (419), (420), (421) or (422):

Formula (403)

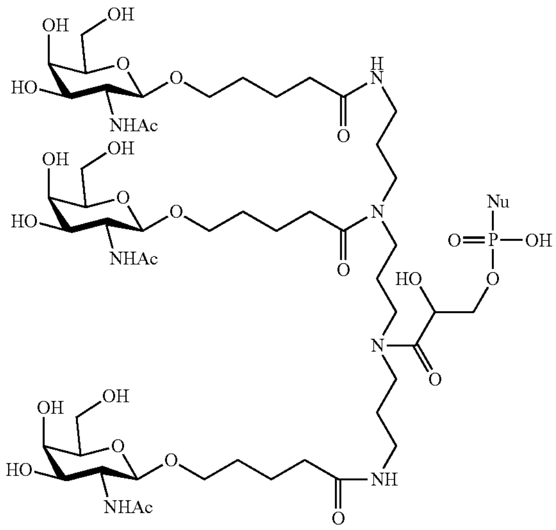

-continued
Formula (404)
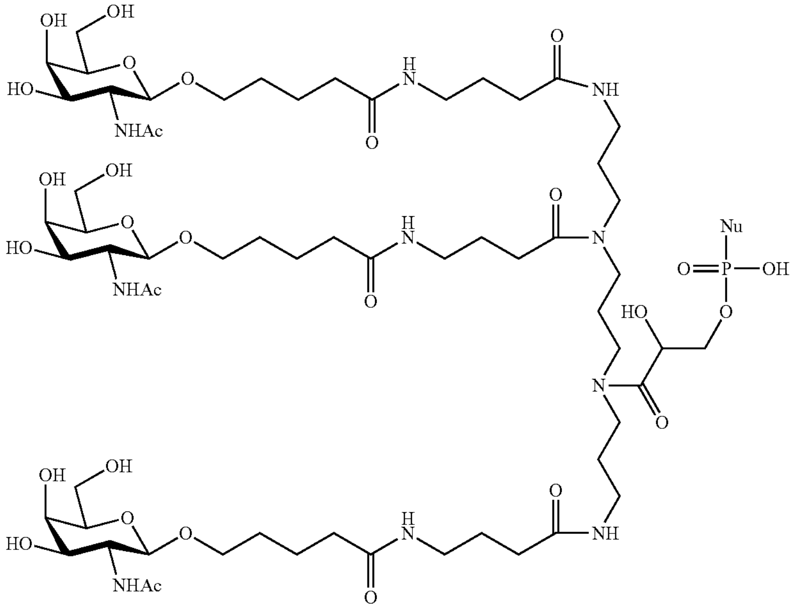
Formula (405)
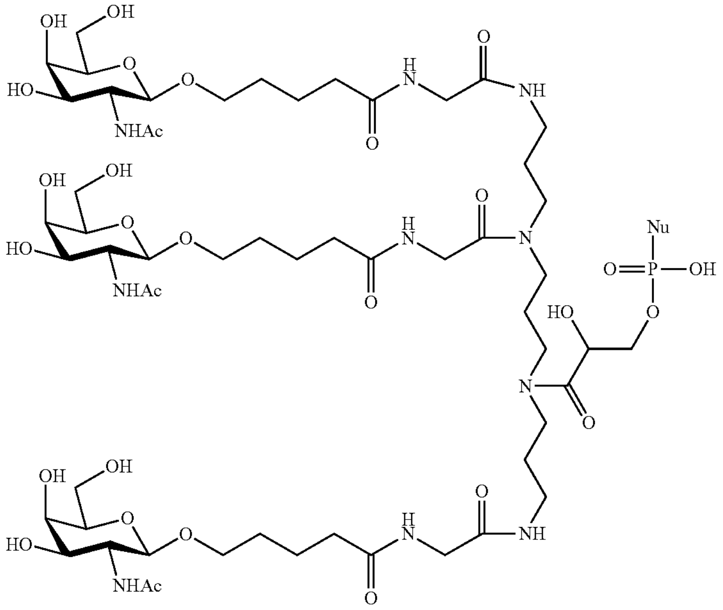

-continued
Formula (406)
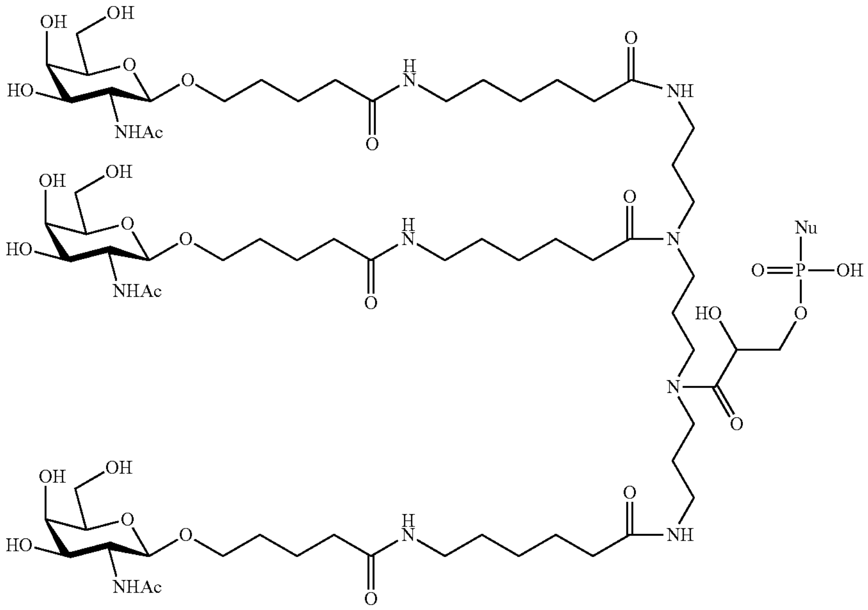
Formula (407)
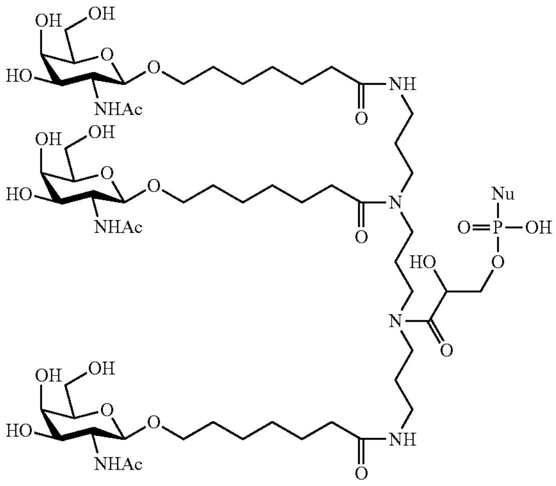
Formula (408)
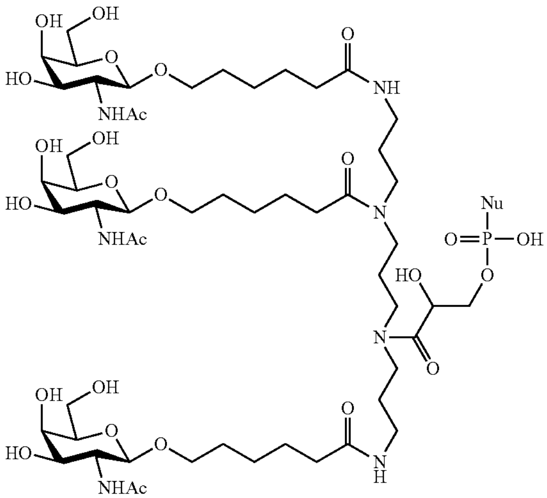
Formula (409)
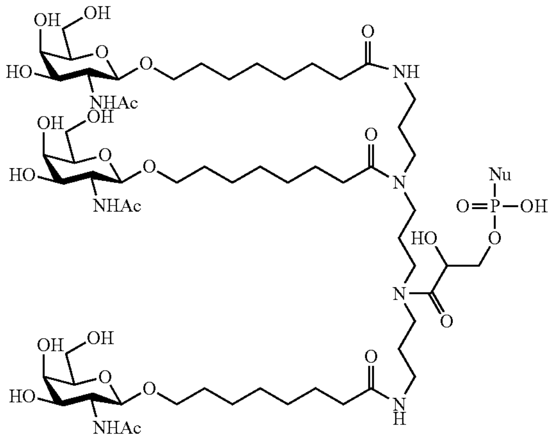
Formula (410)
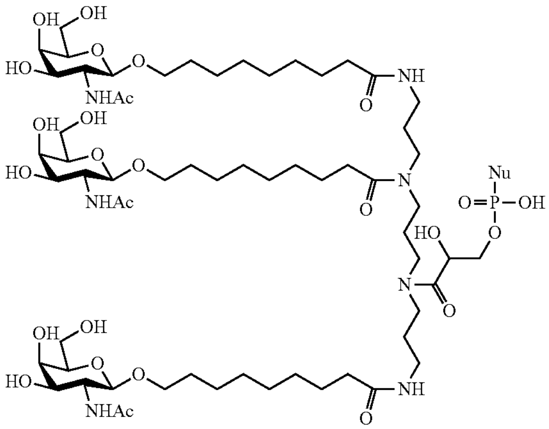

-continued
Formula (411)
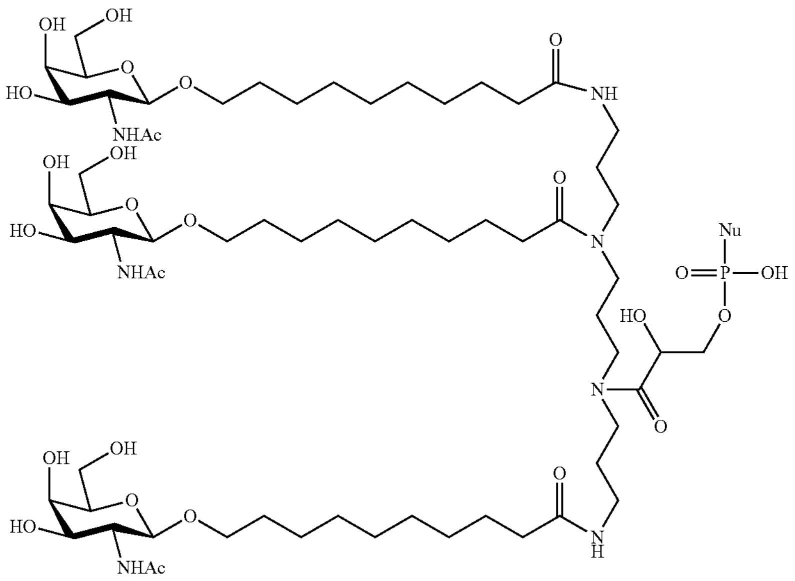
Formula (412)
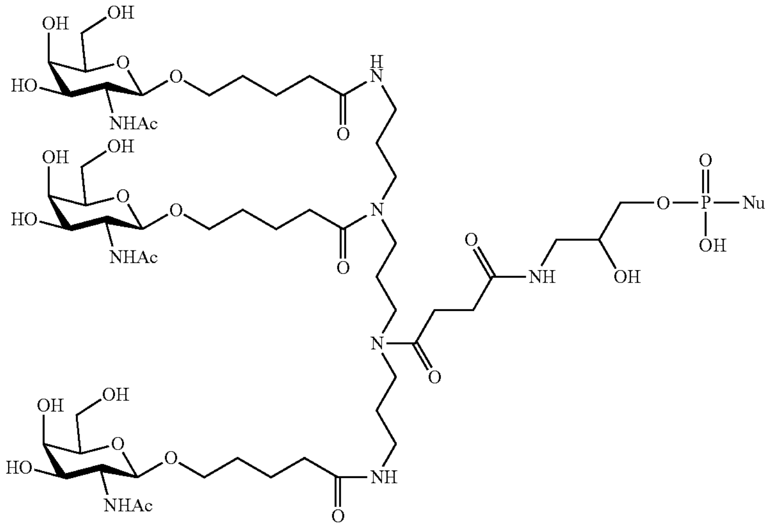
Formula (413)
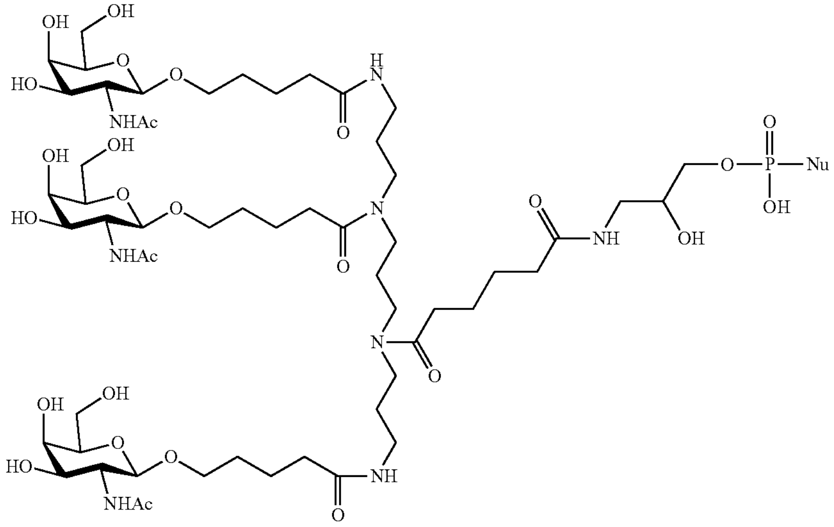

-continued
Formula (414)
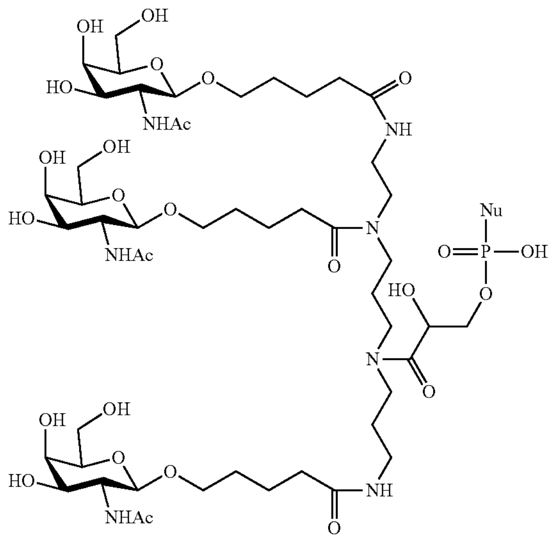
Formula (415)
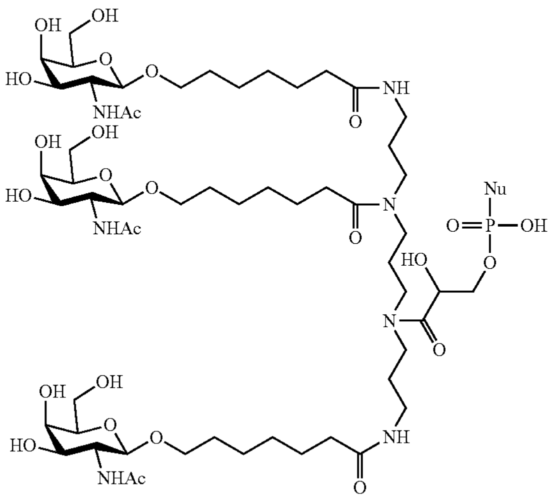
Formula (416)
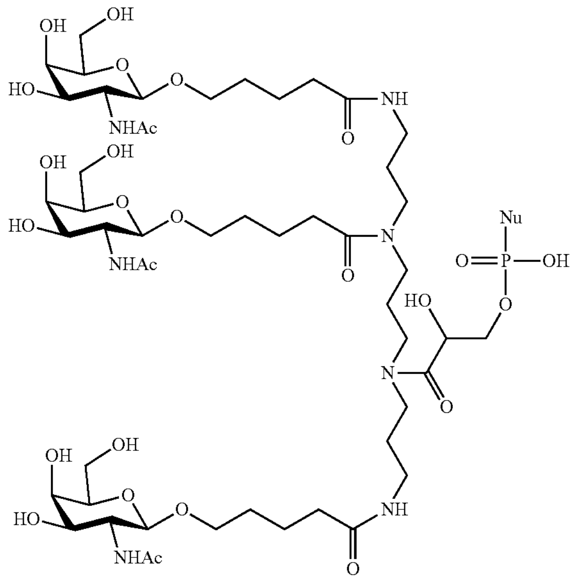

Formula (417)
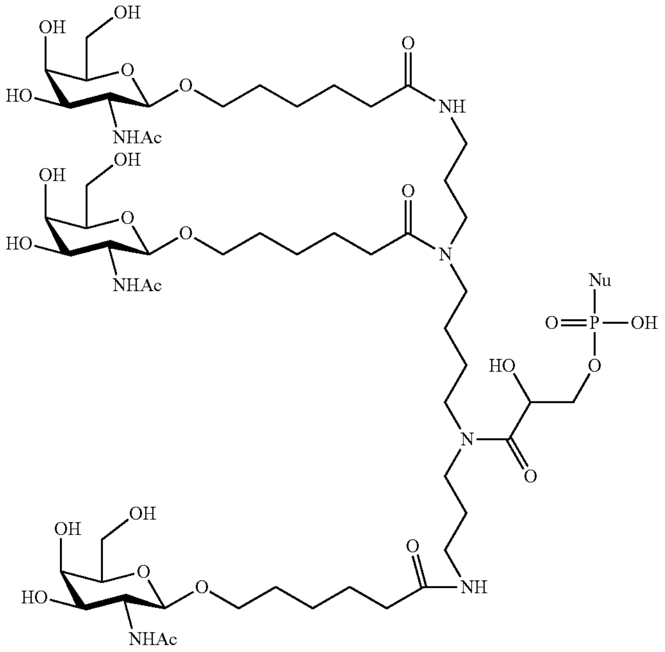
Formula (418)
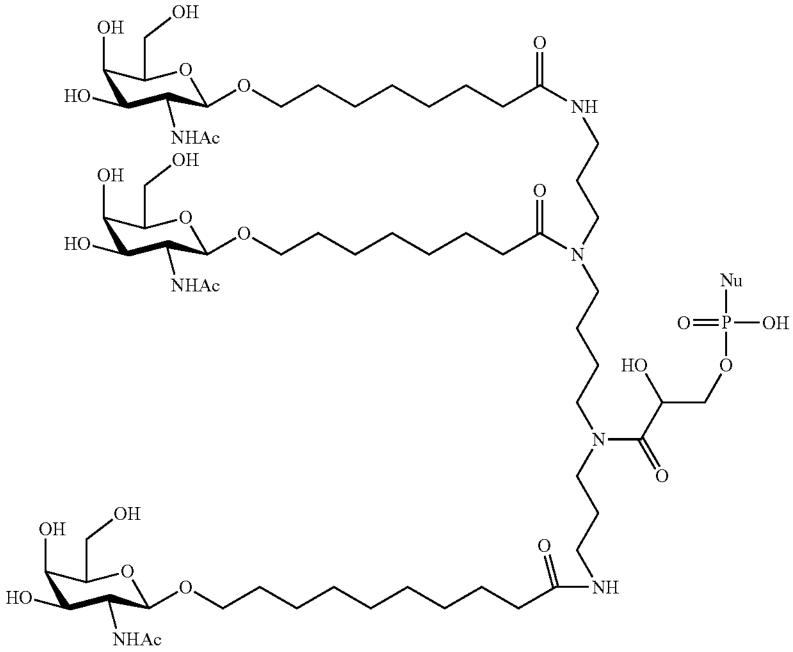

-continued
Formula (419)
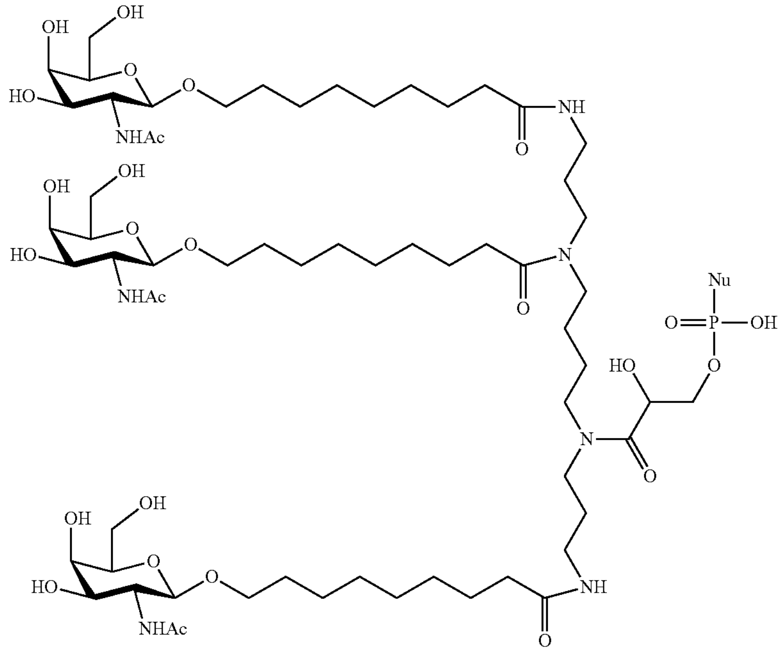
Formula (420)
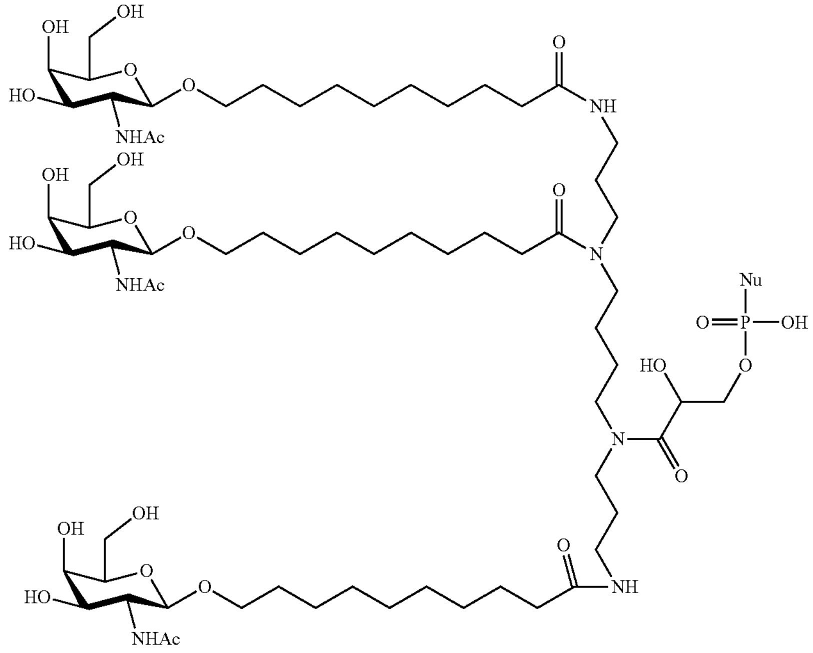

-continued
Formula (421)
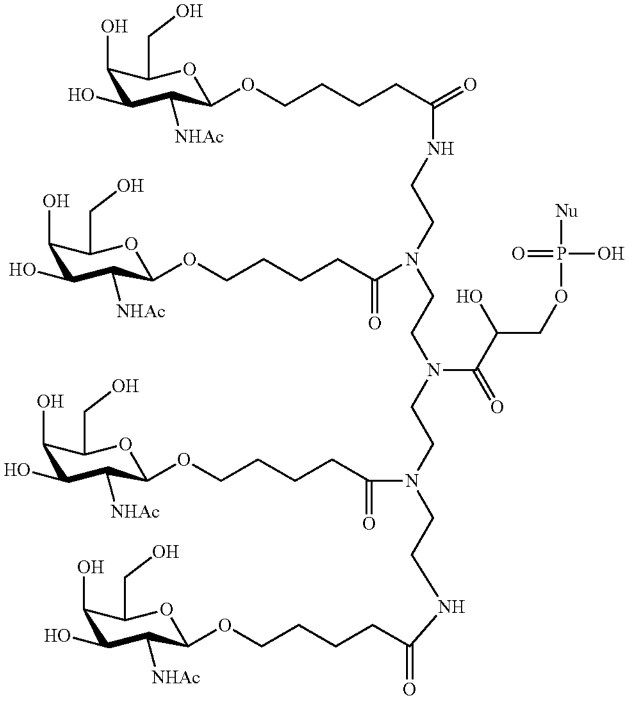
Formula (422)
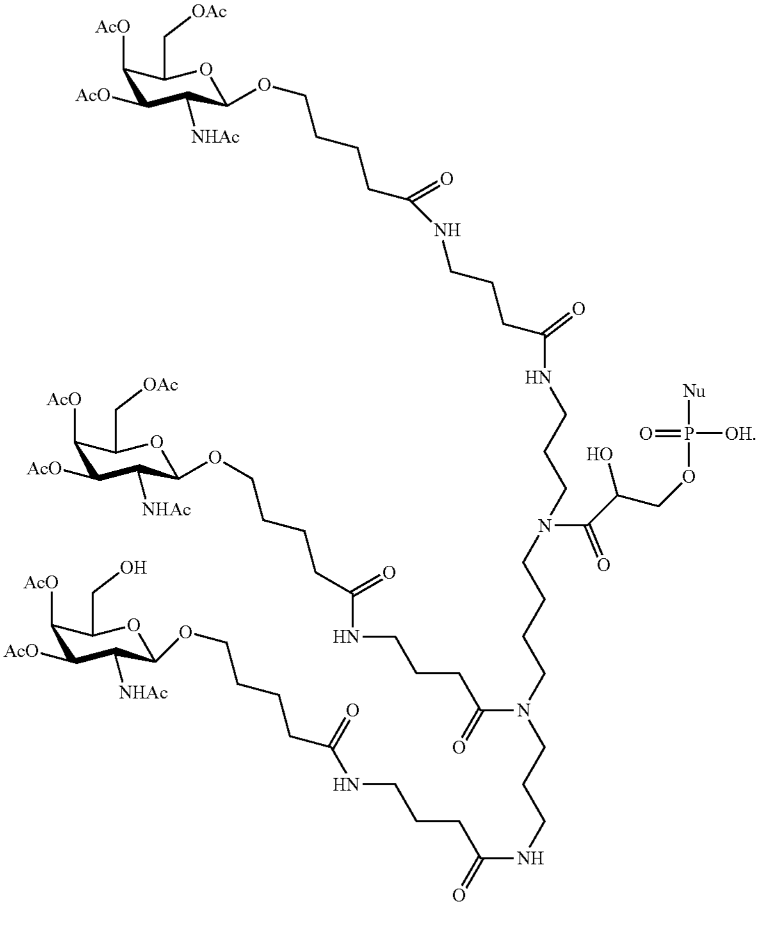

In some embodiments, the P atom in Formula A59 may be linked to any possible position in the siRNA sequence. For example, the P atom in Formula A59 may be linked to any nucleotide in the sense or antisense strand of the siRNA. In some embodiments, the P atom in Formula A59 is linked to any nucleotide in the sense strand of the siRNA. In some embodiments, the P atom in Formula A59 may be linked to a terminal region of the sense or antisense strand of the siRNA. In some embodiments, the P atom in Formula A59 is linked to a terminal region of the sense strand of the siRNA. Said terminal region refers to the first 4 nucleotides counted from one terminal of the sense or antisense strand. In some embodiments, the P atom in Formula A59 is linked to either terminal of the sense or antisense strand of the siRNA. In some embodiments, the P atom in Formula A59 is linked to 3' terminal of the sense strand of the siRNA. In the case where the P atom in Formula A59 is linked to the above position of the sense strand of the siRNA, after having entered into cells, the siRNA conjugate as shown by Formula (308) can release a separate antisense strand of the siRNA during unwinding, thereby blocking the translation of the APOC3 mRNA into a protein and inhibiting the expression of apolipoprotein C3 gene.

In some embodiments, the P atom in Formula A59 may be linked to any possible position of a nucleotide in the siRNA, for example, position 5', position 2', position 3', or the base of the nucleotide. In some embodiments, the P atom in Formula A59 may be linked to position 2', 3', or 5' of a nucleotide in the siRNA by forming a phosphodiester bond. In some embodiments, the P atom in Formula A59 is linked to an oxygen atom formed by dehydrogenation of 3'-hydroxy of the nucleotide at 3' terminal of the sense strand in the siRNA (in this case, the P atom in Formula A59 may be also regarded as the P atom in the phosphate group of the siRNA), or the P atom in Formula A59 is linked to a nucleotide by substituting a hydrogen atom in 2'-hydroxy of a nucleotide of the sense strand in the siRNA, or the P atom in Formula A59 is linked to a nucleotide by substituting a hydrogen atom in 5'-hydroxy of the nucleotide at 5' terminal of the sense strand in the siRNA.

The inventors of the present disclosure have surprisingly found that the siRNA conjugate of the present disclosure exhibits significantly improved stability in plasma and low off-target effect, without significantly reduced silencing activity against APOC3 mRNA, and further shows higher inhibitory effect on blood lipid. Thus, in some embodiments, the siRNA in the siRNA conjugates of the present disclosure is shown in Tables 1, 2, 3, 4, and 5:

TABLE 1

The sequences of first siRNAs in the conjugates of the present disclosure

| siRNA NO. | SEQ ID NO: | Sequence direction 5'-3' |
|---|---|---|
| siAPa1 | 9 | UUAAAAGGGACAGUAUUCU |
| | 10 | AGAAUACUGUCCCUUUUAAGC |
| siAPa2 | 11 | GCUUAAAAGGGACAGUAUUCU |
| | 12 | AGAAUACUGUCCCUUUUAAGCAA |
| siAPa1-M1 | 61 | UmUmAmAmAfAmGfGfGfAmCmAmGmUmAmUmUmCmUm |
| | 62 | AmGfAmAmUmAfCmUfGfUmCmCmCmUfUmUfUmAmAmGmCm |
| siAPa2-M1 | 63 | GmCmUmUmAmAmAfAmGfGfGfAmCmAmGmUmAmUmUmCmUm |
| | 64 | AmGfAmAmUmAfCmUfGfUmCmCmCmUfUmUfUmAmAmGmCmAmAm |
| siAPa1-M2 | 65 | UmUmAmAmAfAmGfGfGfAmCmAmGmUmAmUmUmCmUm |
| | 66 | AmGfAmAmUmAfCmUmGmUmCmCmCmUfUmUfUmAmAmGmCm |
| siAPa2-M2 | 67 | GmCmUmUmAmAmAfAmGfGfGfAmCmAmGmUmAmUmUmCmUm |
| | 68 | AmGfAmAmUmAfCmUmGmUmCmCmCmUfUmUfUmAmAmGmCmAmAm |
| siAPa1-M3 | 69 | UmUmAmAmAmAmGfGfGfAmCmAmGmUmAmUmUmCmUm |
| | 70 | AmGfAmAmUmAfCmUmGmUmCmCmCmUfUmUfUmAmAmGmCm |
| siAPa2-M3 | 71 | GmCmUmUmAmAmAmAmGfGfGfAmCmAmGmUmAmUmUmCmUm |
| | 72 | AmGfAmAmUmAfCmUmGmUmCmCmCmUfUmUfUmAmAmGmCmAmAm |
| siAPa1-M1S | 121 | UmsUmsAmAmAfAmGfGfGfAmCmAmGmUmAmUmUmCmUm |
| | 122 | AmsGfsAmAmUmAfCmUfGfUmCmCmCmUfUmUfUmAmAmsGmsCm |
| siAPa2-M1S | 123 | GmsCmsUmUmAmAmAfAmGfGfGfAmCmAmGmUmAmUmUmCmUm |
| | 124 | AmsGfsAmAmUmAfCmUfGfUmCmCmCmUfUmUfUmAmAmGmCmsAmsAm |

TABLE 1-continued

The sequences of first siRNAs in the conjugates of the present disclosure

| siRNA NO. | SEQ ID NO: | Sequence direction 5'-3' |
|---|---|---|
| siAPa1-M2S | 125 | UmsUmsAmAmAfAmGfGfGfAmCmAmGmUmAmUmUmCmUm |
| | 126 | AmsGfsAmAmUmAfCmUmGmUmCmCmCmUfUmUfUmAmAmsGmsCm |
| siAPa2-M2S | 127 | GmsCmsUmUmAmAmAfAmGfGfGfAmCmAmGmUmAmUmUmCmUm |
| | 128 | AmsGfsAmAmUmAfCmUmGmUmCmCmCmUfUmUfUmAmAmGmCmsAmsAm |
| siAPa1-M3S | 129 | UmsUmsAmAmAmAmGfGfGfAmCmAmGmUmAmUmUmCmUm |
| | 130 | AmsGfsAmAmUmAfCmUmGmUmCmCmCmUfUmUfUmAmAmsGmsCm |
| siAPa2-M3S | 131 | GmsCmsUmUmAmAmAmAmGfGfGfAmCmAmGmUmAmUmUmCmUm |
| | 132 | AmsGfsAmAmUmAfCmUmGmUmCmCmCmUfUmUfUmAmAmGmCmsAmsAm |
| siAPa1-M1P1 | 181 | UmUmAmAmAfAmGfGfGfAmCmAmGmUmAmUmUmCmUm |
| | 182 | P1-AmGfAmAmUmAfCmUfGfUmCmCmCmUfUmUfUmAmAmGmCm |
| siAPa2-M1P1 | 183 | GmCmUmUmAmAmAfAmGfGfGfAmCmAmGmUmAmUmUmCmUm |
| | 184 | P1-AmGfAmAmUmAfCmUfGfUmCmCmCmUfUmUfUmAmAmGmCmAmAm |
| siAPa1-M2P1 | 185 | UmUmAmAmAfAmGfGfGfAmCmAmGmUmAmUmUmCmUm |
| | 186 | P1-AmGfAmAmUmAfCmUmGmUmCmCmCmUfUmUfUmAmAmGmCm |
| siAPa2-M2P1 | 187 | GmCmUmUmAmAmAfAmGfGfGfAmCmAmGmUmAmUmUmCmUm |
| | 188 | P1-AmGfAmAmUmAfCmUmGmUmCmCmCmUfUmUfUmAmAmGmCmAmAm |
| siAPa1-M3P1 | 189 | UmUmAmAmAmAmGfGfGfAmCmAmGmUmAmUmUmCmUm |
| | 190 | P1-AmGfAmAmUmAfCmUmGmUmCmCmCmUfUmUfUmAmAmGmCm |
| siAPa2-M3P1 | 191 | GmCmUmUmAmAmAmAmGfGfGfAmCmAmGmUmAmUmUmCmUm |
| | 192 | P1-AmGfAmAmUmAfCmUmGmUmCmCmCmUfUmUfUmAmAmGmCmAmAm |
| siAPa1-M1SP1 | 193 | UmsUmsAmAmAfAmGfGfGfAmCmAmGmUmAmUmUmCmUm |
| | 194 | P1-AmsGfsAmAmUmAfCmUfGfUmCmCmCmUfUmUfUmAmAmsGmsCm |
| siAPa2-M1SP1 | 195 | GmsCmsUmUmAmAmAfAmGfGfGfAmCmAmGmUmAmUmUmCmUm |
| | 196 | P1-AmsGfsAmAmUmAfCmUfGfUmCmCmCmUfUmUfUmAmAmGmCmsAmsAm |
| siAPa1-M2SP1 | 197 | UmsUmsAmAmAfAmGfGfGfAmCmAmGmUmAmUmUmCmUm |
| | 198 | P1-AmsGfsAmAmUmAfCmUmGmUmCmCmCmUfUmUfUmAmAmsGmsCm |

TABLE 1-continued

The sequences of first siRNAs in the conjugates of the present disclosure

| siRNA NO. | SEQ ID NO: | Sequence direction 5'-3' |
|---|---|---|
| siAPa2-M2SP1 | 199 | GmsCmsUmUmAmAmAfAmGfGfGfAmCmAmGmUmAmUmUmCmUm |
| | 200 | P1-AmsGfsAmAmUmAfCmUmGmUmCmCmCmUfUmUfUmAmAmGmCmsAmsAm |
| siAPa1-M3SP1 | 201 | UmsUmsAmAmAmAmGfGfGfAmCmAmGmUmAmUmUmCmUm |
| | 202 | P1-AmsGfsAmAmUmAfCmUmGmUmCmCmCmUfUmUfUmAmAmsGmsCm |
| siAPa2-M3SP1 | 203 | GmsCmsUmUmAmAmAmAmGfGfGfAmCmAmGmUmAmUmUmCmUm |
| | 204 | P1-AmsGfsAmAmUmAfCmUmGmUmCmCmCmUfUmUfUmAmAmGmCmsAmsAm |
| siAPa1U-M1P1 | 327 | UmUmAmAmAfAmGfGfGfAmCmAmGmUmAmUmUmCmAm |
| | 328 | P1-UmGfAmAmUmAfCmUfGfUmCmCmCmUfUmUfUmAmAmGmCm |
| siAPa2U-M1P1 | 329 | GmCmUmUmAmAmAfAmGfGfGfAmCmAmGmUmAmUmUmCmAm |
| | 330 | P1-UmGfAmAmUmAfCmUfGfUmCmCmCmUfUmUfUmAmAmGmCmAmAm |
| siAPa1U-M2P1 | 331 | UmUmAmAmAfAmGfGfGfAmCmAmGmUmAmUmUmCmAm |
| | 332 | P1-UmGfAmAmUmAfCmUmGmUmCmCmCmUfUmUfUmAmAmGmCm |
| siAPa2U-M2P1 | 333 | GmCmUmUmAmAmAfAmGfGfGfAmCmAmGmUmAmUmUmCmAm |
| | 334 | P1-UmGfAmAmUmAfCmUmGmUmCmCmCmUfUmUfUmAmAmGmCmAmAm |
| siAPa1U-M3P1 | 335 | UmUmAmAmAmAmGfGfGfAmCmAmGmUmAmUmUmCmAm |
| | 336 | P1-UmGfAmAmUmAfCmUmGmUmCmCmCmUfUmUfUmAmAmGmCm |
| siAPa2U-M3P1 | 337 | GmCmUmUmAmAmAmAmGfGfGfAmCmAmGmUmAmUmUmCmAm |
| | 338 | P1-UmGfAmAmUmAfCmUmGmUmCmCmCmUfUmUfUmAmAmGmCmAmAm |
| siAPa1U-M1SP1 | 339 | UmsUmsAmAmAfAmGfGfGfAmCmAmGmUmAmUmUmCmAm |
| | 340 | P1-UmsGfsAmAmUmAfCmUfGfUmCmCmCmUfUmUfUmAmAmsGmsCm |
| siAPa2U-M1SP1 | 341 | GmsCmsUmUmAmAmAfAmGfGfGfAmCmAmGmUmAmUmUmCmAm |
| | 342 | P1-UmsGfsAmAmUmAfCmUfGfUmCmCmCmUfUmUfUmAmAmGmCmsAmsAm |
| siAPa1U-M2SP1 | 343 | UmsUmsAmAmAfAmGfGfGfAmCmAmGmUmAmUmUmCmAm |
| | 344 | P1-UmsGfsAmAmUmAfCmUmGmUmCmCmCmUfUmUfUmAmAmsGmsCm |
| siAPa2U-M2SP1 | 345 | GmsCmsUmUmAmAmAfAmGfGfGfAmCmAmGmUmAmUmUmCmAm |
| | 346 | P1-UmsGfsAmAmUmAfCmUmGmUmCmCmCmUfUmUfUmAmAmGmCmsAmsAm |

TABLE 1-continued

The sequences of first siRNAs in the conjugates of the present disclosure

| siRNA NO. | SEQ ID NO: | Sequence direction 5'-3' |
|---|---|---|
| siAPa1U-M3SP1 | 347 | UmsUmsAmAmAmAmGfGfGfAmCmAmGmUmAmUmUmCmAm |
| | 348 | P1-UmsGfsAmAmUmAfCmUmGmUmCmCmCmUfUmUfUmAmAmsGmsCm |
| siAPa2U-M3SP1 | 349 | GmsCmsUmUmAmAmAmAmGfGfGfAmCmAmGmUmAmUmUmCmAm |
| | 350 | P1-UmsGfsAmAmUmAfCmUmGmUmCmCmCmUfUmUfUmAmAmGmCmsAmsAm |

TABLE 2

The sequences of second siRNAs in the conjugates of the present disclosure

| siRNA NO. | SEQ ID NO: | Sequence direction 5'-3' |
|---|---|---|
| siAPb1 | 21 | ACAGUAUUCUCAGUGCUCU |
| | 22 | AGAGCACUGAGAAUACUGUCC |
| siAPb2 | 23 | GGACAGUAUUCUCAGUGCUCU |
| | 24 | AGAGCACUGAGAAUACUGUCCCU |
| siAPb1-M1 | 73 | AmCmAmGmUfAmUfUfCfUmCmAmGmUmGmCmUmCmUm |
| | 74 | AmGfAmGmCmAfCmUfGfAmGmAmAmUfAmCfUmGmUmCmCm |
| siAPb2-M1 | 75 | GmGmAmCmAmGmUfAmUfUfCfUmCmAmGmUmGmCmUmCmUm |
| | 76 | AmGfAmGmCmAfCmUfGfAmGmAmAmUfAmCfUmGmUmCmCmCmUm |
| siAPb1-M2 | 77 | AmCmAmGmUfAmUfUfCfUmCmAmGmUmGmCmUmCmUm |
| | 78 | AmGfAmGmCmAfCmUmGmAmGmAmAmUfAmCfUmGmUmCmCm |
| siAPb2-M2 | 79 | GmGmAmCmAmGmUfAmUfUfCfUmCmAmGmUmGmCmUmCmUm |
| | 80 | AmGfAmGmCmAfCmUmGmAmGmAmAmUfAmCfUmGmUmCmCmCmUm |
| siAPb1-M3 | 81 | AmCmAmGmUmAmUfUfCfUmCmAmGmUmGmCmUmCmUm |
| | 82 | AmGfAmGmCmAfCmUmGmAmGmAmAmUfAmCfUmGmUmCmCm |
| siAPb2-M3 | 83 | GmGmAmCmAmGmUmAmUfUfCfUmCmAmGmUmGmCmUmCmUm |
| | 84 | AmGfAmGmCmAfCmUmGmAmGmAmAmUfAmCfUmGmUmCmCmCmUm |
| siAPb1-M1S | 133 | AmsCmsAmGmUfAmUfUfCfUmCmAmGmUmGmCmUmCmUm |
| | 134 | AmsGfsAmGmCmAfCmUfGfAmGmAmAmUfAmCfUmGmUmsCmsCm |
| siAPb2-M1S | 135 | GmsGmsAmCmAmGmUfAmUfUfCfUmCmAmGmUmGmCmUmCmUm |
| | 136 | AmsGfsAmGmCmAfCmUfGfAmGmAmAmUfAmCfUmGmUmCmCmsCmsUm |
| siAPb1-M2S | 137 | AmsCmsAmGmUfAmUfUfCfUmCmAmGmUmGmCmUmCmUm |
| | 138 | AmsGfsAmGmCmAfCmUmGmAmGmAmAmUfAmCfUmGmUmsCmsCm |
| siAPb2-M2S | 139 | GmsGmsAmCmAmGmUfAmUfUfCfUmCmAmGmUmGmCmUmCmUm |
| | 140 | AmsGfsAmGmCmAfCmUmGmAmGmAmAmUfAmCfUmGmUmCmCmsCmsUm |

TABLE 2-continued

The sequences of second siRNAs in the conjugates of the present disclosure

| siRNA NO. | SEQ ID NO: | Sequence direction 5'-3' |
|---|---|---|
| siAPb1-M3S | 141 | AmsCmsAmGmUmAmUfUfCfUmCmAmGmUmGmCmUmCmUm |
| | 142 | AmsGfsAmGmCmAfCmUmGmAmGmAmAmUfAmCfUmGmUmsCmsCm |
| siAPb2-M3S | 143 | GmsGmsAmCmAmGmUmAmUfUfCfUmCmAmGmUmGmCmUmCmUm |
| | 144 | AmsGfsAmGmCmAfCmUmGmAmGmAmAmUfAmCfUmGmUmCmCmsCmsUm |
| siAPb1-M1P1 | 205 | AmCmAmGmUfAmUfUfCfUmCmAmGmUmGmCmUmCmUm |
| | 206 | P1-AmGfAmGmCmAfCmUfGfAmGmAmAmUfAmCfUmGmUmCmCm |
| siAPb2-M1P1 | 207 | GmGmAmCmAmGmUfAmUfUfCfUmCmAmGmUmGmCmUmCmUm |
| | 208 | P1-AmGfAmGmCmAfCmUfGfAmGmAmAmUfAmCfUmGmUmCmCmCmUm |
| siAPb1-M2P1 | 209 | AmCmAmGmUfAmUfUfCfUmCmAmGmUmGmCmUmCmUm |
| | 210 | P1-AmGfAmGmCmAfCmUmGmAmGmAmAmUfAmCfUmGmUmCmCm |
| siAPb2-M2P1 | 211 | GmGmAmCmAmGmUfAmUfUfCfUmCmAmGmUmGmCmUmCmUm |
| | 212 | P1-AmGfAmGmCmAfCmUmGmAmGmAmAmUfAmCfUmGmUmCmCmCmUm |
| siAPb1-M3P1 | 213 | AmCmAmGmUmAmUfUfCfUmCmAmGmUmGmCmUmCmUm |
| | 214 | P1-AmGfAmGmCmAfCmUmGmAmGmAmAmUfAmCfUmGmUmCmCm |
| siAPb2-M3P1 | 215 | GmGmAmCmAmGmUmAmUfUfCfUmCmAmGmUmGmCmUmCmUm |
| | 216 | P1-AmGfAmGmCmAfCmUmGmAmGmAmAmUfAmCfUmGmUmCmCmCmUm |
| siAPb1-M1SP1 | 217 | AmsCmsAmGmUfAmUfUfCfUmCmAmGmUmGmCmUmCmUm |
| | 218 | P1-AmsGfsAmGmCmAfCmUfGfAmGmAmAmUfAmCfUmGmUmsCmsCm |
| siAPb2-M1SP1 | 219 | GmsGmsAmCmAmGmUfAmUfUfCfUmCmAmGmUmGmCmUmCmUm |
| | 220 | P1-AmsGfsAmGmCmAfCmUfGfAmGmAmAmUfAmCfUmGmUmCmCmsCmsUm |
| siAPb1-M2SP1 | 221 | AmsCmsAmGmUfAmUfUfCfUmCmAmGmUmGmCmUmCmUm |
| | 222 | P1-AmsGfsAmGmCmAfCmUmGmAmGmAmAmUfAmCfUmGmUmCmCmsCmsUm |
| siAPb2-M2SP1 | 223 | GmsGmsAmCmAmGmUfAmUfUfCfUmCmAmGmUmGmCmUmCmUm |
| | 224 | P1-AmsGfsAmGmCmAfCmUmGmAmGmAmAmUfAmCfUmGmUmCmCmsCmsUm |
| siAPb1-M3SP1 | 225 | AmsCmsAmGmUmAmUfUfCfUmCmAmGmUmGmCmUmCmUm |
| | 226 | P1-AmsGfsAmGmCmAfCmUmGmAmGmAmAmUfAmCfUmGmUmsCmsCm |

TABLE 2-continued

The sequences of second siRNAs in the conjugates of the present disclosure

| siRNA NO. | SEQ ID NO: | Sequence direction 5'-3' |
|---|---|---|
| siAPb2-M3SP1 | 227 | GmsGmsAmCmAmGmUmAmUfUfCfUmCmAmGmUmGmCmUmCmUm |
| | 228 | P1-AmsGfsAmGmCmAfCmUmGmAmGmAmAmUfAmCfUmGmUmCmCmsCmsUm |
| siAPb1U-M1P1 | 351 | AmCmAmGmUfAmUfUfCfUmCmAmGmUmGmCmUmCmAm |
| | 352 | P1-UmGfAmGmCmAfCmUfGfAmGmAmAmUfAmCfUmGmUmCmCm |
| siAPb2U-M1P1 | 353 | GmGmAmCmAmGmUfAmUfUfCfUmCmAmGmUmGmCmUmCmAm |
| | 354 | P1-UmGfAmGmCmAfCmUfGfAmGmAmAmUfAmCfUmGmUmCmCmCmUm |
| siAPb1U-M2P1 | 355 | AmCmAmGmUfAmUfUfCfUmCmAmGmUmGmCmUmCmAm |
| | 356 | P1-UmGfAmGmCmAfCmUmGmAmGmAmAmUfAmCfUmGmUmCmCm |
| siAPb2U-M2P1 | 357 | GmGmAmCmAmGmUfAmUfUfCfUmCmAmGmUmGmCmUmCmAm |
| | 358 | P1-UmGfAmGmCmAfCmUmGmAmGmAmAmUfAmCfUmGmUmCmCmCmUm |
| siAPb1U-M3P1 | 359 | AmCmAmGmUmAmUfUfCfUmCmAmGmUmGmCmUmCmAm |
| | 360 | P1-UmGfAmGmCmAfCmUmGmAmGmAmAmUfAmCfUmGmUmCmCm |
| siAPb2U-M3P1 | 361 | GmGmAmCmAmGmUmAmUfUfCfUmCmAmGmUmGmCmUmCmAm |
| | 362 | P1-UmGfAmGmCmAfCmUmGmAmGmAmAmUfAmCfUmGmUmCmCmCmUm |
| siAPb1U-M1SP1 | 363 | AmsCmsAmGmUfAmUfUfCfUmCmAmGmUmGmCmUmCmAm |
| | 364 | P1-UmsGfsAmGmCmAfCmUfGfAmGmAmAmUfAmCfUmGmUmsCmsCm |
| siAPb2U-M1SP1 | 365 | GmsGmsAmCmAmGmUfAmUfUfCfUmCmAmGmUmGmCmUmCmAm |
| | 366 | P1-UmsGfsAmGmCmAfCmUfGfAmGmAmAmUfAmCfUmGmUmCmCmsCmsUm |
| siAPb1U-M2SP1 | 367 | AmsCmsAmGmUfAmUfUfCfUmCmAmGmUmGmCmUmCmAm |
| | 368 | P1-UmsGfsAmGmCmAfCmUmGmAmGmAmAmUfAmCfUmGmUmCmCmsCmsUm |
| siAPb2U-M2SP1 | 369 | GmsGmsAmCmAmGmUfAmUfUfCfUmCmAmGmUmGmCmUmCmAm |
| | 370 | P1-UmsGfsAmGmCmAfCmUmGmAmGmAmAmUfAmCfUmGmUmCmCmsCmsUm |
| siAPb1U-M3SP1 | 371 | AmsCmsAmGmUmAmUfUfCfUmCmAmGmUmGmCmUmCmAm |
| | 372 | P1-UmsGfsAmGmCmAfCmUmGmAmGmAmAmUfAmCfUmGmUmsCmsCm |
| siAPb2U-M3SP1 | 373 | GmsGmsAmCmAmGmUmAmUfUfCfUmCmAmGmUmGmCmUmCmAm |
| | 374 | P1-UmsGfsAmGmCmAfCmUmGmAmGmAmAmUfAmCfUmGmUmCmCmsCmsUm |

TABLE 3

The sequences of third siRNAs in the conjugates of the present disclosure

| siRNA NO. | SEQ ID NO: | Sequence direction 5'-3' |
|---|---|---|
| siAPc1 | 33 | UAUUCUCAGUGCUCUCCUA |
| | 34 | UAGGAGAGCACUGAGAAUACU |
| siAPc2 | 35 | AGUAUUCUCAGUGCUCUCCUA |
| | 36 | UAGGAGAGCACUGAGAAUACUGU |
| siAPc1- | 85 | UmAmUmUmCfUmCfAfGfUmGmCmUmCmUmCmCmUmAm |
| M1 | 86 | UmAfGmGmAmGfAmGfCfAmCmUmGmAfGmAfAmUmAmCmUm |
| siAPc2- | 87 | AmGmUmAmUmUmCfUmCfAfGfUmGmCmUmCmUmCmCmUmAm |
| M1 | 88 | UmAfGmGmAmGfAmGfCfAmCmUmGmAfGmAfAmUmAmCmUmGmUm |
| siAPc1- | 89 | UmAmUmUmCfUmCfAfGfUmGmCmUmCmUmCmCmUmAm |
| M2 | 90 | UmAfGmGmAmGfAmGmCmAmCmUmGmAfGmAfAmUmAmCmUm |
| siAPc2- | 91 | AmGmUmAmUmUmCfUmCfAfGfUmGmCmUmCmUmCmCmUmAm |
| M2 | 92 | UmAfGmGmAmGfAmGmCmAmCmUmGmAfGmAfAmUmAmCmUmGmUm |
| siAPc1- | 93 | UmAmUmUmCmUmCfAfGfUmGmCmUmCmUmCmCmUmAm |
| M3 | 94 | UmAfGmGmAmGfAmGmCmAmCmUmGmAfGmAfAmUmAmCmUm |
| siAPc2- | 95 | AmGmUmAmUmUmCmUmCfAfGfUmGmCmUmCmUmCmCmUmAm |
| M3 | 96 | UmAfGmGmAmGfAmGmCmAmCmUmGmAfGmAfAmUmAmCmUmGmUm |
| siAPc1- | 145 | UmsAmsUmUmCfUmCfAfGfUmGmCmUmCmUmCmCmUmAm |
| M1S | 146 | UmsAfsGmGmAmGfAmGfCfAmCmUmGmAfGmAfAmUmAmsCmsUm |
| siAPc2- | 147 | AmsGmsUmAmUmUmCfUmCfAfGfUmGmCmUmCmUmCmCmUmAm |
| M1S | 148 | UmsAfsGmGmAmGfAmGfCfAmCmUmGmAfGmAfAmUmAmCmUmsGmsUm |
| siAPc1- | 149 | UmsAmsUmUmCfUmCfAfGfUmGmCmUmCmUmCmCmUmAm |
| M2S | 150 | UmsAfsGmGmAmGfAmGmCmAmCmUmGmAfGmAfAmUmAmsCmsUm |
| siAPc2- | 151 | AmsGmsUmAmUmUmCfUmCfAfGfUmGmCmUmCmUmCmCmUmAm |
| M2S | 152 | UmsAfsGmGmAmGfAmGmCmAmCmUmGmAfGmAfAmUmAmCmUmsGmsUm |
| siAPc1- | 153 | UmsAmsUmUmCmUmCfAfGfUmGmCmUmCmUmCmCmUmAm |
| M3S | 154 | UmsAfsGmGmAmGfAmGmCmAmCmUmGmAfGmAfAmUmAmsCmsUm |
| siAPc2- | 155 | AmsGmsUmAmUmUmCmUmCfAfGfUmGmCmUmCmUmCmCmUmAm |
| M3S | 156 | UmsAfsGmGmAmGfAmGmCmAmCmUmGmAfGmAfAmUmAmCmUmsGmsUm |
| siAPc1- | 229 | UmAmUmUmCfUmCfAfGfUmGmCmUmCmUmCmCmUmAm |
| M1P1 | 230 | P1-UmAfGmGmAmGfAmGfCfAmCmUmGmAfGmAfAmUmAmCmUm |
| siAPc2- | 231 | AmGmUmAmUmUmCfUmCfAfGfUmGmCmUmCmUmCmCmUmAm |
| M1P1 | 232 | P1-UmAfGmGmAmGfAmGfCfAmCmUmGmAfGmAfAmUmAmCmUmGmUm |
| siAPc1- | 233 | UmAmUmUmCfUmCfAfGfUmGmCmUmCmUmCmCmUmAm |
| M2P1 | 234 | P1-UmAfGmGmAmGfAmGmCmAmCmUmGmAfGmAfAmUmAmCmUm |
| siAPc2- | 235 | AmGmUmAmUmUmCfUmCfAfGfUmGmCmUmCmUmCmCmUmAm |
| M2P1 | 236 | P1-UmAfGmGmAmGfAmGmCmAmCmUmGmAfGmAfAmUmAmCmUmGmUm |
| siAPc1- | 237 | UmAmUmUmCmUmCfAfGfUmGmCmUmCmUmCmCmUmAm |
| M3P1 | 238 | P1-UmAfGmGmAmGfAmGmCmAmCmUmGmAfGmAfAmUmAmCmUm |
| siAPc2- | 239 | AmGmUmAmUmUmCmUmCfAfGfUmGmCmUmCmUmCmCmUmAm |
| M3P1 | 240 | P1-UmAfGmGmAmGfAmGmCmAmCmUmGmAfGmAfAmUmAmCmUmGmUm |
| siAPc1- | 241 | UmsAmsUmUmCfUmCfAfGfUmGmCmUmCmUmCmCmUmAm |
| M1SP1 | 242 | P1-UmsAfsGmGmAmGfAmGfCfAmCmUmGmAfGmAfAmUmAmsCmsUm |
| siAPc2- | 243 | AmsGmsUmAmUmUmCfUmCfAfGfUmGmCmUmCmUmCmCmUmAm |
| M1SP1 | 244 | P1-UmsAfsGmGmAmGfAmGfCfAmCmUmGmAfGmAfAmUmAmCmUmsGmsUm |
| siAPc1- | 245 | UmsAmsUmUmCfUmCfAfGfUmGmCmUmCmUmCmCmUmAm |
| M2SP1 | 246 | P1-UmsAfsGmGmAmGfAmGmCmAmCmUmGmAfGmAfAmUmAmsCmsUm |
| siAPc2- | 247 | AmsGmsUmAmUmUmCfUmCfAfGfUmGmCmUmCmUmCmCmUmAm |
| M2SP1 | 248 | P1-UmsAfsGmGmAmGfAmGmCmAmCmUmGmAfGmAfAmUmAmCmUmsGmsUm |
| siAPc1- | 249 | UmsAmsUmUmCmUmCfAfGfUmGmCmUmCmUmCmCmUmAm |
| M3SP1 | 250 | P1-UmsAfsGmGmAmGfAmGmCmAmCmUmGmAfGmAfAmUmAmsCmsUm |

TABLE 3-continued

| The sequences of third siRNAs in the conjugates of the present disclosure | | |
|---|---|---|
| siRNA NO. | SEQ ID NO: | Sequence direction 5'-3' |
| siAPc2- | 251 | AmsGmsUmAmUmUmCmUmCfAfGfUmGmCmUmCmUmCmCmUmAm |
| M3SP1 | 252 | P1-UmsAfsGmGmAmGfAmGmCmAmCmUmGmAfGmAfAmUmAmCmUmsGmsUm |

TABLE 4

| The sequences of fourth siRNAs in the conjugates of the present disclosure | | |
|---|---|---|
| siRNA NO. | SEQ ID NO: | Sequence direction 5'-3' |
| siAPd1 | 45 | AGUAUUCUCAGUGCUCUCC |
| | 46 | GGAGAGCACUGAGAAUACUGU |
| siAPd2 | 47 | ACAGUAUUCUCAGUGCUCUCC |
| | 48 | GGAGAGCACUGAGAAUACUGUCC |
| siAPd1- | 97 | AmGmUmAmUfUmCfUfCfAmGmUmGmCmUmCmUmCmCm |
| M1 | 98 | GmGfAmGmAmGfCmAfCfUmGmAmGmAfAmUfAmCmUmGmUm |
| siAPd2- | 99 | AmCmAmGmUmAmUfUmCfUfCfAmGmUmGmCmUmCmUmCmCm |
| M1 | 100 | GmGfAmGmAmGfCmAfCfUmGmAmGmAfAmUfAmCmUmGmUmCmCm |
| siAPd1- | 101 | AmGmUmAmUfUmCfUfCfAmGmUmGmCmUmCmUmCmCm |
| M2 | 102 | GmGfAmGmAmGfCmAmCmUmGmAmGmAfAmUfAmCmUmGmUm |
| siAPd2- | 103 | AmCmAmGmUmAmUfUmCfUfCfAmGmUmGmCmUmCmUmCmCm |
| M2 | 104 | GmGfAmGmAmGfCmAmCmUmGmAmGmAfAmUfAmCmUmGmUmCmCm |
| siAPd1- | 105 | AmGmUmAmUmUmCfUfCfAmGmUmGmCmUmCmUmCmCm |
| M3 | 106 | GmGfAmGmAmGfCmAmCmUmGmAmGmAfAmUfAmCmUmGmUm |
| siAPd2- | 107 | AmCmAmGmUmAmUmUmCfUfCfAmGmUmGmCmUmCmUmCmCm |
| M3 | 108 | GmGfAmGmAmGfCmAmCmUmGmAmGmAfAmUfAmCmUmGmUmCmCm |
| siAPd1- | 157 | AmsGmsUmAmUfUmCfUfCfAmGmUmGmCmUmCmUmCmCm |
| M1S | 158 | GmsGfsAmGmAmGfCmAfCfUmGmAmGmAfAmUfAmCmUmsGmsUm |
| siAPd2- | 159 | AmsCmsAmGmUmAmUfUmCfUfCfAmGmUmGmCmUmCmUmCmCm |
| M1S | 160 | GmsGfsAmGmAmGfCmAfCfUmGmAmGmAfAmUfAmCmUmGmUmsCmsCm |
| siAPd1- | 161 | AmsGmsUmAmUfUmCfUfCfAmGmUmGmCmUmCmUmCmCm |
| M2S | 162 | GmsGfsAmGmAmGfCmAmCmUmGmAmGmAfAmUfAmCmUmsGmsUm |
| siAPd2- | 163 | AmsCmsAmGmUmAmUfUmCfUfCfAmGmUmGmCmUmCmUmCmCm |
| M2S | 164 | GmsGfsAmGmAmGfCmAmCmUmGmAmGmAfAmUfAmCmUmGmUmsCmsCm |
| siAPd1- | 165 | AmsGmsUmAmUmUmCfUfCfAmGmUmGmCmUmCmUmCmCm |
| M3S | 166 | GmsGfsAmGmAmGfCmAmCmUmGmAmGmAfAmUfAmCmUmsGmsUm |
| siAPd2- | 167 | AmsCmsAmGmUmAmUmUmCfUfCfAmGmUmGmCmUmCmUmCmCm |
| M3S | 168 | GmsGfsAmGmAmGfCmAmCmUmGmAmGmAfAmUfAmCmUmGmUmsCmsCm |
| siAPd1- | 253 | AmGmUmAmUfUmCfUfCfAmGmUmGmCmUmCmUmCmCm |
| M1P1 | 254 | P1-GmGfAmGmAmGfCmAfCfUmGmAmGmAfAmUfAmCmUmGmUm |
| siAPd2- | 255 | AmCmAmGmUmAmUfUmCfUfCfAmGmUmGmCmUmCmUmCmCm |
| M1P1 | 256 | P1-GmGfAmGmAmGfCmAfCfUmGmAmGmAfAmUfAmCmUmGmUmCmCm |
| siAPd1- | 257 | AmGmUmAmUfUmCfUfCfAmGmUmGmCmUmCmUmCmCm |
| M2P1 | 258 | P1-GmGfAmGmAmGfCmAmCmUmGmAmGmAfAmUfAmCmUmGmUm |
| siAPd2- | 259 | AmCmAmGmUmAmUfUmCfUfCfAmGmUmGmCmUmCmUmCmCm |
| M2P1 | 260 | P1-GmGfAmGmAmGfCmAmCmUmGmAmGmAfAmUfAmCmUmGmUmCmCm |
| siAPd1- | 261 | AmGmUmAmUmUmCfUfCfAmGmUmGmCmUmCmUmCmCm |
| M3P1 | 262 | P1-GmGfAmGmAmGfCmAmCmUmGmAmGmAfAmUfAmCmUmGmUm |
| siAPd2- | 263 | AmCmAmGmUmAmUmUmCfUfCfAmGmUmGmCmUmCmUmCmCm |
| M3P1 | 264 | P1-GmGfAmGmAmGfCmAmCmUmGmAmGmAfAmUfAmCmUmGmUmCmCm |

TABLE 4-continued

| The sequences of fourth siRNAs in the conjugates of the present disclosure | | |
|---|---|---|
| siRNA NO. | SEQ ID NO: | Sequence direction 5'-3' |
| siAPd1-M1SP1 | 265 | AmsGmsUmAmUfUmCfUfCfAmGmUmGmCmUmCmUmCmCm |
| | 266 | P1-GmsGfsAmGmAmGfCmAfCfUmGmAmGmAfAmUfAmCmUmsGmsUm |
| siAPd2-M1SP1 | 267 | AmsCmsAmGmUmAmUfUmCfUfCfAmGmUmGmCmUmCmUmCmCm |
| | 268 | P1-GmsGfsAmGmAmGfCmAfCfUmGmAmGmAfAmUfAmCmUmGmUmsCmsCm |
| siAPd1-M2SP1 | 269 | AmsGmsUmAmUfUmCfUfCfAmGmUmGmCmUmCmUmCmCm |
| | 270 | P1-GmsGfsAmGmAmGfCmAmCmUmGmAmGmAfAmUfAmCmUmsGmsUm |
| siAPd2-M2SP1 | 271 | AmsCmsAmGmUmAmUfUmCfUfCfAmGmUmGmCmUmCmUmCmCm |
| | 272 | P1-GmsGfsAmGmAmGfCmAmCmUmGmAmGmAfAmUfAmCmUmGmUmsCmsCm |
| siAPd1-M3SP1 | 273 | AmsGmsUmAmUmUmCfUfCfAmGmUmGmCmUmCmUmCmCm |
| | 274 | P1-GmsGfsAmGmAmGfCmAmCmUmGmAmGmAfAmUfAmCmUmsGmsUm |
| siAPd2-M3SP1 | 275 | AmsCmsAmGmUmAmUmUmCfUfCfAmGmUmGmCmUmCmUmCmCm |
| | 276 | P1-GmsGfsAmGmAmGfCmAmCmUmGmAmGmAfAmUfAmCmUmGmUmsCmsCm |
| siAPd1U-M1P1 | 375 | AmGmUmAmUfUmCfUfCfAmGmUmGmCmUmCmUmCmAm |
| | 376 | P1-UmGfAmGmAmGfCmAfCfUmGmAmGmAfAmUfAmCmUmGmUm |
| siAPd2U-M1P1 | 377 | AmCmAmGmUmAmUfUmCfUfCfAmGmUmGmCmUmCmUmCmAm |
| | 378 | P1-UmGfAmGmAmGfCmAfCfUmGmAmGmAfAmUfAmCmUmGmUmCmCm |
| siAPd1U-M2P1 | 379 | AmGmUmAmUfUmCfUfCfAmGmUmGmCmUmCmUmCmAm |
| | 380 | P1-UmGfAmGmAmGfCmAmCmUmGmAmGmAfAmUfAmCmUmGmUm |
| siAPd2U-M2P1 | 381 | AmCmAmGmUmAmUfUmCfUfCfAmGmUmGmCmUmCmUmCmAm |
| | 382 | P1-UmGfAmGmAmGfCmAmCmUmGmAmGmAfAmUfAmCmUmGmUmCmCm |
| siAPd1U-M3P1 | 383 | AmGmUmAmUmUmCfUfCfAmGmUmGmCmUmCmUmCmAm |
| | 384 | P1-UmGfAmGmAmGfCmAmCmUmGmAmGmAfAmUfAmCmUmGmUm |
| siAPd2U-M3P1 | 385 | AmCmAmGmUmAmUmUmCfUfCfAmGmUmGmCmUmCmUmCmAm |
| | 386 | P1-UmGfAmGmAmGfCmAmCmUmGmAmGmAfAmUfAmCmUmGmUmCmCm |
| siAPd1U-M1SP1 | 387 | AmsGmsUmAmUfUmCfUfCfAmGmUmGmCmUmCmUmCmAm |
| | 388 | P1-UmsGfsAmGmAmGfCmAfCfUmGmAmGmAfAmUfAmCmUmsGmsUm |
| siAPd2U-M1SP1 | 389 | AmsCmsAmGmUmAmUfUmCfUfCfAmGmUmGmCmUmCmUmCmAm |
| | 390 | P1-UmsGfsAmGmAmGfCmAfCfUmGmAmGmAfAmUfAmCmUmGmUmsCmsCm |
| siAPd1U-M2SP1 | 391 | AmsGmsUmAmUfUmCfUfCfAmGmUmGmCmUmCmUmCmAm |
| | 392 | P1-UmsGfsAmGmAmGfCmAmCmUmGmAmGmAfAmUfAmCmUmsGmsUm |
| siAPd2U-M2SP1 | 393 | AmsCmsAmGmUmAmUfUmCfUfCfAmGmUmGmCmUmCmUmCmAm |
| | 394 | P1-UmsGfsAmGmAmGfCmAmCmUmGmAmGmAfAmUfAmCmUmGmUmsCmsCm |
| siAPd1U-M3SP1 | 395 | AmsGmsUmAmUmUmCfUfCfAmGmUmGmCmUmCmUmCmAm |
| | 396 | P1-UmsGfsAmGmAmGfCmAmCmUmGmAmGmAfAmUfAmCmUmsGmsUm |
| siAPd2U-M3SP1 | 397 | AmsCmsAmGmUmAmUmUmCfUfCfAmGmUmGmCmUmCmUmCmAm |
| | 398 | P1-UmsGfsAmGmAmGfCmAmCmUmGmAmGmAfAmUfAmCmUmGmUmsCmsCm |

TABLE 5

| The sequences of fifth siRNAs in the conjugates of the present disclosure | | |
|---|---|---|
| siRNA NO. | SEQ ID NO: | Sequence direction 5'-3' |
| siAPe1 | 57 | GGACAGUAUUCUCAGUGCU |
| | 58 | AGCACUGAGAAUACUGUCCCU |
| siAPe2 | 59 | AGGGACAGUAUUCUCAGUGCU |
| | 60 | AGCACUGAGAAUACUGUCCCUUU |
| siAPe1-M1 | 109 | GmGmAmCmAfGmUfAfUfUmCmUmCmAmGmUmGmCmUm |
| | 110 | AmGfCmAmCmUfGmAfGfAmAmUmAmCfUmGfUmCmCmCmUm |
| siAPe2-M1 | 111 | AmGmGmGmAmCmAfGmUfAfUfUmCmUmCmAmGmUmGmCmUm |
| | 112 | AmGfCmAmCmUfGmAfGfAmAmUmAmCfUmGfUmCmCmCmUmUmUm |

TABLE 5-continued

The sequences of fifth siRNAs in the conjugates of the present disclosure

| siRNA NO. | SEQ ID NO: | Sequence direction 5'-3' |
|---|---|---|
| siAPe1-M2 | 113 | GmGmAmCmAfGmUfAfUfUmCmUmCmAmGmUmGmCmUm |
| | 114 | AmGfCmAmCmUfGmAmGmAmAmUmAmCfUmGfUmCmCmCmUm |
| siAPe2-M2 | 115 | AmGmGmGmAmCmAfGmUfAfUfUmCmUmCmAmGmUmGmCmUm |
| | 116 | AmGfCmAmCmUfGmAmGmAmAmUmAmCfUmGfUmCmCmCmUmUmUm |
| siAPe1-M3 | 117 | GmGmAmCmAmGmUfAfUfUmCmUmCmAmGmUmGmCmUm |
| | 118 | AmGfCmAmCmUfGmAmGmAmAmUmAmCfUmGfUmCmCmCmUm |
| siAPe2-M3 | 119 | AmGmGmGmAmCmAmGmUfAfUfUmCmUmCmAmGmUmGmCmUm |
| | 120 | AmGfCmAmCmUfGmAmGmAmAmUmAmCfUmGfUmCmCmCmUmUmUm |
| siAPe1-M1S | 169 | GmsGmsAmCmAfGmUfAfUfUmCmUmCmAmGmUmGmCmUm |
| | 170 | AmsGfsCmAmCmUfGmAfGfAmAmUmAmCfUmGfUmCmCmsCmsUm |
| siAPe2-M1S | 171 | AmsGmsGmGmAmCmAfGmUfAfUfUmCmUmCmAmGmUmGmCmUm |
| | 172 | AmsGfsCmAmCmUfGmAfGfAmAmUmAmCfUmGfUmCmCmCmUmsUmsUm |
| siAPe1-M2S | 173 | GmsGmsAmCmAfGmUfAfUfUmCmUmCmAmGmUmGmCmUm |
| | 174 | AmsGfsCmAmCmUfGmAmGmAmAmUmAmCfUmGfUmCmCmsCmsUm |
| siAPe2-M2S | 175 | AmsGmsGmGmAmCmAfGmUfAfUfUmCmUmCmAmGmUmGmCmUm |
| | 176 | AmsGfsCmAmCmUfGmAmGmAmAmUmAmCfUmGfUmCmCmCmUmsUmsUm |
| siAPe1-M3S | 177 | GmsGmsAmCmAmGmUfAfUfUmCmUmCmAmGmUmGmCmUm |
| | 178 | AmsGfsCmAmCmUfGmAmGmAmAmUmAmCfUmGfUmCmCmsCmsUm |
| siAPe2-M3S | 179 | AmsGmsGmGmAmCmAmGmUfAfUfUmCmUmCmAmGmUmGmCmUm |
| | 180 | AmsGfsCmAmCmUfGmAmGmAmAmUmAmCfUmGfUmCmCmCmUmsUmsUm |
| siAPe1-M1P1 | 277 | GmGmAmCmAfGmUfAfUfUmCmUmCmAmGmUmGmCmUm |
| | 278 | P1-AmGfCmAmCmUfGmAfGfAmAmUmAmCfUmGfUmCmCmCmUm |
| siAPe2-M1P1 | 279 | AmGmGmGmAmCmAfGmUfAfUfUmCmUmCmAmGmUmGmCmUm |
| | 280 | P1-AmGfCmAmCmUfGmAfGfAmAmUmAmCfUmGfUmCmCmCmUmUmUm |
| siAPe1-M2P1 | 281 | GmGmAmCmAfGmUfAfUfUmCmUmCmAmGmUmGmCmUm |
| | 282 | P1-AmGfCmAmCmUfGmAmGmAmAmUmAmCfUmGfUmCmCmCmUm |
| siAPe2-M2P1 | 283 | AmGmGmGmAmCmAfGmUfAfUfUmCmUmCmAmGmUmGmCmUm |
| | 284 | P1-AmGfCmAmCmUfGmAmGmAmAmUmAmCfUmGfUmCmCmCmUmUmUm |
| siAPe1-M3P1 | 285 | GmGmAmCmAmGmUfAfUfUmCmUmCmAmGmUmGmCmUm |
| | 286 | P1-AmGfCmAmCmUfGmAmGmAmAmUmAmCfUmGfUmCmCmCmUm |
| siAPe2-M3P1 | 287 | AmGmGmGmAmCmAmGmUfAfUfUmCmUmCmAmGmUmGmCmUm |
| | 288 | P1-AmGfCmAmCmUfGmAmGmAmAmUmAmCfUmGfUmCmCmCmUmUmUm |
| siAPe1-M1SP1 | 289 | GmsGmsAmCmAfGmUfAfUfUmCmUmCmAmGmUmGmCmUm |
| | 290 | P1-AmsGfsCmAmCmUfGmAfGfAmAmUmAmCfUmGfUmCmCmsCmsUm |
| siAPe2-M1SP1 | 291 | AmsGmsGmGmAmCmAfGmUfAfUfUmCmUmCmAmGmUmGmCmUm |
| | 292 | P1-AmsGfsCmAmCmUfGmAfGfAmAmUmAmCfUmGfUmCmCmCmUmsUmsUm |
| siAPe1-M2SP1 | 293 | GmsGmsAmCmAfGmUfAfUfUmCmUmCmAmGmUmGmCmUm |
| | 294 | P1-AmsGfsCmAmCmUfGmAmGmAmAmUmAmCfUmGfUmCmCmsCmsUm |
| siAPe2-M2SP1 | 295 | AmsGmsGmGmAmCmAfGmUfAfUfUmCmUmCmAmGmUmGmCmUm |
| | 296 | P1-AmsGfsCmAmCmUfGmAmGmAmAmUmAmCfUmGfUmCmCmCmUmsUmsUm |
| siAPe1-M3SP1 | 297 | GmsGmsAmCmAmGmUfAfUfUmCmUmCmAmGmUmGmCmUm |
| | 298 | P1-AmsGfsCmAmCmUfGmAmGmAmAmUmAmCfUmGfUmCmCmsCmsUm |
| siAPe2-M3SP1 | 299 | AmsGmsGmGmAmCmAmGmUfAfUfUmCmUmCmAmGmUmGmCmUm |
| | 300 | P1-AmsGfsCmAmCmUfGmAmGmAmAmUmAmCfUmGfUmCmCmCmUmsUmsUm |
| siAPe1U-M1P1 | 399 | GmGmAmCmAfGmUfAfUfUmCmUmCmAmGmUmGmCmAm |
| | 400 | P1-UmGfCmAmCmUfGmAfGfAmAmUmAmCfUmGfUmCmCmCmUm |
| siAPe2U-M1P1 | 401 | AmGmGmGmAmCmAfGmUfAfUfUmCmUmCmAmGmUmGmCmAm |
| | 402 | P1-UmGfCmAmCmUfGmAfGfAmAmUmAmCfUmGfUmCmCmCmUmUmUm |
| siAPe1U-M2P1 | 403 | GmGmAmCmAfGmUfAfUfUmCmUmCmAmGmUmGmCmAm |
| | 404 | P1-UmGfCmAmCmUfGmAmGmAmAmUmAmCfUmGfUmCmCmCmUm |

TABLE 5-continued

The sequences of fifth siRNAs in the conjugates of the present disclosure

| siRNA NO. | SEQ ID NO: | Sequence direction 5'-3' |
| --- | --- | --- |
| siAPe2U-M2P1 | 405 | AmGmGmGmAmCmAfGmUfAfUfUmCmUmCmAmGmUmGmCmAm |
| | 406 | P1-UmGfCmAmCmUfGmAmGmAmAmUmAmCfUmGfUmCmCmCmUmUmUm |
| siAPe1U-M3P1 | 407 | GmGmAmCmAmGmUfAfUfUmCmUmCmAmGmUmGmCmAm |
| | 408 | P1-UmGfCmAmCmUfGmAmGmAmAmUmAmCfUmGfUmCmCmCmUm |
| siAPe2U-M3P1 | 409 | AmGmGmGmAmCmAmGmUfAfUfUmCmUmCmAmGmUmGmCmAm |
| | 410 | P1-UmGfCmAmCmUfGmAmGmAmAmUmAmCfUmGfUmCmCmCmUmUmUm |
| siAPe1U-M1SP1 | 411 | GmsGmsAmCmAfGmUfAfUfUmCmUmCmAmGmUmGmCmAm |
| | 412 | P1-UmsGfsCmAmCmUfGmAfGfAmAmUmAmCfUmGfUmCmCmsCmsUm |
| siAPe2U-M1SP1 | 413 | AmsGmsGmGmAmCmAfGmUfAfUfUmCmUmCmAmGmUmGmCmAm |
| | 414 | P1-UmsGfsCmAmCmUfGmAfGfAmAmUmAmCfUmGfUmCmCmCmUmsUmsUm |
| siAPe1U-M2SP1 | 415 | GmsGmsAmCmAfGmUfAfUfUmCmUmCmAmGmUmGmCmAm |
| | 416 | P1-UmsGfsCmAmCmUfGmAmGmAmAmUmAmCfUmGfUmCmCmsCmsUm |
| siAPe2U-M2SP1 | 417 | AmsGmsGmGmAmCmAfGmUfAfUfUmCmUmCmAmGmUmGmCmAm |
| | 418 | P1-UmsGfsCmAmCmUfGmAmGmAmAmUmAmCfUmGfUmCmCmCmUmsUmsUm |
| siAPe1U-M3SP1 | 419 | GmsGmsAmCmAmGmUfAfUfUmCmUmCmAmGmUmGmCmAm |
| | 420 | P1-UmsGfsCmAmCmUfGmAmGmAmAmUmAmCfUmGfUmCmCmsCmsUm |
| siAPe2U-M3SP1 | 421 | AmsGmsGmGmAmCmAmGmUfAfUfUmCmUmCmAmGmUmGmCmAm |
| | 422 | P1-UmsGfsCmAmCmUfGmAmGmAmAmUmAmCfUmGfUmCmCmCmUmsUmsUm |

In the siRNA or siRNA conjugate of the present disclosure, each pair of adjacent nucleotides is linked via a phosphodiester bond or phosphorothioate diester bond. The non-bridging oxygen or sulfur atom in the phosphodiester bond or phosphorothioate diester bond is negatively charged, and may be present in the form of hydroxy or sulfhydryl. Moreover, the hydrogen ion in the hydroxy or sulfhydryl may be partially or completely substituted with a cation. The cation may be any cation, such as a metal cation, an ammonium cation $NH_4^+$ or an organic ammonium cation. In order to increase solubility, in one embodiment, the cation is one or more selected from an alkali metal cation, an ammonium cation formed by a tertiary amine and a quaternary ammonium cation. The alkali metal ion may be $K^+$ and/or $Na^+$, and the cation formed by a tertiary amine may be an ammonium cation formed by triethylamine and/or an ammonium cation formed by N,N-diisopropylethylamine. Thus, the siRNA and the siRNA conjugate of the present disclosure can be at least partially present in the form of salt. In one embodiment, the non-bridging oxygen atom or sulfur atom in the phosphodiester bond or phosphorothioate diester bond at least partly binds to sodium ion, and thus the siRNA and the siRNA conjugate of the present disclosure are present or partially present in the form of sodium salt.

Those skilled in the art clearly know that a modified nucleotide group can be introduced into the siRNA of the present disclosure by a nucleoside monomer with a corresponding modification. The methods for preparing a nucleoside monomer having the corresponding modification and the methods for introducing a modified nucleotide into a siRNA are also well-known to those skilled in the art. All modified nucleoside monomers may be either commercially available or prepared by known methods.

Preparation of the siRNA Conjugate as Shown by Formula (308)

The siRNA conjugate as shown by Formula (308) can be prepared by any appropriate synthetic routes.

In some embodiments, the siRNA conjugate as shown by Formula (308) can be prepared by the following method, comprising: sequentially linking nucleoside monomers in 3' to 5' direction according to the type and sequence of the nucleotides in the sense strand and antisense strands of the siRNA respectively, under the condition for phosphoramidite solid phase synthesis, wherein the step of linking each nucleoside monomer includes a four-step reaction of deprotection, coupling, capping, and oxidation or sulfurization; isolating the sense strand and the antisense strand of the siRNA; and annealing; wherein the siRNA is the above siRNA of the present disclosure.

Moreover, the method further comprises: contacting the compound as shown by Formula (321) with a nucleoside monomer or a nucleotide sequence attached to a solid phase support under coupling reaction condition and in the presence of a coupling agent, thereby linking the compound as shown by Formula (321) to the nucleotide sequence via a coupling reaction. Hereinafter, the compound as shown by Formula (321) is also referred to as a conjugation molecule.

Formula (321)

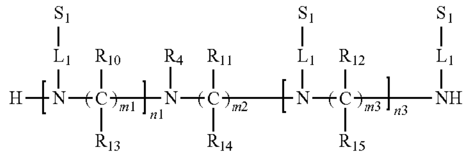

wherein, $R_4$ is a group capable of binding to the siRNA represented by Nu in the compound as shown by Formula (308). In some embodiments, $R_4$ is a group capable of binding to the siRNA represented by Nu via a covalent bond. In some embodiments, $R_4$ is a group comprising any functional group that may be conjugated to the siRNA represented by Nu via a phosphodiester bond by a reaction;

Each $S_1$ is independently a group formed by substituting all active hydroxyls in $M_1$ with the group YCOO—, wherein each Y is independently one selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl; in some embodiments, Y is methyl.

The definitions and options of n1, n3, m1, m2, m3, $R_{10}$, $R_{11}$, $R_{12}$, $R_{13}$, $R_{14}$, $R_{15}$, $L_1$, and $M_1$ are respectively as described above.

$R_4$ is selected to achieve the linkage to the N atom on a nitrogenous backbone and to provide a suitable reaction site for synthesizing the siRNA conjugate as shown by Formula (308). In some embodiments, $R_4$ comprises a $R_2$ linking group or a protected $R_2$ linking group, and a functional group than can react with a siRNA to form a structure as shown by Formula (A59).

In some embodiments, $R_4$ comprises a first functional group that can react with a group on the siRNA represented by Nu or a nucleoside monomer to form a phosphite ester, and a second functional group that can react with a hydroxy group or an amino group to form a covalent bond with, or comprises a solid phase support linked by the covalent bond. In some embodiments, the first functional group is a phosphoramidite, a hydroxy or a protected hydroxy. In some embodiments, the second functional group is a phosphoramidite, a carboxyl or a carboxylate salt. In some embodiments, the second functional group is a solid phase support linked to the rest of the molecule via a covalent bond which is formed by a hydroxy group or an amino group. In some embodiments, the solid phase support is linked via a phosphoester bond, a carboxyl ester bond or an amide bond. In some embodiments, the solid phase support is a resin.

In some embodiments, the first functional group comprises hydroxy, —$OR_k$ or a group as shown by Formula (C3); the second functional group comprises a group as shown by Formula (C1), (C2), (C3), (C1'), or (C3'):

(C1)

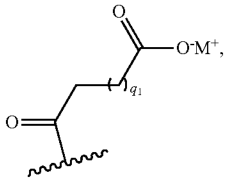

(C2)

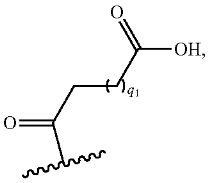

(C3)

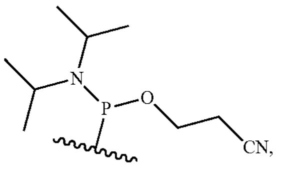

-continued (C1')

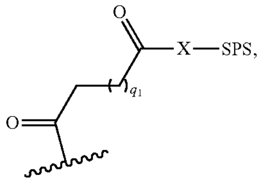

(C3')

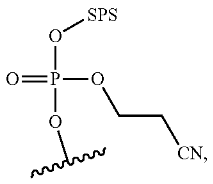

wherein $q_1$ is an integer of 1-4, X is O or NH, $M^+$ is a cation, $R_k$ is a hydroxy protection group, SPS represents a solid phase support, and  represents the site where a group is attached to the rest of the molecule.

In some embodiments, the first functional group comprises a phosphoramidite group, such as the group as shown by Formula (C3). The phosphoramidite group can form a phosphite ester with a hydroxy at any position on a nucleotide (such as a 2'-hydroxy or 3'-hydroxy) by a coupling reaction, and the phosphite ester can form a phosphodiester bond or phosphorothioate ester bond as shown by Formula (A59) via oxidation or sulfurization, so as to conjugate the conjugation molecule to a siRNA. Here, even if the second functional group does not exist, the compound as shown by Formula (321) could still be conjugated to the nucleotide, while not affecting the obtaining of the siRNA conjugate as shown by Formula (308). Under such circumstances, after obtaining a sense or antisense strand of the siRNA by a method such as phosphoramidite solid phase synthesis, the compound as shown by Formula (321) is reacted with a hydroxy on the nucleotide at the terminal of the nucleotide sequence, and a phosphodiester bond linkage or a phosphorothioate bond linkage is formed in the subsequent oxidation or sulfurization process, thereby conjugating the compound as shown by Formula (321) to the siRNA.

In some embodiments, the first functional group comprises a protected hydroxy. In some embodiments, the second functional group comprises a group that can react with a solid phase support to provide a conjugation molecule comprising a solid phase support. In some embodiments, the second functional group comprises a carboxyl, a carboxylate salt or a phosphoramidite, such as the functional group as shown by Formula (C1), (C2) or (C3). When the second functional group comprises a carboxyl or a carboxylate salt, the compound of Formula (321) can react with a hydroxy or an amino group on a solid phase support (such as a resin) via esterification or amidation reaction, to form a conjugation molecule comprising a solid phase support linked via a carboxylate ester bond. When the second functional group comprises a phosphoramidite functional group, the compound of Formula (321) can couple with a hydroxy group on a universal solid phase support (such as a resin), and form a conjugation molecule comprising a solid phase support linked via a phosphodiester bond by oxidation. Next, starting from the above product linked to a solid phase support, the nucleoside monomers are linked sequentially through a phosphoramidite solid phase synthesis method, so as to obtain a sense strand or an antisense strand of the siRNA linked to a conjugation group. In the process of phosphoramidite solid phase synthesis, the first functional group is deprotected, and then coupled with a phosphoramidite group on a nucleoside monomer under coupling reaction condition.

In some embodiments, the first functional group comprises a hydroxy or a protected hydroxy group; the second functional group comprises a solid phase support linked via a carboxylate ester bond, an amide bond, or a phosphoester bond, as shown by Formula (C1') or (C3'). In this case, starting from the compound of Formula (321) in place of a solid phase support, the nucleoside monomers are linked sequentially through a phosphoramidite solid phase synthesis method, so as to obtain a sense strand or an antisense strand of the siRNA linked to a conjugation group.

In some embodiments, the carboxylate may be expressed as $—COO^{-}M^{+}$, wherein $M^{+}$ is a cation such as one selected from a metal cation, an ammonium cation $NH_4^{+}$ and an organic ammonium cation. In one embodiment, the metal cation may be an alkali metal cation, such as $K^{+}$ or $Na^{+}$. In order to increase solubility and facilitate the reaction, in some embodiments, the organic ammonium cation is an ammonium cation formed by a tertiary amine or a quaternary ammonium cation, such as an ammonium cation formed by triethylamine or an ammonium cation formed by N,N-diisopropylethylamine. In some embodiments, the carboxylate is a triethylamine carboxylate or an N,N-diisopropylethylamine carboxylate.

In some embodiments, $R_4$ comprises the structure as shown by Formula (B9), (B10), (B9'), (B10'), (B11), (B12), (B11'), or B(12'):

(B9)

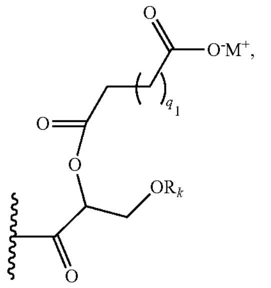

(B10)

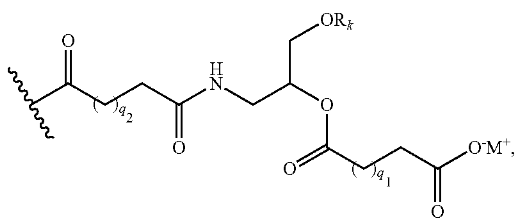

(B9')

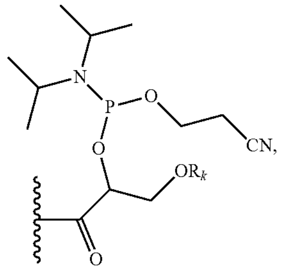

-continued (B10')

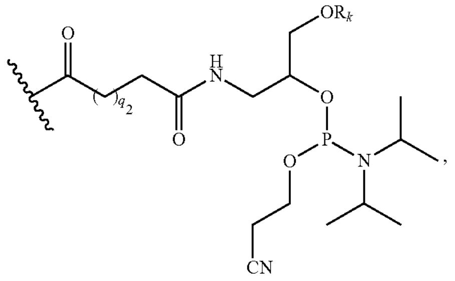

(B11)

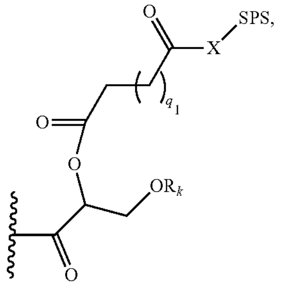

(B12)

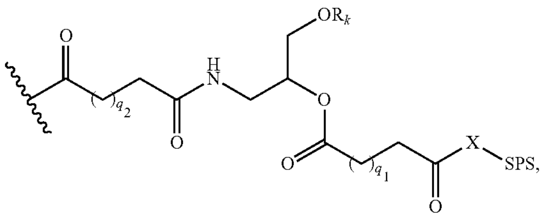

(B11')

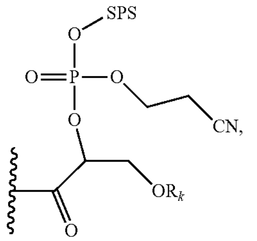

(B12')

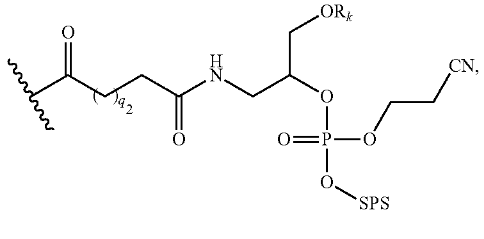

wherein $q_1$ is an integer of 1-4, $q_2$ is an integer of 1-10, X is O or NH, $M^{+}$ is a cation, $R_k$ is a hydroxy protection group, SPS represents a solid phase support, and  represents the site where the group is linked to the rest of the molecule. In some embodiments, $q_1$ is 1 or 2. In some embodiments, $q_2$ is an integer of 1-5. In some embodiments, $R_4$ comprises a structure as shown by Formula (B9) or (B10). In some embodiments, $R_4$ comprises a structure as shown by Formula (B11) or (B12).

In some embodiments, $R_k$ is one or more of Tr (trityl), MMTr (4-methoxytrityl), DMTr (4,4'-dimethoxytrityl), and TMTr (4,4',4'-trimethoxytrityl). In some embodiments, $R_k$ may be DMTr, i.e., 4,4'-dimethoxytrityl.

The definition of $L_1$ is as described above.

In some embodiments, $L_1$ is used to link the $M_1$ targeting group to the N atom on the nitrogenous backbone, thereby providing liver targeting function for the siRNA conjugate as shown by Formula (308). In some embodiments, $L_1$ comprises any one of Formulae (A1)-(A26), and any combination thereof.

According to the above description, those skilled in the art that would easily understand that as compared with the well-known phosphoramidite solid phase synthesis method in the art, the siRNA conjugate as shown by Formula (308) in which the conjugation molecule is linked to any possible position of the nucleotide sequence can be obtained by using the above first functional group and an optional second functional group. For example, the conjugation molecule is linked to a terminal region of the nucleotide sequence, or to a terminal of the nucleotide sequence. Correspondingly, unless otherwise specified, in the following description regarding preparation of the conjugate and/or the conjugation molecule, when referring to the reactions such as “deprotection”, “coupling”, “capping”, “oxidation”, “sulfurization”, it will be understood that the reaction conditions and agents involved in the well-known phosphoramidite solid phase synthesis method in the art would also apply to these reactions. Exemplary reaction conditions and agents will be described in detail hereinafter.

In some embodiments, each $S_1$ is independently a $M_1$. In some embodiments, each $S_1$ is independently a group formed by protecting at least one active hydroxyl group in $M_1$ with a hydroxyl protection group. In some embodiments, each $S_1$ is independently a group formed by protecting all existing active hydroxyl groups in $M_1$ with hydroxyl protection groups. In some embodiments, any hydroxyl protection group known to a skilled one may be used to protect the active hydroxyl group in $M_1$. In some embodiments, the protected hydroxy is expressed as the Formula YCOO—, wherein each Y is independently selected from the group consisting of $C_1$-$C_{10}$ alkyl and $C_6$-$C_{10}$ aryl, which is optionally substituted with one or more substituents selected from the group consisting of halo and $C_1$-$C_6$ alkyl. In some embodiments, each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and $C_1$-$C_6$ alkylphenyl.

In some embodiments, each $S_1$ is independently selected from the group consisting of Formulae (A46)-(A54):

(A46)

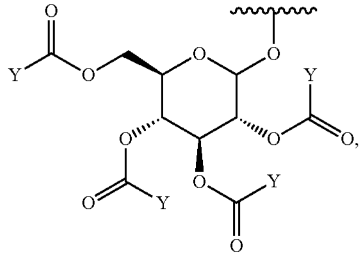

-continued (A47)

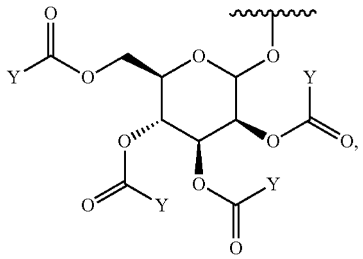

(A48)

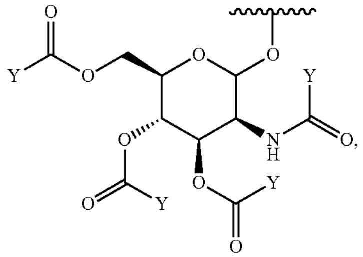

(A49)

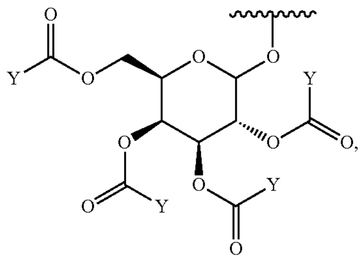

(A50)

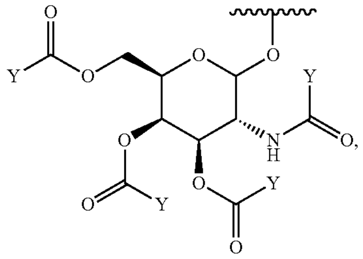

(A51)

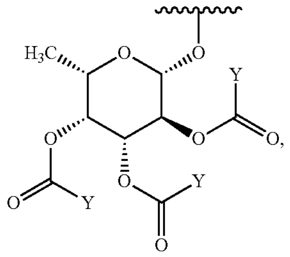

(A52)

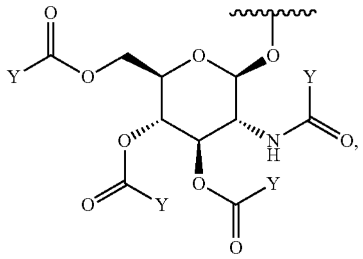

-continued (A53)

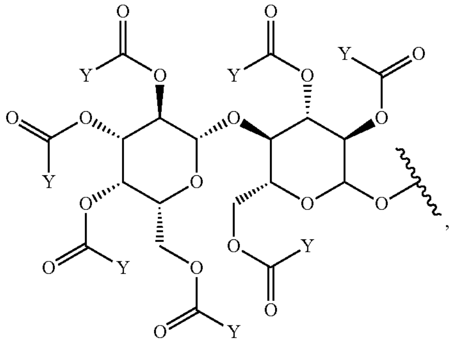

(A54)

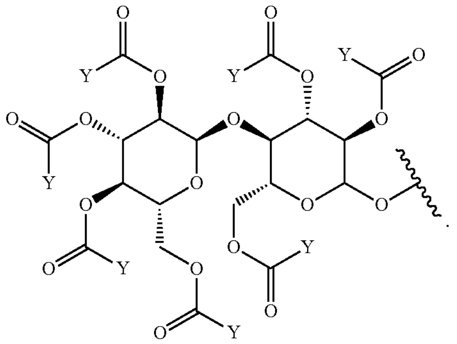

In some embodiments, $S_1$ is A49 or A50.

In some embodiments, each Y is independently one selected from methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl. In some embodiments, Y is methyl.

As mentioned above, the method for preparing the siRNA conjugate as shown by Formula (308) further comprises the following steps: synthesizing the other strand of the siRNA (for example, when a sense strand of the siRNA linked to a conjugation group is synthesized in the above step, the method further comprises synthesizing an antisense strand of the siRNA according to the solid phase synthesis method, vice versa), isolating the sense strand and the antisense strand, and annealing. In particular, in the step of isolating, the solid phase support linked to the nucleotide sequence and/or the conjugation molecule is cleaved, and the necessary protection group is removed (in this case, each $S_1$ group in the compound of Formula (321) is converted to the corresponding $M_1$ targeting group), to afford a sense strand (or an antisense strand) of the siRNA linked to a conjugation group and the corresponding antisense strand (or sense strand). The sense strand and the antisense strand are annealed to form a double-strand RNA structure, thereby affording the siRNA conjugate as shown by Formula (308).

In some embodiments, the method for preparing the siRNA conjugate as shown by Formula (308) comprises the following steps: contacting the compound as shown by Formula (321) with the first nucleoside monomer at 3' terminal of the sense strand or the antisense strand under coupling reaction condition in the presence of a coupling agent, thereby linking the compound as shown by Formula (321) to the first nucleotide in the sequence; sequentially linking nucleoside monomers in 3' to 5' direction to synthesize a sense or antisense strand of the siRNA according to the type and sequence of the nucleotides in the desired sense or antisense strand under the condition for phosphoramidite solid phase synthesis, wherein the compound of Formula (321) is a compound in which $R_4$ comprises a first functional group and a second functional group, wherein the first functional group comprises a protected hydroxyl and the second functional group has a structure as shown by Formula (C1') or (C3'), and the compound of (321) is deprotected before being linked to the first nucleoside monomer; and the linking of each nucleoside monomer comprises a four-step reaction of deprotection, coupling, capping, and oxidation or sulfurization; thus obtaining a sense or antisense strand of the nucleic acid linked to a conjugation group; sequentially linking nucleoside monomers in 3' to 5' direction to synthesize an antisense or sense strand of the nucleic acid according to the type and sequence of the nucleotides in the sense or antisense strand under the condition for phosphoramidite solid phase synthesis; wherein the linking of each nucleoside monomer includes a four-step reaction of deprotection, coupling, capping, and oxidation or sulfurization; removing the protection group and cleaving the solid phase support; isolating and purifying the sense strand and the antisense strand of the nucleic acid; and annealing.

In some embodiments, the method for preparing the siRNA conjugate as shown by Formula (308) comprises the following steps: according to the type and sequence of the nucleotides in the sense or antisense strand of the double-strand siRNA, sequentially linking nucleoside monomers in 3' to 5' direction to synthesize the antisense and sense strand; wherein the linking of each nucleoside monomer includes a four-step reaction of deprotection, coupling, capping, and oxidation or sulfurization, to obtain the sense strand linked to the solid phase support and the antisense strand linked to the solid phase support; contacting the compound as shown by Formula (321) with the sense strand linked to the solid phase support or the antisense strand linked to the solid phase support under coupling reaction condition in the presence of a coupling agent, thereby linking the compound as shown by Formula (321) to the sense strand or antisense strand; wherein the compound as shown by Formula (321) is a compound in which $R_4$ comprises a first functional group which is a phosphoramidite group; removing the protection group and cleaving the solid phase support; respectively isolating and purifying the sense strand or the antisense strand of the siRNA; and annealing, wherein the sense or antisense strand of the siRNA is linked to a conjugation group.

In some embodiments, the P atom in the Formula A59 is linked to the 3' terminal of the sense strand of the siRNA, and the method for preparing the siRNA conjugate as shown by Formula (308) comprises:

(1) removing the hydroxyl protection group $P_k$ in the compound of Formula (321), wherein the compound of Formula (321) is a compound in which $R_4$ comprises a first functional group comprising a protected hydroxyl $OR_k$, and a second functional group having a structure as shown by Formulas ($C_1$') or ($C_3$'); contacting the deprotected product with a nucleoside monomer to afford a nucleoside monomer linked to a solid phase support via a conjugation molecule under coupling reaction condition in the presence of a coupling agent;

(2) starting from the nucleoside monomer linked to a solid phase support via the conjugation molecule, synthesizing a sense strand of the siRNA in 3' to 5' direction by a phosphoramidite solid phase synthesis method;

(3) synthesizing an antisense strand of the siRNA by a phosphoramidite solid phase synthesis method; and (4) isolating the sense strand and the antisense strand of the siRNA and annealing the same to afford the siRNA conjugate as shown by Formula (308).

Therein, in step (1), the method for removing the protection group $R_k$ in the compound of Formula (321) comprises contacting the compound of Formula (321) with a deprotection agent under deprotection condition. The deprotection condition comprises a temperature of 0-50° C., and in some embodiments, 15-35° C., and a reaction time of 30-300 seconds, and in some embodiments, 50-150 seconds. The deprotection agent may be one or more selected from trifluoroacetic acid, trichloroacetic acid, dichloroacetic acid, and monochloroacetic acid, and in some embodiments, dichloroacetic acid. The molar ratio of the deprotection agent to the compound as shown by Formula (321) is 10:1 to 1000:1, and in some embodiments, 50:1 to 500:1.

The coupling reaction condition and the coupling agent may be any condition and agent suitable for the above coupling reaction. In some embodiments, the same condition and agent as those of the coupling reaction in the solid phase synthesis method can be used.

In some embodiments, the coupling reaction condition comprises a reaction temperature of 0-50° C., and in some embodiments, 15-35° C. The molar ratio of the compound of Formula (321) to the nucleoside monomer is 1:1 to 1:50, and in some embodiments, 1:2 to 1:5. The molar ratio of the compound of Formula (321) to the coupling agent may be 1:1 to 1:50, and in some embodiments, 1:3 to 1:10. The reaction time is 200-3,000 seconds, and in some embodiments, 500-1,500 seconds. The coupling agent is one or more selected from 1H-tetrazole, 5-ethylthio-1H-tetrazole and 5-benzylthio-1H-tetrazole, and in some embodiments, is 5-ethylthio-1H-tetrazole. The coupling reaction may be performed in an organic solvent. The organic solvent is one or more selected from anhydrous acetonitrile, anhydrous DMF and anhydrous dichloromethane, and in some embodiments, is anhydrous acetonitrile. With respect to the compound as shown by Formula (321), the amount of the organic solvent is 3-50 L/mol, and in some embodiments, 5-20 L/mol.

In step (2), starting from the nucleoside monomer linked to a solid phase support via a conjugation molecule prepared in the above steps, a sense strand S of the second siRNA conjugate is synthesized in 3' to 5' direction by the phosphoramidite solid phase synthesis method. In this case, the conjugation molecule is linked to 3' terminal of the resultant sense strand.

Other conditions for the solid phase synthesis in steps (2) and (3), including the deprotection condition for the nucleoside monomer, the type and amount of the deprotection agent, the coupling reaction condition, the type and amount of the coupling agent, the capping reaction condition, the type and amount of the capping agent, the oxidation reaction condition, the type and amount of the oxidation agent, the sulfurization reaction condition, and the type and amount of the sulfurization agent, adopt various conventional agents, amounts, and conditions in the art.

In some embodiments, for example, the solid phase synthesis in steps (2) and (3) can use the following conditions:

The deprotection condition for the nucleoside monomer comprises a reaction temperature of 0-50° C., and in some embodiments, 15-35° C., and a reaction time of 30-300 seconds, and in some embodiments, 50-150 seconds. The deprotection agent may be one or more selected from trifluoroacetic acid, trichloroacetic acid, dichloroacetic acid, and monochloroacetic acid, and in some embodiments, is dichloroacetic acid. The molar ratio of the deprotection agent to the protection group 4,4'-dimethoxytrityl on the solid phase support is 2:1 to 100:1, and in some embodiments, 3:1 to 50:1.

The coupling reaction condition comprises a reaction temperature of 0-50° C., and in some embodiments, 15-35° C. The molar ratio of the nucleic acid sequence linked to the solid phase support to the nucleoside monomer is 1:1 to 1:50, and in some embodiments, 1:5 to 1:15. The molar ratio of the nucleic acid sequence linked to the solid phase support to the coupling agent is 1:1 to 1:100, and in some embodiments, 1:50 to 1:80. The selection of the reaction time and the coupling agent is the same as above.

The capping reaction condition comprises a reaction temperature of 0-50° C., and in some embodiments, 15-35° C., and a reaction time of 5-500 seconds, and in some embodiments, 10-100 seconds. The selection of the capping agent is the same as above. The molar ratio of the total amount of the capping agent to the nucleic acid sequence linked to the solid phase support is 1:100 to 100:1, and in some embodiments, is 1:10 to 10:1. In the case where the capping agent uses equimolar acetic anhydride and N-methylimidazole, the molar ratio of acetic anhydride, N-methylimidazole, and the nucleic acid sequence linked to the solid phase support may be 1:1:10-10:10:1, and in some embodiments, is 1:1:2-2:2:1.

The oxidation reaction condition comprises a reaction temperature of 0-50° C., and in some embodiments, 15-35° C., and a reaction time of 1-100 seconds, and in some embodiments, 5-50 seconds. In some embodiments, the oxidation agent is iodine (in some embodiments provided as iodine water). The molar ratio of the oxidation agent to the nucleic acid sequence linked to the solid phase support in the coupling step may be 1:1 to 100:1, and in some embodiments, is 5:1 to 50:1. In some embodiments, the oxidation reaction is performed in a mixed solvent in which the ratio of tetrahydrofuran:water:pyridine is 3:1:1-1:1:3. The sulfurization reaction condition comprises a reaction temperature of 0-50° C., and in some embodiments, 15-35° C., and a reaction time of 50-2,000 seconds, and in some embodiments, 100-1,000 seconds. in some embodiments, the sulfurization agent is xanthane hydride. The molar ratio of the sulfurization agent to the nucleic acid sequence linked to the solid phase support in the coupling step is 10:1 to 1,000:1, and in some embodiments, is 10:1 to 500:1. In some embodiments, the sulfurization reaction is performed in a mixed solvent in which the ratio of acetonitrile:pyridine is 1:3-3:1.

The method further comprises isolating the sense strand and the antisense strand of the siRNA after linking all nucleoside monomers and before the annealing. Methods for isolation are well-known to those skilled in the art and generally comprise cleaving the synthesized nucleotide sequence from the solid phase support, removing the protection groups on the bases, phosphate groups and ligands, purifying, and desalting.

The conventional cleavage and deprotection methods in the synthesis of siRNAs can be used to cleave the synthesized nucleotide sequence from the solid phase support, and remove the protection groups on the bases, phosphate groups and ligands. For example, the resultant nucleotide sequence linked to the solid phase support is contacted with concentrated aqueous ammonia; during deprotection, the protection group YCOO— in groups A46-A54 is converted to a hydroxyl group, and thus the $S_1$ groups are converted to corresponding $M_1$ groups, providing the conjugate as shown by Formula (308); wherein the concentrated aqueous ammonia may be aqueous ammonia of a concentration of 25-30 wt %. With respect to the target siRNA sequence, the amount of the concentrated aqueous ammonia may be 0.2 ml/μmol-0.8 ml/μmol.

When there is at least one 2'-TBDMS protection on the synthesized nucleotide sequence, the method further comprises contacting the nucleotide sequence removed from the solid phase support with triethylamine trihydrofluoride to remove the 2'-TBDMS protection. Here, the resultant target siRNA sequence comprises the corresponding nucleoside having free 2'-hydroxy. With respect to the target siRNA sequence, the amount of pure triethylamine trihydrofluoride is 0.4 ml/mol-1.0 ml/mol. As such, the siRNA conjugate as shown by Formula (308) can be obtained.

Methods for purification and desalination are well-known to those skilled in the art. For example, nucleic acid purification may be performed using a preparative ion chromatography purification column with a gradient elution of NaBr or NaCl; after collection and combination of the product, the desalination may be performed using a reverse phase chromatography purification column.

In the resultant siRNA conjugate as shown by Formula (308), the non-bridging oxygen or sulfur atom in the phosphodiester bond or phosphorothioate diester bond between the nucleotides substantially binds to sodium ion, and the siRNA conjugate is substantially present in the form of a sodium salt. The well-known ion-exchange methods may be used, in which the sodium ion may be replaced with hydrogen ion and/or other cations, thereby providing other forms of siRNA conjugates as shown by Formula (308). The cations are as described above.

During synthesis, the purity and molecular weight of the nucleic acid sequence may be determined at any time, in order to better control the synthesis quality. Such determination methods are well-known to those skilled in the art. For example, the purity of the nucleic acid may be determined by ion exchange chromatography, and the molecular weight may be determined by liquid chromatography-mass spectrometry (LC-MS).

Methods for annealing are also well-known to those skilled in the art. For example, the synthesized sense strand (S strand) and the antisense strand (AS strand) may be simply mixed in water for injection at an equimolar ratio, heated to 70-95° C., and then cooled at room temperature to form a double-stranded structure via hydrogen bond. Hence, the siRNA conjugate as shown by Formula (308) can be obtained.

After having obtained the conjugate, in some embodiments, the synthesized siRNA conjugate as shown by Formula (308) can also be characterized by the means such as molecular weight detection using the methods such as liquid chromatography-mass spectrometry, to confirm that the synthesized siRNA conjugate is the designed siRNA conjugate as shown by Formula (308) of interest, and the sequence of the synthesized siRNA is the sequence of the desired siRNA sequence, for example, one of the sequences listed in Tables 1-5.

The compound as shown by Formula (321) may be obtained by the following preparation method, comprising: contacting a compound as shown by Formula (313) with a cyclic anhydride in an organic solvent under esterification reaction condition in the presence of a base and an esterification catalyst; isolating the compound as shown by Formula (321) by ion exchange:

Formula (313)

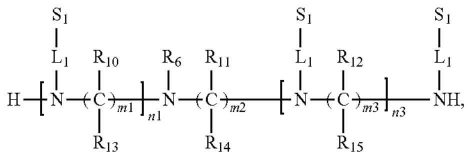

wherein the definitions and options of n1, n3, m1, m2, m3, $R_{10}$, $R_{11}$, $R_{12}$, $R_{13}$, $R_{14}$, $R_{15}$, $L_1$, and $S_1$ are respectively as described above;

$R_6$ is a group for providing $R_4$ of Formula (321); in some embodiments, $R_6$ has a structure as shown by Formula (A61):

(A61)

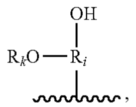

wherein $R_i$ is any group capable of linking to the N atom on the nitrogenous backbone, linking to $R_kO$ and linking to a free hydroxy group; $R_k$ is a hydroxy protection group. In this case, a compound as shown by Formula (321) is obtained, wherein $R_4$ comprises a first functional group which comprises a hydroxy protection group and a second functional group which comprises a structure as shown by Formula (C1) or (C2).

The esterification reaction condition includes a reaction temperature of 0-100° C. and a reaction time of 8-48 hours. In some embodiments, the esterification reaction condition comprises a reaction temperature of 10-40° C. and a reaction time of 20-30 hours.

In some embodiments, the organic solvent comprises one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran, the ether solvent is diethyl ether and/or methyl tertbutyl ether, and the haloalkane solvent is one or more of dichloromethane, trichloromethane and 1,2-dichloroethane. In some embodiments, the organic solvent is dichloromethane. With respect to the compound as shown by Formula (313), the amount of the organic solvent is 3-50 L/mol, and in some embodiments, 5-20 L/mol.

In some embodiments, the cyclic anhydride is one of succinic anhydride, glutaric anhydride, adipic anhydride or pimelic anhydride, and in some embodiments, the cyclic anhydride is succinic anhydride. The molar ratio of the cyclic anhydride to the compound as shown by Formula (313) is 1:1 to 10:1, and in some embodiments, 2:1 to 5:1.

The esterification catalyst may be any catalyst capable of catalyzing esterification reaction, such as 4-dimethylaminopyridine. The molar ratio of the catalyst to the compound as shown by Formula (313) is 1:1 to 10:1, and in some embodiments, is 2:1 to 5:1.

In some embodiments, the base may be any inorganic base, organic base or combination thereof. Considering solubility and product stability, the base may be, for example, an organic base of tertiary amine. In some embodiments, the organic base of tertiary amine is triethylamine or N,N-diisopropylethylamine. The molar ratio of the organic base of tertiary amine to the compound as shown by Formula (313) is 1:1 to 20:1, and in some embodiments, 3:1 to 10:1.

The ion exchange serves the function of converting the compound as shown by Formula (321) into a desired form of carboxylic acid or carboxylic salt and the methods of ion exchange are well-known to those skilled in the art. The above conjugation molecule in which the cation is $M^+$ may be obtained by using suitable ion exchange solution and ion exchange condition, which are omitted herein. In some embodiments, the ion exchange reaction is performed using a triethylamine phosphate solution, and the concentration of the triethylamine phosphate solution is 0.2-0.8 M. In some embodiments, the concentration of the triethylamine phosphate solution is 0.4-0.6 M, and with respect to the compound as shown by Formula (313), the amount of the triethylamine phosphate solution is 3-6 L/mol, and in further embodiments, 4-5 L/mol.

The compound of Formula (321) may be isolated from the reaction mixture using any suitable isolation methods. In some embodiments, the compound of Formula (321) may be isolated by removal of solvent via evaporation followed by chromatography. For example, the following two chromatographic conditions can be used for isolation: (1) normal phase purification of silica gel: 200-300 mesh silica gel filler, gradient elution of 1 wt ‰ triethylamine in dichloromethane:methanol=100:18-100:20; or (2) reverse phase purification: C18 and C8 reverse phase filler, gradient elution of methanol:acetonitrile=0.1:1-1:0.1. In some embodiments, the solvent may be directly removed to obtain a crude product of the compound of Formula (321), which may be directly used in subsequent reactions.

In some embodiments, the method for preparing the compound of Formula (321) further comprises: further contacting the product obtained by the above ion exchanging reaction with a solid phase support with amino or hydroxy groups in an organic solvent under condensation reaction condition in the presence of a condensation agent and an organic base of tertiary amine. In this case, a compound as shown by Formula (321) is obtained, wherein $R_4$ comprises a first functional group which comprises a hydroxy protection group and a second functional group which comprises a structure as shown by Formula (C1').

The solid phase support is one of the supports used in solid phase synthesis of siRNA, some of which are well-known to those skilled in the art. For example, the solid phase support may be selected from the solid phase supports containing active hydroxy or amino functional group(s), and in some embodiments, is an amino or hydroxy resin. In some embodiments, the amino or hydroxy resin has the following parameters: particle size of 100-400 mesh, and surface amino or hydroxy loading of 0.2-0.5 mmol/g. The ratio of the compound as shown by Formula (321) to the solid phase support is 10-400 mol compound/g solid phase support. In some embodiments, the ratio of the compound of Formula (321) to the solid phase support is 50 mol/g to 200 mol/g.

The organic solvent may be any suitable solvent or mixed solvent known to those skilled in the art. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran; the ether solvent is diethyl ether and/or methyl tertbutyl ether; the haloalkane solvent is one or more of dichloromethane, trichloromethane and 1,2-dichloroethane. In some embodiments, the organic solvent is acetonitrile. With respect to the compound of Formula (321), the amount of the organic solvent is 20-200 L/mol, and in some embodiments, 50-100 L/mol.

In some embodiments, the condensation agent may be benzotriazol-1-yl-oxytripyrrolidino phosphonium hexafluorophosphate (PyBop), 3-diethoxyphosphoryl-1,2,3-benzotriazin-4(3H)-one and/or O-benzotriazol-tetramethyluronium hexafluorophosphate. In some embodiments, the condensation agent is O-benzotriazol-tetramethyluronium hexafluorophosphate. The molar ratio of the condensation agent to the compound as shown by Formula (321) is 1:1 to 20:1, and in some embodiments, 1:1 to 5:1.

In some embodiments, the organic base of tertiary amine is triethylamine and/or N,N-diisopropylethylamine, and in some embodiments, N,N-diisopropylethylamine. The molar ratio of the organic base of tertiary amine to the compound as shown by Formula (321) is 1:1 to 20:1, and in some embodiments, 1:1 to 5:1.

In some embodiments, the method for preparing the compound of Formula (321) further comprises: contacting the resultant condensation product with a capping agent and an acylation catalyst in an organic solvent under capping reaction condition, and isolating the compound of Formula (321). The capping reaction is used to remove any active functional group that does not completely react, so as to avoid producing unnecessary by-products in subsequent reactions. The capping reaction condition comprises a reaction temperature of 0-50° C., and in some embodiments, 15-35° C., and a reaction time of 1-10 hours, and in some embodiments, 3-6 hours. The capping agent may be the capping agent used in solid phase synthesis of siRNA, which are well-known to those skilled in the art.

In some embodiments, the capping agent is composed of a capping agent 1 (cap1) and a capping agent 2 (cap2). The cap1 is N-methylimidazole, and in some embodiments, provided as a mixed solution of N-methylimidazole in pyridine/acetonitrile, wherein the volume ratio of pyridine to acetonitrile is 1:10 to 1:1, and in some embodiments, 1:3 to 1:1. In some embodiments, the ratio of the total volume of pyridine and acetonitrile to the volume of N-methylimidazole is 1:1 to 10:1, and in some embodiments, 3:1 to 7:1. The cap2 is acetic anhydride, and in some embodiments, provided as a solution of acetic anhydride in acetonitrile, wherein the volume ratio of acetic anhydride to acetonitrile is 1:1 to 1:10, and in further embodiments, 1:2 to 1:6.

In some embodiments, the ratio of the volume of the mixed solution of N-methylimidazole in pyridine/acetonitrile to the weight of the compound of Formula (321) is 5 ml/g-50 ml/g, and in some embodiments, 15 ml/g-30 ml/g. The ratio of the volume of the solution of acetic anhydride in acetonitrile to the weight of the compound of Formula (321) is 0.5 ml/g-10 ml/g, and in some embodiments, 1 ml/g-5 ml/g.

In some embodiments, the capping agent comprises equimolar acetic anhydride and N-methylimidazole. The organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the organic solvent is acetonitrile. With respect to the compound of Formula (321), the amount of the organic solvent is 10-50 L/mol, and in some embodiments, 5-30 L/mol.

In some embodiments, the acylation catalyst may be selected from any catalyst that may be used for esterification condensation or amidation condensation, such as alkaline heterocyclic compounds. In some embodiments, the acylation catalyst is 4-dimethylaminopyridine. The weight ratio of the catalyst to the compound as shown by Formula (321) may be 0.001:1 to 1:1, and in some embodiments, 0.01:1 to 0.1:1.

In some embodiments, the compound of Formula (321) may be isolated from the reaction mixture by any suitable separation methods. In some embodiments, the compound of Formula (321) may be obtained by thoroughly washing with an organic solvent and filtering to remove unreacted reactants, excess capping agent and other impurities, wherein the organic solvent is selected from acetonitrile, dichloromethane and methanol. In some embodiments, the organic solvent is acetonitrile.

In some embodiments, the preparation method of the conjugation molecule as shown by Formula (321) comprises contacting a compound as shown by Formula (313) with a phosphorodiamidite in an organic solvent under coupling reaction condition in the presence of a coupling agent, and isolating the compound as shown by Formula (321). In this case, a compound as shown by Formula (321) is obtained, wherein $R_4$ comprises a first functional group comprising a hydroxy protection group and a second functional group comprising a structure as shown by Formula (C3).

In some embodiments, the coupling reaction condition comprises: a reaction temperature of 0-50° C., such as 15-35° C.; the molar ratio of the compound of Formula (313) to the phosphorodiamidite of 1:1 to 1:50, such as 1:5 to 1:15; the molar ratio of the compound of Formula (313) to the coupling agent of 1:1 to 1:100, such as 1:50 to 1:80; and a reaction time of 200-3,000 seconds, such as 500-1,500 seconds. The phosphorodiamidite may be, for example, bis(diisopropylamino)(2-cyanoethoxy)phosphine, which may be commercially available or synthesized according to the methods well-known in the art. The coupling agent is one or more selected from 1H-tetrazole, 5-ethylthio-1H-tetrazole and 5-benzylthio-1H-tetrazole, such as 5-ethylthio-1H-tetrazole. The coupling reaction may be performed in an organic solvent. The organic solvent is one or more selected from anhydrous acetonitrile, anhydrous DMF and anhydrous dichloromethane, such as anhydrous acetonitrile. With respect to the compound of Formula (313), the amount of the organic solvent is 3-50 L/mol, such as 5-20 L/mol. By coupling reaction, the hydroxy group in the compound of Formula (313) reacts with the phosphorodiamidite to form a phosphoramidite group. In some embodiments, the solvent may be directly removed to afford a crude product of the compound of Formula (321), which may be directly used in subsequent reactions.

In some embodiments, the preparation method of the compound of Formula (321) further comprises the following steps: further contacting the isolated product with a solid phase support with hydroxy groups in an organic solvent under coupling reaction condition in the presence of a coupling agent, followed by capping, oxidation, and isolation, to afford the compound of Formula (321), wherein $R_4$ comprises a first functional group comprising a hydroxy protection group and a second functional group comprising a structure as shown by Formula (C3').

In some embodiments, the solid phase support is a solid support well-known in the art for solid phase synthesis of nucleic acid, such as, a deprotected commercially available universal solid phase support (NittoPhase®HL UnyLinker™ 300 Oligonucleotide Synthesis Support, Kinovate Life Sciences, as shown by Formula B80):

(B80)

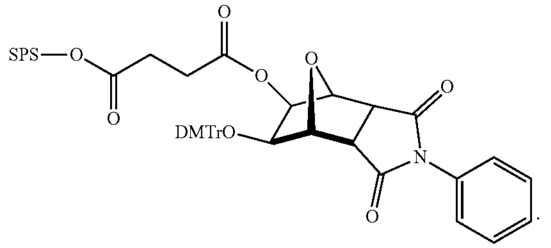

A deprotection reaction is well-known to those skilled in the art. In some embodiments, the deprotection condition comprises a temperature of 0-50° C., such as 15-35° C., and a reaction time of 30-300 seconds, such as 50-150 seconds. The deprotection agent may be one or more selected from of trifluoroacetic acid, trichloroacetic acid, dichloroacetic acid, and monochloroacetic acid. In some embodiments, the deprotection agent is dichloroacetic acid. The molar ratio of the deprotection agent to the protection group -DMTr (4,4'-dimethoxytrityl) on the solid phase support is 2:1 to 100:1, such as 3:1 to 50:1. Through such deprotection, reactive free hydroxy groups are obtained on the surface of the solid phase support, for facilitating the subsequent coupling reaction.

The coupling reaction condition and the coupling agent may be selected as above. Through the coupling reaction, the free hydroxy groups formed in the deprotection react with the phosphoramidite groups, so as to form a phosphite ester linkage.

In some embodiments, the capping reaction condition comprises a temperature of 0-50° C., such as 15-35° C., and a reaction time of 5-500 seconds, such as 10-100 seconds. The capping reaction is carried out in the presence of a capping agent. The selection and amount of the capping agent are as described above.

The oxidation reaction condition comprises a temperature of 0-50° C., such as 15-35° C., and a reaction time of 1-100 seconds, such as 5-50 seconds. The oxidation agent may be, for example, iodine (in some embodiments, provided as iodine water). The molar ratio of the oxidation agent to the nucleic acid sequence linked to the solid phase support is 1:1 to 100:1, such as, may be 5:1 to 50:1. In some embodiments, the oxidation reaction is performed in a mixed solvent in which the ratio of tetrahydrofuran:water:pyridine=3:1:1-1:1:3.

In some embodiments, $R_6$ is one of the groups of Formula B7 or B8:

(B7)

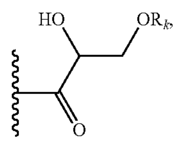

(B8)

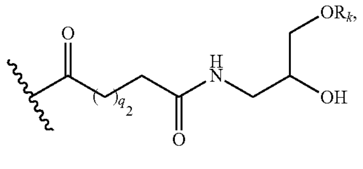

wherein the definition of $q_2$ is as described above.

In this case, the compound as shown by Formula (313) may be obtained by the following preparation method, comprising: contacting the compound as shown by Formula (314) with a compound as shown by Formula (A-1) or (A-2) in an organic solvent under amidation reaction condition in the presence of a condensation agent for amidation reaction and an organic base of tertiary amine, followed by isolation:

Formula (314)

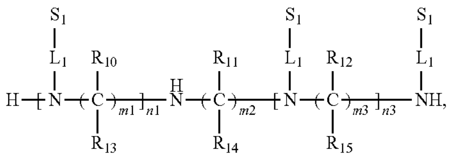

(A-1)

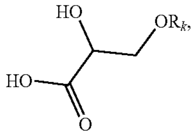

(A-2)

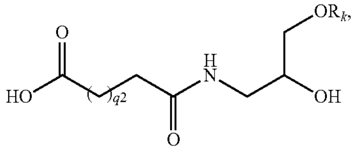

wherein the definitions and options of n1, n3, m1, m2, m3, $R_{10}$, $R_{11}$, $R_{12}$, $R_{13}$, $R_{14}$, $R_{15}$, $L_1$, $S_1$, $q_2$, and $R_k$ are respectively as described above.

The amidation reaction condition comprises a reaction temperature of 0-100° C. and a reaction time of 1-48 hours. In some embodiments, the amidation reaction condition comprises a reaction temperature of 10-40° C. and a reaction time of 2-16 hours.

In some embodiments, the organic solvent is one or more of an alcohol solvent, an epoxy solvent, an ether solvent, an haloalkane solvent, dimethyl sulfoxide, N,N-dimethylformamide, and N,N-diisopropylethylamine. In some embodiments, the alcohol solvent is one or more of methanol, ethanol and propanol, and in some embodiments, ethanol. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. With respect to the compound of Formula (314), the amount of the organic solvent is 3-50 L/mol, and in some embodiments, 3-20 L/mol.

In some embodiments, the condensation agent for amidation reaction is benzotriazol-1-yl-oxytripyrrolidinophosphonium hexafluorophosphate, 3-diethoxyphosphoryl-1,2,3-benzotrizin-4(3H)-one, 4-(4,6-dimethoxytriazin-2-yl)-4-methylmorpholine hydrochloride, 2-ethoxy-1-ethoxycarbonyl-1,2-dihydroquinoline (EEDQ), or O-benzotriazol-tetramethyluronium hexafluorophosphate, and in further embodiments, 3-diethoxyphosphoryl-1,2,3-benzotrizin-4(3H)-one. The molar ratio of the condensation agent for amidation reaction to the compound as shown by Formula (314) is 1:1 to 10:1, and in some embodiments, 2.5:1 to 5:1.

In some embodiments, the organic base of tertiary amine is triethylamine or N,N-diisopropylethylamine, and in some embodiments, N,N-diisopropylethylamine. The molar ratio of the organic base of tertiary amine to the compound as shown by Formula (314) is 3:1 to 20:1, and in some embodiments, 5:1 to 10:1.

The compounds of Formula (A-1) and (A-2) may be prepared by any suitable means. For example, when $R_k$ is a DMTr group, the compound of Formula (A-1) may be prepared by reacting calcium glycerate with DMTrCl. Similarly, the compound of Formula (A-2) may be prepared by firstly contacting 3-amino-1,2-propanediol with a cyclic anhydride and then reacting with DMTrCl, wherein the cyclic anhydride may have 4-13 carbon atoms, and in some embodiments, 4-8 carbon atoms. Those skilled in the art would easily understand that the selections of different cyclic anhydrides correspond to different values for $q_2$ in the compound of Formula (A-2). For example, when the cyclic anhydride is succinic anhydride, $q_2=1$; when the cyclic anhydride is glutaric anhydride, $q_2=2$, and so on.

In some variations, the compound of Formula (313) can also be prepared by sequentially reacting the compound as shown by Formula (314) with the cyclic anhydride, 3-amino-1,2-propanediol and DMTrCl. Those skilled in the art would easily understand that these variations would not affect the structure and function of the compound of Formula (313), and these variations are readily realized by those skilled in the art on the basis of the above methods.

Similarly, the compound of Formula (313) may be isolated from the reaction mixture by any suitable isolation methods. In some embodiments, the compound of Formula (313) may be isolated by removal of solvent via evaporation followed by chromatography. For example, the following chromatographic conditions may be used for isolation: (1) normal phase purification of silica gel: 200-300 mesh silica gel filler, with gradient elution of petroleum ether:ethyl acetate:dichloromethane:N,N-dimethylformamide=1:1:1:0.5-1:1:1:0.6; and (2) reverse phase purification: C18 and C8 reverse phase fillers, with gradient elution of methanol:acetonitrile=0.1:1-1:0.1. In some embodiments, the solvent may be directly removed to afford a crude product of the compound of Formula (313), which may be directly used in subsequent reactions.

In some embodiments, the compound as shown by Formula (314) may be obtained by the following preparation method, comprising: contacting the compound as shown by Formula (320) with the compound as shown by Formula (316) in an organic solvent under condensation reaction condition in the presence of a condensation agent for amidation reaction and an organic base of tertiary amine, followed by isolation:

Formula (316)

$S_1—L_1—OH$

Formula (320)

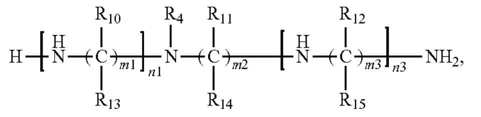

wherein the definitions and options of n1, n3, m1, m2, m3, $R_{10}$, $R_{11}$, $R_{12}$, $R_{13}$, $R_{14}$, and $R_{15}$ are respectively as described above.

The compound of Formula (316) can be, such as, those disclosed in J. Am. Chem. Soc. 2014, 136, 16958-16961. Alternatively, the compounds of Formula (316) may be prepared by those skilled in the art via various methods. For example, some compounds of Formula (316) may be prepared according to the method disclosed in Example 1 of the U.S. Pat. No. 8,106,022B2, which is incorporated herein by reference in its entirety.

In some embodiments, the condensation reaction condition comprises a reaction temperature of 0-100° C. and a reaction time of 0.1-24 hours, and in some embodiments, a reaction temperature of 10-40° C. and a reaction time of 0.5-16 hours.

Considering the structure of the desired product compound of Formula (314), the molar ratio of the compound as shown by Formula (316) to the compound as shown by Formula (320) should be determined based on the sum of n1 and n3 in Formula (320). In some embodiments, for example, when n1+n3=3, to ensure complete reaction without any excess, the molar ratio of the compound as shown by Formula (316) to the compound as shown by Formula (320) may be 3:1 to 3.5:1, and in some embodiments, 3.01:1 to 3.15:1.

In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. With respect to the compound of Formula (320), the amount of the organic solvent may be 3-50 L/mol, and in some embodiments, 5-20 L/mol.

In some embodiments, the condensing agent for amidation reaction is benzotriazol-1-yl-oxytripyrrolidinophosphonium hexafluorophosphate, 3-diethoxyphosphoryloxy-1,2,3-benzotrizin-4(3H)-one (DEPBT), O-benzotriazol-tetramethyluronium hexafluorophosphate, 4-(4,6-dimethoxytriazin-2-yl)-4-methylmorpholine hydrochloride, or 1-hydroxybenzotriazole, and in further embodiments, is a mixture of benzotriazol-1-yl-oxytripyrrolidinophosphonium hexafluorophosphate and 1-hydroxybenzotriazole, wherein benzotriazol-1-yl-oxytripyrrolidinophosphonium hexafluorophosphate and 1-hydroxybenzotriazole are used in equimolar amounts. The molar ratio of the total condensing agent for amidation reaction to the compound as shown by Formula (316) may be 1:1 to 3:1, and in some embodiments, 1.05:1 to 1.5:1.

The organic base of tertiary amine may be N-methylmorpholine, triethylamine or N,N-diisopropylethylamine, and in some embodiments, N-methylmorpholine. The molar ratio of the organic base of tertiary amine to the compound as shown by Formula (316) may be 2:1 to 10:1, and in some embodiments, 2:1 to 5:1.

Similarly, the compound as shown by Formula (314) may be isolated from the reaction mixture by any suitable isolation method. In some embodiments, the compound as shown by Formula (314) may be isolated by removal of solvent via evaporation followed by chromatography, for example, using the following two chromatographic conditions for isolation: (1) normal phase purification of silica gel: 200-300 mesh silica gel filler, with gradient elution of dichloromethane:methanol=100:5-100:7; and (2) reverse phase purification: $C_{18}$ and $C_8$ reverse phase fillers, with gradient elution of methanol:acetonitrile=0.1:1-1:0.1. In some embodiments, the solvent may be directly removed to afford a crude product of the compound of Formula (314), which may be directly used in subsequent reactions.

The compound of Formula (320) may be commercially available, or prepared by those skilled in the art via known methods. For example, in the case where m1=m2=m3=3, n1=1, n3=2, and $R_{10}$, $R_{11}$, $R_{12}$, $R_{13}$, $R_{14}$, and $R_{15}$ are all H, the compound of Formula (320) may be commercially available from Alfa Aesar Inc.

The siRNA conjugate of the present disclosure may also be used in combination with other pharmaceutically acceptable excipients, which may be one or more of various conventional formulations or compounds in the art. For details, please refer to the above description of the pharmaceutical compositions of the present disclosure.

Use of the siRNA, the Pharmaceutical Composition and the Conjugate Comprising the siRNA of the Present Disclosure In some embodiments, the present disclosure provides the use of the siRNA and/or the pharmaceutical composition and/or the siRNA conjugate of the present disclosure in the manufacture of a medicament for treating and/or preventing dyslipidemia.

In some embodiments, the present disclosure provides a method for preventing and/or treating dyslipidemia, comprising administering an effective amount of the siRNA and/or the pharmaceutical composition and/or the siRNA conjugate of the present disclosure to a subject in need thereof.

The purpose of preventing and/or treating dyslipidemia may be achieved through the mechanism of RNA interference by administering the siRNA active ingredient of the present disclosure to a subject in need thereof. Therefore, the siRNA and/or the pharmaceutical composition and/or the siRNA conjugate of the present disclosure may be used for preventing and/or treating dyslipidemia, or for preparing a medicament for preventing and/or treating dyslipidemia.

The dyslipidemia refers to abnormal blood lipid caused by over-expression of APOC3 gene in hepatocytes, and generally manifests itself as increased level(s) of any one or all of lipids (such as triglyceride and cholesterol) and/or lipoprotein in blood. A high level of blood lipid is highly associated with hypertension, cardiovascular disease, diabetes, and other pathological conditions. Hypertriglyceridemia is associated with atherosclerosis, and would lead to pancreatitis. The dyslipidemia of the present disclosure includes, but is not limited to, hypercholesteremia, hypertriglyceridemia or atherosclerosis.

As used herein, the term "administration/administer" refers to the delivery of the siRNA and/or the pharmaceutical composition and/or the siRNA conjugate of the present disclosure into a subject's body by a method or a route that at least partly locates the siRNA and/or the pharmaceutical composition and/or the siRNA conjugate of the present disclosure at a desired site to produce a desired effect. Suitable administration routes for the methods of the present disclosure include topical administration and systemic administration. In general, topical administration results in the delivery of more siRNA conjugate to a particular site as compared with the whole body of the subject; whereas systemic administration results in the delivery of the siRNA and/or the pharmaceutical composition and/or the siRNA conjugate of the present disclosure to substantially the whole body of the subject. Considering that the present disclosure is intended to provide a means for preventing and/or treating dyslipidemia, in some embodiments, an administration mode capable of delivering a medicament to the liver.

The administration to a subject may be achieved by any suitable routes known in the art, including but not limited to, oral and parenteral routes, such as intravenous administration, intramuscular administration, subcutaneous administration, transdermal administration, intratracheal administration (aerosol), pulmonary administration, nasal administration, rectal administration, and topical administration (including buccal administration and sublingual administration). The administration frequency may be once or more times daily, weekly, biweekly, triweekly, monthly, bimonthly, quarterly, semiannually, or yearly.

The dose of the siRNA or the pharmaceutical composition or the siRNA conjugate of the present disclosure may be a conventional dose in the art, which may be determined according to various parameters, especially age, weight and gender of a subject. Toxicity and efficacy may be determined in cell cultures or experimental animals by standard pharmaceutical procedures, for example, by determining $LD_{50}$ (the lethal dose that causes 50% population death) and $ED_{50}$ (the dose that can cause 50% of the maximum response intensity in a graded response, and that causes 50% of the experimental subjects to have a positive response in a qualitative response). The dose range for human may be derived based on data obtained from cell culture analysis and animal studies.

When the siRNA, the pharmaceutical composition and/or the siRNA conjugate of the present disclosure is administered, for example, to male or female, 6 to 12 weeks old, C57BL/6J mice of 18 to 25 g body weight or ob/ob mice of 30 to 45 g body weight, (i) for the siRNA conjugate, the amount of the siRNA thereof may be 0.001 to 100 mg/kg body weight, in further embodiments 0.01 to 50 mg/kg body weight, in more further embodiments 0.05 to 20 mg/kg body weight, in some embodiments 0.05 to 15 mg/kg body weight, and in other embodiments 0.1 to 10 mg/kg body weight; (ii) for a pharmaceutical composition formed from the siRNA and the pharmaceutically acceptable carrier, the amount of the siRNA thereof may be 0.001 to 50 mg/kg body weight, in further embodiments 0.01 to 10 mg/kg body weight, in more further embodiments 0.05 to 5 mg/kg body weight, and in still more further embodiments 0.1 to 3 mg/kg body weight, based on the amount of the siRNA.

In some embodiments, the present disclosure provides a method of inhibiting the expression of APOC3 gene in hepatocytes, comprising contacting an effective amount of the siRNA and/or the pharmaceutical composition and/or the siRNA conjugate of the present disclosure with the hepatocytes, and introducing the siRNA and/or the pharmaceutical composition and/or the siRNA conjugate of the present disclosure into the hepatocytes, so as to realize the purpose of inhibiting the expression of APOC3 gene in hepatocytes through the mechanism of RNA interference. The hepatocytes may be selected from hepatoma cell lines (such as Hep3B, HepG2 and Huh7), and isolated primary hepatocytes. In some embodiments, the hepatocytes are Huh7 hepatoma cells.

In the case where the expression of APOC3 gene in a cell is inhibited by the method of the present disclosure, the amount of the siRNA in the modified siRNA and/or the pharmaceutical composition and/or the siRNA conjugate of the present disclosure is generally such an amount that is sufficient to reduce the expression of the target gene and results in an extracellular concentration of 1 pM to 1 μM, or 0.01 nM to 100 nM, or 0.05 nM to 50 nM, or 0.05 nM to about 5 nM on the surface of the target cells. The amount required to achieve this topical concentration will vary with various factors, including the delivery method, the delivery site, the number of cell layers between the delivery site and the target cells or tissues, the delivery route (topical or systemic), etc. The concentration at the delivery site may be significantly higher than that on the surface of the target cells or tissues.

Kit

The present disclosure provides a kit comprising an effective amount of at least one of the modified siRNA, the pharmaceutical composition, and the siRNA conjugate of the present disclosure.

In some embodiments, the kit of the present disclosure may provide the modified siRNA in a container. In some embodiments, the kit of the present disclosure may comprise a container containing a pharmaceutically acceptable excipient. In some embodiments, the kit may further comprise other ingredients, such as stabilizers or preservatives. In some embodiments, the kit of the present disclosure may comprise at least one additional therapeutic agent in other container different from the container for providing the modified siRNA of the present disclosure. In some embodiments, the kit may comprise an instruction for mixing the modified siRNA with pharmaceutically acceptable carriers and/or excipients or other ingredients (if present).

In the kit of the present disclosure, the modified siRNA and the pharmaceutically acceptable carrier and/or excipient, as well as the modified siRNA, the pharmaceutical composition, and/or the siRNA conjugate and/or the conjugate, and/or the pharmaceutically acceptable excipient may be provided in any form, such as in a liquid form, a dry form or a lyophilized form. In some embodiments, the modified siRNA and the pharmaceutically acceptable carrier and/or excipient, and the pharmaceutical composition and/or conjugate and optional pharmaceutically acceptable excipient(s) are substantially pure and/or sterilized. In some embodiments, the kit of the present disclosure may provide sterilized water.

Hereinafter, the present disclosure will be further illustrated by way of examples, but will not be limited thereto in any respect.

EXAMPLES

Unless otherwise specified, the reagents and culture media used in following examples are all commercially available, and the procedures used such as nucleic acid electrophoresis and real-time PCR are all performed according to the methods described in Molecular Cloning (Cold Spring Harbor Laboratory Press (1989)).

Huh7 cells were purchased from the Stem Cell Bank of Chinese Academy of Science and cultured in DMEM complete media (Hyclone company) containing 10% fetal bovine serum (FBS, Hyclone company) and 1% non-essential amino acid (NEAA, Corning company) at 37° C. in an incubator containing 5% $CO_2$/95% air.

When the siRNA or the siRNA conjugate against APOC3 gene synthesized in the present disclosure or the siRNA or the siRNA conjugate as negative control was used to transfect cells, Lipofectamine™2000 (Invitrogen) was used as a transfection reagent. The specific procedures could refer to the instruction provided by the manufacturer.

Unless otherwise specified, ratios of reagents provided below are all calculated by volume ratio (v/v).

The animal models used are as follows:

Human APOC3 transgenic mice: B6; CBA-Tg(APOC3) 3707Bres/J, purchased from Jackson Laboratory, US;

All the experimental data are expressed as $\overline{X}$, and the data are analyzed with Graphpad prism 5.0 statistical analysis software.

Preparation Example 1: The Preparations of Conjugates 1-11

In this preparation example, Conjugates 1-11 were synthesized. The conjugates were those formed by conjugating L-9 conjugation molecule to the siRNAs as shown in Table 7.

(1-1) Synthesis of Compound L-10:

Compound L-10 was synthesized according to the following method:

(1-1-1) Synthesis of GAL-5 (a terminal segment of the conjugation molecule)

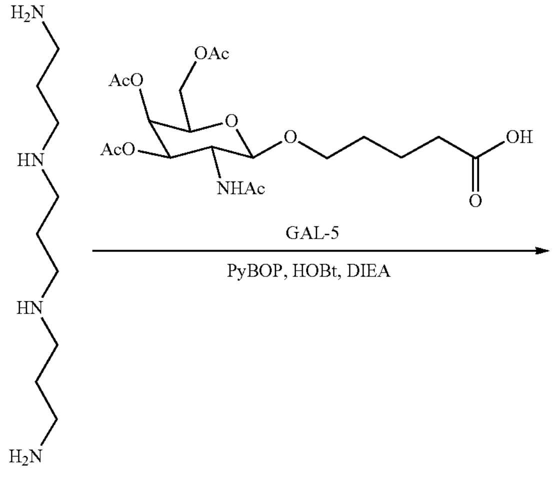

J-0

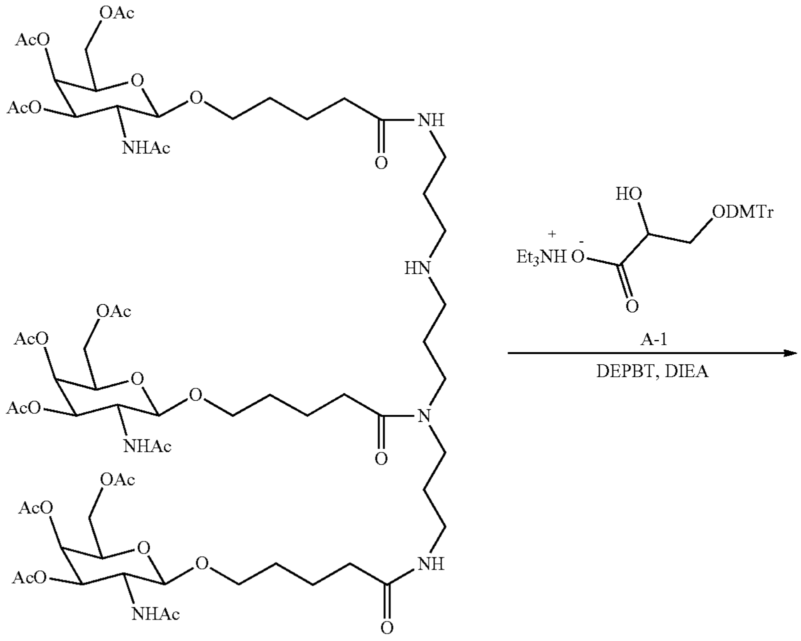

L-8

-continued
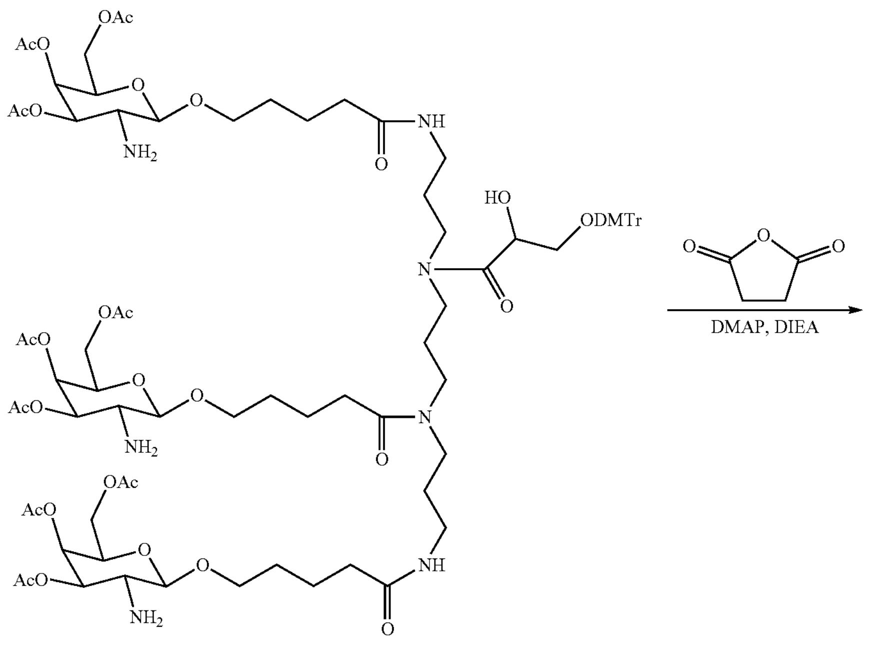
L-7
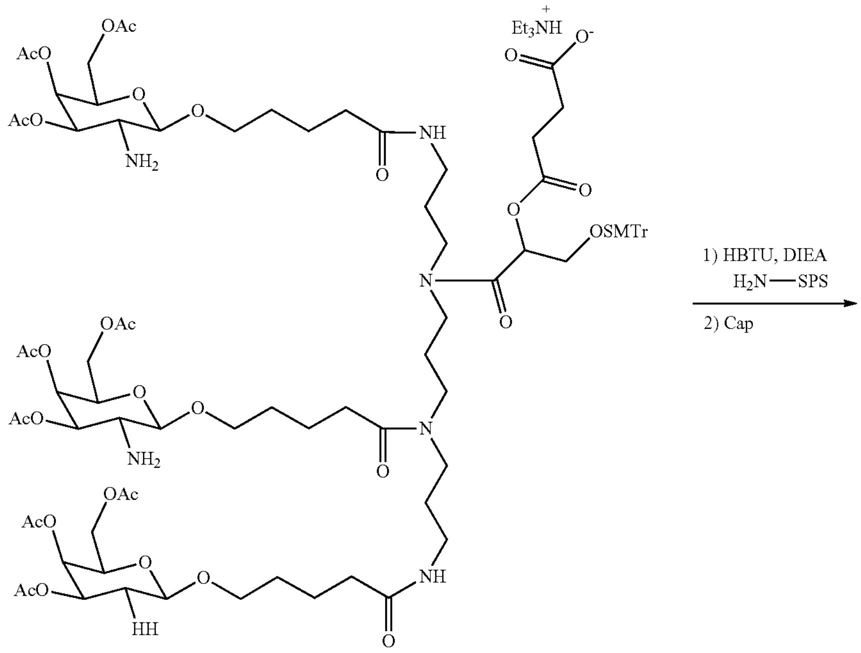

-continued

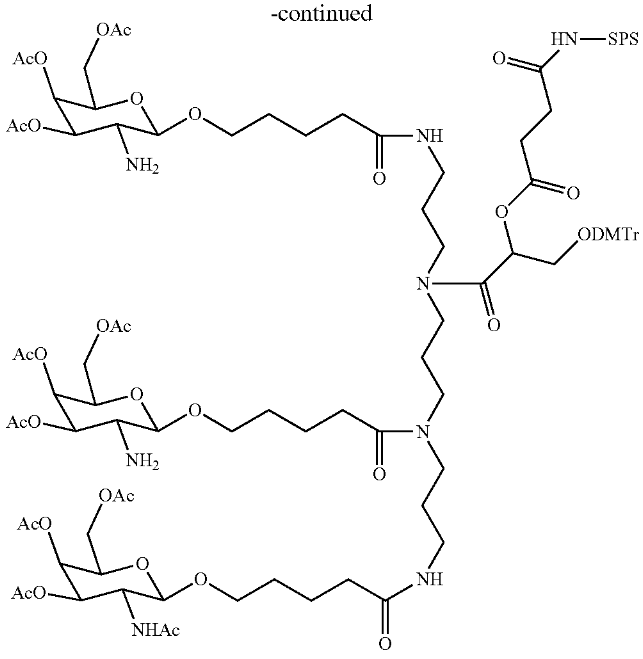

L-10

(1-1-1a) Synthesis of GAL-2

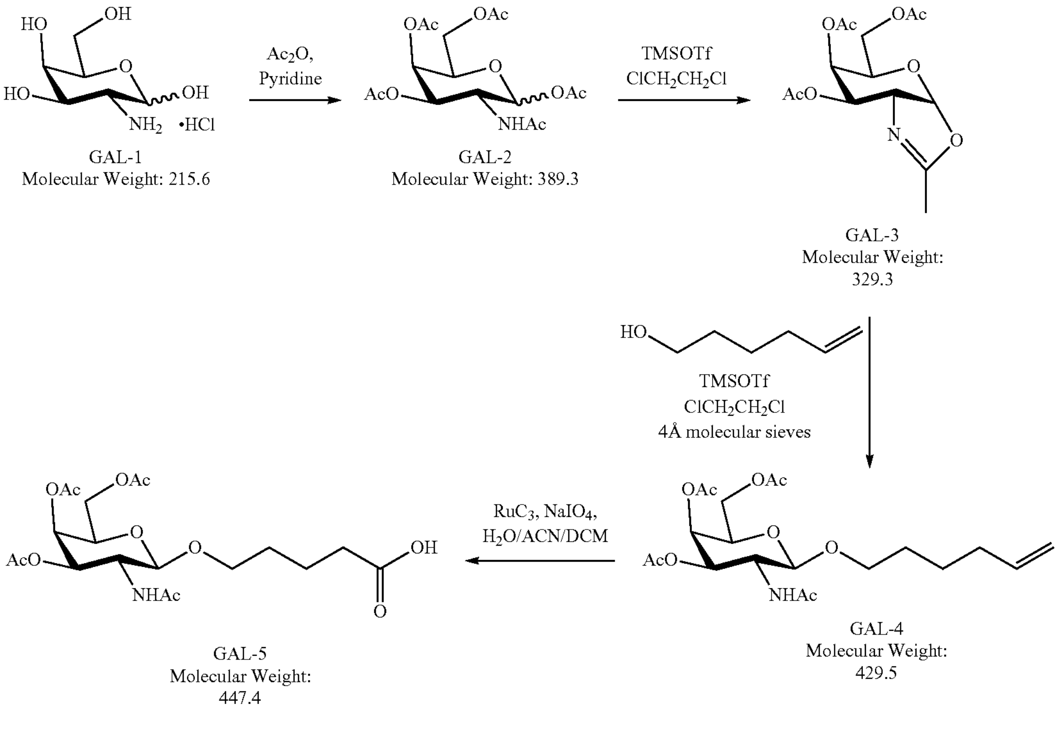

GAL-1
Molecular Weight: 215.6

GAL-2
Molecular Weight: 389.3

GAL-3
Molecular Weight: 329.3

GAL-4
Molecular Weight: 429.5

GAL-5
Molecular Weight: 447.4

100.0 g of GAL-1 (N-acetyl-D-galactosamine hydrochloride, CAS No.: 1772-03-8, purchased from Ning Bo hongxiang bio-chem Co., Ltd., 463.8 mmol) was dissolved in 1000 ml of anhydrous pyridine, to which 540 ml of acetic anhydride (purchased from Enox Inc., 5565.6 mmol) was added in an ice water bath to react under stirring at room temperature for 1.5 hours. The resultant reaction solution was poured into 10 L of ice water and subjected to suction filtration under reduced pressure. The residue was washed with 2 L of ice water, and then added with a mixed solvent of acetonitrile/toluene (v/v ratio of acetonitrile:toluene=1:1) until completely dissolved. The solvent was removed by evaporation to give 130.0 g of product GAL-2 as a white solid.

(1-1-1b) Synthesis of GAL-3

GAL-2 (35.1 g, 90.0 mmol) obtained in step (1-1-1a) was dissolved in 213 ml of anhydrous 1,2-dichloroethane, to which 24.0 g of TMSOTf (CAS No.: 27607-77-8, purchased from Macklin Inc., 108.0 mmol) was added in an ice water bath under nitrogen atmosphere to react at room temperature overnight.

The reaction solution was added with 400 ml dichloromethane for dilution, filtered with diatomite, and then added with 1 L saturated aqueous sodium bicarbonate solution and stirred evenly. An organic phase was isolated. The aqueous phase remained was extracted twice, each with 300 ml of dichloroethane. The organic phases were combined and washed with 300 ml of saturated aqueous sodium bicarbonate solution and 300 ml of saturated brine, respectively. The organic phase was isolated and dried with anhydrous sodium sulfate. The solvent was removed by evaporation to dryness under reduced pressure to give 26.9 g of product GAL-3 as a light yellow viscous syrup.

(1-1-1c) Synthesis of GAL-4

GAL-3 (26.9 g, 81.7 mmol) obtained in step (1-1-1b) was dissolved in 136 ml of anhydrous 1,2-dichloroethane, added with 30 g of dry 4 Å molecular sieve powder followed by 9.0 g of 5-hexen-1-ol (CAS No.: 821-41-0, purchased from Adamas-beta Inc., 89.9 mmol), and stirred at room temperature for 30 minutes. 9.08 g of TMSOTf (40.9 mmol) was added in an ice bath under nitrogen atmosphere to react under stirring at room temperature overnight. The 4 Å molecular sieve powder was removed by filtration. The filtrate was added with 300 ml dichloroethane for dilution, filtered with diatomite, and then added with 500 ml of saturated aqueous sodium bicarbonate solution and stirred for 10 minutes for washing. An organic phase was isolated. The aqueous phase was extracted once with 300 ml of dichloroethane. The organic phases were combined and washed with 300 ml of saturated aqueous sodium bicarbonate solution and 300 ml of saturated brine, respectively. The organic phase was isolated and dried with anhydrous sodium sulfate. The solvent was removed by evaporation to dryness under reduced pressure to give 41.3 g of product GAL-4 as a yellow syrup, which was directly used in the next oxidation reaction without purification.

(1-1-1d) Synthesis of GAL-5

GAL-4 (14.9 g, 34.7 mmol) obtained according to the method described in step (1-1-1c) was dissolved in a mixed solvent of 77 ml of dichloromethane and 77 ml of acetonitrile, added with 103 ml of deionized water and 29.7 g of sodium periodate (CAS No.: 7790-28-5, purchased from Aladdin Inc., 138.8 mmol) respectively, and stirred in an ice bath for 10 minutes. Ruthenium trichloride (CAS No.: 14898-67-0, available from Energy Chemical, 238 mg, 1.145 mmol) was added to react at room temperature overnight. The resultant reaction solution was diluted by adding 300 ml of water under stirring, and adjusted to a pH of about 7.5 by adding saturated sodium bicarbonate. The organic phase was isolated and discarded. The aqueous phase was extracted three times, each with 200 ml of dichloromethane, and the organic phase was discarded. The aqueous phase was adjusted to a pH of about 3 with citric acid solids and extracted three times, each with 200 ml of dichloromethane, and the resultant organic phases were combined and dried with anhydrous sodium sulfate. The solvent was removed by evaporation to dryness under reduced pressure to give 6.85 g of product GAL-5 as a white foamy solid. $^1$H NMR (400 MHz, DMSO) δ 12.01 (br, 1H), 7.83 (d, J=9.2 Hz, 1H), 5.21 (d, J=3.2 Hz, 1H), 4.96 (dd, J=11.2, 3.2 Hz, 1H), 4.49 (d, J=8.4 Hz, 1H), 4.07-3.95 (m, 3H), 3.92-3.85 (m, 1H), 3.74-3.67 (m, 1H), 3.48-3.39 (m, 1H), 2.20 (t, J=6.8 Hz, 2H), 2.11 (s, 3H), 2.00 (s, 3H), 1.90 (s, 3H), 1.77 (s, 3H), 1.55-1.45 (m, 4H).

(1-1-2) Synthesis of L-8

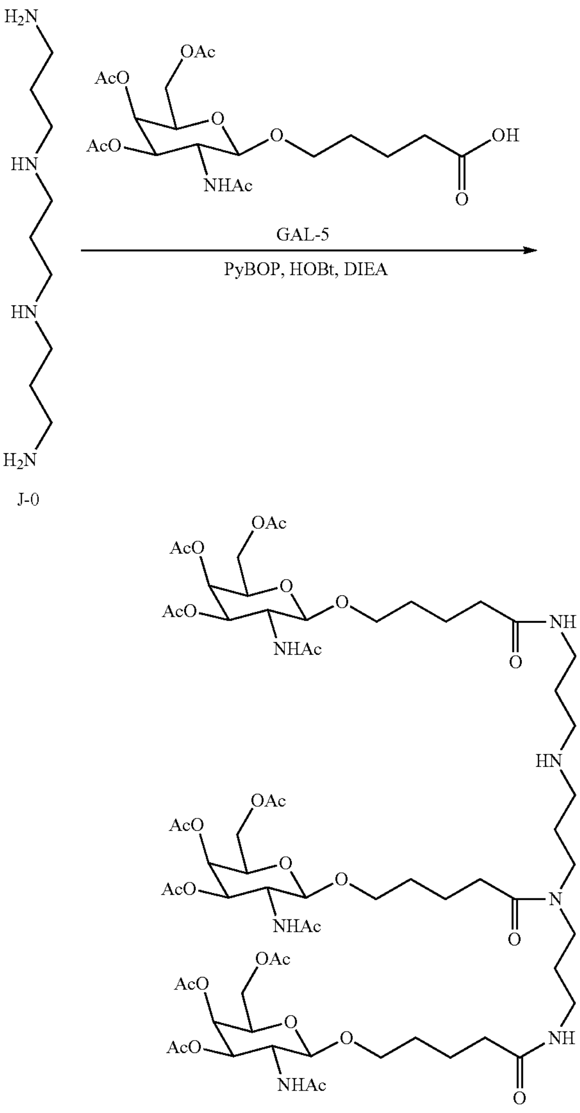

J-0

L-8

J-0 (9.886 g, 52.5 mmol, purchased from Alfa Aesar Inc.) and GAL-5 (72.819 g, 162.75 mmol, obtained by combining several batches of products) obtained in step (1-1-1) were dissolved in 525 ml of dichloromethane, and added with diisopropylethylamine (DIEA, 44.782 g, 346.50 mmol), benzotriazol-1-yl-oxytripyrrolidino phosphonium hexafluorophosphate (PyBOP, 90.158 g, 173.25 mmol) and hydroxybenzotriazole (HOBt, 23.410 g, 173.25 mmol) to react at room temperature for 4 hours. The resultant reaction solution was washed by adding 20 ml of saturated sodium bicarbonate solution and 200 ml of saturated brine. The aqueous phase was extracted twice, each with 100 ml of dichloromethane. The organic phases were combined, dried with anhydrous sodium sulfate, and filtered. Then the solvent was removed by evaporation to dryness under reduced pressure to give a crude product. The crude product was purified by using a normal phase silica gel column (200-300 mesh). The column was added with 10 wt % triethylamine for neutralizing the acidity of silica gel, equilibrated with 1 wt ‰ triethylamine, and eluted with a gradient elution of dichloromethane:methanol=100:25-100:40. The eluate was collected, and the solvent was removed by evaporation to dryness under reduced pressure to give 38.8 g of pure product L-8. $^1$H NMR (400 MHz, DMSO) δ 7.84 (d, J=9.0 Hz, 3H), 7.27-7.23 (m, 1H), 7.13-7.18 (m, 1H), 5.22 (d, J=3.1 Hz, 3H), 4.97 (dd, J=11.3, 3.1 Hz, 3H), 4.48 (d, J=8.4 Hz, 3H), 4.09-3.98 (m, 9H), 3.88 (dd, J=19.3, 9.3 Hz, 3H), 3.75-3.66 (m, 3H), 3.44-3.38 (m, 3H), 3.17-3.30 (m, 4H), 3.10-2.97 (m, 4H), 2.35-2.20 (m, 6H), 2.15-2.08 (m, 9H), 2.07-1.98 (m, 13H), 1.94-1.87 (m, 9H), 1.81-1.74 (m, 9H), 1.65-1.42 (m, 18H). MS m/z: $C_{85}H_{119}N_7O_{30}$, $[M+H]^+$. calculated: 1477.59, measured: 1477.23.

(1-1-3)

(1-1-3a) Synthesis of A-1

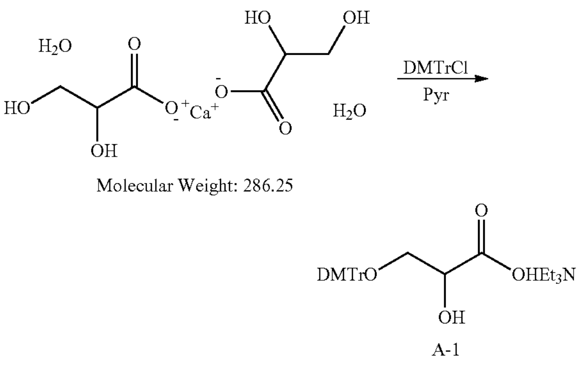

Molecular Weight: 286.25

A-1

Molecular Weight: 509.64

DMTrCl (4,4'-dimethoxytrityl chloride, 101.65 g, 300 mmol) was dissolved in 1000 ml of anhydrous pyridine, and added with calcium DL-glycerate hydrate (28.63 g, 100 mmol) to react at 45° C. for 20 hours. The resultant reaction solution was filtered. The residue was rinsed with 200 ml of DCM, and the filtrate was concentrated to dryness under reduced pressure. The residue was redissolved in 500 ml of dichloromethane and washed twice, each with 200 ml of 0.5 M triethylamine phosphate (pH=7-8). The aqueous phase was extracted twice, each with 200 ml of dichloromethane. The organic phases were combined, dried with anhydrous sodium sulfate, and filtered. The solvent was removed by evaporation to dryness under reduced pressure, and the residue was purified by using a normal phase silica gel column (200-300 mesh). The column was eluted with a gradient elution of petroleum ether:ethyl acetate:dichloromethane:methanol=1:1:1:0.35-1:1:1:0.55. The eluate was collected, and the solvent was removed by evaporation to dryness under reduced pressure. The residue was redissolved in 600 ml of dichloromethane, and washed once with 200 ml of 0.5 M triethylamine phosphate. The aqueous phase was extracted once with 200 ml of dichloromethane. The organic phases were combined, dried with anhydrous sodium sulfate, and filtered. The solvent was removed by evaporation to dryness under reduced pressure, and the residue was dried under reduced pressure in a vacuum oil pump overnight to give 50.7 g of product A-1 as a white solid. $^1$H NMR (400 MHz, DMSO-d6) δ 7.46 (ddd, J=6.5, 2.3, 1.1 Hz, 1H), 7.40-7.28 (m, 7H), 6.89-6.81 (m, 4H), 4.84 (d, J=5.0 Hz, 1H), 4.36-4.24 (m, 1H), 4.29 (s, 6H), 3.92 (dd, J=12.4, 7.0 Hz, 1H), 3.67 (dd, J=12.3, 7.0 Hz, 1H), 2.52 (q, J=6.3 Hz, 6H), 1.03 (t, J=6.3 Hz, 9H). MS m/z: $C_{24}H_{23}O_6$, $[M-H]^-$. calculated: 407.15, measured: 406.92.

(1-1-3b) Synthesis of L-7

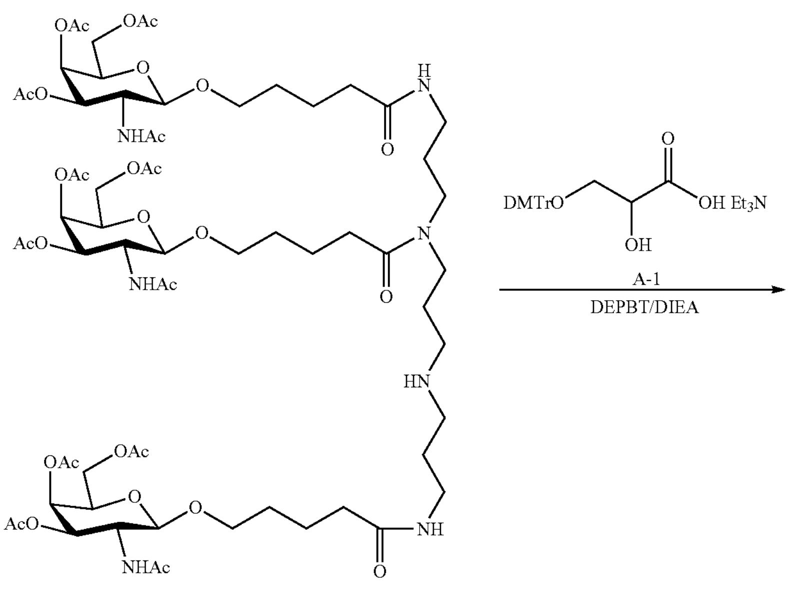

L-8

-continued

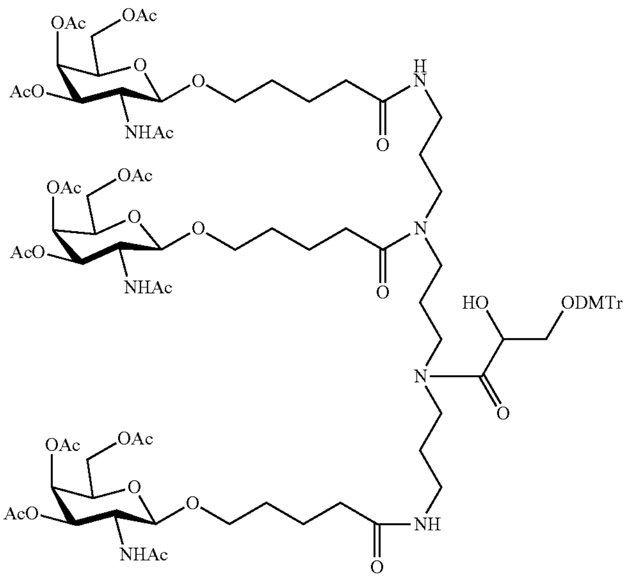

L-7

L-8 (40 g, 27.09 mmol, obtained by combining several batches of products) obtained in step (1-1-2) and A-1 (41.418 g, 81.27 mmol) obtained in step (1-1-3a) were mixed and dissolved in 271 ml of dichloromethane, added with 3-diethoxyphosphoryl-1,2,3-benzotriazin-4(3H)-one (DEPBT) (24.318 g, 81.37 mmol), and further added with diisopropylethylamine (21.007 g, 162.54 mmol) to react under stirring at 25° C. for 1.5 hours. The organic phase was washed with 800 ml of saturated sodium bicarbonate. The aqueous phase was extracted three times, each with 50 ml of dichloromethane. The organic phase was washed with 150 ml of saturated brine, and the aqueous phase was extracted once with 50 ml of dichloromethane, and the organic phases were combined, dried with anhydrous sodium sulfate and filtered. The solvent was removed by evaporation to dryness under reduced pressure, and the residue was foam-dried in a vacuum oil pump overnight to give a crude product. The crude product was subjected to a column purification. The column was filled with 2 kg normal phase silica gel (200-300 mesh), added with 200 ml triethylamine for neutralizing the acidity of silica gel, equilibrated with petroleum ether containing 1 wt % triethylamine, and eluted with a gradient elution of petroleum ether:ethyl acetate:dichloromethane:N,N-dimethylformamide=1:1:1:0.5-1:1:1:0.6. The eluate was collected, and the solvent was removed by evaporation to dryness under reduced pressure to give 40.4 g of pure product L-7. $^1H$ NMR (400 MHz, DMSO) δ 7.90-7.78 (m, 4H), 7.75-7.64 (m, 1H), 7.38-7.18 (m, 9H), 6.91-6.83 (m, 4H), 5.25-5.10 (m, 4H), 4.97 (dd, J=11.2, 3.2 Hz, 3H), 4.48-4.30 (m, 4H), 4.02 (s, 9H), 3.93-3.84 (m, 3H), 3.76-3.66 (m, 9H), 3.45-3.35 (m, 3H), 3.24-2.98 (m, 10H), 2.30-2.20 (m, 2H), 2.11-1.88 (m, 31H), 1.80-1.40 (m, 28H). MS m/z: $C_{90}H_{128}N_7O_{35}$, $[M-DMTr]^+$. calculated: 1564.65, measured: 1564.88.

(1-1-4) Synthesis of L-9

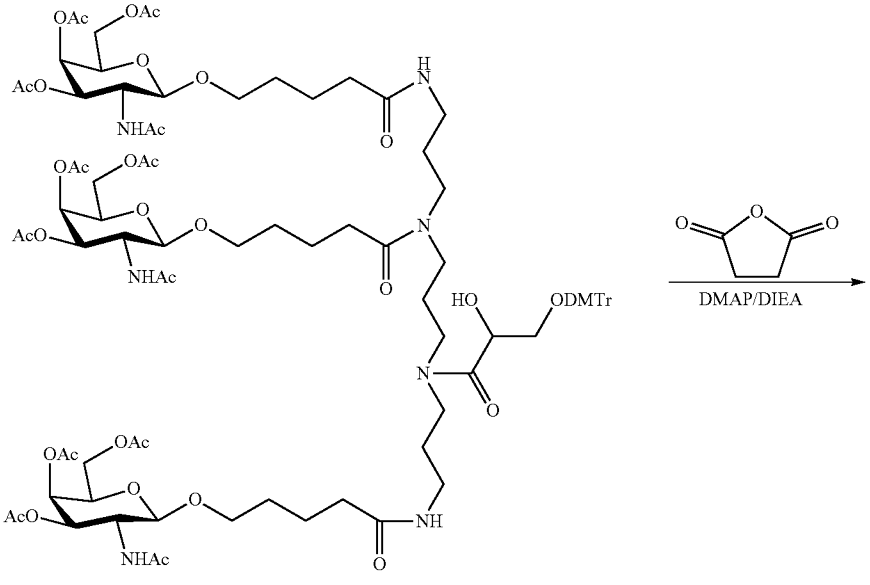

L-7

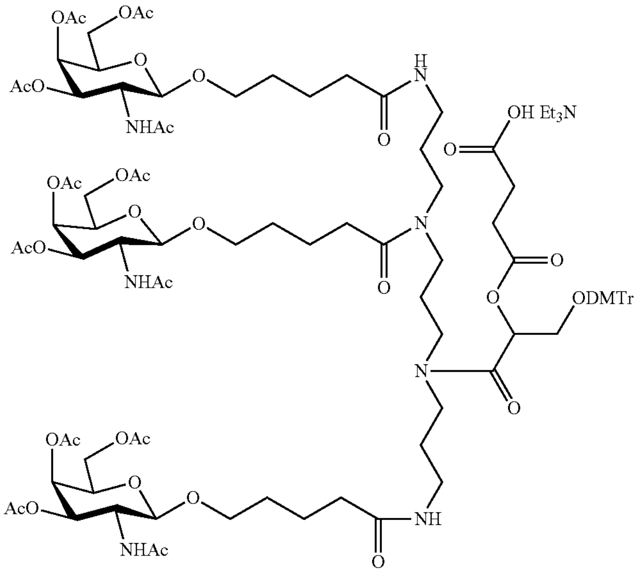

L-9

L-7 (40 g, 21.4247 mmol) obtained in step (1-1-3b), succinic anhydride (4.288 g, 42.8494 mmol) and 4-dimethylaminopyridine (DMAP, 5.235 g, 42.8494 mmol) were mixed and dissolved in 215 ml of dichloromethane, further added with diisopropylethylamine (DIEA, 13.845 g, 107.1235 mmol), and stirred at 25° C. for 24 hours. The resultant reaction solution was washed with 800 ml of 0.5 M triethylamine phosphate. The aqueous phase was extracted three times, each with 5 ml of dichloromethane. The organic phases were combined and evaporated to dryness under reduced pressure to give a crude product. The crude product was subjected to a 10 column purification. The column was filled with 1 kg normal phase silica gel (200-300 mesh), added with 1 wt ‰ triethylamine for neutralizing the acidity of silica gel, equilibrated with dichloromethane, and eluted with a gradient elution of 1 wt ‰ triethylamine in dichloromethane:methanol=100:18-100:20. The eluate was collected, and the solvent was removed by evaporation to dryness under reduced pressure to give 31.0 g of pure product L-9 conjugation molecule. $^1$H NMR (400 MHz, DMSO) δ 8.58 (d, J=4.2 Hz, 1H), 7.94-7.82 (m, 3H), 7.41-7.29 (m, 5H), 7.22 (d, J=8.1 Hz, 5H), 6.89 (d, J=8.3 Hz, 4H), 5.49-5.37 (m, 1H), 5.21 (d, J=3.0 Hz, 3H), 4.97 (d, J=11.1 Hz, 3H), 4.49 (d, J=8.2 Hz, 3H), 4.02 (s, 9H), 3.88 (dd, J=19.4, 9.4 Hz, 3H), 3.77-3.65 (m, 9H), 3.50-3.39 (m, 6H), 3.11-2.90 (m, 5H), 2.61-2.54 (m, 4H), 2.47-2.41 (m, 2H), 2.26-2.17 (m, 2H), 2.15-1.95 (m, 22H), 1.92-1.84 (m, 9H), 1.80-1.70 (m, 10H), 1.65-1.35 (m, 17H), 1.31-1.19 (m, 4H), 0.96 (t, J=7.1 Hz, 9H). MS m/z: $C_{94}H_{13}2N_7O_{38}$, [M-DMTr]$^+$. calculated: 1664.72, measured: 1665.03.

(1-1-5) Synthesis of L-10

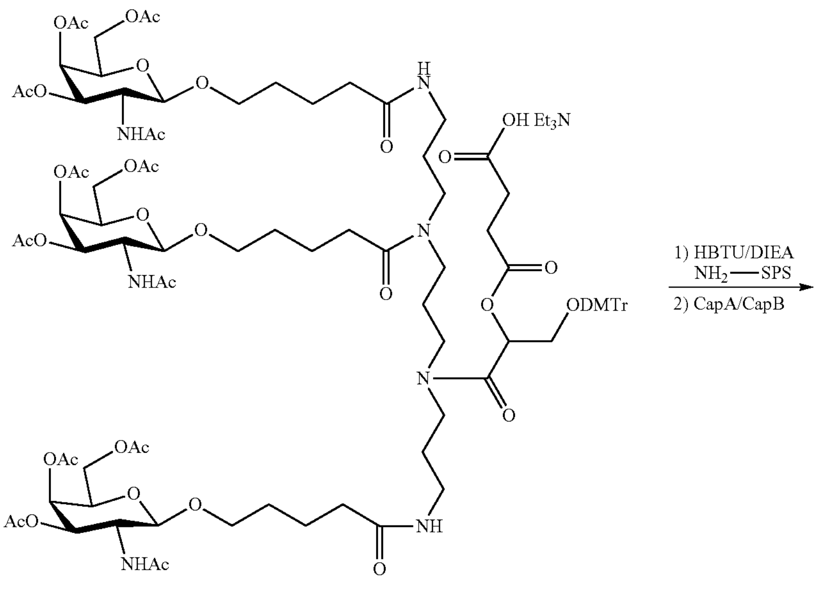

L-9

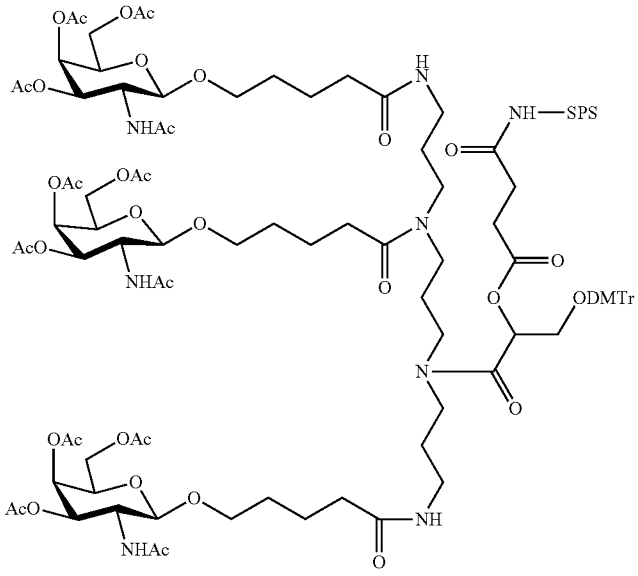

L-10

In this step, Compound L-10 was prepared by linking the L-9 conjugation molecule to a solid phase support.

The L-9 conjugation molecule (22.751 g, 11 mmol) obtained in step (1-1-4), O-benzotriazol-tetramethyluronium hexafluorophosphate (HBTU, 6.257 g, 16.5 mmol) and diisopropylethylamine (DIEA, 2.843 g, 22 mmol) were mixed and dissolved in 900 ml of acetonitrile, and stirred at room temperature for 5 minutes. The resultant reaction solution was added with Aminomethyl resin ($H_2NResin$, 88 g, 100-200 mesh, amino loading: 400 mol/g, purchased from Tianjin Nankai HECHENG S&T Co., Ltd.). A reaction was performed on a shaker at 25° C. and at a rotation speed of 150 rpm/min for 18 hours, followed by filtration. The residue was rinsed twice (each with 300 ml of DCM) and three times (each with 300 ml of acetonitrile), and dried in a vacuum oil pump for 18 hours. Then starting materials (CapA, CapB, 4-dimethylaminopyridine (DMAP) and acetonitrile) were added according to the charge ratio as shown in Table 6 for a capping reaction. The reaction was performed on a shaker at 25° C. and at a rotation speed of 150 rpm/min for 5 hours. The reaction liquid was filtered. The residue was rinsed three times, each with 300 ml of acetonitrile. The solvent was removed by evaporation to dryness under reduced pressure, and the residue was dried under reduced pressure in a vacuum oil pump overnight to give 102 g of Compound L-10 (i.e., the L-9 conjugation molecule linked to a solid phase support), with a loading of 90.8 mol/g.

TABLE 6

| The charge ratio of capping reaction | | | | |
|---|---|---|---|---|
| Starting Materials | Amount | Specs | Lot No. | Manufacturer |
| CapA | 1980 ml | — | — | — |
| CapB | 220 ml | — | — | — |
| DMAP | 1.100 g | analytical pure | I1422139 | Aladdin |
| Acetonitrile | 220 ml | spectroscopic pure | O15161001 | CINC (Shanghai) Co., Ltd |

In the above table, Cap A and Cap B are solutions of capping agents. Cap A is a mixed solution of 20% by volume of N-methylimidazole in pyridine/acetonitrile, wherein the volume ratio of pyridine to acetonitrile is 3:5. Cap B is a solution of 20% by volume of acetic anhydride in acetonitrile.

(1-2) Synthesis of Sense Strands of Conjugates 1-11

Nucleoside monomers were linked one by one in 3' to 5' direction according to the arrangement sequences of nucleotides in the sense strands of Conjugates 1-11 the phosphoramidite solid phase synthesis method, starting the cycles from the Compound L-10 prepared in the above step. The linking of each nucleoside monomer included a four-step reaction of deprotection, coupling, capping, and oxidation or sulfurization. Therein, when two nucleotides are linked via a phosphoester bond, a four-step reaction of deprotection, coupling, capping, and oxidation was included during linking of the later nucleoside monomer; and when two nucleotides is linked via a phosphorothioate linkage, a four-step reaction of deprotection, coupling, capping, and sulfurization was included during linking of the later nucleoside monomer. The synthesis conditions are as follows.

The nucleoside monomers are provided in a 0.1 M acetonitrile solution. The condition for deprotection reaction in each step is identical, i.e., a temperature of 25° C., a reaction time of 70 seconds, a solution of dichloroacetic acid in dichloromethane (3% v/v) as a deprotection reagent, and a molar ratio of dichloroacetic acid to the protection group 4,4'-dimethoxytrityl on the solid phase support of 5:1.

The condition for coupling reaction in each step is identical, including a temperature of 25° C., a molar ratio of the nucleic acid sequence linked to the solid phase support to nucleoside monomers of 1:10, a molar ratio of the nucleic acid sequence linked to the solid phase support to a coupling reagent of 1:65, a reaction time of 600 seconds, and 0.5 M acetonitrile solution of 5-ethylthio-1H-tetrazole (ETT) as a coupling reagent.

The condition for capping reaction in each step is identical, including a temperature of 25° C., a reaction time of 15 seconds, a mixed solution of Cap A and Cap B in a molar ratio of 1:1 as a solution of capping agent, and a molar ratio of the capping agent to the nucleic acid sequence linked to the solid phase support of 1:1:1 (acetic anhydride:N-methylimidazole: the nucleic acid sequence linked to the solid phase support).

The condition for oxidation reaction in each step is identical, including a temperature of 25° C., a reaction time of 15 seconds, and 0.05 M iodine water as an oxidation reagent; and a molar ratio of iodine to the nucleic acid sequence linked to the solid phase support in the coupling step of 30:1. The reaction is carried out in a mixed solvent of tetrahydrofuran:water:pyridine (3:1:1).

The condition for sulfurization reaction in each step is identical, including a temperature of 25° C., a reaction time of 300 seconds, and xanthane hydride as a sulfurization reagent; and a molar ratio of the sulfurization reagent to the nucleic acid sequence linked to the solid phase support in the coupling step of 120:1. The reaction is carried out in a mixed solvent of acetonitrile:pyridine (1:1).

The conditions for cleavage and deprotection are as follows: adding the synthesized nucleotide sequence linked to the support into 25 wt % aqueous ammonia to react at 55° C. for 16 hours, wherein the amount of the aqueous ammonia is 0.5 ml/mol. The liquid was removed, and the residue is concentrated to dryness in vacuum.

Purification and desalination: purification of the nucleic acid is achieved by using a preparative ion chromatography purification column (Source 15Q) with a gradient elution of NaCl. Specifically, eluent A is 20 mM sodium phosphate (pH 8.1), solvent is water/acetonitrile in 9:1 (v/v); eluent B is 1.5 M sodium chloride, 20 mM sodium phosphate (pH 8.1), solvent is water/acetonitrile in 9:1 (v/v); elution gradient: the ratio of eluent A:eluent B=100:0-50:50. The eluate is collected, combined and desalted by using a reverse phase chromatography purification column. The specific condition includes: using a Sephadex column for desalination (filler: Sephadex G25) and eluting with deionized water.

Detection: the purity is determined by ion exchange chromatography (IEX-HPLC); and the molecular weight of the product was analyzed by Liquid Chromatography-Mass Spectrometry (LC-MS). The fact that the measured values were in conformity with the calculated values indicates that the sense strands S of Conjugates 1-11 of which 3' terminal was conjugated to the L-9 conjugation molecule were synthesized.

(1-3) Synthesis of Antisense Strands (1-3A) Preparation of Antisense Strands of Conjugates 1-5

Antisense strands AS of Conjugates 1-5 were synthesized respectively by linking nucleoside monomers one by one in 3' to 5' direction according to the arrangement sequences of nucleotides in the antisense strands of Conjugates 1-5 in the phosphoramidite solid phase synthesis method, starting the cycles from a universal solid phase support (UnyLinker™ loaded NittoPhase®HL Solid Supports, Kinovate Life Sciences Inc.). The reaction conditions of deprotection, coupling, capping, oxidation or sulfurization, cleavage and deprotection, and purification and desalting in the solid phase synthesis method were the same as those used for the synthesis of the sense strands.

Detection: the purity was detected by ion exchange chromatography (IEX-HPLC); and the molecular weight was analyzed by liquid chromatography-mass spectrometry (LC-MS). The fact that the measured values were in conformity with the calculated values indicates that the antisense strands AS having the target sequences were synthesized.

Therein, the vinyl phosphate and 2'-methoxy modified uracil monomer (VP-Um) was synthesized according to the following method:

(1-3-1) Synthesis of VP-U-2
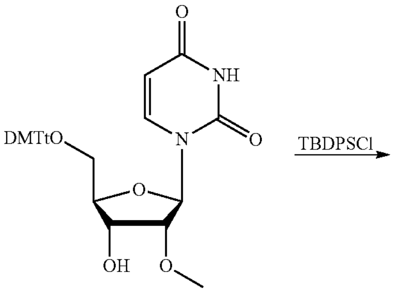
2'-OMe-U
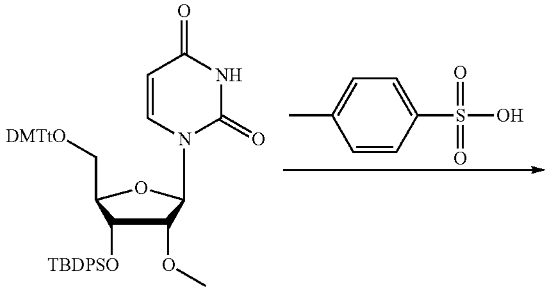
VP-U-1
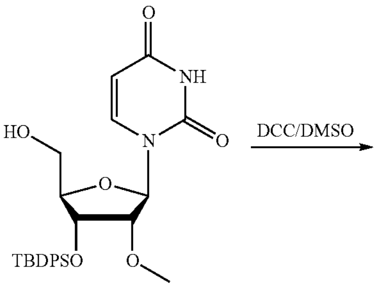
VP-U-2
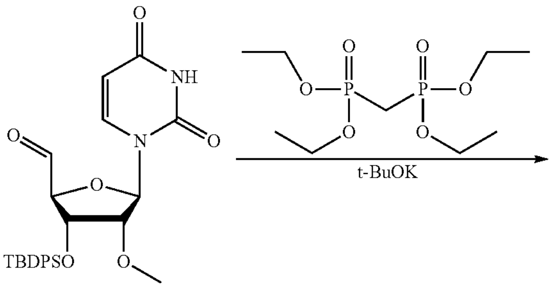
VP-U-3
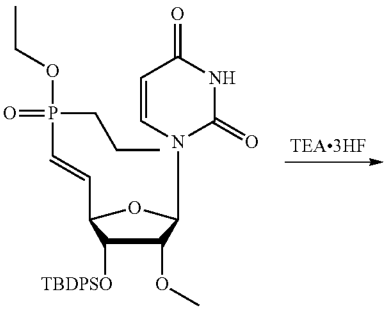
VP-U-4
-continued
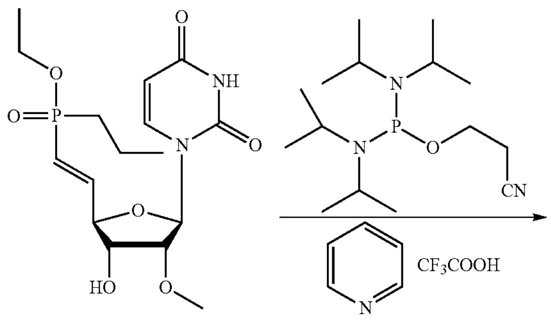
VP-U-5
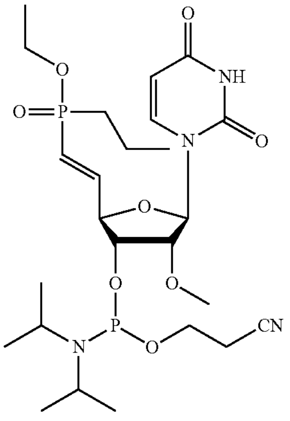
VP-U-6
A VP-U-2 molecule was synthesized according to the following method:
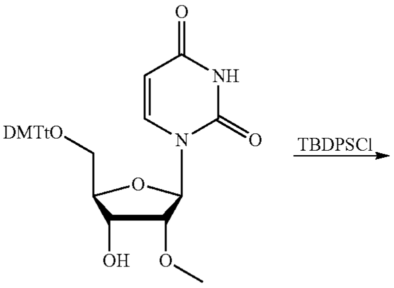
2'-OMe-U
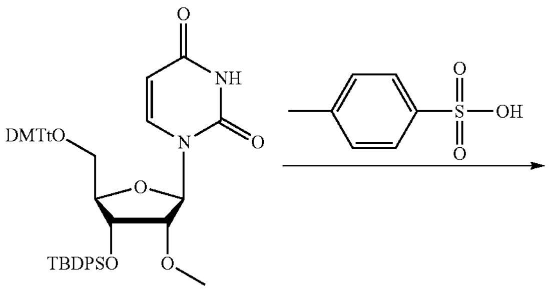
VP-U-1

-continued

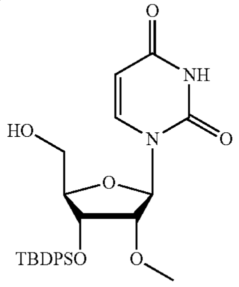

VP-U-2

A 2'-methoxy modified uracil nucleoside (2'-OMe-U, 51.30 g, 91.6 mmol), tert-butyl diphenylchlorosilane (TBDPSCl, 50.35 g, 183.2 mmol), and imidazole (12.47 g, 183.2 mmol) were mixed and dissolved in 450 ml of N,N-dimethylformamide (DMF) to react under stirring at room temperature for 20 hours. DMF was removed by evaporation, and the residue was dissolved with 600 ml of dichloromethane and washed with 300 ml of saturated sodium bicarbonate. The aqueous phase was extracted three times, each with 300 ml of dichloromethane (DCM). The organic phases were combined, washed with 5% oxalic acid until the pH of the aqueous phase was <5. The solvent was evaporated to dryness to give a crude product VP-U-1, which was directly used in the subsequent synthesis of VP-U-2.

The crude product VP-U-1 was dissolved in 100 ml of dichloromethane, and then stirred for 10 minutes in an ice bath. 450 ml of 2% p-toluenesulfonic acid solution (the solvent is a mixed solvent of methanol and dichloromethane in a volume ratio of 3:7) pre-cooled in a refrigerator at 4° C. was added to react for 10 minutes. The reaction was quenched by addition of 200 ml of saturated sodium bicarbonate. The organic phase was washed to pH=8 by addition of saturated sodium bicarbonate solution. The aqueous phases were combined and extracted twice, each with 200 ml of dichloromethane. The organic phases were combined and washed once with 200 ml of saturated brine. The solvent was removed by evaporation to dryness, and the residue was purified by using a normal phase silica gel column (200-300 mesh). The column was packed with petroleum ether and eluted with a gradient elution of petroleum ether:ethyl acetate:dichloromethane:methanol=1:1:1:0.05-1:1:1:0.25. The eluate was collected, the solvent was removed by evaporation to dryness under reduced pressure, and the residue was foam-dried in a vacuum oil pump to give a total of 40.00 g of pure product VP-U-2. $^1$H NMR (400 MHz, DMSO-d6) δ 7.96 (d, J=7.8 Hz, 1H), 7.64 (dtd, J=5.1, 4.0, 2.2 Hz, 4H), 7.41-7.30 (m, 6H), 6.79 (d, J=4.7 Hz, 1H), 5.73 (d, J=7.6 Hz, 1H), 4.94 (t, J=7.0 Hz, 1H), 4.12 (td, J=4.6, 3.9 Hz, 1H), 4.05 (dd, J=4.8, 4.0 Hz, 1H), 3.96 (t, J=4.7 Hz, 1H), 3.68 (ddd, J=11.8, 7.0, 4.6 Hz, 1H), 3.57-3.46 (m, 1H), 3.39 (s, 3H), 1.05 (s, 8H). MS m/z: $C_{26}H_{33}N_2O_6Si$, $[M+H]^+$. calculated: 497.21, measured: 497.45.

(1-3-2) Synthesis of VP-U-4

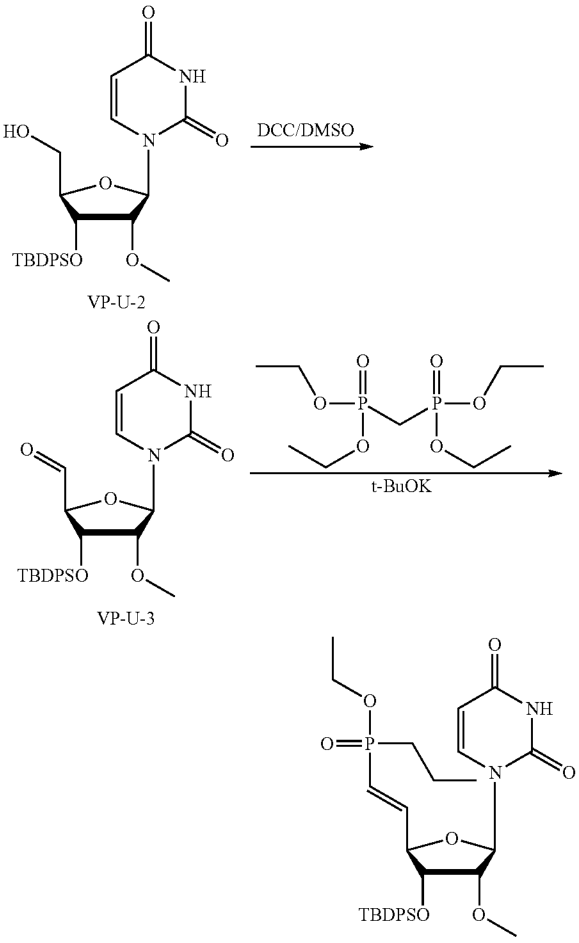

VP-U-2

VP-U-3

VP-U-4

VP-U-2 (19.84 g, 40.0 mmol), dicyclohexylcarbodiimide (DCC, 16.48 g, 80.0 mmol), pyridine (4.20 g, 53.2 mmol), and trifluoroacetic acid (6.61 g, 53.2 mmol) were mixed and dissolved in 200 ml of dimethyl sulfoxide (DMSO) to react under stirring at room temperature for 20 hours. Separately, tetraethyl methylenediphosphate (21.44 g, 74.4 mmol) was dissolved in 120 ml of THF, cooled in an ice bath, added with t-BuOK (11.36 g, 101.2 mmol) at a temperature of the ice bath to react for 10 min, warmed to room temperature to react for 0.5 hour and added into the above reaction solution over about 1 hour. The reaction was carried out at a temperature of the ice bath for 1 hour and then warmed to room temperature to react for 18 hours. The reaction was quenched by addition of water. The aqueous phase was extracted three times, each with 200 ml of dichloromethane. The organic phases were combined and washed once with 200 ml of saturated brine. The solvent was evaporated to dryness, and the residue was purified by using a normal phase silica gel column (200-300 mesh). The column was packed with petroleum ether and eluted with a gradient elution of petroleum ether:ethyl acetate=1:1-1:4. The eluate was collected. The solvent was removed by evaporation to dryness under reduced pressure, and the residue was foam-dried in a vacuum oil pump to give a total of 14.00 g of pure product VP-U-4. $^1$H NMR (400 MHz, DMSO-d6) δ 7.96 (d, J=7.8 Hz, 1H), 7.64 (dtd, J=5.1, 4.0, 2.2 Hz, 4H), 7.41-7.30

(m, 6H), 6.82-6.71 (m, 2H), 5.90 (ddd, J=25.9, 15.0, 1.0 Hz, 1H), 5.73 (d, J=7.6 Hz, 1H), 4.36-4.21 (m, 3H), 4.18 (t, J=4.9 Hz, 1H), 4.05 (ddq, J=9.7, 8.5, 6.9 Hz, 2H), 3.87 (t, J=4.8 Hz, 1H), 3.39 (s, 3H), 1.32 (td, J=6.9, 0.7 Hz, 6H), 1.05 (s, 8H). MS m/z: $C_{31}H_{42}N_2O_8PSi$, $[M+H]^+$. calculated: 629.24, measured: 629.51.

(1-3-3) Sythesis of VP-U-5

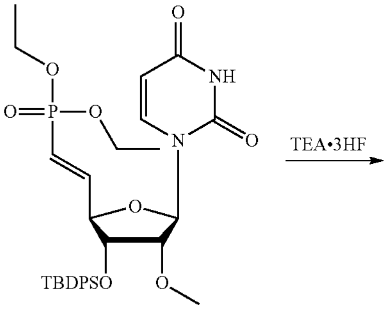

VP-U-4

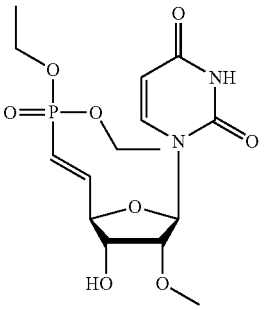

VP-U-5

VP-U-4 (14.00 g, 22.29 mmol) was dissolved in 100 ml of tetrahydrofuran, added with triethylamine trihydrofluoride (17.96 g, 111.45 mmol), and stirred at room temperature for 20 hours to react completely. The solvent was directly evaporated to dryness, the residue was dissolved in dichloromethane, and then the solvent was evaporated to dryness again. The above dissolution and evaporation steps were performed twice, each with 50 ml of dichloromethane, to give a crude product. The crude product was purified by using a normal phase silica gel column (200-300 mesh). The column was packed with petroleum ether and eluted with a gradient elution of petroleum ether:ethyl acetate:dichloromethane:methanol=1:1:1:0.05-1:1:1:0.25. The eluate was collected, the solvent was removed by evaporation to dryness under reduced pressure, and the residue was foam-dried in a vacuum oil pump to give a total of 6.70 g of pure product VP-U-5. $^1$H NMR (400 MHz, DMSO-d6) δ 7.96 (d, J=7.8 Hz, 1H), 6.77 (dd, J=15.0, 6.2 Hz, 1H), 5.99-5.82 (m, 2H), 5.73 (d, J=7.6 Hz, 1H), 5.27 (d, J=5.1 Hz, 1H), 5.10 (dd, J=5.3, 4.7 Hz, 1H), 4.29 (ddq, J=9.8, 8.6, 7.0 Hz, 2H), 4.17 (ddd, J=6.2, 5.2, 1.0 Hz, 1H), 4.12-3.98 (m, 3H), 3.39 (s, 2H), 1.32 (td, J=6.9, 0.6 Hz, 6H). MS m/z: $C_{15}H_{24}N_2O_8P$, $[M+H]^+$. calculated: 391.13, measured: 391.38.

(1-3-4) Synthesis of VP-U-6

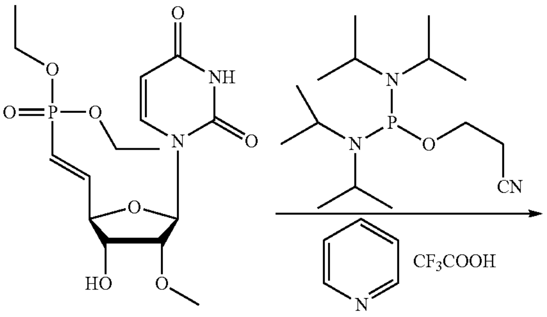

VP-U-5

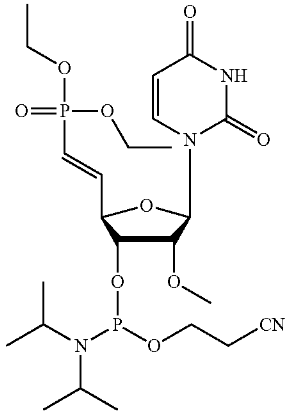

VP-U-6

VP-U-5 (391 mg, 1.0 mmol), pyridine trifluoroacetate (0.232 g, 1.2 mmol), N-methylimidazole (0.099 g, 1.2 mmol), and bis(diisopropylamino)(2-cyanoethoxy)phosphine (0.452 g, 1.5 mmol) were added into 10 ml of anhydrous dichloromethane under argon atmosphere to react under stirring at room temperature for 5 hours. The solvent was evaporated to dryness, and then the residue was purified by column chromatography (200-300 mesh normal phase silica gel, with a gradient elution of dichloromethane:acetonitrile (containing 0.5 wt % triethylamine)=3:1-1:3). The eluate was collected and concentrated to remove the solvent to give a total of 508 mg of target product VP-U-6. $^{31}$P NMR (161 MHz, DMSO-d6) δ 150.34, 150.29, 17.07, 15.50. MS m/z: $C_{24}H_{41}N_4O_9P_2$, $[M+H]^+$. calculated: 591.23, measured: 591.55. The above data indicated that VP-U-6 was the target product VP-Um, which was involved in the synthesis of RNA strands as a nucleoside monomer.

(1-3B) Preparation of Antisense Strands of Conjugates 6 and 8-11

In addition to linking the corresponding nucleoside monomers one by one according to the nucleotide sequences as shown in Table 7 respectively, the method for synthesizing the antisense strands of Conjugates 6 and 8-11 differs from that of the antisense strand of Conjugate 4 only in the modification of the the first nucleotide at 5' terminal. During preparation of the antisense strands according to the phosphoramidite solid phase synthesis method, after the linking of 2'-methoxy modified guanine nucleoside monomer (Gm) as the last nucleoside monomer, the monomer of Formula (CPR-I) (purchased from Suzhou GenePharma Inc. as Cat #13-2601-XX) was linked to 5' terminal of the antisense strand by a four-step reaction of deprotection, coupling, capping, and oxidation, so as to form a 5'-phosphate modification.

(CPR-I)

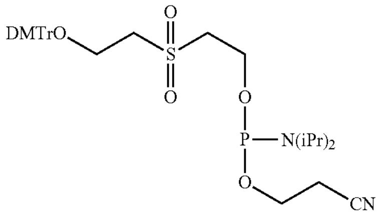

During the synthesis, the universal solid phase support, the conditions of deprotection, coupling, capping, oxidation or sulfurization reaction, cleavage and deprotection, purification and desalting used were the same as those used in the synthesis of the sense strand.

The purity was detected by ion exchange chromatography (IEX-HPLC); and the molecular weight was analyzed by liquid chromatography-mass spectrometry (LC-MS). The fact that the measured values were in conformity with the calculated values indicates that the antisense strands AS having the target sequences were synthesized.

(1-3C) Preparation of an Antisense Strand of Conjugate 7

An antisense strand of Conjugate 7 with a 5'-phosphorothioate modification was prepared by using the same synthesis method as that in step (1-3B), except that the oxidation reaction condition was replaced with a sulfurization reaction condition in the linking of the CPR-I monomer.

(1-4) Synthesis of Conjugates 1-11

For Conjugate 1, the S strand and AS strand were respectively dissolved in water for injection to give a solution of 40 mg/mL. They were mixed in an equimolar ratio, heated at 50° C. for 15 min, cooled at room temperature to produce an annealed product, and then lyophilized to give a lyophilized powder. After the conjugate was diluted to a concentration of 0.2 mg/mL with ultra-pure water (homemade by Milli-Q ultra-pure water instrument, with resistivity of 18.2MΩ*cm (25° C.)), the molecular weight was determined by a liquid chromatography-mass spectrometry (LC-MS) instrument (purchased from Waters Corp., model: LCT Premier). The fact that the measured values were in conformity with the calculated values indicates that the synthesized Conjugate 1 was the designed target double-stranded nucleic acid sequence with the L-9 conjugation molecule.

Conjugates 2-11 were prepared by the same method except that the sense strand of Conjugate 1 was replaced with the sense strands of Conjugates 2-11 as prepared above, and the antisense strand of Conjugate 1 was replaced with the antisense strands of Conjugates 2-11 as prepared above. The molecular weights of the resultant Conjugates 2-11 were respectively determined to confirm that that the measured values were in conformity with the calculated values, indicating that the synthesized conjugates were the designed target double-stranded nucleic acid sequences with the L-9 conjugation molecule.

Conjugates 1-11 have the structure as shown by Formula (403).

TABLE 7 siRNA conjugates

| Conjugate NO: | siRNA NO: | | siRNA Sequences (sequence direction 5'-3') | SEQ ID NO |
|---|---|---|---|---|
| Conjugate 1 | siAPa1UM3SVP | S | UmsUmsAmAmAmAmGfGfGfAmCmAm GmUmAmUmUmCmAm | 301 |
| | | AS | VP- UmsGfsAmAmUmAfCmUmGmUmCmCm CmUfUmUfUmAmAmsGmsCm | 302 |
| Conjugate 2 | siAPe1UM3SVP | S | GmsGmsAmCmAmGmUfAfUfUmCmUm CmAmGmUmGmCmAm | 303 |
| | | AS | VP- UmsGfsCmAmCmUfGmAmGmAmAmUm AmCfUmGfUmCmCmsCmsUm | 304 |
| Conjugate 3 | siAPb1UM3SVP | S | AmsCmsAmGmUmAmUfUfCfUmCmAm GmUmGmCmUmCmAm | 305 |
| | | AS | VP- UmsGfsAmGmCmAfCmUmGmAmGmAm AmUfAmCfUmGmUmsCmsCm | 306 |
| Conjugate 4 | siAPd1UM3SVP | S | AmsGmsUmAmUmUmCfUfCfAmGmUm GmCmUmCmUmCmAm | 307 |
| | | AS | VP- UmsGfsAmGmAmGfCmAmCmUmGmAm GmAfAmUfAmCmUmsGmsUm | 308 |
| Conjugate 5 | siAPc1M3SVP | S | UmsAmsUmUmCmUmCfAfGfUmGmCm UmCmUmCmCmUmAm | 309 |
| | | AS | VP- UmsAfsGmGmAmGfAmGmCmAmCmUm GmAfGmAfAmUmAmsCmsUm | 310 |
| Conjugate 6 | siAPd1UM3SP | S | AmsGmsUmAmUmUmCfUfCfAmGmUm GmCmUmCmUmCmAm | 311 |
| | | AS | P- UmsGfsAmGmAmGfCmAmCmUmGmAm GmAfAmUfAmCmUmsGmsUm | 312 |

TABLE 7-continued

| siRNA conjugates | | | | |
|---|---|---|---|---|
| Conjugate NO: | siRNA NO: | | siRNA Sequences (sequence direction 5'-3') | SEQ ID NO |
| Conjugate 7 | siAPd1UM3SPs | S | AmsGmsUmAmUmUmCfUfCfAmGmUm GmCmUmCmUmCmAm | 313 |
| | | AS | Ps- UmsGfsAmGmAmGfCmAmCmUmGmAm GmAfAmUfAmCmUmsGmsUm | 314 |
| Conjugate 8 | siAPa1M3SP | S | UmsUmsAmAmAmGfGfGfAmCmAm GmUmAmUmUmCmUm | 423 |
| | | AS | P- AmsGfsAmAmUmAfCmUmGmUmCmCm CmUfUmUfUmAmAmsGmsCm | 424 |
| Conjugate 9 | siAPe1M3SP | S | GmsGmsAmCmAmGmUfAfUfUmCmUm CmAmGmUmGmCmUm | 425 |
| | | AS | P- AmsGfsCmAmCmUfGmAmGmAmAmUm AmCfUmGfUmCmCmsCmsUm | 426 |
| Conjugate 10 | siAPb1M3SP | S | AmsCmsAmGmUmAmUfUfCfUmCmAm GmUmGmCmUmCmUm | 427 |
| | | AS | P- AmsGfsAmGmCmAfCmUmGmAmGmAm AmUfAmCfUmGmUmsCmsCm | 428 |
| Conjugate 11 | siAPc1M3SP | S | UmsAmsUmUmCmUmCfAfGfUmGmCm UmCmUmCmCmUmAm | 429 |
| | | AS | P- UmsAfsGmGmAmGfAmGmCmAmCmUm GmAfGmAfAmUmAmsCmsUm | 430 |
| Comparative Conjugate 1 | 65704 | S | GmsCmsUmUmAmAfAmGfGfGfAmCm AmGmUmAmUmUmCmAm | 315 |
| | | AS | UmsGfsAmAmUmAmCmUmGmUmCmCm CmUfUmUmUmAmAmGmCmsAmsAm | 316 |
| Comparative Conjugate 2 | 69535 | S | GmsCmsUmUmAmAmAmAmGfGmGfAmC mAmGmUmAmUmUmCmAm | 317 |
| | | AS | UmsGfsAmAmUmAmCmUmGmUmCmCfC mUfUmUmUmAmAmGmCmsAmsAm | 318 |

Preparation Example 2 Preparation of Comparative Conjugates 1 and 2

In the present preparation example, Comparative Conjugates 1 and 2 were synthesized. The conjugated siRNAs in these conjugates had the sequences as shown in Table 7. The conjugation molecule to be conjugated refers to the (GalNAc)3 conjugation molecule as synthesized in step (2-1) below. The conjugates respectively had the same structures as those of Compounds AD-65704 and AD-69535 in WO2016081444A1.

(2-1) Synthesis of (GalNAc)3 Conjugation Molecule

Compound 30, i.e., the conjugation molecule (referred to as (GalNAc)3 conjugation molecule) containing the above-mentioned linker -$(L^A)$3-trihydroxymethylaminomethane-$L^B$- and N-acetylgalactosamine molecule as the targeting group (wherein each $L^A$ can be linked to one N-acetylgalactosamine molecule so that one linker can be linked to three N-acetylgalactosamine molecules), was synthesized according to the method described in Example 17 of WO2014025805A1. The chemical reaction formulae involved in the synthesis and the structure of $(GalNAc)_3$ conjugation molecule were shown below:

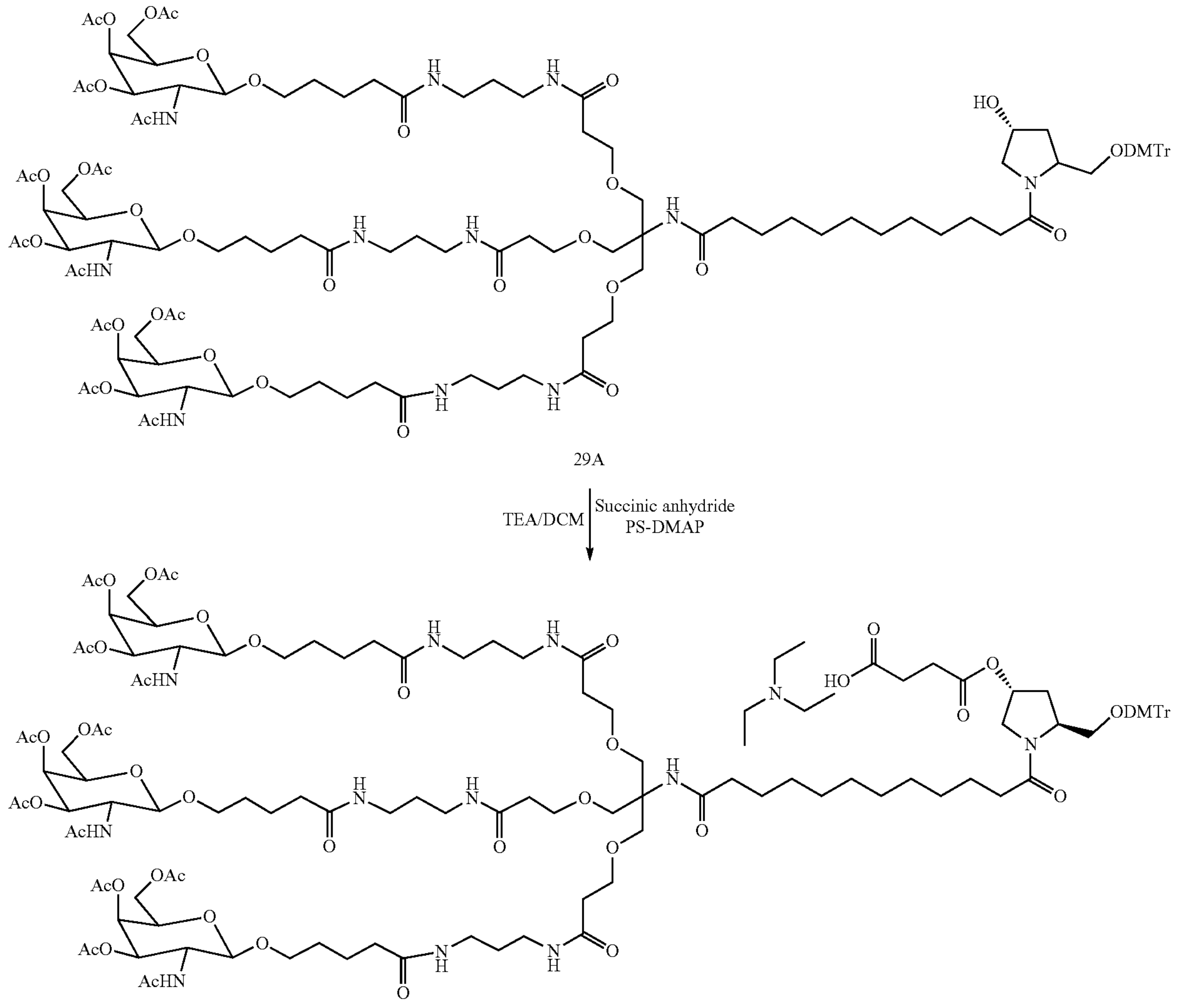

29A

30

(2-2) Preparation of the (GalNAc)3 Conjugation Molecule Linked to a Solid Phase Support The (GalNAc)3 conjugation molecule linked to a solid phase support was prepared by using the same method as that in step (1-1-5) of Preparation Example 1, except that the L-9 conjugation molecule was replaced with the (GalNAc)3 conjugation molecule, thereby obtaining the (GalNAc)3 conjugation molecule linked to a solid phase support.

(2-3) Synthesis of Comparative Conjugates 1 and 2

Comparative Conjugates 1 and 2 were prepared by the same methods as those in steps (1-2), (1-3A) and (1-4) of Preparation Example 1, except that 1) the compound obtained in step (2-2) was used to start the synthesis of the sense strand; 2) during the preparation of the antisense strands according to the phosphoramidite solid phase synthesis method, 2'-methoxy modified uracil nucleoside monomer (Um) was linked as the last nucleoside monomer; and 3) the conjugated siRNAs respectively had the sequences as shown by Nos. (GalNAc)3-65704 and (GalNAc)3-69535 in Table 7.

The molecular weight was determined by a liquid chromatography-mass spectrometry (LC-MS) instrument (purchased from Waters Corp., model: LCT Premier). The fact that the measured values were in conformity with the calculated values confirms that the synthesized conjugates were the designed target compounds having the structures as shown by Formula (305).

Experimental Example 1: Detection of the Inhibitory Activity of the siRNA Conjugates in In Vitro Cell System

Experimental Example 1-1 the Inhibitory Effect of the siRNA Conjugates on the Expression Level of APOC3 mRNA in Huh 7

In this experimental example, the inhibition efficiencies of Conjugates 1-5 against the expression level of APOC3 mRNA in in vitro Huh 7 cell lines were investigated.

Conjugates 1-5 were transfected to human hepatoma cell lines Huh7 by using Lipofectamine™ 2000. The final concentrations of the siRNA conjugates (based on the amount of the siRNA) were 0.5 nM, 0.125 nM and 0.03125 nM, respectively. The siRNA conjugates were provided in the form of solutions. In particular, prior to the experiment, the siRNA conjugates were dissolved in DEPC water to give solutions with the desired concentrations. The cells not being transfected with the siRNA conjugates were used as a blank control, with two replicate wells per concentration.

The expression levels of APOC3 mRNAs in Huh 7 cells transfected with Conjugates 1-5 at various concentrations were measured by Quantitative Real-Time PCR, respectively. Specific steps were as follows: 24 hours after cultivation of the transfected cells, the total RNA was extracted and obtained by using Trizol (Thermo Fisher) according to the standard procedure for total RNA extraction; 1 g of the total RNA was taken and reverse transcribed into cDNA by using a reverse transcription kit (Promega, Cat No. A3500) according to the procedures in the instruction thereof. The expression level of APOC3 mRNA was measured by using 2×Ultra SYBR Mixture (with ROX) kit (Beijing Cowin Biosicences Co., Ltd, Cat No. CW0956) with the cDNA as a template according to the procedures in the instruction. Therein, the PCR primers of for amplifying APOC3 and GAPDH as an internal control gene are shown in Table 8.

TABLE 8

Sequences of the primers for detection

| Genes | Upstream Primers | Downstream Primers |
|---|---|---|
| Human APOC3 | 5'-GTGACCGATGGCTTCAGTTC-3' (SEQ ID NO: 319) | 5'-ATGGATAGGCAGGTGGACTT-3' (SEQ ID NO: 320) |
| Human GAPDH | 5'-GGTCGGAGTCAACGGATTT-3' (EQ ID NO: 321) | 5'-CCAGCATCGCCCCACTTGA-3' (SEQ ID NO: 322) |

The expression level of APOC3 mRNA was calculated by the following equation:

The expression level of APOC3 mRNA=(the expression level of APOC3 mRNA in the test group/the expression level of GAPDH mRNA in the test group)/(the expression level of APOC3 mRNA in the control group/the expression level of GAPDH mRNA in the control group)×100%.

The inhibition rates of the conjugates against the expression level of APOC3 mRNA were calculated by the following equation:

The inhibition rate=(1−the expression level of APOC3 mRNA)×100%. Therein, the test groups are respectively the Huh7 cells treated with Conjugates 1-5 at various concentrations, and the control group is the Huh 7 cells untreated with the conjugates.

FIG. 1 is a histogram showing the expression levels of APOC3 mRNA in untransfected Huh7 cells and in Huh7 cells transfected with different conjugates at different final concentrations (the expression levels used those of human GAPDH as reference, and were normalized against the blank control).

As can be seen from FIG. 1, the siRNA conjugates of the present disclosure exhibited higher inhibitory activity in Huh7 cell lines; the conjugates at 0.5 nM showed inhibition rates of more than 60% against the expression levels of APOC3 mRNA. All of the siRNA conjugates of the present disclosure at all concentration exhibited higher inhibitory activity than that of Comparative Conjugate 1.

Experimental Example 1-2: Determination of $IC_{50}$ of siRNA Conjugates Against APOC3 mRNA in Huh7 Cell Lines This experimental example determined the $IC_{50}$ values of Conjugates 6 and 8-11 against APOC3 mRNA in Huh7 cell lines.

Conjugates 6 and 8-11 were transfected by the same method as that in Experimental Example 1-1, and the expression level of APOC3 mRNA in each group was measured, except that the final concentrations of the conjugates (calculated based on the concentrations of siRNAs) were from 3 nM to 0.004 nM (three-fold serial dilutions of 7 concentrations). The dose-response curves were plotted by the expression levels of APOC3 mRNA measured at different concentrations of the conjugates, and the curves were fitted using the function log(inhibitor) vs. response Variable slope of Graphpad 5.0 software. The $IC_{50}$ of each conjugate was calculated based on the dose-response curve.

$$Y = \text{Bot} + \frac{\text{Top} - \text{Bot}}{1 + 10^{(LogIC_{50} - X) \times HillSlope}}$$

wherein:

Y is the expression level of remaining mRNA,

X is the logarithm of the concentration of transfected conjugates,

Bot is the Y value at the bottom of the steady stage,

Top is the Y value at the top of the steady stage, $LogIC_{50}$ is the X value at which Y is the median value between the bottom and the top, and HillSlope is the slope of the curve.

The $IC_{50}$ values of Conjugates 6 and 8-11 in in vitro Huh 7 cells were measured to be 0.01002 nM, 0.008159 nM, 0.05375 nM, 0.01933 nM, and 0.01949 nM, respectively, indicating that the siRNA conjugates of the present disclosure exhibited higher inhibitory activity against the expression levels of the target mRNA in vitro.

Experimental Example 2 this Experiment Investigated the In Vivo Effects of Reducing Blood Lipid Content of the siRNA Conjugates of the Present Disclosure

Experimental Example 2-1 this Experiment Investigated the In Vivo Effects of Conjugates 2, 4 and 5 for Reducing the Contents of Total Cholesterol (CHO) and Triglyceride (TG) in Serum of Human APOC3 Transgenic Mice Human APOC3 transgenic mice (B6; CBA-Tg(APOC3) 3707Bres/J) with serum TG content >2 mmol/L were randomly divided into groups (7 mice per group) as follows: (1) normal saline control group; (2) Conjugate 2: 3 mg/kg group; (3) Conjugate 2: 1 mg/kg group; (4) Conjugate 4: 3 mg/kg group; (5) Conjugate 4: 1 mg/kg group; (6) Conjugate 5: 3 mg/kg group; and (7) Conjugate 5: 1 mg/kg group. The administration dosages for all animals were calculated according to the body weight and subcutaneously injected as single administration, wherein the siRNA conjugates were provided in 0.9 wt % NaCl aqueous solutions with concentrations of 0.6 mg/ml and 0.2 mg/ml. In particular, prior to the experiments, the siRNA conjugates were dissolved in the 0.9 wt % NaCl aqueous solution to give solutions with the desired concentrations. The administration volumes for normal saline and the siRNA conjugates were 5 mL/kg.

The blood was taken from mouse orbital venous plexus before administration (marked as day 0) and on days 7, 14, 21, 28, 35, 42, 49, 63, 77, 91, 112, 133, 147, 161, 175, and 189 after administration respectively. The contents of total cholesterol (CHO) and triglyceride (TG) in serum were measured at each time point.

About 100 μl blood was taken from the orbit each time, and the serum was not less than 20 μl after centrifugation. The contents of total cholesterol (CHO) and triglyceride (TG) in serum were further measured by using a PM1P000/3 full-automatic serum biochemical analyzer (SABA).

The normalized blood lipid level=(the blood lipid content in the test group after administration/the blood lipid content in the test group before administration)×100%.

The inhibition rate against blood lipid level=(1−the blood lipid content in the test group after administration/the blood lipid content in the test group before administration)×100%. Blood lipid refers to total cholesterol (CHO) or triglyceride (TG).

FIGS. 2A to 2D are diagrams showing the changes of total cholesterol (CHO) level and triglyceride (TG) level over time in serum of human APOC3 trangenic mice administered with normal saline and Conjugates 2, 4 and 5 at different doses. In these figures, the test group before administration was marked as day DO; and the respective CHO levels and TG levels in serum were normalized relative to the value on day DO.

Figure 2A:
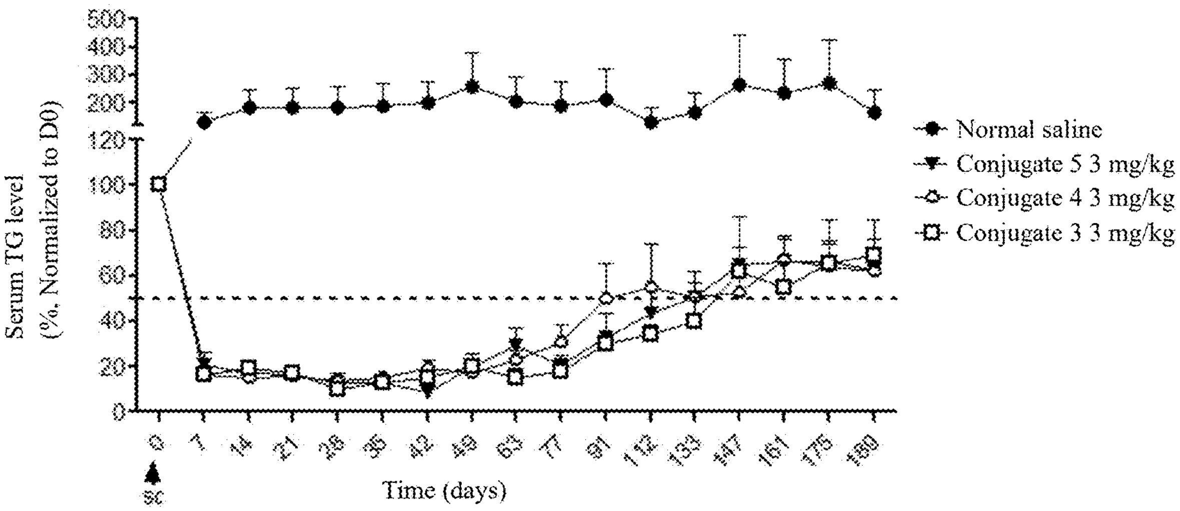
FIGS. 2A-7D are diagrams showing the changes of total cholesterol (CHO) level and triglyceride (TG) level over time in serum of human APOC3 trangenic mice administered with normal saline and various conjugates at different doses.

As can be seen from FIG. 2A, the three conjugates in the 3 mg/kg dose groups after single administration show inhibition rates of 70% to 90% against TG over a period of up to 77 days, and inhibition rates of about 50% or lower against TG over a period of up to 147 days.

Figure 2B:
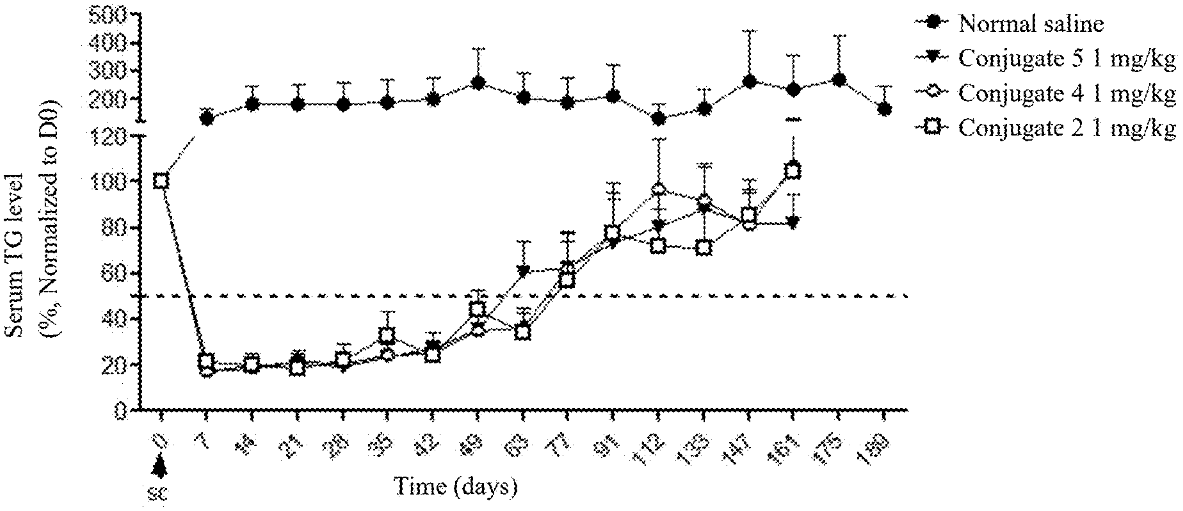

As can be seen from FIG. 2B, the three conjugates in the 1 mg/kg dose groups show inhibition rates of about 80% against TG on day 7 after single administration, and continuously show the effects of reducing the TG content by no less than 50% over a period of up to 49 days.

Figure 2C:
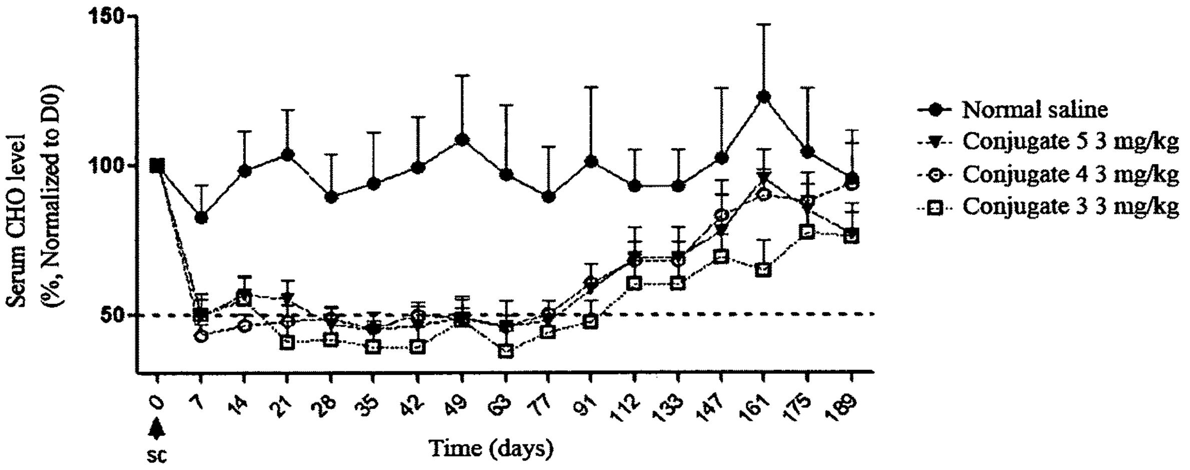

As can be seen from FIG. 2C, after single administration, the three conjugates in the 3 mg/kg dose groups substantially maintain inhibition rates of about 50% against CHO over a period of up to 77 days.

Figure 2D:
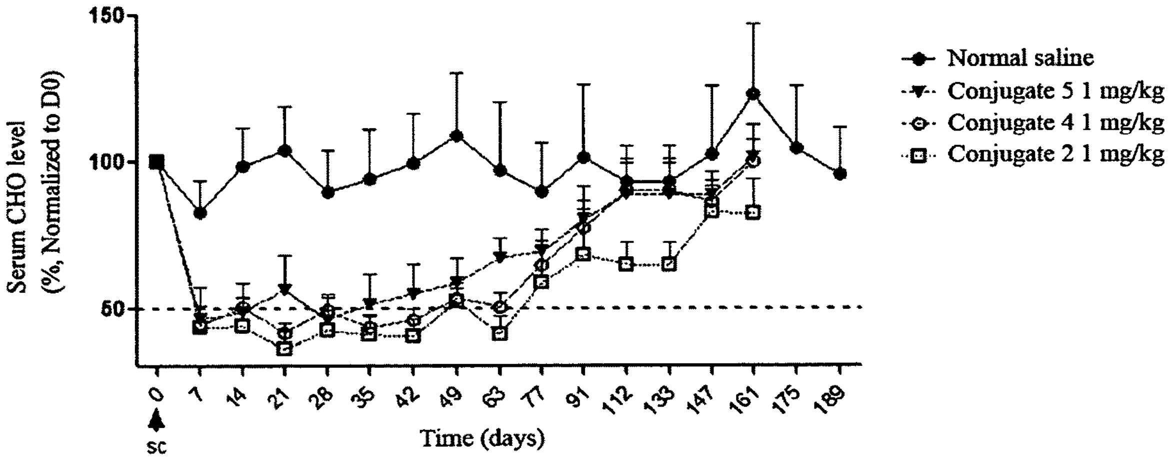

As can be seen from FIG. 2D, the three conjugates in the 1 mg/kg dose groups still show the effects of reducing CHO content by at least about 50% on day 35 after single administration.

The results of FIGS. 2A to 2D show that Conjugates 2, 4 and 5 show the effects of significantly reducing the contents of TG and CHO in mouse serum at different time points after administration, indicating that the siRNA conjugates of the present disclosure could stably and effectively reduce blood lipid level over a longer time period.

Experimental Example 2-2: This Experiment Investigated the In Vivo Effects of Conjugate 1 for Reducing the Contents of Total Cholesterol (CHO) and Triglyceride (TG) in Serum of Human APOC3 Transgenic Mice The measurement was conducted by the same method as that in Experimental Example 2-1, except that each test group included 6 mice; the conjugates to be administered were Conjugate 1 and Comparative Conjugate 2; and the test continued until day 112 after administration.

Figure 3A:
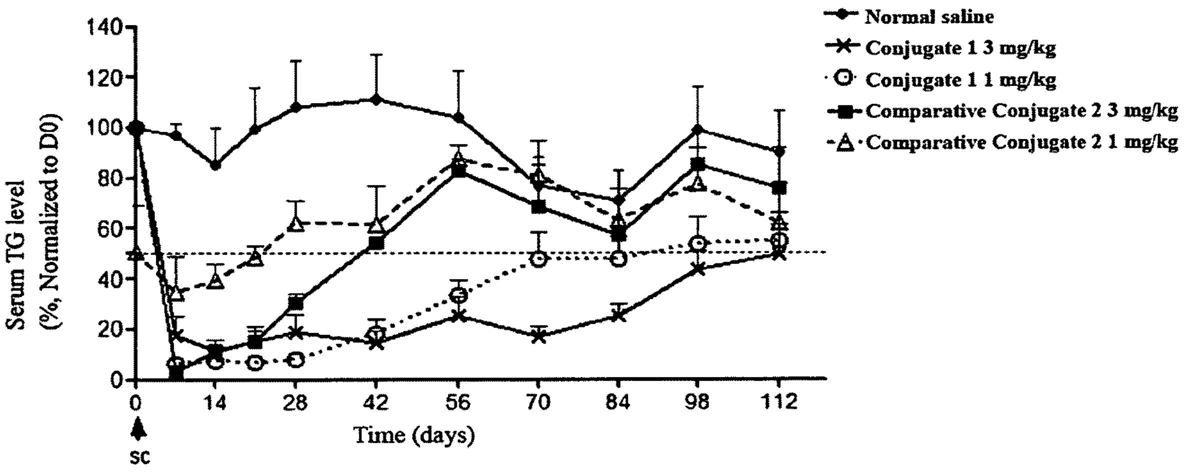
Figure 3B:
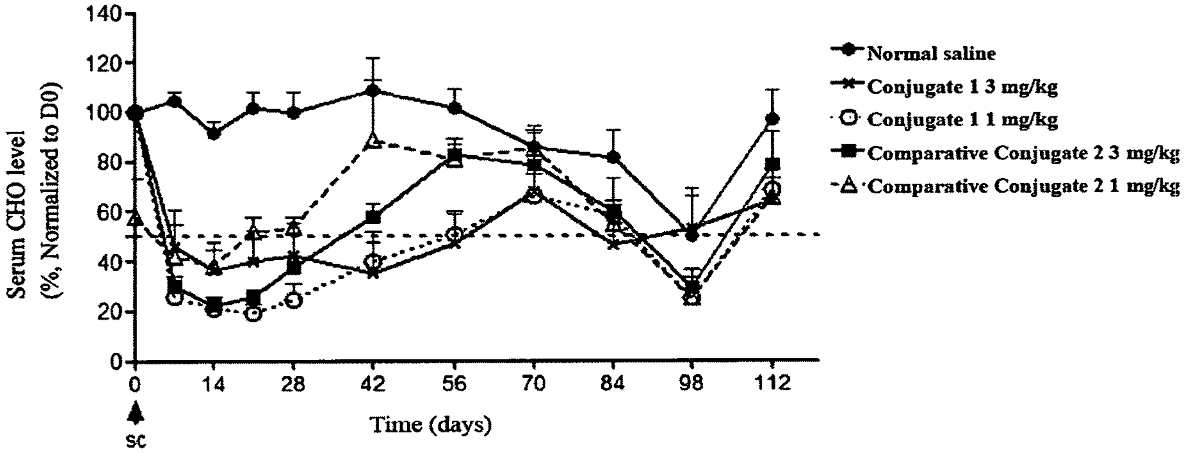

FIGS. 3A to 3B are diagrams showing the changes of total cholesterol (CHO) level and triglyceride (TG) level over time in serum of human APOC3 trangenic mice administered with normal saline and Conjugate 1 and Comparative Conjugate 2 at different doses. In these figures, the test group before administration was marked as day DO; and the respective CHO levels and TG levels in serum were normalized relative to the value on day DO.

As can be seen from FIGS. 3A to 3B, in both of the 3 mg/kg dose group and the 1 mg/kg dose group, Conjugate 1 could significantly reduce the TG and CHO levels in the transgenic mice over a period of up to 112 days, and such reduction effects are significantly superior to that of Comparative conjugative 2. In both of the 3 mg/kg dose group and the 1 mg/kg dose group, Conjugate 1 shows inhibition rates of 50% or higher against TG and CHO over 56 days after single administration, and the inhibitory effects on TG are more significant: the two doses of Conjugate 1 continuously maintain the TG level of about 50% over a period of up to 112 days.

Experimental Example 2-3: This Experiment Investigated the In Vivo Effects of Conjugate 3 for Reducing the Contents of Total Cholesterol (CHO) and Triglyceride (TG) in Serum of Human APOC3 Transgenic Mice The measurement was conducted by the same method as that in Experimental Example 2-1, except that each test group included 6 mice; the conjugate to be administered was Conjugate 3; Conjugate 3 was dissolved in 1×PBS buffer solution in place of normal saline (NS) to give a solution with the desired concentration; 1×PBS buffer solution was used as the blank control in the experiment; and the test continued until day 112 after administration.

Figure 4A:
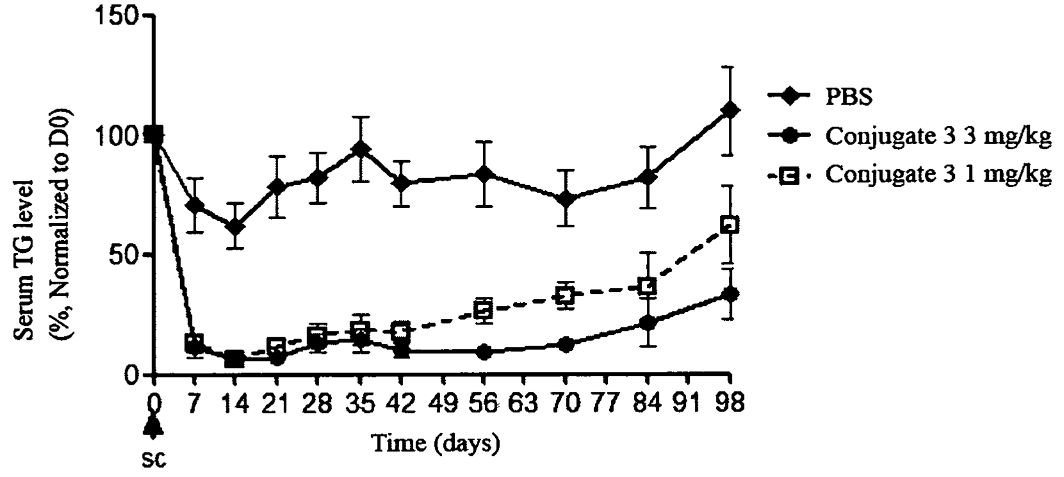
Figure 4B:
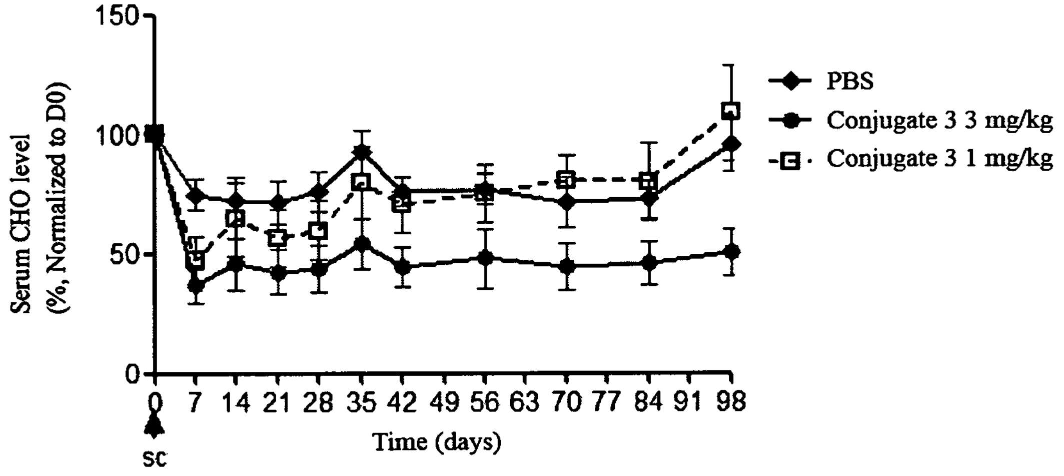

FIGS. 4A to 4B are diagrams showing the changes of the total cholesterol (CHO) level and triglyceride (TG) level over time in serum of human APOC3 trangenic mice administered with PBS and Conjugate 3 at different doses. In these figures, the test group before administration was marked as day D0; and the respective CHO levels and TG levels in serum were normalized relative to the value on day D0.

As can be seen from FIG. 4A, in the 3 mg/kg dose group, Conjugate 3 shows an inhibition rate of up to 93.6% against TG on day 14 after single administration, and still shows an inhibition rate of 66.4% against TG on day 98 after administration. In the 1 mg/kg dose group, Conjugate 3 shows an inhibition rate of up to 93.3% against TG on day 14 after single administration, and still shows an inhibition rate of 37.7% against TG on day 98 after administration.

As can be seen from FIG. 4B, in the 3 mg/kg dose group, Conjugate 3 shows an inhibition rate of up to 63.0% against CHO on day 7 after single administration, and still shows an inhibition rate of 49.2% against CHO on day 98 after administration. In the 1 mg/kg dose group, Conjugate 3 shows an inhibition rate of up to 52.2% against CHO on day 7 after single administration.

The results of FIGS. 4A to 4B show that Conjugate 3 could significantly reduce the TG and CHO levels in the transgenic mice over a period of up to 98 days, and such reduction effects have obvious dose-dependent effect.

Experimental Example 2-4: This Experiment Investigated the In Vivo Effects of Conjugate 4 for Reducing the Contents of Total Cholesterol (CHO) and Triglyceride (TG) in Serum of Human APOC3 Transgenic Mice The measurement was conducted by the same method as that in Experimental Example 2-1, except that each test group included 8 mice; the conjugate to be administered was Conjugate 4; Conjugate 4 was administered at three doses of 0.3 mg/kg, 1 mg/kg and 3 mg/kg, respectively, while the administration volume remained unchanged; and the test continued until day 133 after administration.

Figure 5A:
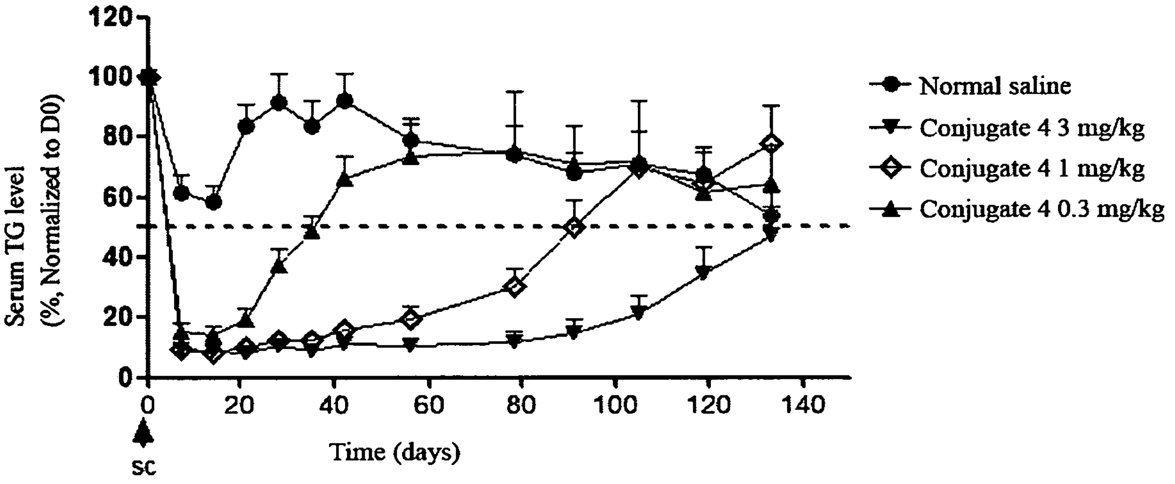
Figure 5B:
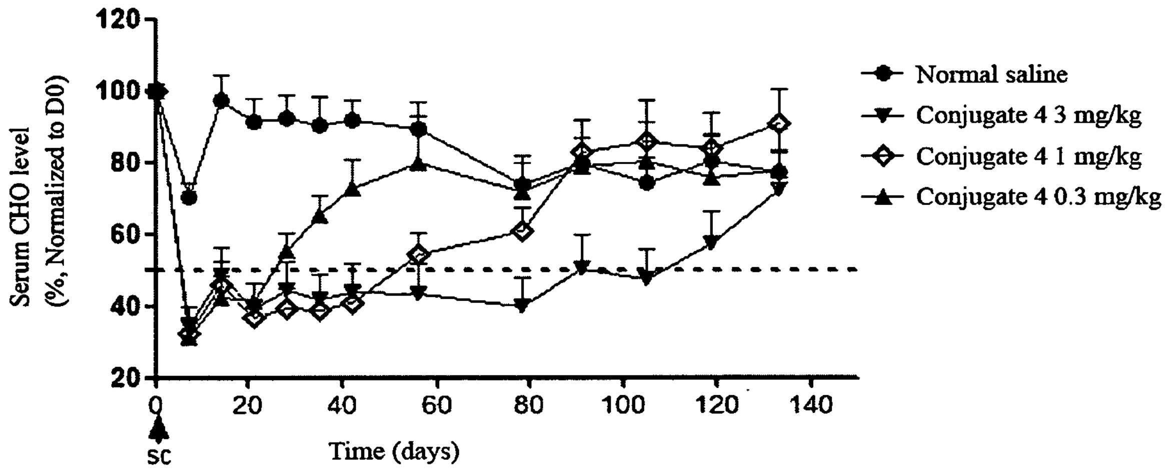
Figure 6A:
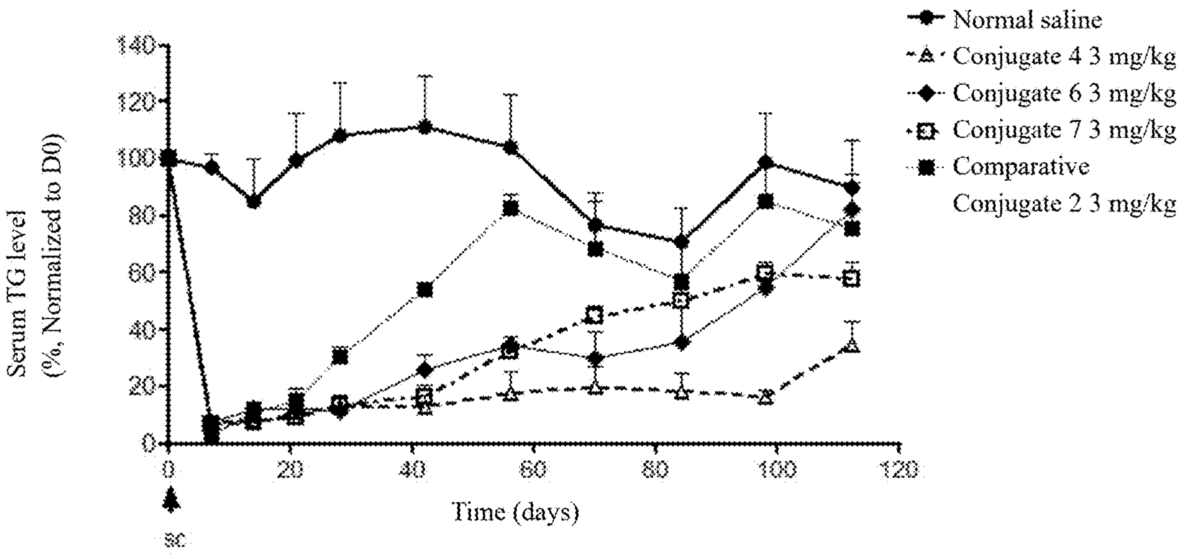
Figure 6B:
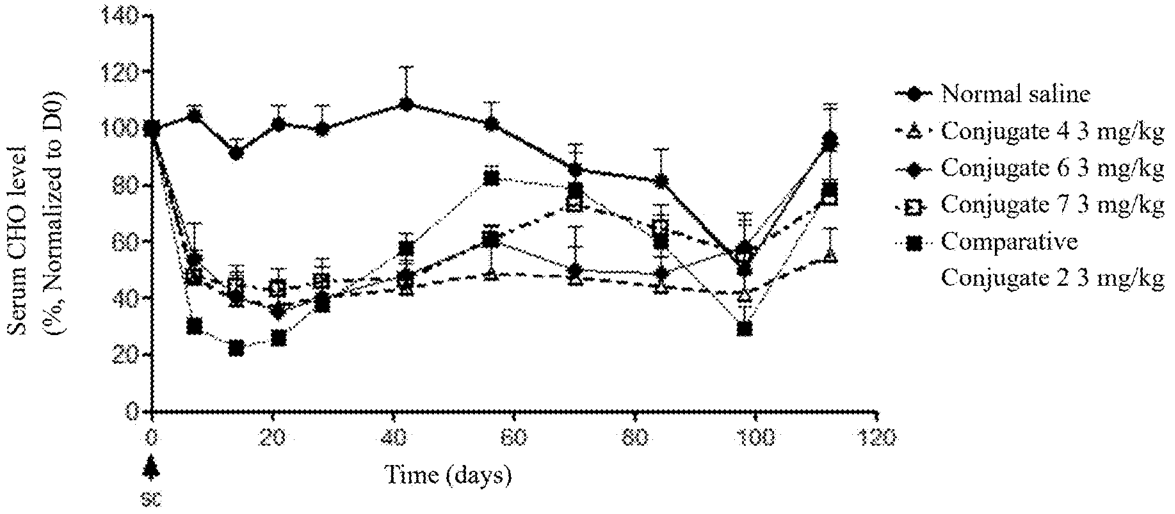
Figure 6C:
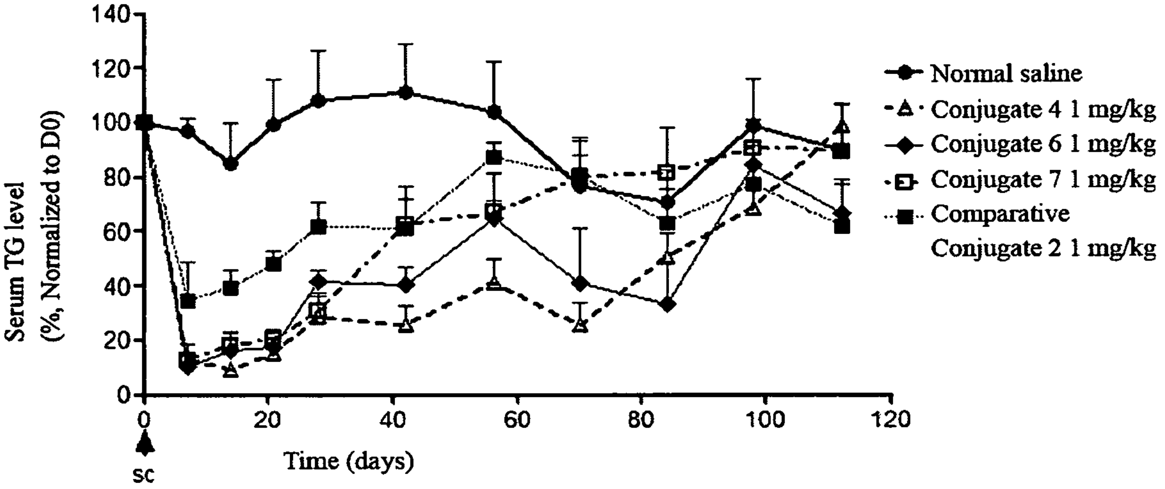
Figure 6D:
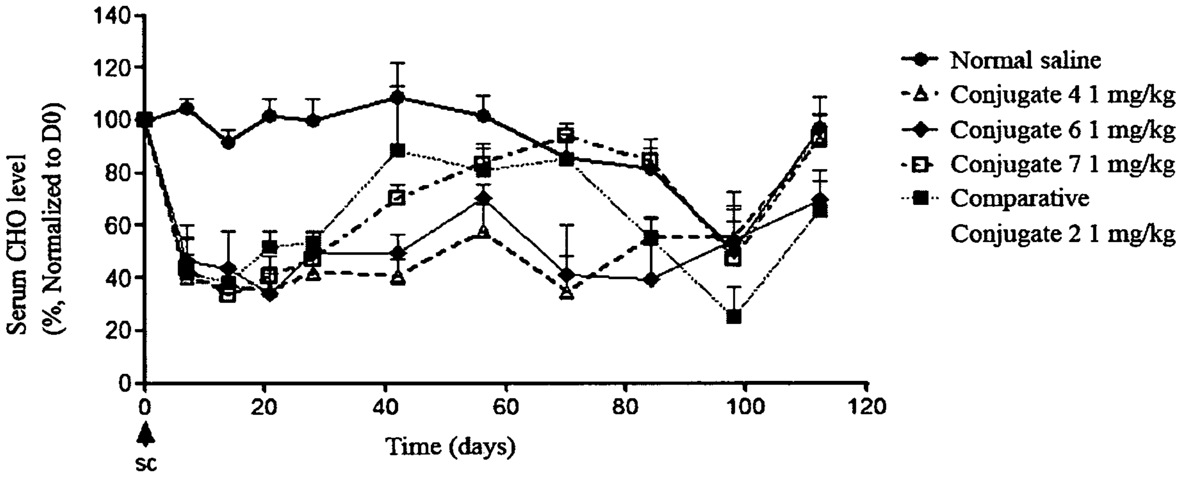
Figure 7A:
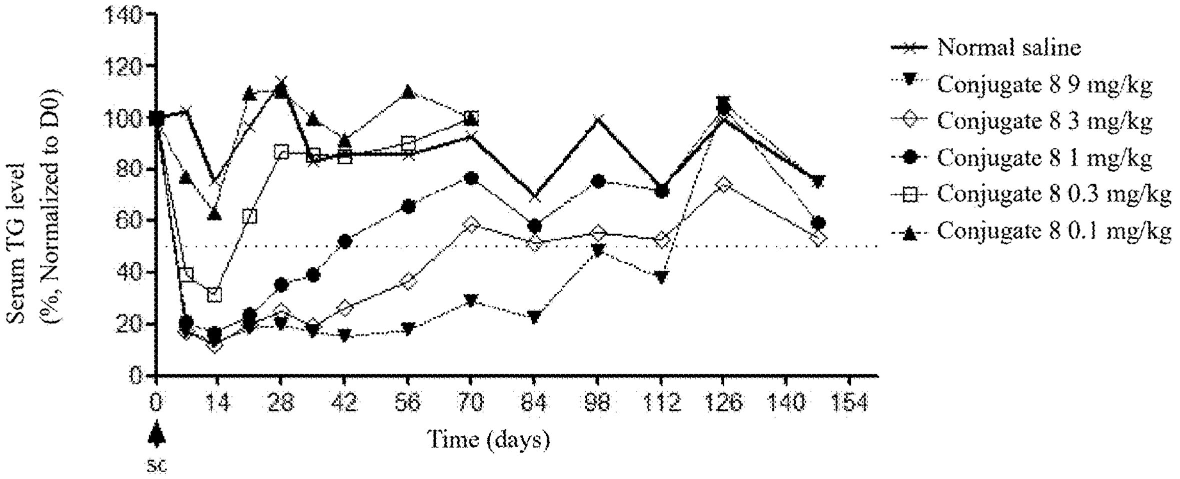
Figure 7B:
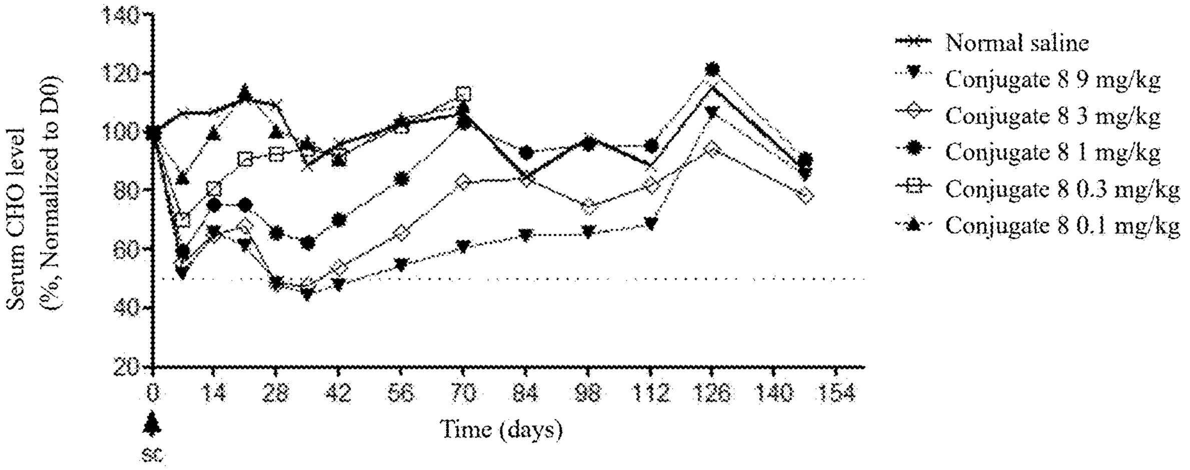
Figure 7C:
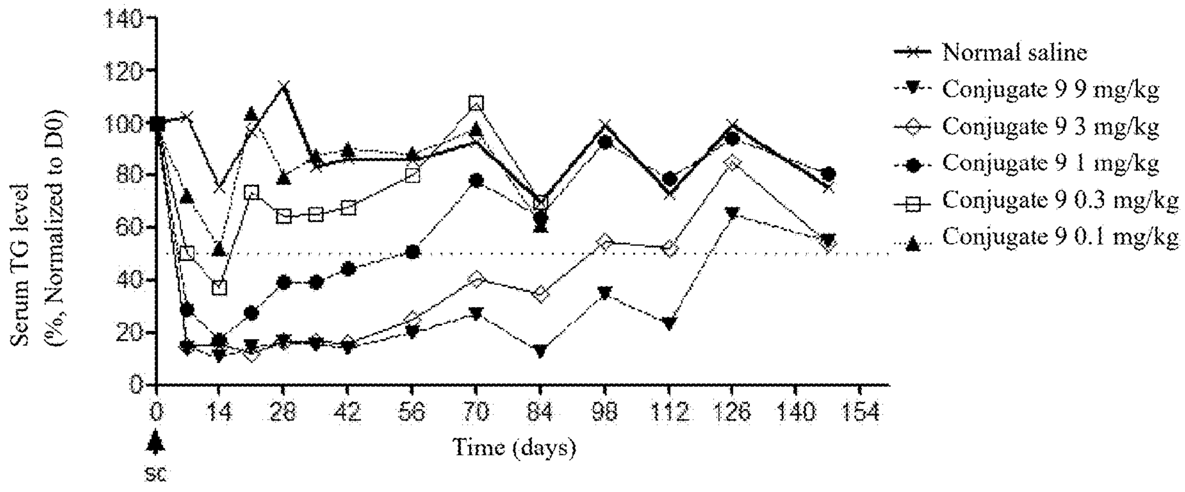
Figure 7D:
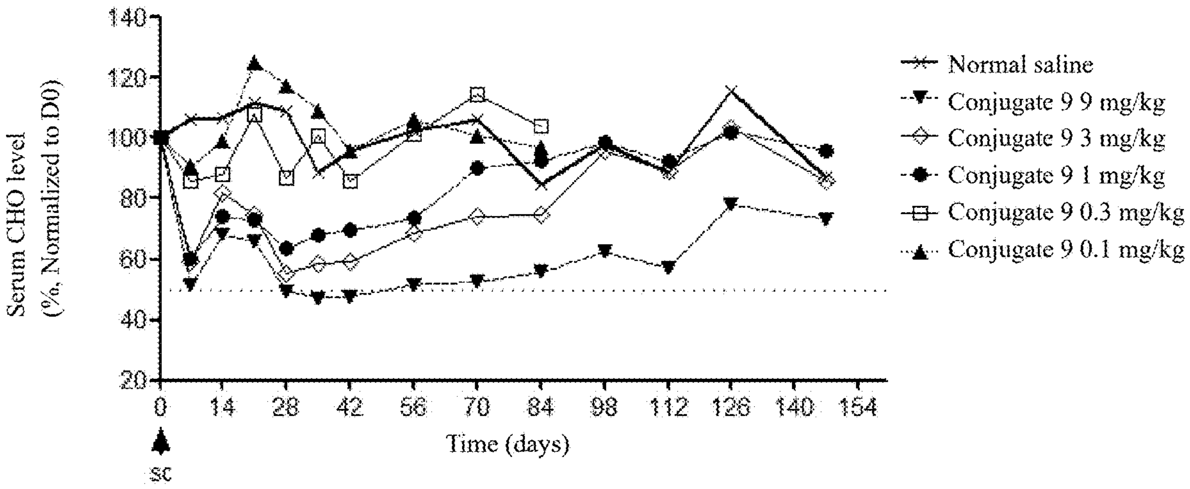

FIGS. 5A to 5B are diagrams showing the changes of the total cholesterol (CHO) level and triglyceride (TG) level over time in serum of human APOC3 trangenic mice administered with normal saline and Conjugate 4 at different doses. In these figures, the test group before administration was marked as day DO; and the respective of CHO levels and TG levels in serum were normalized relative to the value on day DO. As can be seen from the results of FIGS. 5A to 5B, Conjugate 4 at the three doses shows the effects of significantly reducing lipid in human APOC3 trangenic mice, and the reduction effects are dose-dependent. Conjugate 4 in the 3 mg/kg dose group still shows an inhibition rate of up to 50% against TG on day 133.

Experimental Example 2-5: This Experiment Investigated the In Vivo Effects of Conjugates 4, 6 and 7 for Reducing the Contents of Total Cholesterol (CHO) and Triglyceride (TG) in Serum of Human APOC3 Transgenic Mice The measurement was conducted by the same method as that in Experimental Example 2-1, except that each test group included 6 mice; the conjugates to be administered were Conjugates 4, 6 and 7 and Comparative Conjugate 2; and the test continued until day 112 after administration.

FIGS. 6A to 6D are diagrams showing the changes of the total cholesterol (CHO) level and triglyceride (TG) level in serum of human APOC3 trangenic mice administered with normal saline and Conjugates 4, 6 and 7 and Comparative Conjugate 2 at different doses. In these figures, the test group before administration was marked as day DO; and the respective of CHO levels and TG levels in serum were normalized relative to the value on day DO.

As can be seen from the results of FIGS. 6A to 6D, Conjugates 4, 6 and 7 at the two doses show the effects of significantly reducing blood lipid in human APOC3 trangenic mice. Conjugates 4, 6 and 7 in the 3 mg/kg dose group continuously maintain inhibition rates of 50% or higher against TG and inhibition rates of 30% or higher against CHO on day 84 after administration. It is noteworthy that Conjugates 4, 6 and 7 at the doses of 3 mg/kg and 1 mg/kg continuously show higher inhibitory effects on TG than those of Comparative Conjugate 2; and the same tendency is also observed for the inhibitory effect on CHO.

Experimental Example 2-6: This Experiment Investigated the In Vivo Effects of Conjugates 8 and 9 at Different Doses for Reducing the Contents of Total Cholesterol (CHO) and Triglyceride (TG) in Serum of Human APOC3 Transgenic Mice The measurement was conducted by the same method as that in Experimental Example 2-1, except that each test group included 8 mice; the conjugates to be administered were Conjugates 8 and 9; the conjugates were administered at five doses of 0.1 mg/kg, 0.3 mg/kg, 1 mg/kg, 3 mg/kg, and 9 mg/kg, respectively; and the administration volume remained unchanged while the concentrations of the conjugate solutions were correspondingly adjusted; and the test continued until day 147 after administration.

FIGS. 7A to 7D are diagrams showing the the changes of the total cholesterol (CHO) level and triglyceride (TG) level over time in serum of human APOC3 trangenic mice administered with normal saline and Conjugates 8 and 9 at different doses. In these figures, the test group before administration was marked as day DO; and the respective of CHO levels and TG levels in serum were normalized relative to the value on day DO.

As can be seen from the results of FIGS. 7A to 7D, Conjugates 8 and 9 at the five doses show the effects of significantly reducing lipid in human APOC3 trangenic mice, and the reduction effects are dose-dependent.

Further, $ED_{50}$ values of Conjugates 8 and 9 for inhibiting TG level at different time points in human APOC3 transgenic mice were measured based on the inhibition rates of the conjugates at different doses against TG at different time points.

The dose-response curves were plotted according to the serum TG levels measured at different time points when using Conjugates 8 and 9 at different doses, and the curves were fitted using the function log(inhibitor) vs. response Variable slope of Graphpad 5.0 software. The $ED_{50}$ value of each conjugate was calculated based on the dose-response curve.

$$Y = \text{Bot} + \frac{\text{Top} - \text{Bot}}{1 + 10^{(LogED_{50} - X) \times HillSlope}}$$

wherein:

Y is the measured serum TG level (normalized relative to the TG level on day D0), X is the logarithm of the dose of transfected conjugates at the same time point, Bot is the Y value at the bottom of the steady stage, Top is the Y value at the top of the steady stage, $LogED_{50}$ is the X value at which Y is the median value between the bottom and the top, and HillSlope is the slope of the curve.

The calculated $ED_{50}$ values of Conjugates 8 and 9 for inhibiting TG at different time points after single administration were shown in Table 9.

TABLE 9

$ED_{50}$ values (mg/kg) of Conjugates 8 and 9 for inhibiting TG at different time points

| Conjugate | Day 7 | Day 14 | Day 21 | Day 28 | Day 35 | Day 42 | Day 56 | Day 70 |
|---|---|---|---|---|---|---|---|---|
| Conjugate 8 | 0.27 | 0.16 | 0.53 | 0.94 | 0.90 | 1.22 | 1.95 | 3.93 |
| Conjugate 9 | 0.32 | 0.11 | 0.60 | 0.58 | 0.64 | 0.73 | 1.11 | 2.82 |

According to the results shown in Table 9, it can be seen that for human APOC3 transgenic mouse, even half a month after administration, a single subcutaneous injection of 0.16 mg/kg Conjugate 8 or 0.11 mg/kg Conjugate 9 could still realize the efficacy of reducing half of the TG content; and even one month after administration, a single subcutaneous injection of less than 1 mg/kg of the conjugates of the present disclosure could still realize the effect of reducing half of the TG content.

Experimental Example 3: This Experimental Example Investigated Inhibition Rate of Conjugate 4 Against the Expression Level of APOC3 mRNA in the In Vivo Liver Tissue of Human APOC3 Transgenic Mice Prior to the experiments, the serum triglyceride (TG) contents in human APOC3 transgenic mice (B6; CBA-Tg (APOC3)3707Bres/J) were measured. Transgenic mice with serum TG content >2 mmol/L were selected and randomly divided into groups. Each of the test groups included 5 mice; and the blank control group (administered with NS) included 4 mice. Conjugate 4 and normal saline (NS) were respectively administered to the mice in groups. The administration dosages for all animals were calculated according to the body weight and subcutaneously injected as single administration. The siRNA conjugate was administered at two doses of 1 mg/kg and 0.1 mg/kg (based on the amount of the siRNA), wherein the siRNA conjugates were provided in 0.9 wt % NaCl aqueous solutions with concentrations of 0.2 mg/ml and 0.02 mg/ml concentration and the administration volume is 5 mL/kg. The mice were sacrificed on day 14 after administration and the liver tissues were collected and stored in RNA later (Sigma Aldrich). Subsequently, the liver tissues were homogenized with a tissue homogenizer, and then the total RNAs in the liver tissues were extracted and obtained by using Trizol (Thermo Fisher) according to the standard procedure for total RNA extraction.

The expression levels of APOC3 mRNA in liver tissues were measured by the same Quantitative Real-Time PCR method as that used in Experimental Example 1-1, except that in this fluorescent qPCR method, β-actin gene was used as an internal control gene, and the expression levels of APOC3 and β-actin were determined by using the primers for APOC3 and β-actin, respectively.

The sequences of the primers for detection were shown in Table 10.

TABLE 10

Sequences of the primers for detection

| Genes | Upstream Primers | Downstream Primers |
|---|---|---|
| Human APOC3 | 5'-GTGACCGATGGCTTCAGTTC-3' (SEQ ID NO: 323) | 5'- ATGGATAGGCAGGTGGACTT-3' (SEQ ID NO: 324) |
| Mouse β-actin | 5'-AGCTTCTTTGCAGCTCCTTCGTTG-3' (SEQ ID NO: 325) | 5'-TTCTGACCCATTCCCACCATCACA-3' (SEQ ID NO: 326) |

The expression levels of APOC3 mRNA in liver and the inhibition rate of the conjugate against APOC3 mRNA were calculated by the same methods as those used in Experimental Example 1-1. In this experiment, the mice in the control group were administered with normal Saline (NS); and the mice in the test groups were administered with the siRNA conjugate at different concentrations, respectively.

Figure 8:
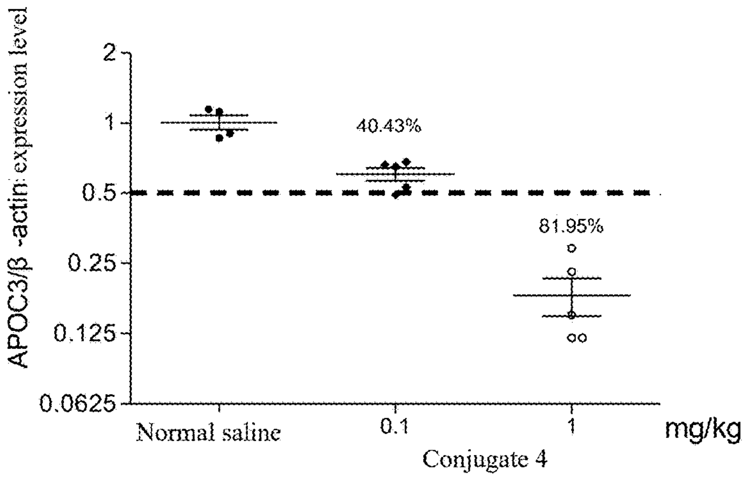
FIG. 8 is a scatterplot showing the expression levels of APOC3 mRNA in the in vivo liver tissues of human APOC3 trangenic mice administered with normal saline and Conjugate 4 at different doses.

FIG. 8 is a scatterplot showing the expression levels of APOC3 mRNA in the in vivo liver tissues of human APOC3 trangenic mice administered with normal saline (NS) and Conjugate 4 at different doses (the expression levels used those of mouse β-actin gene as reference, and were normalized against the blank control NS).

The results shows that single administration of 1 mg/kg and 0.1 mg/kg of Conjugate 4 could have significantly inhibitory effect on human APOC3 gene in transgenic mice. In particular, 1 mg/kg Conjugate 4 shows an inhibition rate of up to 82.0% against APOC3 mRNA, and 0.1 mg/kg Conjugate 4 shows an inhibition rate of 40.4% against APOC3 mRNA.

Some embodiments of the present disclosure are described in detail above, but the present disclosure is not limited to the specific details of the above embodiments. Various simple variations to the technical solutions of the present disclosure can be made within the scope of the technical concept of the present disclosure, and these simple variations are also within the scope of the present disclosure.

It is to be noted that each of the specific technical features described in the above embodiments can be combined in any suitable manner provided that no contradiction is caused. In order to avoid unnecessary repetition, various possible combination manners are no longer described in the present disclosure.

In addition, various different embodiments of the present disclosure may also be combined as long as it does not deviate from the idea of the present disclosure, which should also be regarded as the disclosure of the present disclosure.

INCORPORATION BY REFERENCE

All publications, patents and patent applications mentioned in this description are incorporated herein by reference to the extent as if each publication, patent and patent application were specifically and separately incorporated herein by reference.

The invention claimed is:

1. A siRNA conjugate having a structure as shown by Formula (308):

Formula (308)

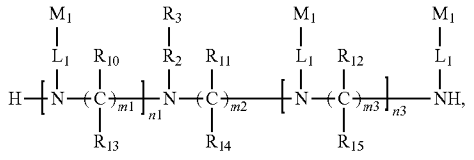

wherein n1 is an integer of 1-2, and n3 is an integer of 0-1, and n1+n3=2-3;

m1, m2, and m3 independently of one another are an integer of 2-10;

$R_{10}$, $R_{11}$, $R_{12}$, $R_{13}$, $R_{14}$, and $R_{15}$ independently of one another are H, or selected from the group consisting of $C_1$-$C_{10}$ alkyl, $C_1$-$C_{10}$ haloalkyl, and $C_1$-$C_{10}$ alkoxy;

$R_3$ is a group having a structure as shown by Formula (A59):

Formula (A59)

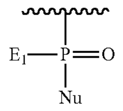

wherein, $E_1$ is OH, SH or $BH_2$;

Nu is a siRNA;

the siRNA comprises a sense strand and an antisense strand; each nucleotide in the siRNA is independently a modified or unmodified nucleotide; wherein the sense strand comprises a nucleotide sequence I, and the antisense strand comprises a nucleotide sequence II; the nucleotide sequence I and the nucleotide sequence II are at least partly reverse complementary to form a double-stranded region; the nucleotide sequence I and the nucleotide sequence II are the sequences selected from one of the following groups i)-v):

i) the nucleotide sequence I and the nucleotide sequence as shown by SEQ ID NO: 1 have an equal length and no more than 3 nucleotide differences, and the nucleotide sequence II and the nucleotide sequence as shown by SEQ ID NO: 2 have an equal length and no more than 3 nucleotide differences; the nucleotide sequence I comprises a nucleotide $Z_{a3}$ at the position corresponding to $Z_{a1}$; the nucleotide sequence II comprises a nucleotide $Z_{a4}$ at the position corresponding to $Z_{a2}$, wherein $Z_{a4}$ is the first nucleotide at 5' terminal of the antisense strand;

(SEQ ID NO: 1)
5'-UUAAAAGGGACAGUAUUCZ$_{a1}$-3', (SEQ ID NO: 2)
5'-Z$_{a2}$GAAUACUGUCCCUUUUAA-3', wherein $Z_{a1}$ is A, $Z_{a2}$ is U, the nucleotide difference between the nucleotide sequence II and the nucleotide sequence as shown by SEQ ID NO: 2 includes a difference at the position $Z_{a4}$, and $Z_{a4}$ is selected from A, C or G; or ii) the nucleotide sequence I and the nucleotide sequence as shown by SEQ ID NO: 13 have an equal length and no more than 3 nucleotide differences, and the nucleotide sequence II and the nucleotide sequence as shown by SEQ ID NO: 14 have an equal length and no more than 3 nucleotide differences; the nucleotide sequence I comprises a nucleotide $Z_{b3}$ at the position corresponding to $Z_{b1}$; the nucleotide sequence II comprises a nucleotide $Z_{b4}$ at the position corresponding to $Z_{b2}$, wherein $Z_{b4}$ is the first nucleotide at 5' terminal of the antisense strand;

(SEQ ID NO: 13)
5'-ACAGUAUUCUCAGUGCUCZ$_{b1}$-3', (SEQ ID NO: 14)
5'-Z$_{b2}$GAGCACUGAGAAUACUGU-3', wherein $Z_{b1}$ is A, $Z_{b2}$ is U, the nucleotide difference between the nucleotide sequence II and the nucleotide sequence as shown by SEQ ID NO: 14 includes a difference at the position $Z_{b4}$, and $Z_{b4}$ is selected from A, C or G; or iii) the nucleotide sequence I and the nucleotide sequence as shown by SEQ ID NO: 25 have an equal length and no more than 3 nucleotide differences, and the nucleotide sequence II and the nucleotide sequence as shown by SEQ ID NO: 26 have an equal length and no more than 3 nucleotide differences; the nucleotide sequence I comprises a nucleotide $Z_{c3}$ at the position corresponding to $Z_{c1}$; the nucleotide sequence II comprises a nucleotide $Z_{c4}$ at the position corresponding to $Z_{c2}$, wherein $Z_{c4}$ is the first nucleotide at 5' terminal of the antisense strand;

(SEQ ID NO: 25)
5'-UAUUCUCAGUGCUCUCCUZ$_{c1}$-3', (SEQ ID NO: 26)
5'-Z$_{c2}$AGGAGAGCACUGAGAAUA-3', wherein $Z_{c1}$ is A, $Z_{c2}$ is U, the nucleotide difference between the nucleotide sequence II and the nucleotide sequence as shown by SEQ ID NO: 26 includes a difference at the position $Z_{c4}$, and $Z_{c4}$ is selected from A, C or G; or iv) the nucleotide sequence I and the nucleotide sequence as shown by SEQ ID NO: 37 have an equal length and no more than 3 nucleotide differences, and the nucleotide sequence II and the nucleotide sequence as shown by SEQ ID NO: 38 have an equal length and no more than 3 nucleotide differences; the nucleotide sequence I comprises a nucleotide $Z_{d3}$ at the position corresponding to $Z_{d1}$; the nucleotide sequence II comprises a nucleotide $Z_{d4}$ at the position corresponding to $Z_{d2}$, wherein $Z_{d4}$ is the first nucleotide at 5' terminal of the antisense strand;

(SEQ ID NO: 37)
5'-AGUAUUCUCAGUGCUCUCZ$_{d1}$-3', (SEQ ID NO: 38)
5'-Z$_{d2}$GAGAGCACUGAGAAUACU-3', wherein $Z_{d1}$ is A, $Z_{d2}$ is U, the nucleotide difference between the nucleotide sequence II and the nucleotide sequence as shown by SEQ ID NO: 38 includes a difference at the position $Z_{d4}$, and $Z_{d4}$ is selected from A, C or G; or v) the nucleotide sequence I and the nucleotide sequence as shown by SEQ ID NO: 49 have an equal length and no more than 3 nucleotide differences, and the nucleotide sequence II and the nucleotide sequence as shown by SEQ ID NO: 50 have an equal length and no more than 3 nucleotide differences; the nucleotide sequence I comprises a nucleotide $Z_{e3}$ at the position corresponding to $Z_{e1}$; the nucleotide sequence II comprises a nucleotide $Z_{e4}$ at the position corresponding to $Z_{e2}$, wherein $Z_{e4}$ is the first nucleotide at 5' terminal of the antisense strand;

(SEQ ID NO: 49)
5'-GGACAGUAUUCUCAGUGCZ$_{e1}$-3', (SEQ ID NO: 50)
5'-Z$_{e2}$GCACUGAGAAUACUGUCC-3', wherein $Z_{e1}$ is A, $Z_{e2}$ is U, the nucleotide difference between the nucleotide sequence II and the nucleotide sequence as shown by SEQ ID NO: 50 includes a difference at the position $Z_{e4}$, and $Z_{e4}$ is selected from A, C or G;

$R_2$ is a linear alkylene of 1 to 20 carbon atoms in length, wherein one or more carbon atoms are optionally replaced with one or more groups selected from the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene; and wherein $R_2$ optionally has any one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —N($C_1$-$C_{10}$ alkyl) ($C_1$-$C_{10}$ alkylphenyl), —NH($C_1$-$C_{10}$ alkylphenyl), cyano, nitro, —$CO_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2$NH($C_1$-$C_{10}$ alkyl), —$SO_2$NH(phenyl), —NH$SO_2$($C_1$-$C_{10}$ alkyl), —NH$SO_2$(phenyl), and —NH$SO_2$($C_1$-$C_{10}$ haloalkyl);

each $L_1$ is a linear alkylene of 1 to 70 carbon atoms in length, wherein one or more carbon atoms are optionally replaced with one or more groups selected from the group consisting of: C(O), NH, O, S, CH═N, $S(O)_2$, $C_2$-$C_{10}$ alkenylene, $C_2$-$C_{10}$ alkynylene, $C_6$-$C_{10}$ arylene, $C_3$-$C_{18}$ heterocyclylene, and $C_5$-$C_{10}$ heteroarylene; and wherein $L_1$ optionally has any one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —N($C_1$-$C_{10}$ alkyl)($C_1$-$C_{10}$ alkyl), —NH($C_1$-$C_{10}$ alkyl), —N($C_1$-$C_{10}$ alkyl) ($C_1$-$C_{10}$ alkylphenyl), —NH($C_1$-$C_{10}$ alkylphenyl), cyano, nitro, —$CO_2H$, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2NH$($C_1$-$C_{10}$ alkyl), —$SO_2NH$(phenyl), —$NHSO_2$($C_1$-$C_{10}$ alkyl), —$NHSO_2$(phenyl), and —$NHSO_2$($C_1$-$C_{10}$ haloalkyl);

represents the site where a group is linked to the rest of the molecule; and $M_1$ represents a targeting group.

2. The siRNA conjugate according to claim 1, wherein each $L_1$ is independently selected from the linkage combinations of one or more of the groups of Formulae (A1)-(A26):

(A1)

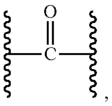

(A2)

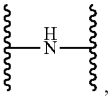

(A3)

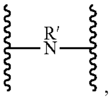

(A4)

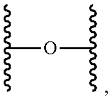

(A5)

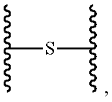

(A6)

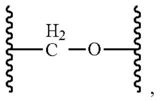

-continued (A7)

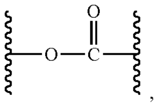

(A8)

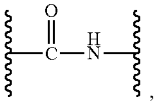

(A9)

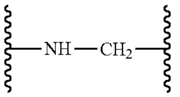

(A10)

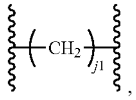

(A11)

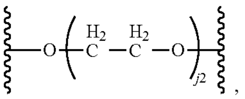

(A12)

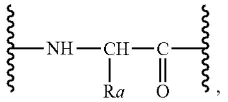

(A13)

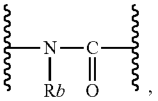

(A14)

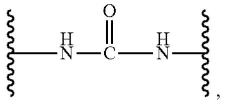

(A15)

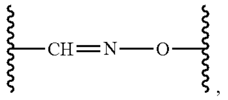

(A16)

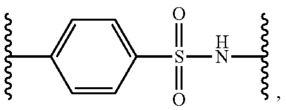

(A17)

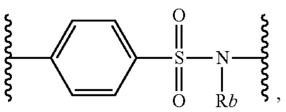

(A18)

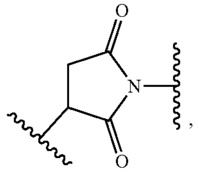

-continued
(A19)
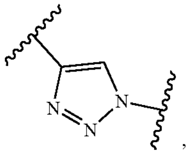
(A20)
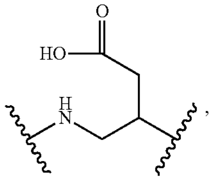
(A21)
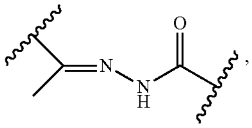
(A22)
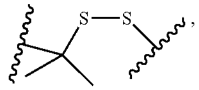
(A23)
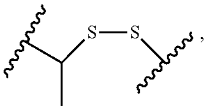
(A24)
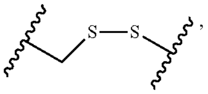
(A25)
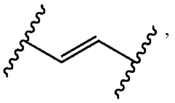
and
(A26)
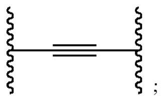
wherein j1 is an integer of 1-20;
j2 is an integer of 1-20;
R' is a $C_1$-$C_{10}$ alkyl;
Ra is selected from the group consisting of the groups of Formulae (A27)-(A45) or any combination thereof:
(A27)
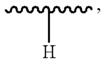
(A28)
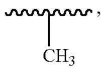
(A29)
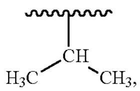
-continued
(A30)
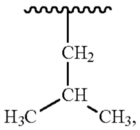
(A31)
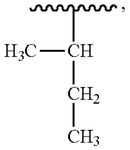
(A32)
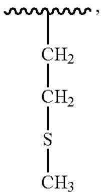
(A33)
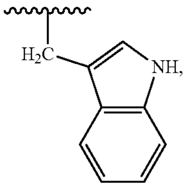
(A34)
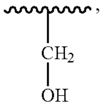
(A35)
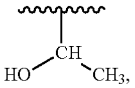
(A36)
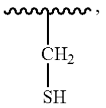
(A37)
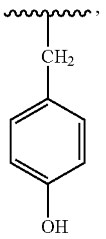
(A38)
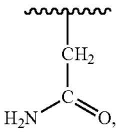

-continued (A39)

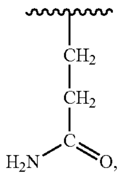

(A40)

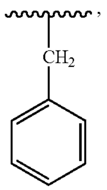

(A41)

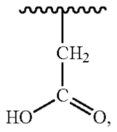

(A42)

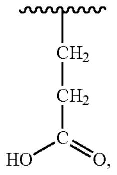

(A43)

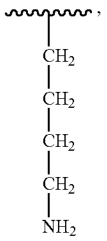

(A44)

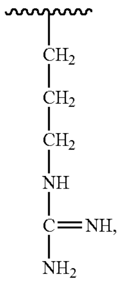

and (A45)

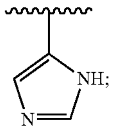

Rb is a $C_1$-$C_{10}$ alkyl; or $L_1$ is selected from the linkage combinations of one or more of Formulae (A1), (A4), (A5), (A6), (A8), (A10), (A11), and (A13); or $L_1$ is selected from the linkage combinations of at least two of Formulae (A1), (A4), (A8), (A10) and (All); or $L_1$ is selected from the linkage combinations of at least two of Formulae (A1), (A8), and (A10); or $L_1$ has a length of 3 to 25 atoms; or $L_1$ has a length of 4 to 15 atoms.

3. The siRNA conjugate according to claim 2, wherein j1 is an integer of 2-10; j2 is an integer of 2-10; R' is a $C_1$-$C_4$ alkyl; Ra is one of A27, A28, A29, A30, and A31; and Rb is a $C_1$-$C_5$ alkyl; or j1 is an integer of 3-5; j2 is an integer of 3-5; R' is one of methyl, ethyl, and isopropyl;

Ra is a group as shown by Formula A27 or A28; and Rb is one of methyl, ethyl, isopropyl, and butyl.

4. The siRNA conjugate according to claim 1, wherein m1, m2 and m3 independently of one another are an integer of 2-5, and/or m1=m2=m3.

5. The siRNA conjugate according to claim 1, wherein each of the targeting groups is independently a ligand that has affinity to the asialoglycoprotein receptor on the surface of mammalian hepatocyte; or each of the targeting groups is independently an asialoglycoprotein or a saccharide; or each of the targeting groups is independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, L-4-thioribose; or at least one or each of the targeting groups is galactose or N-acetylgalactosamine.

6. The siRNA conjugate according to claim 1, wherein $R_2$ comprises both a site linking to the N atom on the nitrogenous backbone and a site linking to the P atom in $R_3$; or in $R_2$, the site linking to the N atom on the nitrogenous backbone forms an amide bond with the N atom, and the site linking to the P atom in $R_3$ forms a phosphoester bond with the P atom; or $R_2$ is a functional group having a structure as shown by any one of Formula (B5),(B6),(B5') or (B6).

7. The siRNA conjugate according to claim 1, wherein the conjugate has a structure as shown by Formula (403), (404), (405), (406), (407), (408), (409), (410), (411), (412), (413), (414), (415), (416), (417), (418), (419), (420), (421), or (422).

8. The siRNA conjugate according to claim 1, wherein the P atom in Formula A59 is linked to a terminal region of the sense or antisense strand of the siRNA, and the terminal region refers to the first 4 nucleotides counted from one terminal of the sense or antisense strand; or the P atom in Formula A59 is linked to one terminal of the sense or antisense strand of the siRNA; or the P atom in Formula A59 is linked to 3' terminal of the sense strand of the siRNA; or the P atom in Formula A59 is linked to position 2', 3', or 5' of a nucleotide in the siRNA by forming a phosphodiester bond.

9. The siRNA conjugate according to claim 1, wherein i) the nucleotide sequence I has no more than 1 nucleotide difference from the nucleotide sequence as shown by SEQ ID NO: 1, and/or the nucleotide sequence II has no more than 1 nucleotide difference from the nucleotide sequence as shown by SEQ ID NO: 2; or ii) the nucleotide sequence I has no more than 1 nucleotide difference from the nucleotide sequence as shown by SEQ ID NO: 13, and/or the nucleotide sequence II has no more than 1 nucleotide difference from the nucleotide sequence as shown by SEQ ID NO: 14; or iii) the nucleotide sequence I has no more than 1 nucleotide difference from the nucleotide sequence as shown by SEQ ID NO: 25, and/or the nucleotide sequence II has no more than 1 nucleotide difference from the nucleotide sequence as shown by SEQ ID NO: 26; or iv) the nucleotide sequence I has no more than 1 nucleotide difference from the nucleotide sequence as shown by SEQ ID NO: 37, and/or the nucleotide sequence II has no more than 1 nucleotide difference from the nucleotide sequence as shown by SEQ ID NO: 38; or v) the nucleotide sequence I has no more than 1 nucleotide difference from the nucleotide sequence as shown by SEQ ID NO: 49, and/or the nucleotide sequence II has no more than 1 nucleotide difference from the nucleotide sequence as shown by SEQ ID NO: 50.

10. The siRNA conjugate according to claim 9, wherein the sense strand further comprises a nucleotide sequence III, the antisense strand further comprises a nucleotide sequence IV; and the nucleotide sequence III and the nucleotide sequence IV independently of one another have a length of 1 to 4 nucleotides; the nucleotide sequence III is linked to 5' terminal of the nucleotide sequence I, the nucleotide sequence IV is linked to 3' terminal of the nucleotide sequence II; the nucleotide sequence III and the nucleotide sequence IV have an equal length, and are substantially reverse complementary or completely reverse complementary to each other; the "substantially reverse complementary" means that there is no more than 1 base mispairing between two nucleotide sequences; and the "completely reverse complementary" means that there is no mispairing between two nucleotide sequences, wherein i) the nucleotide sequence I is the nucleotide sequence as shown by SEQ ID NO: 3; the nucleotide sequence II is the nucleotide sequence as shown by SEQ ID NO: 4; and the nucleotide sequence III and the nucleotide sequence IV both have a length of 1 nucleotide, and the base of the nucleotide sequence III is C; or the nucleotide sequence III and the nucleotide sequence IV both have a length of 2 nucleotides, and in the direction from 5' terminal to 3' terminal, the bases of the nucleotide sequence III is GC; or the nucleotide sequence III and the nucleotide sequence IV both have a length of 3 nucleotides, and in the direction from 5' terminal to 3' terminal, the bases of the nucleotide sequence III is UGC; or the nucleotide sequence III and the nucleotide sequence IV both have a length of 4 nucleotides, and in the direction from 5' terminal to 3' terminal, the bases of the nucleotide sequence III is UUGC; or ii) the nucleotide sequence I is the nucleotide sequence as shown by SEQ ID NO: 15; the nucleotide sequence II is the nucleotide sequence as shown by SEQ ID NO: 16; and the nucleotide sequence III and the nucleotide sequence IV both have a length of 1 nucleotide, and the base of the nucleotide sequence III is G; or the nucleotide sequence III and the nucleotide sequence IV both have a length of 2 nucleotides, and in the direction from 5' terminal to 3' terminal, the bases of the nucleotide sequence III is GG; or the nucleotide sequence III and the nucleotide sequence IV both have a length of 3 nucleotides, and in the direction from 5' terminal to 3' terminal, the bases of the nucleotide sequence III is AGG; or the nucleotide sequence III and the nucleotide sequence IV both have a length of 4 nucleotides, and in the direction from 5' terminal to 3' terminal, the bases of the nucleotide sequence III is AGGG; or iii) the nucleotide sequence I is the nucleotide sequence as shown by SEQ ID NO: 25; the nucleotide sequence II is the nucleotide sequence as shown by SEQ ID NO: 26; and the nucleotide sequence III and the nucleotide sequence IV both have a length of 1 nucleotide, and the base of the nucleotide sequence III is G; or the nucleotide sequence III and the nucleotide sequence IV both have a length of 2 nucleotides, and in the direction from 5' terminal to 3' terminal, the bases of the nucleotide sequence III is AG; or the nucleotide sequence III and the nucleotide sequence IV both have a length of 3 nucleotides, and in the direction from 5' terminal to 3' terminal, the bases of the nucleotide sequence III is CAG; or the nucleotide sequence III and the nucleotide sequence IV both have a length of 4 nucleotides, and in the direction from 5' terminal to 3' terminal, the bases of the nucleotide sequence III is ACAG; or iv) the nucleotide sequence I is the nucleotide sequence as shown by SEQ ID NO: 39; the nucleotide sequence II is the nucleotide sequence as shown by SEQ ID NO: 40; and the nucleotide sequence III and the nucleotide sequence IV both have a length of 1 nucleotide, and the base of the nucleotide sequence III is C; or the nucleotide sequence III and the nucleotide sequence IV both have a length of 2 nucleotides, and in the direction from 5' terminal to 3' terminal, the bases of the nucleotide sequence III is AC; or the nucleotide sequence III and the nucleotide sequence IV both have a length of 3 nucleotides, and in the direction from 5' terminal to 3' terminal, the bases of the nucleotide sequence III is GAC; or the nucleotide sequence III and the nucleotide sequence IV both have a length of 4 nucleotides, and in the direction from 5' terminal to 3' terminal, the bases of the nucleotide sequence III is GGAC; or v) the nucleotide sequence I is the nucleotide sequence as shown by SEQ ID NO. 51; the nucleotide sequence II is the nucleotide sequence as shown by SEQ ID NO: 52; and the nucleotide sequence III and the nucleotide sequence IV both have a length of 1 nucleotide, and the base of the nucleotide sequence III is G; or the nucleotide sequence III and the nucleotide sequence IV both have a length of 2 nucleotides, and in the direction from 5' terminal to 3' terminal, the bases of the nucleotide sequence III is AG; or the nucleotide sequence III and the nucleotide sequence IV both have a length of 3 nucleotides, and in the direction from 5' terminal to 3' terminal, the bases of the nucleotide sequence III is AAG; or the nucleotide sequence III and the nucleotide sequence IV both have a length of 4 nucleotides, and in the direction from 5' terminal to 3' terminal, the bases of the nucleotide sequence III is AAAG.

11. The siRNA conjugate according to claim 9, wherein the antisense strand further comprises a nucleotide sequence V, which has a length of 1 to 3 nucleotides and is linked to 3' terminal of the antisense strand, thereby forming a 3' overhang terminal of the antisense strand; or the nucleotide sequence V has a length of 2 nucleotides; or the nucleotide sequence V is 2 consecutive thymine deoxyribonucleotides or 2 consecutive uracil ribonucleotides; or the nucleotide sequence V is complementary to the nucleotides at the corresponding positions of the target mRNA.

12. The siRNA conjugate according to claim 9, wherein the sense strand of the siRNA comprises the nucleotide sequence as shown by SEQ ID NO: 5, and the antisense strand of the siRNA comprises the nucleotide sequence as shown by SEQ ID NO: 6; or the sense strand of the siRNA comprises the nucleotide sequence as shown by SEQ ID NO: 7, and the antisense strand of the siRNA comprises the nucleotide sequence as shown by SEQ ID NO: 8; or the sense strand of the siRNA comprises the nucleotide sequence as shown by SEQ ID NO: 17, and the antisense strand of the siRNA comprises the nucleotide sequence as shown by SEQ ID NO: 18; or the sense strand of the siRNA comprises the nucleotide sequence as shown by SEQ ID NO: 19, and the antisense strand of the siRNA comprises the nucleotide sequence as shown by SEQ ID NO: 20; or the sense strand of the siRNA comprises the nucleotide sequence as shown by SEQ ID NO: 29, and the antisense strand of the siRNA comprises the nucleotide sequence as shown by SEQ ID NO: 30; or the sense strand of the siRNA comprises the nucleotide sequence as shown by SEQ ID NO: 31, and the antisense strand of the siRNA comprises the nucleotide sequence as shown by SEQ ID NO: 32; or the sense strand of the siRNA comprises the nucleotide sequence as shown by SEQ ID NO: 41, and the antisense strand of the siRNA comprises the nucleotide sequence as shown by SEQ ID NO: 42; or the sense strand of the siRNA comprises the nucleotide sequence as shown by SEQ ID NO: 43, and the antisense strand of the siRNA comprises the nucleotide sequence as shown by SEQ ID NO: 44; or the sense strand of the siRNA comprises the nucleotide sequence as shown by SEQ ID NO: 53, and the antisense strand of the siRNA comprises the nucleotide sequence as shown by SEQ ID NO: 54; or the sense strand of the siRNA comprises the nucleotide sequence as shown by SEQ ID NO: 55, and the antisense strand of the siRNA comprises the nucleotide sequence as shown by SEQ ID NO: 56.

13. The siRNA conjugate according to claim 9, wherein the siRNA is siAPa1, siAPa2, siAPb1, siAPb2, siAPc1, siAPc2, siAPd1, siAPd2, siAPe1, or siAPe2.

14. The siRNA conjugate according to claim 9, wherein each nucleotide in the sense strand and antisense strand is independently a fluoro modified nucleotide or a non-fluoro modified nucleotide; or the fluoro modified nucleotides are located in the nucleotide sequence I and the nucleotide sequence II; and in the direction from 5' terminal to 3' terminal, the nucleotides at positions 7, 8 and 9 of the nucleotide sequence I are fluoro modified nucleotides; and in the direction from 5' terminal to 3' terminal, the nucleotides at positions 2, 6, 14, and 16 of the nucleotide sequence II are fluoro modified nucleotides; or in the direction from 5' terminal to 3' terminal, the nucleotides at positions 7, 8 and 9 or at positions 5, 7, 8 and 9 of the nucleotide sequence I in the sense strand are fluoro modified nucleotides, and the nucleotides at the other positions in the sense strand are non-fluoro modified nucleotides; in the direction from 5' terminal to 3' terminal, the nucleotides at positions 2, 6, 14 and 16 or at positions 2, 6, 8, 9, 14, and 16 of the nucleotide sequence II in the antisense strand are fluoro modified nucleotides, and the nucleotides at the other positions in the antisense strand are non-fluoro modified nucleotides.

15. The siRNA conjugate according to claim 14, wherein each non-fluoro modified nucleotide is independently a nucleotide formed by substituting the 2'-hydroxy of the ribose group of the nucleotide with a non-fluoro group, or a nucleotide analogue; or the nucleotide formed by substituting the 2'-hydroxy of the ribose group with a non-fluoro group is selected from the group consisting of 2'-alkoxy modified nucleotide, 2'-substituted alkoxy modified nucleotide, 2'-alkyl modified nucleotide, 2'-substituted alkyl modified nucleotide, 2'-amino modified nucleotide, 2'-substituted amino modified nucleotide, and 2'-deoxy nucleotide; and the nucleotide analogue is selected from the group consisting of an isonucleotide, locked nucleic acid (LNA), ethylene-bridged nucleic acid (ENA), constrained ethyl bridged nucleic acid (cET), unlocked nucleic acid (UNA), and glycerol nucleic acid (GNA); or each non-fluoro modified nucleotide is a methoxy modified nucleotide, wherein the methoxy modified nucleotide refers to a nucleotide formed by substituting 2'-hydroxy of the ribose group with a methoxy group, wherein LNA, ENA, cET, UNA and GNA are represented by Formulae (212), (213), (14), (15) and (16), respectively:

(12)

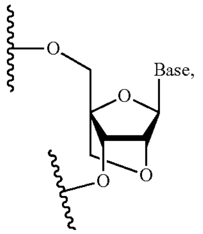

(13)

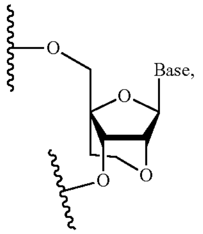

-continued (14)

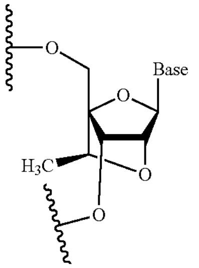

(15)

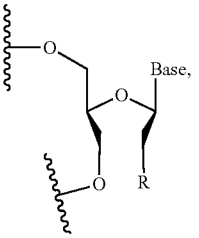

(16)

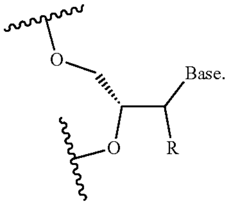

16. The siRNA conjugate according to claim 14, wherein in the direction from 5' terminal to 3' terminal, the nucleotides at positions 5, 7, 8 and 9 of the nucleotide sequence I in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 8, 9, 14 and 16 of the nucleotide sequence II in the antisense strand of the siRNA are fluoro modified nucleotides, and the nucleotides at the other positions in the antisense strand of the siRNA are methoxy modified nucleotides; or in the direction from 5' terminal to 3' terminal, the nucleotides at positions 5, 7, 8 and 9 of the nucleotide sequence I in the sense strand of the siRNA are fluoro modified nucleotides, and the nucleotides at the other positions of the sense strand of the siRNA are methoxy modified nucleotides; and in the direction from 5' terminal to 3' terminal, the nucleotides at positions 2, 6, 14 and 16 of the nucleotide sequence II in the antisense strand of the siRNA are fluoro modified nucleotides, and the nucleotides at the other positions in the antisense strand are methoxy modified nucleotides; or in the direction from 5' terminal to 3' terminal, the nucleotides at positions 7, 8 and 9 of the nucleotide sequence I in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14 and 16 of the nucleotide sequence II in the antisense strand of the siRNA are fluoro modified nucleotides, and the nucleotides at the other positions in the antisense strand of the siRNA are methoxy modified nucleotides.

17. The siRNA conjugate according to claim 9, wherein the siRNA is any one of siAPa1-M1, siAPa2-M1, siAPa1-M2, siAPa2-M2, siAPa1-M3, siAPa2-M3, siAPb1-M1, siAPb2-M1, siAPb1-M2, siAPb2-M2, siAPb1-M3, siAPb2-M3, siAPc1-M1, siAPc2-M1, siAPc1-M2, siAPc2-M2, siAPc1-M3, siAPc2-M3, siAPd1-M1, siAPd2-M1, siAPd1-M2, siAPd2-M2, siAPd1-M3, siAPd2-M3, siAPe1-M1, siAPe2-M1, siAPe1-M2, siAPe2-M2, siAPe1-M3, and siAPe2-M3.

18. The siRNA conjugate according to claim 9, wherein in the siRNA, at least one phosphate group is a phosphorothioate group, and the phosphorothioate linkage is located in at least one of the group consisting of the following positions:

the position between the first and second nucleotides at 5' terminal of the sense strand;

the position between the second and third nucleotides at 5' terminal of the sense strand;

the position between the first and second nucleotides at 3' terminal of the sense strand;

the position between the second and third nucleotides at 3' terminal of the sense strand;

the position between the first and second nucleotides at 5' terminal of the antisense strand;

the position between the second and third nucleotides at 5' terminal of the antisense strand;

the position between the first and second nucleotides at 3' terminal of the antisense strand; and the position between the second and third nucleotides at 3' terminal of the antisense strand.

19. The siRNA conjugate according to claim 9, wherein the siRNA is any one of siAPa1-M1S, siAPa2-M1S, siAPa1-M2S, siAPa2-M2S, siAPa1-M3S, siAPa2-M3S, siAPb1-M1S, siAPb2-M1S, siAPb1-M2S, siAPb2-M2S, siAPb1-M3S, siAPb2-M3S, siAPc1-M1S, siAPc2-M1S, siAPc1-M2S, siAPc2-M2S, siAPc1-M3S, siAPc2-M3S, siAPd1-M1S, siAPd2-M1S, siAPd1-M2S, siAPd2-M2S, siAPd1-M3S, siAPd2-M3S, siAPe1-M1S, siAPe2-M1S, siAPe1-M2S, siAPe2-M2S, siAPe1-M3S, and siAPe2-M3S.

20. The siRNA conjugate according to claim 9, wherein the nucleotide at 5'-terminal of the antisense strand of the siRNA is a 5'-phosphate nucleotide or a 5'-phosphate analogue modified nucleotide; or the 5'-phosphate nucleotide is a nucleotide having a structure as shown by Formula (2); and the 5'-phosphate analogue modified nucleotide is a nucleotide having a structure as shown by any one of Formulae (3) to (6):

Formula (2)

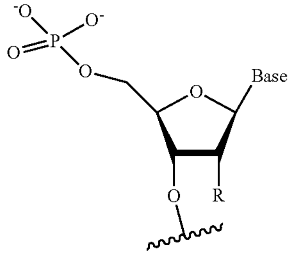

-continued

Formula (3)

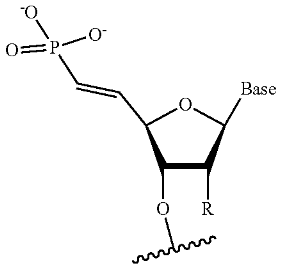

Formula (4)

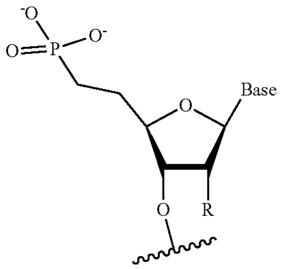

Formula (5)

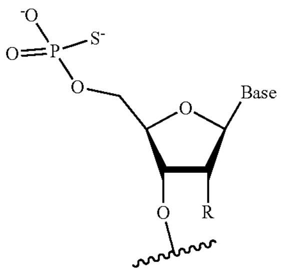

Formula (6)

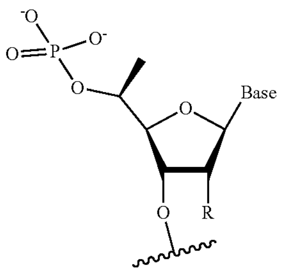

wherein R is selected from H, OH, methoxy or F;

"Base" represents a base selected from A, U, C, G, or T.

21. The siRNA conjugate according to claim 9, wherein the siRNA is any one of siAPa1-M1P1, siAPa2-M1P1, siAPa1-M2P1, siAPa2-M2P1, siAPa1-M3P1, siAPa2-M3P1, siAPa1-M1SP1, siAPa2-M1SP1, siAPa1-M2SP1, siAPa2-M2SP1, siAPa1-M3SP1, siAPa2-M3SP1, siAPa1U-M1P1, siAPa2U-M1P1, siAPa1U-M2P1, siAPa2U-M2P1, siAPa1U-M3P1, siAPa2U-M3P1, siAPa1U-M1SP1, siAPa2U-M1SP1, siAPa1U-M2SP1, siAPa2U-M2SP1, siAPa1U-M3SP1, siAPa2U-M3SP1, siAPb1-M1P1, siAPb2-M1P1, siAPb1-M2P1, siAPb2-M2P1, siAPb1-M3P1, siAPb2-M3P1, siAPb1-M1SP1, siAPb2-M1SP1, siAPb1-M2SP1, siAPb2-M2SP1, siAPb1-M3SP1, siAPb2-M3SP1, siAPb1U-M1P1, siAPb2U-M1P1, siAPb1U-M2P1, siAPb2U-M2P1, siAPb1U-M3P1, siAPb2U-M3P1, siAPb1U-M1SP1, siAPb2U-M1SP1, siAPb1U-M2SP1, siAPb2U-M2SP1, siAPb1U-M3SP1, siAPb2U-M3SP1, siAPc1-M1P1, siAPc2-M1P1, siAPc1-M2P1, siAPc2-M2P1, siAPc1-M3P1, siAPc2-M3P1, siAPc1-M1SP1, siAPc2-M1SP1, siAPc1-M2SP1, siAPc2-M2SP1, siAPc1-M3SP1, siAPc2-M3SP1, siAPd1-M1P1, siAPd2-M1P1, siAPd1-M2P1, siAPd2-M2P1, siAPd1-M3P1, siAPd2-M3P1, siAPd1-M1SP1, siAPd2-M1SP1, siAPd1-M2SP1, siAPd2-M2SP1, siAPd1-M3SP1, siAPd2-M3SP1, siAPd1U-M1P1, siAPd2U-M1P1, siAPd1U-M2P1, siAPd2U-M2P1, siAPd1U-M3P1, siAPd2U-M3P1, siAPd1U-M1SP1, siAPd2U-M1SP1, siAPd1U-M2SP1, siAPd2U-M2SP1, siAPd1U-M3SP1, siAPd2U-M3SP1, siAPe1-M1P1, siAPe2-M1P1, siAPe1-M2P1, siAPe2-M2P1, siAPe1-M3P1, siAPe2-M3P1, siAPe1-M1SP1, siAPe2-M1SP1, siAPe1-M2SP1, siAPe2-M2SP1, siAPe1-M3SP1, siAPe2-M3SP1, siAPe1U-M1P1, siAPe2U-M1P1, siAPe1U-M2P1, siAPe2U-M2P1, siAPe1U-M3P1, siAPe2U-M3P1, siAPe1U-M1SP1, siAPe2U-M1SP1, siAPe1U-M2SP1, siAPe2U-M2SP1, siAPe1U-M3SP1, and siAPe2U-M3SP1.

22. A method for treating dyslipidemia, comprising subcutaneously administering an effective amount of the siRNA conjugate according to claim 1 to a subject suffering from dyslipidemia.

23. The method of claim 22, wherein the dyslipidemia is hypercholesteremia, hypertriglyceridemia or atherosclerosis.

24. A method for inhibiting the expression of APOC3 gene in hepatocytes, comprising contacting an effective amount of the siRNA conjugate according to claim 1 with the hepatocytes, wherein when the contacting is in vivo, the siRNA conjugate is subcutaneously administered.

* * * * *

SEQUENCE LISTING

```
<160> NUMBER OF SEQ ID NOS: 430

<210> SEQ ID NO 1
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Za1, Za1 is A
<220> FEATURE:
<223> OTHER INFORMATION: siRNA
```

```
<400> SEQUENCE: 1

uuaaaaggga caguauucn                                                19


<210> SEQ ID NO 2
<211> LENGTH: 19
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Za2, Za2 is U
<220> FEATURE:
<223> OTHER INFORMATION: siRNA

<400> SEQUENCE: 2

ngaauacugu cccuuuuaa                                                19


<210> SEQ ID NO 3
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Za3, Za3 is selected from A, U, G or C
<220> FEATURE:
<223> OTHER INFORMATION: siRNA

<400> SEQUENCE: 3

uuaaaaggga caguauucn                                                19


<210> SEQ ID NO 4
<211> LENGTH: 19
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Za4, Za4 is a nucleotide complementary to
      Za3, Za3 is selected from A, U, G or C
<220> FEATURE:
<223> OTHER INFORMATION: siRNA

<400> SEQUENCE: 4

ngaauacugu cccuuuuaa                                                19


<210> SEQ ID NO 5
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Za3, Za3 is selected from A, U, G or C
<220> FEATURE:
<223> OTHER INFORMATION: siRNA

<400> SEQUENCE: 5

uuaaaaggga caguauucn                                                19


<210> SEQ ID NO 6
<211> LENGTH: 21
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Za4, Za4 is a nucleotide complementary to
```

Za3, Za3 is selected from A, U, G or C
<220> FEATURE:
<223> OTHER INFORMATION: siRNA

<400> SEQUENCE: 6
ngaauacugu cccuuuuaag c 21

<210> SEQ ID NO 7
<211> LENGTH: 21
<212> TYPE: RNA
<213> ORGANISM: Artificial Sequence
<220> FEATURE:
<221> NAME/KEY: misc_feature
<222> LOCATION: (21)..(21)
<223> OTHER INFORMATION: n is Za3, Za3 is selected from A, U, G or C
<220> FEATURE:
<223> OTHER INFORMATION: siRNA

<400> SEQUENCE: 7
gcuuaaaagg gacaguauuc n 21

<210> SEQ ID NO 8
<211> LENGTH: 23
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Za4, Za4 is a nucleotide complementary to
Za3, Za3 is selected from A, U, G or C
<220> FEATURE:
<223> OTHER INFORMATION: siRNA

<400> SEQUENCE: 8
ngaauacugu cccuuuuaag caa 23

<210> SEQ ID NO 9
<211> LENGTH: 19
<212> TYPE: RNA
<213> ORGANISM: Artificial Sequence
<220> FEATURE:
<223> OTHER INFORMATION: siRNA

<400> SEQUENCE: 9
uuaaaaggga caguauucu 19

<210> SEQ ID NO 10
<211> LENGTH: 21
<212> TYPE: RNA
<213> ORGANISM: Artificial Sequence
<220> FEATURE:
<223> OTHER INFORMATION: siRNA

<400> SEQUENCE: 10
agaauacugu cccuuuuaag c 21

<210> SEQ ID NO 11
<211> LENGTH: 21
<212> TYPE: RNA
<213> ORGANISM: Artificial Sequence
<220> FEATURE:
<223> OTHER INFORMATION: siRNA

<400> SEQUENCE: 11
gcuuaaaagg gacaguauuc u 21

<210> SEQ ID NO 12

<211> LENGTH: 23
<212> TYPE: RNA
<213> ORGANISM: Artificial Sequence
<220> FEATURE:
<223> OTHER INFORMATION: siRNA

<400> SEQUENCE: 12
agaauacugu cccuuuuaag caa 23

<210> SEQ ID NO 13
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Zb1, Zb1 is A
<220> FEATURE:
<223> OTHER INFORMATION: siRNA

<400> SEQUENCE: 13
acaguauucu cagugcucn 19

<210> SEQ ID NO 14
<211> LENGTH: 19
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Zb2, Zb2 is U
<220> FEATURE:
<223> OTHER INFORMATION: siRNA

<400> SEQUENCE: 14
ngagcacuga gaauacugu 19

<210> SEQ ID NO 15
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Zb3, Zb3 is selected from A, U, G or C
<220> FEATURE:
<223> OTHER INFORMATION: siRNA

<400> SEQUENCE: 15
acaguauucu cagugcucn 19

<210> SEQ ID NO 16
<211> LENGTH: 19
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Zb4, Zb4 is a nucleotide complementary to
Zb3, Zb3 is selected from A, U, G or C
<220> FEATURE:
<223> OTHER INFORMATION: siRNA

<400> SEQUENCE: 16
ngagcacuga gaauacugu 19

<210> SEQ ID NO 17
<211> LENGTH: 19
<212> TYPE: RNA

<213> ORGANISM: Artificial Sequence
<220> FEATURE:
<221> NAME/KEY: misc_feature
<222> LOCATION: (19)..(19)
<223> OTHER INFORMATION: n is Zb3, Zb3 is selected from A, U, G or C
<220> FEATURE:
<223> OTHER INFORMATION: siRNA

<400> SEQUENCE: 17
acaguauucu cagugcucn 19

<210> SEQ ID NO 18
<211> LENGTH: 21
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Zb4, Zb4 is a nucleotide complementary to
Zb3, Zb3 is selected from A, U, G or C
<220> FEATURE:
<223> OTHER INFORMATION: siRNA

<400> SEQUENCE: 18
ngagcacuga gaauacuguc c 21

<210> SEQ ID NO 19
<211> LENGTH: 21
<212> TYPE: RNA
<213> ORGANISM: Artificial Sequence
<220> FEATURE:
<221> NAME/KEY: misc_feature
<222> LOCATION: (21)..(21)
<223> OTHER INFORMATION: n is Zb3, Zb3 is selected from A, U, G or C
<220> FEATURE:
<223> OTHER INFORMATION: siRNA

<400> SEQUENCE: 19
ggacaguauu cucagugcuc n 21

<210> SEQ ID NO 20
<211> LENGTH: 23
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Zb4, Zb4 is a nucleotide complementary to
Zb3, Zb3 is selected from A, U, G or C
<220> FEATURE:
<223> OTHER INFORMATION: siRNA

<400> SEQUENCE: 20
ngagcacuga gaauacuguc ccu 23

<210> SEQ ID NO 21
<211> LENGTH: 19
<212> TYPE: RNA
<213> ORGANISM: Artificial Sequence
<220> FEATURE:
<223> OTHER INFORMATION: siRNA

<400> SEQUENCE: 21
acaguauucu cagugcucu 19

<210> SEQ ID NO 22
<211> LENGTH: 21
<212> TYPE: RNA
<213> ORGANISM: Artificial Sequence
<220> FEATURE:
<223> OTHER INFORMATION: siRNA

<400> SEQUENCE: 22
agagcacuga gaauacuguc c 21

<210> SEQ ID NO 23
<211> LENGTH: 21
<212> TYPE: RNA
<213> ORGANISM: Artificial Sequence
<220> FEATURE:
<223> OTHER INFORMATION: siRNA

<400> SEQUENCE: 23
ggacaguauu cucagugcuc u 21

<210> SEQ ID NO 24
<211> LENGTH: 23
<212> TYPE: RNA
<213> ORGANISM: Artificial Sequence
<220> FEATURE:
<223> OTHER INFORMATION: siRNA

<400> SEQUENCE: 24
agagcacuga gaauacuguc ccu 23

<210> SEQ ID NO 25
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Zc1, Zc1 is A
<220> FEATURE:
<223> OTHER INFORMATION: siRNA

<400> SEQUENCE: 25
uauucucagu gcucuccun 19

<210> SEQ ID NO 26
<211> LENGTH: 19
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Zc2, Zc2 is U
<220> FEATURE:
<223> OTHER INFORMATION: siRNA

<400> SEQUENCE: 26
naggagagca cugagaaua 19

<210> SEQ ID NO 27
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Zc3, Zc3 is selected from A, U, G or C
<220> FEATURE:
<223> OTHER INFORMATION: siRNA

<400> SEQUENCE: 27
uauucucagu gcucuccun 19

<210> SEQ ID NO 28
<211> LENGTH: 19
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Zc4, Zc4 is a nucleotide complementary to Zc3, Zc3 is selected from A, U, G or C
<220> FEATURE:
<223> OTHER INFORMATION: siRNA

<400> SEQUENCE: 28
naggagagca cugagaaua 19

<210> SEQ ID NO 29
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Zc3, Zc3 is selected from A, U, G or C
<220> FEATURE:
<223> OTHER INFORMATION: siRNA

<400> SEQUENCE: 29
uauucucagu gcucuccun 19

<210> SEQ ID NO 30
<211> LENGTH: 21
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Zc4, Zc4 is a nucleotide complementary to Zc3, Zc3 is selected from A, U, G or C
<220> FEATURE:
<223> OTHER INFORMATION: siRNA

<400> SEQUENCE: 30
naggagagca cugagaauac u 21

<210> SEQ ID NO 31
<211> LENGTH: 21
<212> TYPE: RNA
<213> ORGANISM: Artificial Sequence
<220> FEATURE:
<221> NAME/KEY: misc_feature
<222> LOCATION: (21)..(21)
<223> OTHER INFORMATION: n is Zc3, Zc3 is selected from A, U, G or C
<220> FEATURE:
<223> OTHER INFORMATION: siRNA

<400> SEQUENCE: 31
aguauucuca gugcucuccu n 21

<210> SEQ ID NO 32
<211> LENGTH: 23
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Zc4, Zc4 is a nucleotide complementary to Zc3, Zc3 is selected from A, U, G or C
<220> FEATURE:
<223> OTHER INFORMATION: siRNA

<400> SEQUENCE: 32
naggagagca cugagaauac ugu 23

<210> SEQ ID NO 33
<211> LENGTH: 19
<212> TYPE: RNA
<213> ORGANISM: Artificial Sequence
<220> FEATURE:
<223> OTHER INFORMATION: siRNA

<400> SEQUENCE: 33
uauucucagu gcucuccua 19

<210> SEQ ID NO 34
<211> LENGTH: 21
<212> TYPE: RNA
<213> ORGANISM: Artificial Sequence
<220> FEATURE:
<223> OTHER INFORMATION: siRNA

<400> SEQUENCE: 34
uaggagagca cugagaauac u 21

<210> SEQ ID NO 35
<211> LENGTH: 21
<212> TYPE: RNA
<213> ORGANISM: Artificial Sequence
<220> FEATURE:
<223> OTHER INFORMATION: siRNA

<400> SEQUENCE: 35
aguauucuca gugcucuccu a 21

<210> SEQ ID NO 36
<211> LENGTH: 23
<212> TYPE: RNA
<213> ORGANISM: Artificial Sequence
<220> FEATURE:
<223> OTHER INFORMATION: siRNA

<400> SEQUENCE: 36
uaggagagca cugagaauac ugu 23

<210> SEQ ID NO 37
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Zd1, Zd1 is A
<220> FEATURE:
<223> OTHER INFORMATION: siRNA

<400> SEQUENCE: 37
aguauucuca gugcucucn 19

<210> SEQ ID NO 38
<211> LENGTH: 19
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Zd2, Zd2 is U
<220> FEATURE:
<223> OTHER INFORMATION: siRNA

<400> SEQUENCE: 38
ngagagcacu gagaauacu 19

<210> SEQ ID NO 39
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Zd3, Zd3 is selected from A, U, G or C
<220> FEATURE:
<223> OTHER INFORMATION: siRNA

<400> SEQUENCE: 39
aguauucuca gugcucucn 19

<210> SEQ ID NO 40
<211> LENGTH: 19
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Zd4, Zd4 is a nucleotide complementary to Zd3, Zd3 is selected from A, U, G or C
<220> FEATURE:
<223> OTHER INFORMATION: siRNA

<400> SEQUENCE: 40
ngagagcacu gagaauacu 19

<210> SEQ ID NO 41
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Zd3, Zd3 is selected from A, U, G or C
<220> FEATURE:
<223> OTHER INFORMATION: siRNA

<400> SEQUENCE: 41
aguauucuca gugcucucn 19

<210> SEQ ID NO 42
<211> LENGTH: 21
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Zd4, Zd4 is a nucleotide complementary to Zd3, Zd3 is selected from A, U, G or C
<220> FEATURE:
<223> OTHER INFORMATION: siRNA

<400> SEQUENCE: 42
ngagagcacu gagaauacug u 21

<210> SEQ ID NO 43
<211> LENGTH: 21
<212> TYPE: RNA
<213> ORGANISM: Artificial Sequence
<220> FEATURE:
<221> NAME/KEY: misc_feature
<222> LOCATION: (21)..(21)

<223> OTHER INFORMATION: n is Zd3, Zd3 is selected from A, U, G or C
<220> FEATURE:
<223> OTHER INFORMATION: siRNA

<400> SEQUENCE: 43
acaguauucu cagugcucuc n 21

<210> SEQ ID NO 44
<211> LENGTH: 23
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Zd4, Zd4 is a nucleotide complementary to
Zd3, Zd3 is selected from A, U, G or C
<220> FEATURE:
<223> OTHER INFORMATION: siRNA

<400> SEQUENCE: 44
ngagagcacu gagaauacug ucc 23

<210> SEQ ID NO 45
<211> LENGTH: 19
<212> TYPE: RNA
<213> ORGANISM: Artificial Sequence
<220> FEATURE:
<223> OTHER INFORMATION: siRNA

<400> SEQUENCE: 45
aguauucuca gugcucucc 19

<210> SEQ ID NO 46
<211> LENGTH: 21
<212> TYPE: RNA
<213> ORGANISM: Artificial Sequence
<220> FEATURE:
<223> OTHER INFORMATION: siRNA

<400> SEQUENCE: 46
ggagagcacu gagaa uacug u 21

<210> SEQ ID NO 47
<211> LENGTH: 21
<212> TYPE: RNA
<213> ORGANISM: Artificial Sequence
<220> FEATURE:
<223> OTHER INFORMATION: siRNA

<400> SEQUENCE: 47
acaguauucu cagugcucuc c 21

<210> SEQ ID NO 48
<211> LENGTH: 23
<212> TYPE: RNA
<213> ORGANISM: Artificial Sequence
<220> FEATURE:
<223> OTHER INFORMATION: siRNA

<400> SEQUENCE: 48
ggagagcacu gagaauacug ucc 23

<210> SEQ ID NO 49
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Ze1, Ze1 is A
<220> FEATURE:
<223> OTHER INFORMATION: siRNA

<400> SEQUENCE: 49
ggacaguauu cucagugcn 19

<210> SEQ ID NO 50
<211> LENGTH: 19
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Ze2, Ze2 is U
<220> FEATURE:
<223> OTHER INFORMATION: siRNA

<400> SEQUENCE: 50
ngcacugaga auacugucc 19

<210> SEQ ID NO 51
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Ze3, Ze3 is selected from A, U, G or C
<220> FEATURE:
<223> OTHER INFORMATION: siRNA

<400> SEQUENCE: 51
ggacaguauu cucagugcn 19

<210> SEQ ID NO 52
<211> LENGTH: 19
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Ze4, Ze4 is a nucleotide complementary to
Ze3, Ze3 is selected from A, U, G or C
<220> FEATURE:
<223> OTHER INFORMATION: siRNA

<400> SEQUENCE: 52
ngcacugaga auacugucc 19

<210> SEQ ID NO 53
<211> LENGTH: 19
<212> TYPE: RNA
<213> ORGANISM: Artificial Sequence
<220> FEATURE:
<221> NAME/KEY: misc_feature
<222> LOCATION: (19)..(19)
<223> OTHER INFORMATION: n is Ze3, Ze3 is selected from A, U, G or C
<220> FEATURE:
<223> OTHER INFORMATION: siRNA

<400> SEQUENCE: 53
ggacaguauu cucagugcn 19

<210> SEQ ID NO 54
<211> LENGTH: 21
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Ze4, Ze4 is a nucleotide complementary to
Ze3, Ze3 is selected from A, U, G or C
<220> FEATURE:
<223> OTHER INFORMATION: siRNA

<400> SEQUENCE: 54
ngcacugaga auacuguccc u 21

<210> SEQ ID NO 55
<211> LENGTH: 21
<212> TYPE: RNA
<213> ORGANISM: Artificial Sequence
<220> FEATURE:
<221> NAME/KEY: misc_feature
<222> LOCATION: (21)..(21)
<223> OTHER INFORMATION: n is Ze3, Ze3 is selected from A, U, G or C
<220> FEATURE:
<223> OTHER INFORMATION: siRNA

<400> SEQUENCE: 55
agggacagua uucucagugc n 21

<210> SEQ ID NO 56
<211> LENGTH: 23
<212> TYPE: RNA
<213> ORGANISM: Artificial Sequence
<220> FEATURE:
<221> NAME/KEY: misc_feature
<222> LOCATION: (1)..(1)
<223> OTHER INFORMATION: n is Ze4, Ze4 is a nucleotide complementary to
Ze3, Ze3 is selected from A, U, G or C
<220> FEATURE:
<223> OTHER INFORMATION: siRNA

<400> SEQUENCE: 56
ngcacugaga auacuguccc uuu 23

<210> SEQ ID NO 57
<211> LENGTH: 19
<212> TYPE: RNA
<213> ORGANISM: Artificial Sequence
<220> FEATURE:
<223> OTHER INFORMATION: siRNA

<400> SEQUENCE: 57
ggacaguauu cucagugcu 19

<210> SEQ ID NO 58
<211> LENGTH: 21
<212> TYPE: RNA
<213> ORGANISM: Artificial Sequence
<220> FEATURE:
<223> OTHER INFORMATION: siRNA

<400> SEQUENCE: 58
agcacugaga auacuguccc u 21

<210> SEQ ID NO 59
<211> LENGTH: 21
<212> TYPE: RNA
<213> ORGANISM: Artificial Sequence
<220> FEATURE:
<223> OTHER INFORMATION: siRNA

<400> SEQUENCE: 59

-continued agggacagua uucucagugc u 21

<210> SEQ ID NO 60
<211> LENGTH: 23
<212> TYPE: RNA
<213> ORGANISM: Artificial Sequence
<220> FEATURE:
<223> OTHER INFORMATION: siRNA

<400> SEQUENCE: 60
agcacugaga auacuguccc uuu 23

<210> SEQ ID NO 61
<211> LENGTH: 19
<212> TYPE: RNA
<213> ORGANISM: Artificial Sequence
<220> FEATURE:
<223> OTHER INFORMATION: siRNA

<400> SEQUENCE: 61
uuaaaaggga caguauucu 19

<210> SEQ ID NO 62
<211> LENGTH: 21
<212> TYPE: RNA
<213> ORGANISM: Artificial Sequence
<220> FEATURE:
<223> OTHER INFORMATION: siRNA

<400> SEQUENCE: 62
agaauacugu cccuuuuaag c 21

<210> SEQ ID NO 63
<211> LENGTH: 21
<212> TYPE: RNA
<213> ORGANISM: Artificial Sequence
<220> FEATURE:
<223> OTHER INFORMATION: siRNA

<400> SEQUENCE: 63
gcuuaaaagg gacaguauuc u 21

<210> SEQ ID NO 64
<211> LENGTH: 23
<212> TYPE: RNA
<213> ORGANISM: Artificial Sequence
<220> FEATURE:
<223> OTHER INFORMATION: siRNA

<400> SEQUENCE: 64
agaauacugu cccuuuuaag caa 23

<210> SEQ ID NO 65
<211> LENGTH: 19
<212> TYPE: RNA
<213> ORGANISM: Artificial Sequence
<220> FEATURE:
<223> OTHER INFORMATION: siRNA

<400> SEQUENCE: 65
uuaaaaggga caguauucu 19

<210> SEQ ID NO 66
<211> LENGTH: 21
<212> TYPE: RNA
<213> ORGANISM: Artificial Sequence
<220> FEATURE:
<223> OTHER INFORMATION: siRNA

<400> SEQUENCE: 66
agaauacugu cccuuuuaag c 21

<210> SEQ ID NO 67
<211> LENGTH: 21
<212> TYPE: RNA
<213> ORGANISM: Artificial Sequence
<220> FEATURE:
<223> OTHER INFORMATION: siRNA

<400> SEQUENCE: 67
gcuuaaaagg gacaguauuc u 21

<210> SEQ ID NO 68
<211> LENGTH: 23
<212> TYPE: RNA
<213> ORGANISM: Artificial Sequence
<220> FEATURE:
<223> OTHER INFORMATION: siRNA

<400> SEQUENCE: 68
agaauacugu cccuuuuaag caa 23

<210> SEQ ID NO 69
<211> LENGTH: 19
<212> TYPE: RNA
<213> ORGANISM: Artificial Sequence
<220> FEATURE:
<223> OTHER INFORMATION: siRNA

<400> SEQUENCE: 69
uuaaaaggga caguauucu 19

<210> SEQ ID NO 70
<211> LENGTH: 21
<212> TYPE: RNA
<213> ORGANISM: Artificial Sequence
<220> FEATURE:
<223> OTHER INFORMATION: siRNA

<400> SEQUENCE: 70
agaauacugu cccuuuuaag c 21

<210> SEQ ID NO 71
<211> LENGTH: 21
<212> TYPE: RNA
<213> ORGANISM: Artificial Sequence
<220> FEATURE:
<223> OTHER INFORMATION: siRNA

<400> SEQUENCE: 71
gcuuaaaagg gacaguauuc u 21

<210> SEQ ID NO 72
<211> LENGTH: 23
<212> TYPE: RNA
<213> ORGANISM: Artificial Sequence
<220> FEATURE:
<223> OTHER INFORMATION: siRNA

<400> SEQUENCE: 72
agaauacugu cccuuuuaag caa 23

<210> SEQ ID NO 73
<211> LENGTH: 19
<212> TYPE: RNA
<213> ORGANISM: Artificial Sequence
<220> FEATURE:
<223> OTHER INFORMATION: siRNA

<400> SEQUENCE: 73
acaguauucu cagugcucu 19

<210> SEQ ID NO 74
<211> LENGTH: 21
<212> TYPE: RNA
<213> ORGANISM: Artificial Sequence
<220> FEATURE:
<223> OTHER INFORMATION: siRNA

<400> SEQUENCE: 74
agagcacuga gaauacuguc c 21

<210> SEQ ID NO 75
<211> LENGTH: 21
<212> TYPE: RNA
<213> ORGANISM: Artificial Sequence
<220> FEATURE:
<223> OTHER INFORMATION: siRNA

<400> SEQUENCE: 75
ggacaguauu cucagugcuc u 21

<210> SEQ ID NO 76
<211> LENGTH: 23
<212> TYPE: RNA
<213> ORGANISM: Artificial Sequence
<220> FEATURE:
<223> OTHER INFORMATION: siRNA

<400> SEQUENCE: 76
agagcacuga gaauacuguc ccu 23

<210> SEQ ID NO 77
<211> LENGTH: 19
<212> TYPE: RNA
<213> ORGANISM: Artificial Sequence
<220> FEATURE:
<223> OTHER INFORMATION: siRNA

<400> SEQUENCE: 77
acaguauucu cagugcucu 19

<210> SEQ ID NO 78
<211> LENGTH: 21
<212> TYPE: RNA
<213> ORGANISM: Artificial Sequence
<220> FEATURE:
<223> OTHER INFORMATION: siRNA

<400> SEQUENCE: 78
agagcacuga gaauacuguc c 21

<210> SEQ ID NO 79
<211> LENGTH: 21
<212> TYPE: RNA
<213> ORGANISM: Artificial Sequence
<220> FEATURE:
<223> OTHER INFORMATION: siRNA

<400> SEQUENCE: 79
ggacaguauu cucagugcuc u 21

<210> SEQ ID NO 80
<211> LENGTH: 23
<212> TYPE: RNA
<213> ORGANISM: Artificial Sequence
<220> FEATURE:
<223> OTHER INFORMATION: siRNA

<400> SEQUENCE: 80
agagcacuga gaauacuguc ccu 23

<210> SEQ ID NO 81
<211> LENGTH: 19
<212> TYPE: RNA
<213> ORGANISM: Artificial Sequence
<220> FEATURE:
<223> OTHER INFORMATION: siRNA

<400> SEQUENCE: 81
acaguauucu cagugcucu 19

<210> SEQ ID NO 82
<211> LENGTH: 21
<212> TYPE: RNA
<213> ORGANISM: Artificial Sequence
<220> FEATURE:
<223> OTHER INFORMATION: siRNA

<400> SEQUENCE: 82
agagcacuga gaauacuguc c 21

<210> SEQ ID NO 83
<211> LENGTH: 21
<212> TYPE: RNA
<213> ORGANISM: Artificial Sequence
<220> FEATURE:
<223> OTHER INFORMATION: siRNA

<400> SEQUENCE: 83
ggacaguauu cucagugcuc u 21

<210> SEQ ID NO 84
<211> LENGTH: 23
<212> TYPE: RNA
<213> ORGANISM: Artificial Sequence
<220> FEATURE:
<223> OTHER INFORMATION: siRNA

<400> SEQUENCE: 84
agagcacuga gaauacuguc ccu 23

<210> SEQ ID NO 85
<211> LENGTH: 19
<212> TYPE: RNA
<213> ORGANISM: Artificial Sequence
<220> FEATURE:
<223> OTHER INFORMATION: siRNA

<400> SEQUENCE: 85
uauucucagu gcucuccua 19

<210> SEQ ID NO 86

<211> LENGTH: 21
<212> TYPE: RNA
<213> ORGANISM: Artificial Sequence
<220> FEATURE:
<223> OTHER INFORMATION: siRNA

<400> SEQUENCE: 86
uaggagagca cugagaauac u 21

<210> SEQ ID NO 87
<211> LENGTH: 21
<212> TYPE: RNA
<213> ORGANISM: Artificial Sequence
<220> FEATURE:
<223> OTHER INFORMATION: siRNA

<400> SEQUENCE: 87
aguauucuca gugcucuccu a 21

<210> SEQ ID NO 88
<211> LENGTH: 23
<212> TYPE: RNA
<213> ORGANISM: Artificial Sequence
<220> FEATURE:
<223> OTHER INFORMATION: siRNA

<400> SEQUENCE: 88
uaggagagca cugagaauac ugu 23

<210> SEQ ID NO 89
<211> LENGTH: 19
<212> TYPE: RNA
<213> ORGANISM: Artificial Sequence
<220> FEATURE:
<223> OTHER INFORMATION: siRNA

<400> SEQUENCE: 89
uauucucagu gcucuccua 19

<210> SEQ ID NO 90
<211> LENGTH: 21
<212> TYPE: RNA
<213> ORGANISM: Artificial Sequence
<220> FEATURE:
<223> OTHER INFORMATION: siRNA

<400> SEQUENCE: 90
uaggagagca cugagaauac u 21

<210> SEQ ID NO 91
<211> LENGTH: 21
<212> TYPE: RNA
<213> ORGANISM: Artificial Sequence
<220> FEATURE:
<223> OTHER INFORMATION: siRNA

<400> SEQUENCE: 91
aguauucuca gugcucuccu a 21

<210> SEQ ID NO 92
<211> LENGTH: 23
<212> TYPE: RNA
<213> ORGANISM: Artificial Sequence
<220> FEATURE:
<223> OTHER INFORMATION: siRNA

<400> SEQUENCE: 92
uaggagagca cugagaauac ugu 23

<210> SEQ ID NO 93
<211> LENGTH: 19
<212> TYPE: RNA
<213> ORGANISM: Artificial Sequence
<220> FEATURE:
<223> OTHER INFORMATION: siRNA

<400> SEQUENCE: 93
uauucucagu gcucuccua 19

<210> SEQ ID NO 94
<211> LENGTH: 21
<212> TYPE: RNA
<213> ORGANISM: Artificial Sequence
<220> FEATURE:
<223> OTHER INFORMATION: siRNA

<400> SEQUENCE: 94
uaggagagca cugagaauac u 21

<210> SEQ ID NO 95
<211> LENGTH: 21
<212> TYPE: RNA
<213> ORGANISM: Artificial Sequence
<220> FEATURE:
<223> OTHER INFORMATION: siRNA

<400> SEQUENCE: 95
aguauucuca gugcucuccu a 21

<210> SEQ ID NO 96
<211> LENGTH: 23
<212> TYPE: RNA
<213> ORGANISM: Artificial Sequence
<220> FEATURE:
<223> OTHER INFORMATION: siRNA

<400> SEQUENCE: 96
uaggagagca cugagaauac ugu 23

<210> SEQ ID NO 97
<211> LENGTH: 19
<212> TYPE: RNA
<213> ORGANISM: Artificial Sequence
<220> FEATURE:
<223> OTHER INFORMATION: siRNA

<400> SEQUENCE: 97
aguauucuca gugcucucc 19

<210> SEQ ID NO 98
<211> LENGTH: 21
<212> TYPE: RNA
<213> ORGANISM: Artificial Sequence
<220> FEATURE:
<223> OTHER INFORMATION: siRNA

<400> SEQUENCE: 98
ggagagcacu gagaauacug u 21

<210> SEQ ID NO 99
<211> LENGTH: 21
<212> TYPE: RNA

-continued

<213> ORGANISM: Artificial Sequence
<220> FEATURE:
<223> OTHER INFORMATION: siRNA

<400> SEQUENCE: 99
acaguauucu cagugcucuc c 21

<210> SEQ ID NO 100
<211> LENGTH: 23
<212> TYPE: RNA
<213> ORGANISM: Artificial Sequence
<220> FEATURE:
<223> OTHER INFORMATION: siRNA

<400> SEQUENCE: 100
ggagagcacu gagaauacug ucc 23

<210> SEQ ID NO 101
<211> LENGTH: 19
<212> TYPE: RNA
<213> ORGANISM: Artificial Sequence
<220> FEATURE:
<223> OTHER INFORMATION: siRNA

<400> SEQUENCE: 101
aguauucuca gugcucucc 19

<210> SEQ ID NO 102
<211> LENGTH: 21
<212> TYPE: RNA
<213> ORGANISM: Artificial Sequence
<220> FEATURE:
<223> OTHER INFORMATION: siRNA

<400> SEQUENCE: 102
ggagagcacu gagaauacug u 21

<210> SEQ ID NO 103
<211> LENGTH: 21
<212> TYPE: RNA
<213> ORGANISM: Artificial Sequence
<220> FEATURE:
<223> OTHER INFORMATION: siRNA

<400> SEQUENCE: 103
acaguauucu cagugcucuc c 21

<210> SEQ ID NO 104
<211> LENGTH: 23
<212> TYPE: RNA
<213> ORGANISM: Artificial Sequence
<220> FEATURE:
<223> OTHER INFORMATION: siRNA

<400> SEQUENCE: 104
ggagagcacu gagaauacug ucc 23

<210> SEQ ID NO 105
<211> LENGTH: 19
<212> TYPE: RNA
<213> ORGANISM: Artificial Sequence
<220> FEATURE:
<223> OTHER INFORMATION: siRNA

<400> SEQUENCE: 105
aguauucuca gugcucucc 19

<210> SEQ ID NO 106
<211> LENGTH: 21
<212> TYPE: RNA
<213> ORGANISM: Artificial Sequence
<220> FEATURE:
<223> OTHER INFORMATION: siRNA

<400> SEQUENCE: 106
ggagagcacu gagaauacug u 21

<210> SEQ ID NO 107
<211> LENGTH: 21
<212> TYPE: RNA
<213> ORGANISM: Artificial Sequence
<220> FEATURE:
<223> OTHER INFORMATION: siRNA

<400> SEQUENCE: 107
acaguauucu cagugcucuc c 21

<210> SEQ ID NO 108
<211> LENGTH: 23
<212> TYPE: RNA
<213> ORGANISM: Artificial Sequence
<220> FEATURE:
<223> OTHER INFORMATION: siRNA

<400> SEQUENCE: 108
ggagagcacu gagaauacug ucc 23

<210> SEQ ID NO 109
<211> LENGTH: 19
<212> TYPE: RNA
<213> ORGANISM: Artificial Sequence
<220> FEATURE:
<223> OTHER INFORMATION: siRNA

<400> SEQUENCE: 109
ggacaguauu cucagugcu 19

<210> SEQ ID NO 110
<211> LENGTH: 21
<212> TYPE: RNA
<213> ORGANISM: Artificial Sequence
<220> FEATURE:
<223> OTHER INFORMATION: siRNA

<400> SEQUENCE: 110
agcacugaga auacuguccc u 21

<210> SEQ ID NO 111
<211> LENGTH: 21
<212> TYPE: RNA
<213> ORGANISM: Artificial Sequence
<220> FEATURE:
<223> OTHER INFORMATION: siRNA

<400> SEQUENCE: 111
agggacagua uucucagugc u 21

<210> SEQ ID NO 112
<211> LENGTH: 23
<212> TYPE: RNA
<213> ORGANISM: Artificial Sequence
<220> FEATURE:

<223> OTHER INFORMATION: siRNA

<400> SEQUENCE: 112
agcacugaga auacuguccc uuu 23

<210> SEQ ID NO 113
<211> LENGTH: 19
<212> TYPE: RNA
<213> ORGANISM: Artificial Sequence
<220> FEATURE:
<223> OTHER INFORMATION: siRNA

<400> SEQUENCE: 113
ggacaguauu cucagugcu 19

<210> SEQ ID NO 114
<211> LENGTH: 21
<212> TYPE: RNA
<213> ORGANISM: Artificial Sequence
<220> FEATURE:
<223> OTHER INFORMATION: siRNA

<400> SEQUENCE: 114
agcacugaga auacuguccc u 21

<210> SEQ ID NO 115
<211> LENGTH: 21
<212> TYPE: RNA
<213> ORGANISM: Artificial Sequence
<220> FEATURE:
<223> OTHER INFORMATION: siRNA

<400> SEQUENCE: 115
agggacagua uucucagugc u 21

<210> SEQ ID NO 116
<211> LENGTH: 23
<212> TYPE: RNA
<213> ORGANISM: Artificial Sequence
<220> FEATURE:
<223> OTHER INFORMATION: siRNA

<400> SEQUENCE: 116
agcacugaga auacuguccc uuu 23

<210> SEQ ID NO 117
<211> LENGTH: 19
<212> TYPE: RNA
<213> ORGANISM: Artificial Sequence
<220> FEATURE:
<223> OTHER INFORMATION: siRNA

<400> SEQUENCE: 117
ggacaguauu cucagugcu 19

<210> SEQ ID NO 118
<211> LENGTH: 21
<212> TYPE: RNA
<213> ORGANISM: Artificial Sequence
<220> FEATURE:
<223> OTHER INFORMATION: siRNA

<400> SEQUENCE: 118
agcacugaga auacuguccc u 21

<210> SEQ ID NO 119
<211> LENGTH: 21
<212> TYPE: RNA
<213> ORGANISM: Artificial Sequence
<220> FEATURE:
<223> OTHER INFORMATION: siRNA

<400> SEQUENCE: 119
agggacagua uucucagugc u 21

<210> SEQ ID NO 120
<211> LENGTH: 23
<212> TYPE: RNA
<213> ORGANISM: Artificial Sequence
<220> FEATURE:
<223> OTHER INFORMATION: siRNA

<400> SEQUENCE: 120
agcacugaga auacuguccc uuu 23

<210> SEQ ID NO 121
<211> LENGTH: 19
<212> TYPE: RNA
<213> ORGANISM: Artificial Sequence
<220> FEATURE:
<223> OTHER INFORMATION: siRNA

<400> SEQUENCE: 121
uuaaaaggga caguauucu 19

<210> SEQ ID NO 122
<211> LENGTH: 21
<212> TYPE: RNA
<213> ORGANISM: Artificial Sequence
<220> FEATURE:
<223> OTHER INFORMATION: siRNA

<400> SEQUENCE: 122
agaauacugu cccuuuuaag c 21

<210> SEQ ID NO 123
<211> LENGTH: 21
<212> TYPE: RNA
<213> ORGANISM: Artificial Sequence
<220> FEATURE:
<223> OTHER INFORMATION: siRNA

<400> SEQUENCE: 123
gcuuaaaagg gacaguauuc u 21

<210> SEQ ID NO 124
<211> LENGTH: 23
<212> TYPE: RNA
<213> ORGANISM: Artificial Sequence
<220> FEATURE:
<223> OTHER INFORMATION: siRNA

<400> SEQUENCE: 124
agaauacugu cccuuuuaag caa 23

<210> SEQ ID NO 125
<211> LENGTH: 19
<212> TYPE: RNA
<213> ORGANISM: Artificial Sequence
<220> FEATURE:
<223> OTHER INFORMATION: siRNA

<400> SEQUENCE: 125
uuaaaaggga caguauucu 19

<210> SEQ ID NO 126
<211> LENGTH: 21
<212> TYPE: RNA
<213> ORGANISM: Artificial Sequence
<220> FEATURE:
<223> OTHER INFORMATION: siRNA

<400> SEQUENCE: 126
agaauacugu cccuuuuaag c 21

<210> SEQ ID NO 127
<211> LENGTH: 21
<212> TYPE: RNA
<213> ORGANISM: Artificial Sequence
<220> FEATURE:
<223> OTHER INFORMATION: siRNA

<400> SEQUENCE: 127
gcuuaaaagg gacaguauuc u 21

<210> SEQ ID NO 128
<211> LENGTH: 23
<212> TYPE: RNA
<213> ORGANISM: Artificial Sequence
<220> FEATURE:
<223> OTHER INFORMATION: siRNA

<400> SEQUENCE: 128
agaauacugu cccuuuuaag caa 23

<210> SEQ ID NO 129
<211> LENGTH: 19
<212> TYPE: RNA
<213> ORGANISM: Artificial Sequence
<220> FEATURE:
<223> OTHER INFORMATION: siRNA

<400> SEQUENCE: 129
uuaaaaggga caguauucu 19

<210> SEQ ID NO 130
<211> LENGTH: 21
<212> TYPE: RNA
<213> ORGANISM: Artificial Sequence
<220> FEATURE:
<223> OTHER INFORMATION: siRNA

<400> SEQUENCE: 130
agaauacugu cccuuuuaag c 21

<210> SEQ ID NO 131
<211> LENGTH: 21
<212> TYPE: RNA
<213> ORGANISM: Artificial Sequence
<220> FEATURE:
<223> OTHER INFORMATION: siRNA

<400> SEQUENCE: 131
gcuuaaaagg gacaguauuc u 21

<210> SEQ ID NO 132
<211> LENGTH: 23

<212> TYPE: RNA
<213> ORGANISM: Artificial Sequence
<220> FEATURE:
<223> OTHER INFORMATION: siRNA

<400> SEQUENCE: 132
agaauacugu cccuuuuaag caa 23

<210> SEQ ID NO 133
<211> LENGTH: 19
<212> TYPE: RNA
<213> ORGANISM: Artificial Sequence
<220> FEATURE:
<223> OTHER INFORMATION: siRNA

<400> SEQUENCE: 133
acaguauucu cagugcucu 19

<210> SEQ ID NO 134
<211> LENGTH: 21
<212> TYPE: RNA
<213> ORGANISM: Artificial Sequence
<220> FEATURE:
<223> OTHER INFORMATION: siRNA

<400> SEQUENCE: 134
agagcacuga gaauacuguc c 21

<210> SEQ ID NO 135
<211> LENGTH: 21
<212> TYPE: RNA
<213> ORGANISM: Artificial Sequence
<220> FEATURE:
<223> OTHER INFORMATION: siRNA

<400> SEQUENCE: 135
ggacaguauu cucagugcuc u 21

<210> SEQ ID NO 136
<211> LENGTH: 23
<212> TYPE: RNA
<213> ORGANISM: Artificial Sequence
<220> FEATURE:
<223> OTHER INFORMATION: siRNA

<400> SEQUENCE: 136
agagcacuga gaauacuguc ccu 23

<210> SEQ ID NO 137
<211> LENGTH: 19
<212> TYPE: RNA
<213> ORGANISM: Artificial Sequence
<220> FEATURE:
<223> OTHER INFORMATION: siRNA

<400> SEQUENCE: 137
acaguauucu cagugcucu 19

<210> SEQ ID NO 138
<211> LENGTH: 21
<212> TYPE: RNA
<213> ORGANISM: Artificial Sequence
<220> FEATURE:
<223> OTHER INFORMATION: siRNA

<400> SEQUENCE: 138

-continued agagcacuga gaauacuguc c 21

<210> SEQ ID NO 139
<211> LENGTH: 21
<212> TYPE: RNA
<213> ORGANISM: Artificial Sequence
<220> FEATURE:
<223> OTHER INFORMATION: siRNA

<400> SEQUENCE: 139
ggacaguauu cucagugcuc u 21

<210> SEQ ID NO 140
<211> LENGTH: 23
<212> TYPE: RNA
<213> ORGANISM: Artificial Sequence
<220> FEATURE:
<223> OTHER INFORMATION: siRNA

<400> SEQUENCE: 140
agagcacuga gaauacuguc ccu 23

<210> SEQ ID NO 141
<211> LENGTH: 19
<212> TYPE: RNA
<213> ORGANISM: Artificial Sequence
<220> FEATURE:
<223> OTHER INFORMATION: siRNA

<400> SEQUENCE: 141
acaguauucu cagugcucu 19

<210> SEQ ID NO 142
<211> LENGTH: 21
<212> TYPE: RNA
<213> ORGANISM: Artificial Sequence
<220> FEATURE:
<223> OTHER INFORMATION: siRNA

<400> SEQUENCE: 142
agagcacuga gaauacuguc c 21

<210> SEQ ID NO 143
<211> LENGTH: 21
<212> TYPE: RNA
<213> ORGANISM: Artificial Sequence
<220> FEATURE:
<223> OTHER INFORMATION: siRNA

<400> SEQUENCE: 143
ggacaguauu cucagugcuc u 21

<210> SEQ ID NO 144
<211> LENGTH: 23
<212> TYPE: RNA
<213> ORGANISM: Artificial Sequence
<220> FEATURE:
<223> OTHER INFORMATION: siRNA

<400> SEQUENCE: 144
agagcacuga gaauacuguc ccu 23

<210> SEQ ID NO 145
<211> LENGTH: 19
<212> TYPE: RNA
<213> ORGANISM: Artificial Sequence -continued
<220> FEATURE:
<223> OTHER INFORMATION: siRNA

<400> SEQUENCE: 145
uauucucagu gcucuccua 19

<210> SEQ ID NO 146
<211> LENGTH: 21
<212> TYPE: RNA
<213> ORGANISM: Artificial Sequence
<220> FEATURE:
<223> OTHER INFORMATION: siRNA

<400> SEQUENCE: 146
uaggagagca cugagaauac u 21

<210> SEQ ID NO 147
<211> LENGTH: 21
<212> TYPE: RNA
<213> ORGANISM: Artificial Sequence
<220> FEATURE:
<223> OTHER INFORMATION: siRNA

<400> SEQUENCE: 147
aguauucuca gugcucuccu a 21

<210> SEQ ID NO 148
<211> LENGTH: 23
<212> TYPE: RNA
<213> ORGANISM: Artificial Sequence
<220> FEATURE:
<223> OTHER INFORMATION: siRNA

<400> SEQUENCE: 148
uaggagagca cugagaauac ugu 23

<210> SEQ ID NO 149
<211> LENGTH: 19
<212> TYPE: RNA
<213> ORGANISM: Artificial Sequence
<220> FEATURE:
<223> OTHER INFORMATION: siRNA

<400> SEQUENCE: 149
uauucucagu gcucuccua 19

<210> SEQ ID NO 150
<211> LENGTH: 21
<212> TYPE: RNA
<213> ORGANISM: Artificial Sequence
<220> FEATURE:
<223> OTHER INFORMATION: siRNA

<400> SEQUENCE: 150
uaggagagca cugagaauac u 21

<210> SEQ ID NO 151
<211> LENGTH: 21
<212> TYPE: RNA
<213> ORGANISM: Artificial Sequence
<220> FEATURE:
<223> OTHER INFORMATION: siRNA

<400> SEQUENCE: 151
aguauucuca gugcucuccu a 21

<210> SEQ ID NO 152
<211> LENGTH: 23
<212> TYPE: RNA
<213> ORGANISM: Artificial Sequence
<220> FEATURE:
<223> OTHER INFORMATION: siRNA

<400> SEQUENCE: 152
uaggagagca cugagaauac ugu 23

<210> SEQ ID NO 153
<211> LENGTH: 19
<212> TYPE: RNA
<213> ORGANISM: Artificial Sequence
<220> FEATURE:
<223> OTHER INFORMATION: siRNA

<400> SEQUENCE: 153
uauucucagu gcucuccua 19

<210> SEQ ID NO 154
<211> LENGTH: 21
<212> TYPE: RNA
<213> ORGANISM: Artificial Sequence
<220> FEATURE:
<223> OTHER INFORMATION: siRNA

<400> SEQUENCE: 154
uaggagagca cugagaauac u 21

<210> SEQ ID NO 155
<211> LENGTH: 21
<212> TYPE: RNA
<213> ORGANISM: Artificial Sequence
<220> FEATURE:
<223> OTHER INFORMATION: siRNA

<400> SEQUENCE: 155
aguauucuca gugcucuccu a 21

<210> SEQ ID NO 156
<211> LENGTH: 23
<212> TYPE: RNA
<213> ORGANISM: Artificial Sequence
<220> FEATURE:
<223> OTHER INFORMATION: siRNA

<400> SEQUENCE: 156
uaggagagca cugagaauac ugu 23

<210> SEQ ID NO 157
<211> LENGTH: 19
<212> TYPE: RNA
<213> ORGANISM: Artificial Sequence
<220> FEATURE:
<223> OTHER INFORMATION: siRNA

<400> SEQUENCE: 157
aguauucuca gugcucucc 19

<210> SEQ ID NO 158
<211> LENGTH: 21
<212> TYPE: RNA
<213> ORGANISM: Artificial Sequence
<220> FEATURE:
<223> OTHER INFORMATION: siRNA

<400> SEQUENCE: 158
ggagagcacu gagaauacug u 21

<210> SEQ ID NO 159
<211> LENGTH: 21
<212> TYPE: RNA
<213> ORGANISM: Artificial Sequence
<220> FEATURE:
<223> OTHER INFORMATION: siRNA

<400> SEQUENCE: 159
acaguauucu cagugcucuc c 21

<210> SEQ ID NO 160
<211> LENGTH: 23
<212> TYPE: RNA
<213> ORGANISM: Artificial Sequence
<220> FEATURE:
<223> OTHER INFORMATION: siRNA

<400> SEQUENCE: 160
ggagagcacu gagaauacug ucc 23

<210> SEQ ID NO 161
<211> LENGTH: 19
<212> TYPE: RNA
<213> ORGANISM: Artificial Sequence
<220> FEATURE:
<223> OTHER INFORMATION: siRNA

<400> SEQUENCE: 161
aguauucuca gugcucucc 19

<210> SEQ ID NO 162
<211> LENGTH: 21
<212> TYPE: RNA
<213> ORGANISM: Artificial Sequence
<220> FEATURE:
<223> OTHER INFORMATION: siRNA

<400> SEQUENCE: 162
ggagagcacu gagaauacug u 21

<210> SEQ ID NO 163
<211> LENGTH: 21
<212> TYPE: RNA
<213> ORGANISM: Artificial Sequence
<220> FEATURE:
<223> OTHER INFORMATION: siRNA

<400> SEQUENCE: 163
acaguauucu cagugcucuc c 21

<210> SEQ ID NO 164
<211> LENGTH: 23
<212> TYPE: RNA
<213> ORGANISM: Artificial Sequence
<220> FEATURE:
<223> OTHER INFORMATION: siRNA

<400> SEQUENCE: 164
ggagagcacu gagaauacug ucc 23

<210> SEQ ID NO 165

<211> LENGTH: 19
<212> TYPE: RNA
<213> ORGANISM: Artificial Sequence
<220> FEATURE:
<223> OTHER INFORMATION: siRNA

<400> SEQUENCE: 165
aguauucuca gugcucucc 19

<210> SEQ ID NO 166
<211> LENGTH: 21
<212> TYPE: RNA
<213> ORGANISM: Artificial Sequence
<220> FEATURE:
<223> OTHER INFORMATION: siRNA

<400> SEQUENCE: 166
ggagagcacu gagaauacug u 21

<210> SEQ ID NO 167
<211> LENGTH: 19
<212> TYPE: RNA
<213> ORGANISM: Artificial Sequence
<220> FEATURE:
<223> OTHER INFORMATION: siRNA

<400> SEQUENCE: 167
aguauucuca gugcucucc 19

<210> SEQ ID NO 168
<211> LENGTH: 23
<212> TYPE: RNA
<213> ORGANISM: Artificial Sequence
<220> FEATURE:
<223> OTHER INFORMATION: siRNA

<400> SEQUENCE: 168
ggagagcacu gagaauacug ucc 23

<210> SEQ ID NO 169
<211> LENGTH: 19
<212> TYPE: RNA
<213> ORGANISM: Artificial Sequence
<220> FEATURE:
<223> OTHER INFORMATION: siRNA

<400> SEQUENCE: 169
ggacaguauu cucagugcu 19

<210> SEQ ID NO 170
<211> LENGTH: 21
<212> TYPE: RNA
<213> ORGANISM: Artificial Sequence
<220> FEATURE:
<223> OTHER INFORMATION: siRNA

<400> SEQUENCE: 170
agcacugaga auacuguccc u 21

<210> SEQ ID NO 171
<211> LENGTH: 21
<212> TYPE: RNA
<213> ORGANISM: Artificial Sequence
<220> FEATURE:
<223> OTHER INFORMATION: siRNA

<400> SEQUENCE: 171
agggacagua uucucagugc u 21

<210> SEQ ID NO 172
<211> LENGTH: 23
<212> TYPE: RNA
<213> ORGANISM: Artificial Sequence
<220> FEATURE:
<223> OTHER INFORMATION: siRNA

<400> SEQUENCE: 172
agcacugaga auacuguccc uuu 23

<210> SEQ ID NO 173
<211> LENGTH: 19
<212> TYPE: RNA
<213> ORGANISM: Artificial Sequence
<220> FEATURE:
<223> OTHER INFORMATION: siRNA

<400> SEQUENCE: 173
ggacaguauu cucagugcu 19

<210> SEQ ID NO 174
<211> LENGTH: 21
<212> TYPE: RNA
<213> ORGANISM: Artificial Sequence
<220> FEATURE:
<223> OTHER INFORMATION: siRNA

<400> SEQUENCE: 174
agcacugaga auacuguccc u 21

<210> SEQ ID NO 175
<211> LENGTH: 21
<212> TYPE: RNA
<213> ORGANISM: Artificial Sequence
<220> FEATURE:
<223> OTHER INFORMATION: siRNA

<400> SEQUENCE: 175
agggacagua uucucagugc u 21

<210> SEQ ID NO 176
<211> LENGTH: 23
<212> TYPE: RNA
<213> ORGANISM: Artificial Sequence
<220> FEATURE:
<223> OTHER INFORMATION: siRNA

<400> SEQUENCE: 176
agcacugaga auacuguccc uuu 23

<210> SEQ ID NO 177
<211> LENGTH: 19
<212> TYPE: RNA
<213> ORGANISM: Artificial Sequence
<220> FEATURE:
<223> OTHER INFORMATION: siRNA

<400> SEQUENCE: 177
ggacaguauu cucagugcu 19

<210> SEQ ID NO 178
<211> LENGTH: 21
<212> TYPE: RNA

<213> ORGANISM: Artificial Sequence
<220> FEATURE:
<223> OTHER INFORMATION: siRNA

<400> SEQUENCE: 178
agcacugaga auacuguccc u 21

<210> SEQ ID NO 179
<211> LENGTH: 21
<212> TYPE: RNA
<213> ORGANISM: Artificial Sequence
<220> FEATURE:
<223> OTHER INFORMATION: siRNA

<400> SEQUENCE: 179
agggacagua uucucagugc u 21

<210> SEQ ID NO 180
<211> LENGTH: 23
<212> TYPE: RNA
<213> ORGANISM: Artificial Sequence
<220> FEATURE:
<223> OTHER INFORMATION: siRNA

<400> SEQUENCE: 180
agcacugaga auacuguccc uuu 23

<210> SEQ ID NO 181
<211> LENGTH: 19
<212> TYPE: RNA
<213> ORGANISM: Artificial Sequence
<220> FEATURE:
<223> OTHER INFORMATION: siRNA

<400> SEQUENCE: 181
uuaaaaggga caguauucu 19

<210> SEQ ID NO 182
<211> LENGTH: 21
<212> TYPE: RNA
<213> ORGANISM: Artificial Sequence
<220> FEATURE:
<223> OTHER INFORMATION: siRNA

<400> SEQUENCE: 182
agaauacugu cccuuuuaag c 21

<210> SEQ ID NO 183
<211> LENGTH: 21
<212> TYPE: RNA
<213> ORGANISM: Artificial Sequence
<220> FEATURE:
<223> OTHER INFORMATION: siRNA

<400> SEQUENCE: 183
gcuuaaaagg gacaguauuc u 21

<210> SEQ ID NO 184
<211> LENGTH: 23
<212> TYPE: RNA
<213> ORGANISM: Artificial Sequence
<220> FEATURE:
<223> OTHER INFORMATION: siRNA

<400> SEQUENCE: 184
agaauacugu cccuuuuaag caa 23

<210> SEQ ID NO 185
<211> LENGTH: 19
<212> TYPE: RNA
<213> ORGANISM: Artificial Sequence
<220> FEATURE:
<223> OTHER INFORMATION: siRNA

<400> SEQUENCE: 185
uuaaaaggga caguauucu 19

<210> SEQ ID NO 186
<211> LENGTH: 21
<212> TYPE: RNA
<213> ORGANISM: Artificial Sequence
<220> FEATURE:
<223> OTHER INFORMATION: siRNA

<400> SEQUENCE: 186
agaauacugu cccuuuuaag c 21

<210> SEQ ID NO 187
<211> LENGTH: 21
<212> TYPE: RNA
<213> ORGANISM: Artificial Sequence
<220> FEATURE:
<223> OTHER INFORMATION: siRNA

<400> SEQUENCE: 187
gcuuaaaagg gacaguauuc u 21

<210> SEQ ID NO 188
<211> LENGTH: 23
<212> TYPE: RNA
<213> ORGANISM: Artificial Sequence
<220> FEATURE:
<223> OTHER INFORMATION: siRNA

<400> SEQUENCE: 188
agaauacugu cccuuuuaag caa 23

<210> SEQ ID NO 189
<211> LENGTH: 19
<212> TYPE: RNA
<213> ORGANISM: Artificial Sequence
<220> FEATURE:
<223> OTHER INFORMATION: siRNA

<400> SEQUENCE: 189
uuaaaaggga caguauucu 19

<210> SEQ ID NO 190
<211> LENGTH: 21
<212> TYPE: RNA
<213> ORGANISM: Artificial Sequence
<220> FEATURE:
<223> OTHER INFORMATION: siRNA

<400> SEQUENCE: 190
agaauacugu cccuuuuaag c 21

<210> SEQ ID NO 191
<211> LENGTH: 21
<212> TYPE: RNA
<213> ORGANISM: Artificial Sequence
<220> FEATURE:

-continued

<223> OTHER INFORMATION: siRNA

<400> SEQUENCE: 191
gcuuaaaagg gacaguauuc u 21

<210> SEQ ID NO 192
<211> LENGTH: 23
<212> TYPE: RNA
<213> ORGANISM: Artificial Sequence
<220> FEATURE:
<223> OTHER INFORMATION: siRNA

<400> SEQUENCE: 192
agaauacugu cccuuuuaag caa 23

<210> SEQ ID NO 193
<211> LENGTH: 19
<212> TYPE: RNA
<213> ORGANISM: Artificial Sequence
<220> FEATURE:
<223> OTHER INFORMATION: siRNA

<400> SEQUENCE: 193
uuaaaaggga caguauucu 19

<210> SEQ ID NO 194
<211> LENGTH: 21
<212> TYPE: RNA
<213> ORGANISM: Artificial Sequence
<220> FEATURE:
<223> OTHER INFORMATION: siRNA

<400> SEQUENCE: 194
agaauacugu cccuuuuaag c 21

<210> SEQ ID NO 195
<211> LENGTH: 21
<212> TYPE: RNA
<213> ORGANISM: Artificial Sequence
<220> FEATURE:
<223> OTHER INFORMATION: siRNA

<400> SEQUENCE: 195
gcuuaaaagg gacaguauuc u 21

<210> SEQ ID NO 196
<211> LENGTH: 23
<212> TYPE: RNA
<213> ORGANISM: Artificial Sequence
<220> FEATURE:
<223> OTHER INFORMATION: siRNA

<400> SEQUENCE: 196
agaauacugu cccuuuuaag caa 23

<210> SEQ ID NO 197
<211> LENGTH: 19
<212> TYPE: RNA
<213> ORGANISM: Artificial Sequence
<220> FEATURE:
<223> OTHER INFORMATION: siRNA

<400> SEQUENCE: 197
uuaaaaggga caguauucu 19

<210> SEQ ID NO 198
<211> LENGTH: 21
<212> TYPE: RNA
<213> ORGANISM: Artificial Sequence
<220> FEATURE:
<223> OTHER INFORMATION: siRNA

<400> SEQUENCE: 198
agaauacugu cccuuuuaag c 21

<210> SEQ ID NO 199
<211> LENGTH: 21
<212> TYPE: RNA
<213> ORGANISM: Artificial Sequence
<220> FEATURE:
<223> OTHER INFORMATION: siRNA

<400> SEQUENCE: 199
gcuuaaaagg gacaguauuc u 21

<210> SEQ ID NO 200
<211> LENGTH: 23
<212> TYPE: RNA
<213> ORGANISM: Artificial Sequence
<220> FEATURE:
<223> OTHER INFORMATION: siRNA

<400> SEQUENCE: 200
agaauacugu cccuuuuaag caa 23

<210> SEQ ID NO 201
<211> LENGTH: 19
<212> TYPE: RNA
<213> ORGANISM: Artificial Sequence
<220> FEATURE:
<223> OTHER INFORMATION: siRNA

<400> SEQUENCE: 201
uuaaaaggga caguauucu 19

<210> SEQ ID NO 202
<211> LENGTH: 21
<212> TYPE: RNA
<213> ORGANISM: Artificial Sequence
<220> FEATURE:
<223> OTHER INFORMATION: siRNA

<400> SEQUENCE: 202
agaauacugu cccuuuuaag c 21

<210> SEQ ID NO 203
<211> LENGTH: 21
<212> TYPE: RNA
<213> ORGANISM: Artificial Sequence
<220> FEATURE:
<223> OTHER INFORMATION: siRNA

<400> SEQUENCE: 203
gcuuaaaagg gacaguauuc u 21

<210> SEQ ID NO 204
<211> LENGTH: 23
<212> TYPE: RNA
<213> ORGANISM: Artificial Sequence
<220> FEATURE:
<223> OTHER INFORMATION: siRNA

<400> SEQUENCE: 204
agaauacugu cccuuuuaag caa 23

<210> SEQ ID NO 205
<211> LENGTH: 19
<212> TYPE: RNA
<213> ORGANISM: Artificial Sequence
<220> FEATURE:
<223> OTHER INFORMATION: siRNA

<400> SEQUENCE: 205
acaguauucu cagugcucu 19

<210> SEQ ID NO 206
<211> LENGTH: 21
<212> TYPE: RNA
<213> ORGANISM: Artificial Sequence
<220> FEATURE:
<223> OTHER INFORMATION: siRNA

<400> SEQUENCE: 206
agagcacuga gaauacuguc c 21

<210> SEQ ID NO 207
<211> LENGTH: 21
<212> TYPE: RNA
<213> ORGANISM: Artificial Sequence
<220> FEATURE:
<223> OTHER INFORMATION: siRNA

<400> SEQUENCE: 207
ggacaguauu cucagugcuc u 21

<210> SEQ ID NO 208
<211> LENGTH: 23
<212> TYPE: RNA
<213> ORGANISM: Artificial Sequence
<220> FEATURE:
<223> OTHER INFORMATION: siRNA

<400> SEQUENCE: 208
agagcacuga gaauacuguc ccu 23

<210> SEQ ID NO 209
<211> LENGTH: 19
<212> TYPE: RNA
<213> ORGANISM: Artificial Sequence
<220> FEATURE:
<223> OTHER INFORMATION: siRNA

<400> SEQUENCE: 209
acaguauucu cagugcucu 19

<210> SEQ ID NO 210
<211> LENGTH: 21
<212> TYPE: RNA
<213> ORGANISM: Artificial Sequence
<220> FEATURE:
<223> OTHER INFORMATION: siRNA

<400> SEQUENCE: 210
agagcacuga gaauacuguc c 21

<210> SEQ ID NO 211
<211> LENGTH: 21

<212> TYPE: RNA
<213> ORGANISM: Artificial Sequence
<220> FEATURE:
<223> OTHER INFORMATION: siRNA

<400> SEQUENCE: 211
ggacaguauu cucagugcuc u 21

<210> SEQ ID NO 212
<211> LENGTH: 23
<212> TYPE: RNA
<213> ORGANISM: Artificial Sequence
<220> FEATURE:
<223> OTHER INFORMATION: siRNA

<400> SEQUENCE: 212
agagcacuga gaauacuguc ccu 23

<210> SEQ ID NO 213
<211> LENGTH: 19
<212> TYPE: RNA
<213> ORGANISM: Artificial Sequence
<220> FEATURE:
<223> OTHER INFORMATION: siRNA

<400> SEQUENCE: 213
acaguauucu cagugcucu 19

<210> SEQ ID NO 214
<211> LENGTH: 21
<212> TYPE: RNA
<213> ORGANISM: Artificial Sequence
<220> FEATURE:
<223> OTHER INFORMATION: siRNA

<400> SEQUENCE: 214
agagcacuga gaauacuguc c 21

<210> SEQ ID NO 215
<211> LENGTH: 21
<212> TYPE: RNA
<213> ORGANISM: Artificial Sequence
<220> FEATURE:
<223> OTHER INFORMATION: siRNA

<400> SEQUENCE: 215
ggacaguauu cucagugcuc u 21

<210> SEQ ID NO 216
<211> LENGTH: 23
<212> TYPE: RNA
<213> ORGANISM: Artificial Sequence
<220> FEATURE:
<223> OTHER INFORMATION: siRNA

<400> SEQUENCE: 216
agagcacuga gaauacuguc ccu 23

<210> SEQ ID NO 217
<211> LENGTH: 19
<212> TYPE: RNA
<213> ORGANISM: Artificial Sequence
<220> FEATURE:
<223> OTHER INFORMATION: siRNA

<400> SEQUENCE: 217

-continued acaguauucu cagugcucu 19

<210> SEQ ID NO 218
<211> LENGTH: 21
<212> TYPE: RNA
<213> ORGANISM: Artificial Sequence
<220> FEATURE:
<223> OTHER INFORMATION: siRNA

<400> SEQUENCE: 218
agagcacuga gaauacuguc c 21

<210> SEQ ID NO 219
<211> LENGTH: 21
<212> TYPE: RNA
<213> ORGANISM: Artificial Sequence
<220> FEATURE:
<223> OTHER INFORMATION: siRNA

<400> SEQUENCE: 219
ggacaguauu cucagugcuc u 21

<210> SEQ ID NO 220
<211> LENGTH: 23
<212> TYPE: RNA
<213> ORGANISM: Artificial Sequence
<220> FEATURE:
<223> OTHER INFORMATION: siRNA

<400> SEQUENCE: 220
agagcacuga gaauacuguc ccu 23

<210> SEQ ID NO 221
<211> LENGTH: 19
<212> TYPE: RNA
<213> ORGANISM: Artificial Sequence
<220> FEATURE:
<223> OTHER INFORMATION: siRNA

<400> SEQUENCE: 221
acaguauucu cagugcucu 19

<210> SEQ ID NO 222
<211> LENGTH: 21
<212> TYPE: RNA
<213> ORGANISM: Artificial Sequence
<220> FEATURE:
<223> OTHER INFORMATION: siRNA

<400> SEQUENCE: 222
agagcacuga gaauacuguc c 21

<210> SEQ ID NO 223
<211> LENGTH: 21
<212> TYPE: RNA
<213> ORGANISM: Artificial Sequence
<220> FEATURE:
<223> OTHER INFORMATION: siRNA

<400> SEQUENCE: 223
ggacaguauu cucagugcuc u 21

<210> SEQ ID NO 224
<211> LENGTH: 23
<212> TYPE: RNA
<213> ORGANISM: Artificial Sequence
<220> FEATURE:
<223> OTHER INFORMATION: siRNA

<400> SEQUENCE: 224
agagcacuga gaauacuguc ccu 23

<210> SEQ ID NO 225
<211> LENGTH: 19
<212> TYPE: RNA
<213> ORGANISM: Artificial Sequence
<220> FEATURE:
<223> OTHER INFORMATION: siRNA

<400> SEQUENCE: 225
acaguauucu cagugcucu 19

<210> SEQ ID NO 226
<211> LENGTH: 21
<212> TYPE: RNA
<213> ORGANISM: Artificial Sequence
<220> FEATURE:
<223> OTHER INFORMATION: siRNA

<400> SEQUENCE: 226
agagcacuga gaauacuguc c 21

<210> SEQ ID NO 227
<211> LENGTH: 21
<212> TYPE: RNA
<213> ORGANISM: Artificial Sequence
<220> FEATURE:
<223> OTHER INFORMATION: siRNA

<400> SEQUENCE: 227
ggacaguauu cucagugcuc u 21

<210> SEQ ID NO 228
<211> LENGTH: 23
<212> TYPE: RNA
<213> ORGANISM: Artificial Sequence
<220> FEATURE:
<223> OTHER INFORMATION: siRNA

<400> SEQUENCE: 228
agagcacuga gaauacuguc ccu 23

<210> SEQ ID NO 229
<211> LENGTH: 19
<212> TYPE: RNA
<213> ORGANISM: Artificial Sequence
<220> FEATURE:
<223> OTHER INFORMATION: siRNA

<400> SEQUENCE: 229
uauucucagu gcucuccua 19

<210> SEQ ID NO 230
<211> LENGTH: 21
<212> TYPE: RNA
<213> ORGANISM: Artificial Sequence
<220> FEATURE:
<223> OTHER INFORMATION: siRNA

<400> SEQUENCE: 230
uaggagagca cugagaauac u 21

<210> SEQ ID NO 231
<211> LENGTH: 21
<212> TYPE: RNA
<213> ORGANISM: Artificial Sequence
<220> FEATURE:
<223> OTHER INFORMATION: siRNA

<400> SEQUENCE: 231
aguauucuca gugcucuccu a 21

<210> SEQ ID NO 232
<211> LENGTH: 23
<212> TYPE: RNA
<213> ORGANISM: Artificial Sequence
<220> FEATURE:
<223> OTHER INFORMATION: siRNA

<400> SEQUENCE: 232
uaggagagca cugagaauac ugu 23

<210> SEQ ID NO 233
<211> LENGTH: 19
<212> TYPE: RNA
<213> ORGANISM: Artificial Sequence
<220> FEATURE:
<223> OTHER INFORMATION: siRNA

<400> SEQUENCE: 233
uauucucagu gcucuccua 19

<210> SEQ ID NO 234
<211> LENGTH: 21
<212> TYPE: RNA
<213> ORGANISM: Artificial Sequence
<220> FEATURE:
<223> OTHER INFORMATION: siRNA

<400> SEQUENCE: 234
uaggagagca cugagaauac u 21

<210> SEQ ID NO 235
<211> LENGTH: 21
<212> TYPE: RNA
<213> ORGANISM: Artificial Sequence
<220> FEATURE:
<223> OTHER INFORMATION: siRNA

<400> SEQUENCE: 235
aguauucuca gugcucuccu a 21

<210> SEQ ID NO 236
<211> LENGTH: 23
<212> TYPE: RNA
<213> ORGANISM: Artificial Sequence
<220> FEATURE:
<223> OTHER INFORMATION: siRNA

<400> SEQUENCE: 236
uaggagagca cugagaauac ugu 23

<210> SEQ ID NO 237
<211> LENGTH: 19
<212> TYPE: RNA
<213> ORGANISM: Artificial Sequence
<220> FEATURE:
<223> OTHER INFORMATION: siRNA

<400> SEQUENCE: 237
uauucucagu gcucuccua 19

<210> SEQ ID NO 238
<211> LENGTH: 21
<212> TYPE: RNA
<213> ORGANISM: Artificial Sequence
<220> FEATURE:
<223> OTHER INFORMATION: siRNA

<400> SEQUENCE: 238
uaggagagca cugagaauac u 21

<210> SEQ ID NO 239
<211> LENGTH: 21
<212> TYPE: RNA
<213> ORGANISM: Artificial Sequence
<220> FEATURE:
<223> OTHER INFORMATION: siRNA

<400> SEQUENCE: 239
aguauucuca gugcucuccu a 21

<210> SEQ ID NO 240
<211> LENGTH: 23
<212> TYPE: RNA
<213> ORGANISM: Artificial Sequence
<220> FEATURE:
<223> OTHER INFORMATION: siRNA

<400> SEQUENCE: 240
uaggagagca cugagaauac ugu 23

<210> SEQ ID NO 241
<211> LENGTH: 19
<212> TYPE: RNA
<213> ORGANISM: Artificial Sequence
<220> FEATURE:
<223> OTHER INFORMATION: siRNA

<400> SEQUENCE: 241
uauucucagu gcucuccua 19

<210> SEQ ID NO 242
<211> LENGTH: 21
<212> TYPE: RNA
<213> ORGANISM: Artificial Sequence
<220> FEATURE:
<223> OTHER INFORMATION: siRNA

<400> SEQUENCE: 242
uaggagagca cugagaauac u 21

<210> SEQ ID NO 243
<211> LENGTH: 21
<212> TYPE: RNA
<213> ORGANISM: Artificial Sequence
<220> FEATURE:
<223> OTHER INFORMATION: siRNA

<400> SEQUENCE: 243
aguauucuca gugcucuccu a 21

<210> SEQ ID NO 244

<211> LENGTH: 23
<212> TYPE: RNA
<213> ORGANISM: Artificial Sequence
<220> FEATURE:
<223> OTHER INFORMATION: siRNA

<400> SEQUENCE: 244
uaggagagca cugagaauac ugu 23

<210> SEQ ID NO 245
<211> LENGTH: 19
<212> TYPE: RNA
<213> ORGANISM: Artificial Sequence
<220> FEATURE:
<223> OTHER INFORMATION: siRNA

<400> SEQUENCE: 245
uauucucagu gcucuccua 19

<210> SEQ ID NO 246
<211> LENGTH: 21
<212> TYPE: RNA
<213> ORGANISM: Artificial Sequence
<220> FEATURE:
<223> OTHER INFORMATION: siRNA

<400> SEQUENCE: 246
uaggagagca cugagaauac u 21

<210> SEQ ID NO 247
<211> LENGTH: 21
<212> TYPE: RNA
<213> ORGANISM: Artificial Sequence
<220> FEATURE:
<223> OTHER INFORMATION: siRNA

<400> SEQUENCE: 247
aguauucuca gugcucuccu a 21

<210> SEQ ID NO 248
<211> LENGTH: 23
<212> TYPE: RNA
<213> ORGANISM: Artificial Sequence
<220> FEATURE:
<223> OTHER INFORMATION: siRNA

<400> SEQUENCE: 248
uaggagagca cugagaauac ugu 23

<210> SEQ ID NO 249
<211> LENGTH: 19
<212> TYPE: RNA
<213> ORGANISM: Artificial Sequence
<220> FEATURE:
<223> OTHER INFORMATION: siRNA

<400> SEQUENCE: 249
uauucucagu gcucuccua 19

<210> SEQ ID NO 250
<211> LENGTH: 21
<212> TYPE: RNA
<213> ORGANISM: Artificial Sequence
<220> FEATURE:
<223> OTHER INFORMATION: siRNA

<400> SEQUENCE: 250
uaggagagca cugagaauac u 21

<210> SEQ ID NO 251
<211> LENGTH: 21
<212> TYPE: RNA
<213> ORGANISM: Artificial Sequence
<220> FEATURE:
<223> OTHER INFORMATION: siRNA

<400> SEQUENCE: 251
aguauucuca gugcucuccu a 21

<210> SEQ ID NO 252
<211> LENGTH: 23
<212> TYPE: RNA
<213> ORGANISM: Artificial Sequence
<220> FEATURE:
<223> OTHER INFORMATION: siRNA

<400> SEQUENCE: 252
uaggagagca cugagaauac ugu 23

<210> SEQ ID NO 253
<211> LENGTH: 19
<212> TYPE: RNA
<213> ORGANISM: Artificial Sequence
<220> FEATURE:
<223> OTHER INFORMATION: siRNA

<400> SEQUENCE: 253
aguauucuca gugcucucc 19

<210> SEQ ID NO 254
<211> LENGTH: 21
<212> TYPE: RNA
<213> ORGANISM: Artificial Sequence
<220> FEATURE:
<223> OTHER INFORMATION: siRNA

<400> SEQUENCE: 254
ggagagcacu gagaauacug u 21

<210> SEQ ID NO 255
<211> LENGTH: 21
<212> TYPE: RNA
<213> ORGANISM: Artificial Sequence
<220> FEATURE:
<223> OTHER INFORMATION: siRNA

<400> SEQUENCE: 255
acaguauucu cagugcucuc c 21

<210> SEQ ID NO 256
<211> LENGTH: 23
<212> TYPE: RNA
<213> ORGANISM: Artificial Sequence
<220> FEATURE:
<223> OTHER INFORMATION: siRNA

<400> SEQUENCE: 256
ggagagcacu gagaauacug ucc 23

<210> SEQ ID NO 257
<211> LENGTH: 19
<212> TYPE: RNA

<213> ORGANISM: Artificial Sequence
<220> FEATURE:
<223> OTHER INFORMATION: siRNA

<400> SEQUENCE: 257
aguauucuca gugcucucc 19

<210> SEQ ID NO 258
<211> LENGTH: 21
<212> TYPE: RNA
<213> ORGANISM: Artificial Sequence
<220> FEATURE:
<223> OTHER INFORMATION: siRNA

<400> SEQUENCE: 258
ggagagcacu gagaauacug u 21

<210> SEQ ID NO 259
<211> LENGTH: 21
<212> TYPE: RNA
<213> ORGANISM: Artificial Sequence
<220> FEATURE:
<223> OTHER INFORMATION: siRNA

<400> SEQUENCE: 259
acaguauucu cagugcucuc c 21

<210> SEQ ID NO 260
<211> LENGTH: 23
<212> TYPE: RNA
<213> ORGANISM: Artificial Sequence
<220> FEATURE:
<223> OTHER INFORMATION: siRNA

<400> SEQUENCE: 260
ggagagcacu gagaauacug ucc 23

<210> SEQ ID NO 261
<211> LENGTH: 19
<212> TYPE: RNA
<213> ORGANISM: Artificial Sequence
<220> FEATURE:
<223> OTHER INFORMATION: siRNA

<400> SEQUENCE: 261
aguauucuca gugcucucc 19

<210> SEQ ID NO 262
<211> LENGTH: 21
<212> TYPE: RNA
<213> ORGANISM: Artificial Sequence
<220> FEATURE:
<223> OTHER INFORMATION: siRNA

<400> SEQUENCE: 262
ggagagcacu gagaauacug u 21

<210> SEQ ID NO 263
<211> LENGTH: 21
<212> TYPE: RNA
<213> ORGANISM: Artificial Sequence
<220> FEATURE:
<223> OTHER INFORMATION: siRNA

<400> SEQUENCE: 263
acaguauucu cagugcucuc c 21

<210> SEQ ID NO 264
<211> LENGTH: 23
<212> TYPE: RNA
<213> ORGANISM: Artificial Sequence
<220> FEATURE:
<223> OTHER INFORMATION: siRNA

<400> SEQUENCE: 264
ggagagcacu gagaauacug ucc 23

<210> SEQ ID NO 265
<211> LENGTH: 19
<212> TYPE: RNA
<213> ORGANISM: Artificial Sequence
<220> FEATURE:
<223> OTHER INFORMATION: siRNA

<400> SEQUENCE: 265
aguauucuca gugcucucc 19

<210> SEQ ID NO 266
<211> LENGTH: 21
<212> TYPE: RNA
<213> ORGANISM: Artificial Sequence
<220> FEATURE:
<223> OTHER INFORMATION: siRNA

<400> SEQUENCE: 266
ggagagcacu gagaauacug u 21

<210> SEQ ID NO 267
<211> LENGTH: 21
<212> TYPE: RNA
<213> ORGANISM: Artificial Sequence
<220> FEATURE:
<223> OTHER INFORMATION: siRNA

<400> SEQUENCE: 267
acaguauucu cagugcucuc c 21

<210> SEQ ID NO 268
<211> LENGTH: 23
<212> TYPE: RNA
<213> ORGANISM: Artificial Sequence
<220> FEATURE:
<223> OTHER INFORMATION: siRNA

<400> SEQUENCE: 268
ggagagcacu gagaauacug ucc 23

<210> SEQ ID NO 269
<211> LENGTH: 19
<212> TYPE: RNA
<213> ORGANISM: Artificial Sequence
<220> FEATURE:
<223> OTHER INFORMATION: siRNA

<400> SEQUENCE: 269
aguauucuca gugcucucc 19

<210> SEQ ID NO 270
<211> LENGTH: 21
<212> TYPE: RNA
<213> ORGANISM: Artificial Sequence
<220> FEATURE:

<223> OTHER INFORMATION: siRNA

<400> SEQUENCE: 270
ggagagcacu gagaauacug u 21

<210> SEQ ID NO 271
<211> LENGTH: 21
<212> TYPE: RNA
<213> ORGANISM: Artificial Sequence
<220> FEATURE:
<223> OTHER INFORMATION: siRNA

<400> SEQUENCE: 271
acaguauucu cagugcucuc c 21

<210> SEQ ID NO 272
<211> LENGTH: 23
<212> TYPE: RNA
<213> ORGANISM: Artificial Sequence
<220> FEATURE:
<223> OTHER INFORMATION: siRNA

<400> SEQUENCE: 272
ggagagcacu gagaauacug ucc 23

<210> SEQ ID NO 273
<211> LENGTH: 21
<212> TYPE: RNA
<213> ORGANISM: Artificial Sequence
<220> FEATURE:
<223> OTHER INFORMATION: siRNA

<400> SEQUENCE: 273
acaguauucu cagugcucuc c 21

<210> SEQ ID NO 274
<211> LENGTH: 23
<212> TYPE: RNA
<213> ORGANISM: Artificial Sequence
<220> FEATURE:
<223> OTHER INFORMATION: siRNA

<400> SEQUENCE: 274
ggagagcacu gagaauacug ucc 23

<210> SEQ ID NO 275
<211> LENGTH: 21
<212> TYPE: RNA
<213> ORGANISM: Artificial Sequence
<220> FEATURE:
<223> OTHER INFORMATION: siRNA

<400> SEQUENCE: 275
acaguauucu cagugcucuc c 21

<210> SEQ ID NO 276
<211> LENGTH: 23
<212> TYPE: RNA
<213> ORGANISM: Artificial Sequence
<220> FEATURE:
<223> OTHER INFORMATION: siRNA

<400> SEQUENCE: 276
ggagagcacu gagaauacug ucc 23

-continued

<210> SEQ ID NO 277
<211> LENGTH: 19
<212> TYPE: RNA
<213> ORGANISM: Artificial Sequence
<220> FEATURE:
<223> OTHER INFORMATION: siRNA

<400> SEQUENCE: 277
ggacaguauu cucagugcu 19

<210> SEQ ID NO 278
<211> LENGTH: 21
<212> TYPE: RNA
<213> ORGANISM: Artificial Sequence
<220> FEATURE:
<223> OTHER INFORMATION: siRNA

<400> SEQUENCE: 278
agcacugaga auacuguccc u 21

<210> SEQ ID NO 279
<211> LENGTH: 21
<212> TYPE: RNA
<213> ORGANISM: Artificial Sequence
<220> FEATURE:
<223> OTHER INFORMATION: siRNA

<400> SEQUENCE: 279
agggacagua uucucagugc u 21

<210> SEQ ID NO 280
<211> LENGTH: 23
<212> TYPE: RNA
<213> ORGANISM: Artificial Sequence
<220> FEATURE:
<223> OTHER INFORMATION: siRNA

<400> SEQUENCE: 280
agcacugaga auacuguccc uuu 23

<210> SEQ ID NO 281
<211> LENGTH: 19
<212> TYPE: RNA
<213> ORGANISM: Artificial Sequence
<220> FEATURE:
<223> OTHER INFORMATION: siRNA

<400> SEQUENCE: 281
ggacaguauu cucagugcu 19

<210> SEQ ID NO 282
<211> LENGTH: 21
<212> TYPE: RNA
<213> ORGANISM: Artificial Sequence
<220> FEATURE:
<223> OTHER INFORMATION: siRNA

<400> SEQUENCE: 282
agcacugaga auacuguccc u 21

<210> SEQ ID NO 283
<211> LENGTH: 21
<212> TYPE: RNA
<213> ORGANISM: Artificial Sequence
<220> FEATURE:
<223> OTHER INFORMATION: siRNA

<400> SEQUENCE: 283
agggacagua uucucagugc u 21

<210> SEQ ID NO 284
<211> LENGTH: 23
<212> TYPE: RNA
<213> ORGANISM: Artificial Sequence
<220> FEATURE:
<223> OTHER INFORMATION: siRNA

<400> SEQUENCE: 284
agcacugaga auacuguccc uuu 23

<210> SEQ ID NO 285
<211> LENGTH: 19
<212> TYPE: RNA
<213> ORGANISM: Artificial Sequence
<220> FEATURE:
<223> OTHER INFORMATION: siRNA

<400> SEQUENCE: 285
ggacaguauu cucagugcu 19

<210> SEQ ID NO 286
<211> LENGTH: 21
<212> TYPE: RNA
<213> ORGANISM: Artificial Sequence
<220> FEATURE:
<223> OTHER INFORMATION: siRNA

<400> SEQUENCE: 286
agcacugaga auacuguccc u 21

<210> SEQ ID NO 287
<211> LENGTH: 21
<212> TYPE: RNA
<213> ORGANISM: Artificial Sequence
<220> FEATURE:
<223> OTHER INFORMATION: siRNA

<400> SEQUENCE: 287
agggacagua uucucagugc u 21

<210> SEQ ID NO 288
<211> LENGTH: 23
<212> TYPE: RNA
<213> ORGANISM: Artificial Sequence
<220> FEATURE:
<223> OTHER INFORMATION: siRNA

<400> SEQUENCE: 288
agcacugaga auacuguccc uuu 23

<210> SEQ ID NO 289
<211> LENGTH: 19
<212> TYPE: RNA
<213> ORGANISM: Artificial Sequence
<220> FEATURE:
<223> OTHER INFORMATION: siRNA

<400> SEQUENCE: 289
ggacaguauu cucagugcu 19

<210> SEQ ID NO 290
<211> LENGTH: 21

<212> TYPE: RNA
<213> ORGANISM: Artificial Sequence
<220> FEATURE:
<223> OTHER INFORMATION: siRNA

<400> SEQUENCE: 290
agcacugaga auacuguccc u 21

<210> SEQ ID NO 291
<211> LENGTH: 21
<212> TYPE: RNA
<213> ORGANISM: Artificial Sequence
<220> FEATURE:
<223> OTHER INFORMATION: siRNA

<400> SEQUENCE: 291
agggacagua uucucagugc u 21

<210> SEQ ID NO 292
<211> LENGTH: 23
<212> TYPE: RNA
<213> ORGANISM: Artificial Sequence
<220> FEATURE:
<223> OTHER INFORMATION: siRNA

<400> SEQUENCE: 292
agcacugaga auacuguccc uuu 23

<210> SEQ ID NO 293
<211> LENGTH: 19
<212> TYPE: RNA
<213> ORGANISM: Artificial Sequence
<220> FEATURE:
<223> OTHER INFORMATION: siRNA

<400> SEQUENCE: 293
ggacaguauu cucagugcu 19

<210> SEQ ID NO 294
<211> LENGTH: 21
<212> TYPE: RNA
<213> ORGANISM: Artificial Sequence
<220> FEATURE:
<223> OTHER INFORMATION: siRNA

<400> SEQUENCE: 294
agcacugaga auacuguccc u 21

<210> SEQ ID NO 295
<211> LENGTH: 21
<212> TYPE: RNA
<213> ORGANISM: Artificial Sequence
<220> FEATURE:
<223> OTHER INFORMATION: siRNA

<400> SEQUENCE: 295
agggacagua uucucagugc u 21

<210> SEQ ID NO 296
<211> LENGTH: 23
<212> TYPE: RNA
<213> ORGANISM: Artificial Sequence
<220> FEATURE:
<223> OTHER INFORMATION: siRNA

<400> SEQUENCE: 296

-continued agcacugaga auacuguccc uuu 23

<210> SEQ ID NO 297
<211> LENGTH: 19
<212> TYPE: RNA
<213> ORGANISM: Artificial Sequence
<220> FEATURE:
<223> OTHER INFORMATION: siRNA

<400> SEQUENCE: 297
ggacaguauu cucagugcu 19

<210> SEQ ID NO 298
<211> LENGTH: 21
<212> TYPE: RNA
<213> ORGANISM: Artificial Sequence
<220> FEATURE:
<223> OTHER INFORMATION: siRNA

<400> SEQUENCE: 298
agcacugaga auacuguccc u 21

<210> SEQ ID NO 299
<211> LENGTH: 21
<212> TYPE: RNA
<213> ORGANISM: Artificial Sequence
<220> FEATURE:
<223> OTHER INFORMATION: siRNA

<400> SEQUENCE: 299
agggacagua uucucagugc u 21

<210> SEQ ID NO 300
<211> LENGTH: 23
<212> TYPE: RNA
<213> ORGANISM: Artificial Sequence
<220> FEATURE:
<223> OTHER INFORMATION: siRNA

<400> SEQUENCE: 300
agcacugaga auacuguccc uuu 23

<210> SEQ ID NO 301
<211> LENGTH: 19
<212> TYPE: RNA
<213> ORGANISM: Artificial Sequence
<220> FEATURE:
<223> OTHER INFORMATION: siRNA

<400> SEQUENCE: 301
uuaaaaggga caguauuca 19

<210> SEQ ID NO 302
<211> LENGTH: 21
<212> TYPE: RNA
<213> ORGANISM: Artificial Sequence
<220> FEATURE:
<223> OTHER INFORMATION: siRNA

<400> SEQUENCE: 302
ugaauacugu cccuuuuaag c 21

<210> SEQ ID NO 303
<211> LENGTH: 19
<212> TYPE: RNA
<213> ORGANISM: Artificial Sequence
<220> FEATURE:
<223> OTHER INFORMATION: siRNA

<400> SEQUENCE: 303
ggacaguauu cucagugca 19

<210> SEQ ID NO 304
<211> LENGTH: 21
<212> TYPE: RNA
<213> ORGANISM: Artificial Sequence
<220> FEATURE:
<223> OTHER INFORMATION: siRNA

<400> SEQUENCE: 304
ugcacugaga auacuguccc u 21

<210> SEQ ID NO 305
<211> LENGTH: 19
<212> TYPE: RNA
<213> ORGANISM: Artificial Sequence
<220> FEATURE:
<223> OTHER INFORMATION: siRNA

<400> SEQUENCE: 305
acaguauucu cagugcuca 19

<210> SEQ ID NO 306
<211> LENGTH: 21
<212> TYPE: RNA
<213> ORGANISM: Artificial Sequence
<220> FEATURE:
<223> OTHER INFORMATION: siRNA

<400> SEQUENCE: 306
ugagcacuga gaauacuguc c 21

<210> SEQ ID NO 307
<211> LENGTH: 19
<212> TYPE: RNA
<213> ORGANISM: Artificial Sequence
<220> FEATURE:
<223> OTHER INFORMATION: siRNA

<400> SEQUENCE: 307
aguauucuca gugcucuca 19

<210> SEQ ID NO 308
<211> LENGTH: 21
<212> TYPE: RNA
<213> ORGANISM: Artificial Sequence
<220> FEATURE:
<223> OTHER INFORMATION: siRNA

<400> SEQUENCE: 308
ugagagcacu gagaauacug u 21

<210> SEQ ID NO 309
<211> LENGTH: 19
<212> TYPE: RNA
<213> ORGANISM: Artificial Sequence
<220> FEATURE:
<223> OTHER INFORMATION: siRNA

<400> SEQUENCE: 309
uauucucagu gcucuccua 19

<210> SEQ ID NO 310
<211> LENGTH: 21
<212> TYPE: RNA
<213> ORGANISM: Artificial Sequence
<220> FEATURE:
<223> OTHER INFORMATION: siRNA

<400> SEQUENCE: 310
uaggagagca cugagaauac u 21

<210> SEQ ID NO 311
<211> LENGTH: 19
<212> TYPE: RNA
<213> ORGANISM: Artificial Sequence
<220> FEATURE:
<223> OTHER INFORMATION: siRNA

<400> SEQUENCE: 311
aguauucuca gugcucuca 19

<210> SEQ ID NO 312
<211> LENGTH: 21
<212> TYPE: RNA
<213> ORGANISM: Artificial Sequence
<220> FEATURE:
<223> OTHER INFORMATION: siRNA

<400> SEQUENCE: 312
ugagagcacu gagaauacug u 21

<210> SEQ ID NO 313
<211> LENGTH: 19
<212> TYPE: RNA
<213> ORGANISM: Artificial Sequence
<220> FEATURE:
<223> OTHER INFORMATION: siRNA

<400> SEQUENCE: 313
aguauucuca gugcucuca 19

<210> SEQ ID NO 314
<211> LENGTH: 21
<212> TYPE: RNA
<213> ORGANISM: Artificial Sequence
<220> FEATURE:
<223> OTHER INFORMATION: siRNA

<400> SEQUENCE: 314
ugagagcacu gagaauacug u 21

<210> SEQ ID NO 315
<211> LENGTH: 21
<212> TYPE: RNA
<213> ORGANISM: Artificial Sequence
<220> FEATURE:
<223> OTHER INFORMATION: siRNA

<400> SEQUENCE: 315
gcuuaaaagg gacaguauuc a 21

<210> SEQ ID NO 316
<211> LENGTH: 23
<212> TYPE: RNA
<213> ORGANISM: Artificial Sequence
<220> FEATURE:
<223> OTHER INFORMATION: siRNA

<400> SEQUENCE: 316
ugaauacugu cccuuuuaag caa 23

<210> SEQ ID NO 317
<211> LENGTH: 21
<212> TYPE: RNA
<213> ORGANISM: Artificial Sequence
<220> FEATURE:
<223> OTHER INFORMATION: siRNA

<400> SEQUENCE: 317
gcuuaaaagg gacaguauuc a 21

<210> SEQ ID NO 318
<211> LENGTH: 23
<212> TYPE: RNA
<213> ORGANISM: Artificial Sequence
<220> FEATURE:
<223> OTHER INFORMATION: siRNA

<400> SEQUENCE: 318
ugaauacugu cccuuuuaag caa 23

<210> SEQ ID NO 319
<211> LENGTH: 20
<212> TYPE: DNA
<213> ORGANISM: Artificial Sequence
<220> FEATURE:
<223> OTHER INFORMATION: siRNA
<220> FEATURE:
<223> OTHER INFORMATION: primer

<400> SEQUENCE: 319
gtgaccgatg gcttcagttc 20

<210> SEQ ID NO 320
<211> LENGTH: 20
<212> TYPE: DNA
<213> ORGANISM: Artificial Sequence
<220> FEATURE:
<223> OTHER INFORMATION: siRNA
<220> FEATURE:
<223> OTHER INFORMATION: primer

<400> SEQUENCE: 320
atggataggc aggtggactt 20

<210> SEQ ID NO 321
<211> LENGTH: 19
<212> TYPE: DNA
<213> ORGANISM: Artificial Sequence
<220> FEATURE:
<223> OTHER INFORMATION: siRNA
<220> FEATURE:
<223> OTHER INFORMATION: primer

<400> SEQUENCE: 321
ggtcggagtc aacggattt 19

<210> SEQ ID NO 322
<211> LENGTH: 19
<212> TYPE: DNA
<213> ORGANISM: Artificial Sequence
<220> FEATURE:
<223> OTHER INFORMATION: siRNA
<220> FEATURE:

<223> OTHER INFORMATION: primer

<400> SEQUENCE: 322
ccagcatcgc cccacttga 19

<210> SEQ ID NO 323
<211> LENGTH: 20
<212> TYPE: DNA
<213> ORGANISM: Artificial Sequence
<220> FEATURE:
<223> OTHER INFORMATION: siRNA
<220> FEATURE:
<223> OTHER INFORMATION: primer

<400> SEQUENCE: 323
gtgaccgatg gcttcagttc 20

<210> SEQ ID NO 324
<211> LENGTH: 20
<212> TYPE: DNA
<213> ORGANISM: Artificial Sequence
<220> FEATURE:
<223> OTHER INFORMATION: siRNA
<220> FEATURE:
<223> OTHER INFORMATION: primer

<400> SEQUENCE: 324
atggataggc aggtggactt 20

<210> SEQ ID NO 325
<211> LENGTH: 24
<212> TYPE: DNA
<213> ORGANISM: Artificial Sequence
<220> FEATURE:
<223> OTHER INFORMATION: siRNA
<220> FEATURE:
<223> OTHER INFORMATION: primer

<400> SEQUENCE: 325
agcttctttg cagctccttc gttg 24

<210> SEQ ID NO 326
<211> LENGTH: 24
<212> TYPE: DNA
<213> ORGANISM: Artificial Sequence
<220> FEATURE:
<223> OTHER INFORMATION: siRNA
<220> FEATURE:
<223> OTHER INFORMATION: primer

<400> SEQUENCE: 326
ttctgaccca ttcccaccat caca 24

<210> SEQ ID NO 327
<211> LENGTH: 19
<212> TYPE: RNA
<213> ORGANISM: Artificial Sequence
<220> FEATURE:
<223> OTHER INFORMATION: siRNA

<400> SEQUENCE: 327
uuaaaaggga caguauuca 19

<210> SEQ ID NO 328
<211> LENGTH: 21
<212> TYPE: RNA
<213> ORGANISM: Artificial Sequence
<220> FEATURE:
<223> OTHER INFORMATION: siRNA

<400> SEQUENCE: 328
ugaauacugu cccuuuuaag c 21

<210> SEQ ID NO 329
<211> LENGTH: 21
<212> TYPE: RNA
<213> ORGANISM: Artificial Sequence
<220> FEATURE:
<223> OTHER INFORMATION: siRNA

<400> SEQUENCE: 329
gcuuaaaagg gacaguauuc a 21

<210> SEQ ID NO 330
<211> LENGTH: 23
<212> TYPE: RNA
<213> ORGANISM: Artificial Sequence
<220> FEATURE:
<223> OTHER INFORMATION: siRNA

<400> SEQUENCE: 330
ugaauacugu cccuuuuaag caa 23

<210> SEQ ID NO 331
<211> LENGTH: 19
<212> TYPE: RNA
<213> ORGANISM: Artificial Sequence
<220> FEATURE:
<223> OTHER INFORMATION: siRNA

<400> SEQUENCE: 331
uuaaaaggga caguauuca 19

<210> SEQ ID NO 332
<211> LENGTH: 21
<212> TYPE: RNA
<213> ORGANISM: Artificial Sequence
<220> FEATURE:
<223> OTHER INFORMATION: siRNA

<400> SEQUENCE: 332
ugaauacugu cccuuuuaag c 21

<210> SEQ ID NO 333
<211> LENGTH: 21
<212> TYPE: RNA
<213> ORGANISM: Artificial Sequence
<220> FEATURE:
<223> OTHER INFORMATION: siRNA

<400> SEQUENCE: 333
gcuuaaaagg gacaguauuc a 21

<210> SEQ ID NO 334
<211> LENGTH: 23
<212> TYPE: RNA
<213> ORGANISM: Artificial Sequence
<220> FEATURE:
<223> OTHER INFORMATION: siRNA

<400> SEQUENCE: 334
ugaauacugu cccuuuuaag caa 23

<210> SEQ ID NO 335
<211> LENGTH: 19
<212> TYPE: RNA
<213> ORGANISM: Artificial Sequence
<220> FEATURE:
<223> OTHER INFORMATION: siRNA

<400> SEQUENCE: 335
uuaaaaggga caguauuca 19

<210> SEQ ID NO 336
<211> LENGTH: 21
<212> TYPE: RNA
<213> ORGANISM: Artificial Sequence
<220> FEATURE:
<223> OTHER INFORMATION: siRNA

<400> SEQUENCE: 336
ugaauacugu cccuuuuaag c 21

<210> SEQ ID NO 337
<211> LENGTH: 21
<212> TYPE: RNA
<213> ORGANISM: Artificial Sequence
<220> FEATURE:
<223> OTHER INFORMATION: siRNA

<400> SEQUENCE: 337
gcuuaaaagg gacaguauuc a 21

<210> SEQ ID NO 338
<211> LENGTH: 23
<212> TYPE: RNA
<213> ORGANISM: Artificial Sequence
<220> FEATURE:
<223> OTHER INFORMATION: siRNA

<400> SEQUENCE: 338
ugaauacugu cccuuuuaag caa 23

<210> SEQ ID NO 339
<211> LENGTH: 19
<212> TYPE: RNA
<213> ORGANISM: Artificial Sequence
<220> FEATURE:
<223> OTHER INFORMATION: siRNA

<400> SEQUENCE: 339
uuaaaaggga caguauuca 19

<210> SEQ ID NO 340
<211> LENGTH: 21
<212> TYPE: RNA
<213> ORGANISM: Artificial Sequence
<220> FEATURE:
<223> OTHER INFORMATION: siRNA

<400> SEQUENCE: 340
ugaauacugu cccuuuuaag c 21

<210> SEQ ID NO 341
<211> LENGTH: 21
<212> TYPE: RNA
<213> ORGANISM: Artificial Sequence
<220> FEATURE:
<223> OTHER INFORMATION: siRNA

<400> SEQUENCE: 341
gcuuaaaagg gacaguauuc a 21

<210> SEQ ID NO 342
<211> LENGTH: 23
<212> TYPE: RNA
<213> ORGANISM: Artificial Sequence
<220> FEATURE:
<223> OTHER INFORMATION: siRNA

<400> SEQUENCE: 342
ugaauacugu cccuuuuaag caa 23

<210> SEQ ID NO 343
<211> LENGTH: 19
<212> TYPE: RNA
<213> ORGANISM: Artificial Sequence
<220> FEATURE:
<223> OTHER INFORMATION: siRNA

<400> SEQUENCE: 343
uuaaaaggga caguauuca 19

<210> SEQ ID NO 344
<211> LENGTH: 21
<212> TYPE: RNA
<213> ORGANISM: Artificial Sequence
<220> FEATURE:
<223> OTHER INFORMATION: siRNA

<400> SEQUENCE: 344
ugaauacugu cccuuuuaag c 21

<210> SEQ ID NO 345
<211> LENGTH: 21
<212> TYPE: RNA
<213> ORGANISM: Artificial Sequence
<220> FEATURE:
<223> OTHER INFORMATION: siRNA

<400> SEQUENCE: 345
gcuuaaaagg gacaguauuc a 21

<210> SEQ ID NO 346
<211> LENGTH: 23
<212> TYPE: RNA
<213> ORGANISM: Artificial Sequence
<220> FEATURE:
<223> OTHER INFORMATION: siRNA

<400> SEQUENCE: 346
ugaauacugu cccuuuuaag caa 23

<210> SEQ ID NO 347
<211> LENGTH: 19
<212> TYPE: RNA
<213> ORGANISM: Artificial Sequence
<220> FEATURE:
<223> OTHER INFORMATION: siRNA

<400> SEQUENCE: 347
uuaaaaggga caguauuca 19

<210> SEQ ID NO 348

<211> LENGTH: 21
<212> TYPE: RNA
<213> ORGANISM: Artificial Sequence
<220> FEATURE:
<223> OTHER INFORMATION: siRNA

<400> SEQUENCE: 348
ugaauacugu cccuuuuaag c 21

<210> SEQ ID NO 349
<211> LENGTH: 21
<212> TYPE: RNA
<213> ORGANISM: Artificial Sequence
<220> FEATURE:
<223> OTHER INFORMATION: siRNA

<400> SEQUENCE: 349
gcuuaaaagg gacaguauuc a 21

<210> SEQ ID NO 350
<211> LENGTH: 23
<212> TYPE: RNA
<213> ORGANISM: Artificial Sequence
<220> FEATURE:
<223> OTHER INFORMATION: siRNA

<400> SEQUENCE: 350
ugaauacugu cccuuuuaag caa 23

<210> SEQ ID NO 351
<211> LENGTH: 19
<212> TYPE: RNA
<213> ORGANISM: Artificial Sequence
<220> FEATURE:
<223> OTHER INFORMATION: siRNA

<400> SEQUENCE: 351
acaguauucu cagugcuca 19

<210> SEQ ID NO 352
<211> LENGTH: 21
<212> TYPE: RNA
<213> ORGANISM: Artificial Sequence
<220> FEATURE:
<223> OTHER INFORMATION: siRNA

<400> SEQUENCE: 352
ugagcacuga gaauacuguc c 21

<210> SEQ ID NO 353
<211> LENGTH: 21
<212> TYPE: RNA
<213> ORGANISM: Artificial Sequence
<220> FEATURE:
<223> OTHER INFORMATION: siRNA

<400> SEQUENCE: 353
ggacaguauu cucagugcuc a 21

<210> SEQ ID NO 354
<211> LENGTH: 23
<212> TYPE: RNA
<213> ORGANISM: Artificial Sequence
<220> FEATURE:
<223> OTHER INFORMATION: siRNA

<400> SEQUENCE: 354
ugagcacuga gaauacuguc ccu 23

<210> SEQ ID NO 355
<211> LENGTH: 19
<212> TYPE: RNA
<213> ORGANISM: Artificial Sequence
<220> FEATURE:
<223> OTHER INFORMATION: siRNA

<400> SEQUENCE: 355
acaguauucu cagugcuca 19

<210> SEQ ID NO 356
<211> LENGTH: 21
<212> TYPE: RNA
<213> ORGANISM: Artificial Sequence
<220> FEATURE:
<223> OTHER INFORMATION: siRNA

<400> SEQUENCE: 356
ugagcacuga gaauacuguc c 21

<210> SEQ ID NO 357
<211> LENGTH: 21
<212> TYPE: RNA
<213> ORGANISM: Artificial Sequence
<220> FEATURE:
<223> OTHER INFORMATION: siRNA

<400> SEQUENCE: 357
ggacaguauu cucagugcuc a 21

<210> SEQ ID NO 358
<211> LENGTH: 23
<212> TYPE: RNA
<213> ORGANISM: Artificial Sequence
<220> FEATURE:
<223> OTHER INFORMATION: siRNA

<400> SEQUENCE: 358
ugagcacuga gaauacuguc ccu 23

<210> SEQ ID NO 359
<211> LENGTH: 19
<212> TYPE: RNA
<213> ORGANISM: Artificial Sequence
<220> FEATURE:
<223> OTHER INFORMATION: siRNA

<400> SEQUENCE: 359
acaguauucu cagugcuca 19

<210> SEQ ID NO 360
<211> LENGTH: 21
<212> TYPE: RNA
<213> ORGANISM: Artificial Sequence
<220> FEATURE:
<223> OTHER INFORMATION: siRNA

<400> SEQUENCE: 360
ugagcacuga gaauacuguc c 21

<210> SEQ ID NO 361
<211> LENGTH: 21
<212> TYPE: RNA

<213> ORGANISM: Artificial Sequence
<220> FEATURE:
<223> OTHER INFORMATION: siRNA

<400> SEQUENCE: 361
ggacaguauu cucagugcuc a 21

<210> SEQ ID NO 362
<211> LENGTH: 23
<212> TYPE: RNA
<213> ORGANISM: Artificial Sequence
<220> FEATURE:
<223> OTHER INFORMATION: siRNA

<400> SEQUENCE: 362
ugagcacuga gaauacuguc ccu 23

<210> SEQ ID NO 363
<211> LENGTH: 19
<212> TYPE: RNA
<213> ORGANISM: Artificial Sequence
<220> FEATURE:
<223> OTHER INFORMATION: siRNA

<400> SEQUENCE: 363
acaguauucu cagugcuca 19

<210> SEQ ID NO 364
<211> LENGTH: 21
<212> TYPE: RNA
<213> ORGANISM: Artificial Sequence
<220> FEATURE:
<223> OTHER INFORMATION: siRNA

<400> SEQUENCE: 364
ugagcacuga gaauacuguc c 21

<210> SEQ ID NO 365
<211> LENGTH: 21
<212> TYPE: RNA
<213> ORGANISM: Artificial Sequence
<220> FEATURE:
<223> OTHER INFORMATION: siRNA

<400> SEQUENCE: 365
ggacaguauu cucagugcuc a 21

<210> SEQ ID NO 366
<211> LENGTH: 23
<212> TYPE: RNA
<213> ORGANISM: Artificial Sequence
<220> FEATURE:
<223> OTHER INFORMATION: siRNA

<400> SEQUENCE: 366
ugagcacuga gaauacuguc ccu 23

<210> SEQ ID NO 367
<211> LENGTH: 19
<212> TYPE: RNA
<213> ORGANISM: Artificial Sequence
<220> FEATURE:
<223> OTHER INFORMATION: siRNA

<400> SEQUENCE: 367
acaguauucu cagugcuca 19

<210> SEQ ID NO 368
<211> LENGTH: 21
<212> TYPE: RNA
<213> ORGANISM: Artificial Sequence
<220> FEATURE:
<223> OTHER INFORMATION: siRNA

<400> SEQUENCE: 368
ugagcacuga gaauacuguc c 21

<210> SEQ ID NO 369
<211> LENGTH: 21
<212> TYPE: RNA
<213> ORGANISM: Artificial Sequence
<220> FEATURE:
<223> OTHER INFORMATION: siRNA

<400> SEQUENCE: 369
ggacaguauu cucagugcuc a 21

<210> SEQ ID NO 370
<211> LENGTH: 23
<212> TYPE: RNA
<213> ORGANISM: Artificial Sequence
<220> FEATURE:
<223> OTHER INFORMATION: siRNA

<400> SEQUENCE: 370
ugagcacuga gaauacuguc ccu 23

<210> SEQ ID NO 371
<211> LENGTH: 19
<212> TYPE: RNA
<213> ORGANISM: Artificial Sequence
<220> FEATURE:
<223> OTHER INFORMATION: siRNA

<400> SEQUENCE: 371
acaguauucu cagugcuca 19

<210> SEQ ID NO 372
<211> LENGTH: 21
<212> TYPE: RNA
<213> ORGANISM: Artificial Sequence
<220> FEATURE:
<223> OTHER INFORMATION: siRNA

<400> SEQUENCE: 372
ugagcacuga gaauacuguc c 21

<210> SEQ ID NO 373
<211> LENGTH: 21
<212> TYPE: RNA
<213> ORGANISM: Artificial Sequence
<220> FEATURE:
<223> OTHER INFORMATION: siRNA

<400> SEQUENCE: 373
ggacaguauu cucagugcuc a 21

<210> SEQ ID NO 374
<211> LENGTH: 23
<212> TYPE: RNA
<213> ORGANISM: Artificial Sequence
<220> FEATURE:

<223> OTHER INFORMATION: siRNA

<400> SEQUENCE: 374
ugagcacuga gaauacuguc ccu 23

<210> SEQ ID NO 375
<211> LENGTH: 19
<212> TYPE: RNA
<213> ORGANISM: Artificial Sequence
<220> FEATURE:
<223> OTHER INFORMATION: siRNA

<400> SEQUENCE: 375
aguauucuca gugcucuca 19

<210> SEQ ID NO 376
<211> LENGTH: 21
<212> TYPE: RNA
<213> ORGANISM: Artificial Sequence
<220> FEATURE:
<223> OTHER INFORMATION: siRNA

<400> SEQUENCE: 376
ugagagcacu gagaauacug u 21

<210> SEQ ID NO 377
<211> LENGTH: 21
<212> TYPE: RNA
<213> ORGANISM: Artificial Sequence
<220> FEATURE:
<223> OTHER INFORMATION: siRNA

<400> SEQUENCE: 377
acaguauucu cagugcucuc a 21

<210> SEQ ID NO 378
<211> LENGTH: 23
<212> TYPE: RNA
<213> ORGANISM: Artificial Sequence
<220> FEATURE:
<223> OTHER INFORMATION: siRNA

<400> SEQUENCE: 378
ugagagcacu gagaauacug ucc 23

<210> SEQ ID NO 379
<211> LENGTH: 19
<212> TYPE: RNA
<213> ORGANISM: Artificial Sequence
<220> FEATURE:
<223> OTHER INFORMATION: siRNA

<400> SEQUENCE: 379
aguauucuca gugcucuca 19

<210> SEQ ID NO 380
<211> LENGTH: 21
<212> TYPE: RNA
<213> ORGANISM: Artificial Sequence
<220> FEATURE:
<223> OTHER INFORMATION: siRNA

<400> SEQUENCE: 380
ugagagcacu gagaauacug u 21

-continued

<210> SEQ ID NO 381
<211> LENGTH: 21
<212> TYPE: RNA
<213> ORGANISM: Artificial Sequence
<220> FEATURE:
<223> OTHER INFORMATION: siRNA

<400> SEQUENCE: 381
acaguauucu cagugcucuc a 21

<210> SEQ ID NO 382
<211> LENGTH: 23
<212> TYPE: RNA
<213> ORGANISM: Artificial Sequence
<220> FEATURE:
<223> OTHER INFORMATION: siRNA

<400> SEQUENCE: 382
ugagagcacu gagaauacug ucc 23

<210> SEQ ID NO 383
<211> LENGTH: 19
<212> TYPE: RNA
<213> ORGANISM: Artificial Sequence
<220> FEATURE:
<223> OTHER INFORMATION: siRNA

<400> SEQUENCE: 383
aguauucuca gugcucuca 19

<210> SEQ ID NO 384
<211> LENGTH: 21
<212> TYPE: RNA
<213> ORGANISM: Artificial Sequence
<220> FEATURE:
<223> OTHER INFORMATION: siRNA

<400> SEQUENCE: 384
ugagagcacu gagaauacug u 21

<210> SEQ ID NO 385
<211> LENGTH: 21
<212> TYPE: RNA
<213> ORGANISM: Artificial Sequence
<220> FEATURE:
<223> OTHER INFORMATION: siRNA

<400> SEQUENCE: 385
acaguauucu cagugcucuc a 21

<210> SEQ ID NO 386
<211> LENGTH: 23
<212> TYPE: RNA
<213> ORGANISM: Artificial Sequence
<220> FEATURE:
<223> OTHER INFORMATION: siRNA

<400> SEQUENCE: 386
ugagagcacu gagaauacug ucc 23

<210> SEQ ID NO 387
<211> LENGTH: 19
<212> TYPE: RNA
<213> ORGANISM: Artificial Sequence
<220> FEATURE:
<223> OTHER INFORMATION: siRNA

<400> SEQUENCE: 387
aguauucuca gugcucuca 19

<210> SEQ ID NO 388
<211> LENGTH: 21
<212> TYPE: RNA
<213> ORGANISM: Artificial Sequence
<220> FEATURE:
<223> OTHER INFORMATION: siRNA

<400> SEQUENCE: 388
ugagagcacu gagaauacug u 21

<210> SEQ ID NO 389
<211> LENGTH: 21
<212> TYPE: RNA
<213> ORGANISM: Artificial Sequence
<220> FEATURE:
<223> OTHER INFORMATION: siRNA

<400> SEQUENCE: 389
acaguauucu cagugcucuc a 21

<210> SEQ ID NO 390
<211> LENGTH: 23
<212> TYPE: RNA
<213> ORGANISM: Artificial Sequence
<220> FEATURE:
<223> OTHER INFORMATION: siRNA

<400> SEQUENCE: 390
ugagagcacu gagaauacug ucc 23

<210> SEQ ID NO 391
<211> LENGTH: 19
<212> TYPE: RNA
<213> ORGANISM: Artificial Sequence
<220> FEATURE:
<223> OTHER INFORMATION: siRNA

<400> SEQUENCE: 391
aguauucuca gugcucuca 19

<210> SEQ ID NO 392
<211> LENGTH: 21
<212> TYPE: RNA
<213> ORGANISM: Artificial Sequence
<220> FEATURE:
<223> OTHER INFORMATION: siRNA

<400> SEQUENCE: 392
ugagagcacu gagaauacug u 21

<210> SEQ ID NO 393
<211> LENGTH: 21
<212> TYPE: RNA
<213> ORGANISM: Artificial Sequence
<220> FEATURE:
<223> OTHER INFORMATION: siRNA

<400> SEQUENCE: 393
acaguauucu cagugcucuc a 21

<210> SEQ ID NO 394
<211> LENGTH: 23

<212> TYPE: RNA
<213> ORGANISM: Artificial Sequence
<220> FEATURE:
<223> OTHER INFORMATION: siRNA

<400> SEQUENCE: 394
ugagagcacu gagaauacug ucc 23

<210> SEQ ID NO 395
<211> LENGTH: 19
<212> TYPE: RNA
<213> ORGANISM: Artificial Sequence
<220> FEATURE:
<223> OTHER INFORMATION: siRNA

<400> SEQUENCE: 395
aguauucuca gugcucuca 19

<210> SEQ ID NO 396
<211> LENGTH: 21
<212> TYPE: RNA
<213> ORGANISM: Artificial Sequence
<220> FEATURE:
<223> OTHER INFORMATION: siRNA

<400> SEQUENCE: 396
ugagagcacu gagaauacug u 21

<210> SEQ ID NO 397
<211> LENGTH: 21
<212> TYPE: RNA
<213> ORGANISM: Artificial Sequence
<220> FEATURE:
<223> OTHER INFORMATION: siRNA

<400> SEQUENCE: 397
acaguauucu cagugcucuc a 21

<210> SEQ ID NO 398
<211> LENGTH: 23
<212> TYPE: RNA
<213> ORGANISM: Artificial Sequence
<220> FEATURE:
<223> OTHER INFORMATION: siRNA

<400> SEQUENCE: 398
ugagagcacu gagaauacug ucc 23

<210> SEQ ID NO 399
<211> LENGTH: 19
<212> TYPE: RNA
<213> ORGANISM: Artificial Sequence
<220> FEATURE:
<223> OTHER INFORMATION: siRNA

<400> SEQUENCE: 399
ggacaguauu cucagugca 19

<210> SEQ ID NO 400
<211> LENGTH: 21
<212> TYPE: RNA
<213> ORGANISM: Artificial Sequence
<220> FEATURE:
<223> OTHER INFORMATION: siRNA

<400> SEQUENCE: 400
ugcacugaga auacuguccc u 21

<210> SEQ ID NO 401
<211> LENGTH: 21
<212> TYPE: RNA
<213> ORGANISM: Artificial Sequence
<220> FEATURE:
<223> OTHER INFORMATION: siRNA

<400> SEQUENCE: 401
agggacagua uucucagugc a 21

<210> SEQ ID NO 402
<211> LENGTH: 23
<212> TYPE: RNA
<213> ORGANISM: Artificial Sequence
<220> FEATURE:
<223> OTHER INFORMATION: siRNA

<400> SEQUENCE: 402
ugcacugaga auacuguccc uuu 23

<210> SEQ ID NO 403
<211> LENGTH: 19
<212> TYPE: RNA
<213> ORGANISM: Artificial Sequence
<220> FEATURE:
<223> OTHER INFORMATION: siRNA

<400> SEQUENCE: 403
ggacaguauu cucagugca 19

<210> SEQ ID NO 404
<211> LENGTH: 21
<212> TYPE: RNA
<213> ORGANISM: Artificial Sequence
<220> FEATURE:
<223> OTHER INFORMATION: siRNA

<400> SEQUENCE: 404
ugcacugaga auacuguccc u 21

<210> SEQ ID NO 405
<211> LENGTH: 21
<212> TYPE: RNA
<213> ORGANISM: Artificial Sequence
<220> FEATURE:
<223> OTHER INFORMATION: siRNA

<400> SEQUENCE: 405
agggacagua uucucagugc a 21

<210> SEQ ID NO 406
<211> LENGTH: 23
<212> TYPE: RNA
<213> ORGANISM: Artificial Sequence
<220> FEATURE:
<223> OTHER INFORMATION: siRNA

<400> SEQUENCE: 406
ugcacugaga auacuguccc uuu 23

<210> SEQ ID NO 407
<211> LENGTH: 19
<212> TYPE: RNA
<213> ORGANISM: Artificial Sequence
<220> FEATURE:
<223> OTHER INFORMATION: siRNA

<400> SEQUENCE: 407
ggacaguauu cucagugca 19

<210> SEQ ID NO 408
<211> LENGTH: 21
<212> TYPE: RNA
<213> ORGANISM: Artificial Sequence
<220> FEATURE:
<223> OTHER INFORMATION: siRNA

<400> SEQUENCE: 408
ugcacugaga auacuguccc u 21

<210> SEQ ID NO 409
<211> LENGTH: 21
<212> TYPE: RNA
<213> ORGANISM: Artificial Sequence
<220> FEATURE:
<223> OTHER INFORMATION: siRNA

<400> SEQUENCE: 409
agggacagua uucucagugc a 21

<210> SEQ ID NO 410
<211> LENGTH: 23
<212> TYPE: RNA
<213> ORGANISM: Artificial Sequence
<220> FEATURE:
<223> OTHER INFORMATION: siRNA

<400> SEQUENCE: 410
ugcacugaga auacuguccc uuu 23

<210> SEQ ID NO 411
<211> LENGTH: 19
<212> TYPE: RNA
<213> ORGANISM: Artificial Sequence
<220> FEATURE:
<223> OTHER INFORMATION: siRNA

<400> SEQUENCE: 411
ggacaguauu cucagugca 19

<210> SEQ ID NO 412
<211> LENGTH: 21
<212> TYPE: RNA
<213> ORGANISM: Artificial Sequence
<220> FEATURE:
<223> OTHER INFORMATION: siRNA

<400> SEQUENCE: 412
ugcacugaga auacuguccc u 21

<210> SEQ ID NO 413
<211> LENGTH: 21
<212> TYPE: RNA
<213> ORGANISM: Artificial Sequence
<220> FEATURE:
<223> OTHER INFORMATION: siRNA

<400> SEQUENCE: 413
agggacagua uucucagugc a 21

<210> SEQ ID NO 414
<211> LENGTH: 23
<212> TYPE: RNA
<213> ORGANISM: Artificial Sequence
<220> FEATURE:
<223> OTHER INFORMATION: siRNA

<400> SEQUENCE: 414
ugcacugaga auacuguccc uuu 23

<210> SEQ ID NO 415
<211> LENGTH: 19
<212> TYPE: RNA
<213> ORGANISM: Artificial Sequence
<220> FEATURE:
<223> OTHER INFORMATION: siRNA

<400> SEQUENCE: 415
ggacaguauu cucagugca 19

<210> SEQ ID NO 416
<211> LENGTH: 21
<212> TYPE: RNA
<213> ORGANISM: Artificial Sequence
<220> FEATURE:
<223> OTHER INFORMATION: siRNA

<400> SEQUENCE: 416
ugcacugaga auacuguccc u 21

<210> SEQ ID NO 417
<211> LENGTH: 21
<212> TYPE: RNA
<213> ORGANISM: Artificial Sequence
<220> FEATURE:
<223> OTHER INFORMATION: siRNA

<400> SEQUENCE: 417
agggacagua uucucagugc a 21

<210> SEQ ID NO 418
<211> LENGTH: 23
<212> TYPE: RNA
<213> ORGANISM: Artificial Sequence
<220> FEATURE:
<223> OTHER INFORMATION: siRNA

<400> SEQUENCE: 418
ugcacugaga auacuguccc uuu 23

<210> SEQ ID NO 419
<211> LENGTH: 19
<212> TYPE: RNA
<213> ORGANISM: Artificial Sequence
<220> FEATURE:
<223> OTHER INFORMATION: siRNA

<400> SEQUENCE: 419
ggacaguauu cucagugca 19

<210> SEQ ID NO 420
<211> LENGTH: 21
<212> TYPE: RNA
<213> ORGANISM: Artificial Sequence
<220> FEATURE:
<223> OTHER INFORMATION: siRNA

<400> SEQUENCE: 420
ugcacugaga auacuguccc u 21

<210> SEQ ID NO 421
<211> LENGTH: 21
<212> TYPE: RNA
<213> ORGANISM: Artificial Sequence
<220> FEATURE:
<223> OTHER INFORMATION: siRNA

<400> SEQUENCE: 421
agggacagua uucucagugc a 21

<210> SEQ ID NO 422
<211> LENGTH: 23
<212> TYPE: RNA
<213> ORGANISM: Artificial Sequence
<220> FEATURE:
<223> OTHER INFORMATION: siRNA

<400> SEQUENCE: 422
ugcacugaga auacuguccc uuu 23

<210> SEQ ID NO 423
<211> LENGTH: 19
<212> TYPE: RNA
<213> ORGANISM: Artificial Sequence
<220> FEATURE:
<223> OTHER INFORMATION: siRNA

<400> SEQUENCE: 423
uuaaaaggga caguauucu 19

<210> SEQ ID NO 424
<211> LENGTH: 21
<212> TYPE: RNA
<213> ORGANISM: Artificial Sequence
<220> FEATURE:
<223> OTHER INFORMATION: siRNA

<400> SEQUENCE: 424
agaauacugu cccuuuuaag c 21

<210> SEQ ID NO 425
<211> LENGTH: 19
<212> TYPE: RNA
<213> ORGANISM: Artificial Sequence
<220> FEATURE:
<223> OTHER INFORMATION: siRNA

<400> SEQUENCE: 425
ggacaguauu cucagugcu 19

<210> SEQ ID NO 426
<211> LENGTH: 21
<212> TYPE: RNA
<213> ORGANISM: Artificial Sequence
<220> FEATURE:
<223> OTHER INFORMATION: siRNA

<400> SEQUENCE: 426
agcacugaga auacuguccc u 21

<210> SEQ ID NO 427

-continued

```
<211> LENGTH: 19
<212> TYPE: RNA
<213> ORGANISM: Artificial Sequence
<220> FEATURE:
<223> OTHER INFORMATION: siRNA

<400> SEQUENCE: 427

acaguauucu cagugcucu                                               19


<210> SEQ ID NO 428
<211> LENGTH: 21
<212> TYPE: RNA
<213> ORGANISM: Artificial Sequence
<220> FEATURE:
<223> OTHER INFORMATION: siRNA

<400> SEQUENCE: 428

agagcacuga gaauacuguc c                                            21


<210> SEQ ID NO 429
<211> LENGTH: 19
<212> TYPE: RNA
<213> ORGANISM: Artificial Sequence
<220> FEATURE:
<223> OTHER INFORMATION: siRNA

<400> SEQUENCE: 429

uauucucagu gcucuccua                                               19


<210> SEQ ID NO 430
<211> LENGTH: 21
<212> TYPE: RNA
<213> ORGANISM: Artificial Sequence
<220> FEATURE:
<223> OTHER INFORMATION: siRNA

<400> SEQUENCE: 430

uaggagagca cugagaauac u                                            21
```